United States Patent
Kim et al.

(10) Patent No.: US 10,392,347 B2
(45) Date of Patent: Aug. 27, 2019

(54) 2,4-DIHYDROXY-NICOTINAMIDES AS APJ AGONISTS

(71) Applicant: BRISTOL-MYERS SQUIBB COMPANY, Princeton, NJ (US)

(72) Inventors: Soong-Hoon Kim, Titusville, NJ (US); Hannguang J. Chao, Nashua, NH (US); Heather Finlay, Skillman, NJ (US); Ji Jiang, West Windsor, NJ (US); James A. Johnson, Pennington, NJ (US); R. Michael Lawrence, Yardley, NJ (US); Michael C. Myers, Newtown, PA (US); Monique Phillips, Ewing, NJ (US); George O. Tora, Langhorne, PA (US); Wei Meng, Pennington, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 15/767,364

(22) PCT Filed: Oct. 13, 2016

(86) PCT No.: PCT/US2016/056769
§ 371 (c)(1),
(2) Date: Apr. 11, 2018

(87) PCT Pub. No.: WO2017/066402
PCT Pub. Date: Apr. 20, 2017

(65) Prior Publication Data
US 2018/0297954 A1  Oct. 18, 2018

Related U.S. Application Data

(60) Provisional application No. 62/241,367, filed on Oct. 14, 2015, provisional application No. 62/270,659, filed on Dec. 22, 2015.

(51) Int. Cl.
| C07D 213/82 | (2006.01) |
| C07D 401/06 | (2006.01) |
| C07D 401/14 | (2006.01) |
| C07D 405/14 | (2006.01) |
| C07D 413/12 | (2006.01) |
| C07D 413/14 | (2006.01) |
| C07D 417/12 | (2006.01) |
| C07D 417/14 | (2006.01) |
| C07D 491/107 | (2006.01) |
| C07D 498/10 | (2006.01) |
| C07D 401/12 | (2006.01) |
| C07D 471/10 | (2006.01) |

(52) U.S. Cl.
CPC ......... *C07D 213/82* (2013.01); *C07D 401/06* (2013.01); *C07D 401/12* (2013.01); *C07D 401/14* (2013.01); *C07D 405/14* (2013.01); *C07D 413/12* (2013.01); *C07D 413/14* (2013.01); *C07D 417/12* (2013.01); *C07D 417/14* (2013.01); *C07D 471/10* (2013.01); *C07D 491/107* (2013.01); *C07D 498/10* (2013.01)

(58) Field of Classification Search
CPC ... C07D 213/82; C07D 401/06; C07D 401/14
See application file for complete search history.

(56) References Cited

U.S. PATENT DOCUMENTS

| 6,310,069 B1 | 10/2001 | Lohray et al. |
| 7,732,613 B2 | 6/2010 | Kim |
| 2008/0171756 A1 | 7/2008 | Shaw et al. |
| 2016/0355507 A1 | 12/2016 | Johnson et al. |

FOREIGN PATENT DOCUMENTS

| CH | 602 664 | 7/1978 | |
| EP | 693477 | * 1/1996 | ........... C07D 213/82 |
| GB | 2 263 639 A | 4/1993 | |
| JP | 2004339159 A | 12/2004 | |
| KR | 2017009185 | 2/2017 | |
| WO | WO2002/06242 A2 | 1/2002 | |
| WO | WO2003/043992 A1 | 5/2003 | |
| WO | WO2003/094839 A2 | 11/2003 | |

(Continued)

OTHER PUBLICATIONS

Machine translation for EP 693477 (Year: 1996).*

(Continued)

*Primary Examiner* — Emily A Bernhardt
(74) *Attorney, Agent, or Firm* — Hong Liu

(57) ABSTRACT

The present invention provides compounds of Formula (I): wherein all variables are as defined in the specification, and compositions comprising any of such novel compounds. These compounds are APJ agonists which may be used as medicaments.

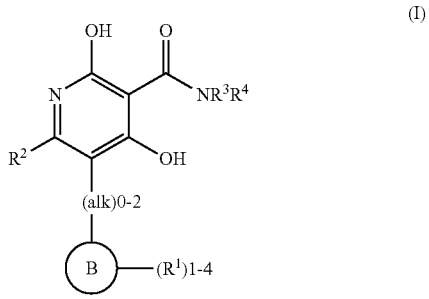

10 Claims, No Drawings

(56) References Cited

FOREIGN PATENT DOCUMENTS

| WO | WO2003/099211 A2 | 12/2003 |
|----|----|----|
| WO | WO2005/026148 A1 | 3/2005 |
| WO | WO2005/041888 A2 | 5/2005 |
| WO | WO2005/060654 A2 | 7/2005 |
| WO | WO2007/037543 A1 | 5/2007 |
| WO | WO2007/064797 A2 | 6/2007 |
| WO | WO207/124397 A2 | 11/2007 |
| WO | WO2008/052861 A2 | 5/2008 |
| WO | WO2008/052863 A2 | 5/2008 |
| WO | WO2008/103277 A2 | 8/2008 |
| WO | WO2009/129120 A2 | 10/2009 |
| WO | WO2010/072696 A2 | 7/2010 |
| WO | WO2010/132999 A1 | 11/2010 |
| WO | WO2012/020742 A1 | 2/2012 |
| WO | WO2012/163489 A1 | 12/2012 |
| WO | WO2012/163490 A1 | 12/2012 |
| WO | WO2014/004676 A1 | 1/2014 |
| WO | WO2014/067603 A1 | 5/2014 |
| WO | WO2014/160185 A2 | 10/2014 |
| WO | WO2014/207100 A1 | 12/2014 |
| WO | WO2014/207601 A1 | 12/2014 |
| WO | WO2015/079028 A1 | 6/2015 |
| WO | WO2015/184011 A2 | 12/2015 |
| WO | WO2015/188073 A1 | 12/2015 |
| WO | WO2016/074757 A1 | 5/2016 |
| WO | WO2016/171249 A1 | 10/2016 |
| WO | WO2016/187308 A1 | 11/2016 |
| WO | WO2016/196771 A1 | 12/2016 |
| WO | WO2017/091513 A1 | 6/2017 |
| WO | WO2017/096130 A1 | 6/2017 |
| WO | WO2017/106396 A1 | 6/2017 |
| WO | WO2017/165640 A1 | 9/2017 |
| WO | WO2017/218617 A1 | 12/2017 |
| WO | WO2017/218633 A1 | 12/2017 |
| WO | WO2018/071622 A1 | 4/2018 |

OTHER PUBLICATIONS

Cao, J. et al., "Targeting Drugs to APJ Receptor: The Prospect of Treatment of Hypertension and Other Cardiovascular Diseases", Current Drug Targets, vol. 16, pp. 148-155 (2015).

Maloney, Patrick R., et al., Discovery of 4-oxo-6-((pyrimidin-2-ylthio)methyl)-4H-pyran-3-yl4-nitrobenzoate (ML221) as a functional antagonist of the apelin (APJ) receptor, Bioorganic & Medicinal Chemistry Letters, vol. 22, pp. 6656-6660 (2012).

* cited by examiner

2,4-DIHYDROXY-NICOTINAMIDES AS APJ AGONISTS

CROSS REFERENCE TO RELATED APPLICATIONS

This application is a 371 application of PCT/US2016/056769, filed Oct. 13, 2016, which claims priority of U.S. Provisional Application Ser. No. 62/241,367, filed on Oct. 14, 2015 and U.S. Provisional Application Ser. No. 62/270,659, filed on Dec. 22, 2015, each of which is fully incorporated herein in its entirety.

FIELD OF THE INVENTION

The present invention provides novel 2,4-dihydroxy-nicotinamides, and their analogues thereof, which are APJ agonists, compositions containing them, and methods of using them, for example, for the treatment or prophylaxis of heart failure, atherosclerosis, ischemic heart disease and related conditions.

BACKGROUND OF THE INVENTION

Heart failure (HF) and related complications constitute major health burden in developed countries with an estimated prevalence of 5,700,000 in the United States alone (Roger, V. L. et al., Circulation, 125(1):e2-e220 (2012)). Despite considerable advances in recent two decades, the prognosis remains very poor, with survival rates of only ~50% within 5-years of diagnosis (Roger, V. L. et al., JAMA, 292(3):344-350 (2004)). In addition to poor survival, the impaired quality of life and recurrent hospitalizations constitute clear unmet medical need for development of novel treatment options.

HF is a clinical syndrome characterized by the inability of the heart to deliver sufficient supply of blood and oxygen to meet the metabolic demands of organs in the body. Main symptoms associated with HF include shortness of breath due to pulmonary edema, fatigue, reduced tolerance to exercise and lower extremity edemas. The etiology of HF is highly complex with multiple associated risk factors and potential causes.

Among the leading causes of HF are coronary artery disease and cardiac ischemia, acute myocardial infarction, intrinsic cardiomyopathies and chronic uncontrolled hypertension. HF can develop either acutely (functional impairment post myocardial infarction) or as a chronic condition, characterized by long-term maladaptive cardiac tissue remodeling, hypertrophy and cardiac dysfunction (for example due to uncontrolled long-term hypertension). According to the diagnostic criteria and type of ventricular dysfunction, HF is classified to two major groups, HF with "reduced ejection fraction" (HFrEF) or HF with "preserved ejection fraction" (HFpEF). Both types are associated with similar signs and symptoms, but differ in the type of ventricular functional impairment (Borlaug, B. A. et al., Eur. Heart J., 32(6):670-679 (2011)).

APJ receptor (APLNR) and its endogenous peptidic ligand apelin have been implicated as important modulators of cardiovascular function and candidates for therapeutic intervention in HF (for review see Japp, A. G. et al., Biochem. Pharmacol., 75(10):1882-1892 (2008)).

Accumulated evidence from preclinical disease models and human heart failure patients have implicated apelin and APJ agonism as beneficial in the setting of HF. Mice lacking Apelin or APJ gene have impaired myocyte contractility (Charo, D. N. et al., Am. J. Physiol. Heart Circ. Physiol., 297(5):H1904-H1913 (2009)). Apelin knockout (KO) mice develop progressive cardiac dysfunction with aging and are more susceptible to HF in the model of trans-aortic constriction (TAC) (Kuba, K. et al., Circ. Res., 101(4):e32-42 (2007)). The functional impairment in chronic HF is a result of prolonged demand on the heart and is associated with maladaptive cardiac remodeling, manifested by the cardiac hypertrophy, increased inflammation and interstitial fibrosis which eventually lead to decrease in cardiac performance.

Acute administration of apelin increases cardiac output in rodents under normal conditions and also in models of heart failure (Berry, M. F., Circulation, 110(11 Suppl. 1):11187-11193 (2004)). Increased cardiac output is a result of direct augmentation of cardiac contractility and reduced peripheral vascular resistance in the arterial and venous beds (Ashley, E. A., Cardiovasc. Res., 65(1):73-82 (2005)). Reduction in the vascular resistance leads to lower pre-load and after-load on the heart and thus lesser work load (Cheng, X. et al., Eur. J. Pharmacol., 470(3):171-175 (2003)). Similar to rodent studies, acute infusion of apelin to healthy human subjects and patients with heart failure produces similar hemodynamic responses with increased cardiac output and increased vasodilatory response in peripheral and coronary arteries (Japp, A. G. et al., Circulation, 121(16):1818-1827 (2010)).

The mechanisms underlying inotropic action of apelin are not well understood, but appear to be distinct from clinically used $\beta_1$-adrenergic agonists (dobutamine) due to lack of increase in heart rate. The vasodilatory action of apelin is primarily mediated via endothelial nitric oxide synthase pathways (Tatemoto, K., Regul. Pept., 99(2-3):87-92 (2001)). Apelin is induced under hypoxic conditions, promotes angiogenesis and has been shown to limit the infarct size in ischemia-reperfusion models (Simpkin, J. C., Basic Res. Cardiol., 102(6):518-528 (2007)).

In addition to aforementioned studies evaluating acute administration of apelin, several studies have clearly demonstrated beneficial effects of prolonged administration of apelin in a number of chronic rodent models of HF, including the angiotensin II model, TAC model and rat Dahl salt-sensitive model (Siddiquee, K. et al., J. Hypertens., 29(4):724-731 (2011); Scimia, M. C. et al., Nature, 488 (7411):394-398 (2012); Koguchi, W. et al., Circ. J., 76(1):137-144 (2012)). In these studies, prolonged apelin infusion reduced cardiac hypertrophy and cardiac fibrosis, and was associated with improvement in cardiac performance.

Genetic evidence is also emerging that polymorphisms in the APJ gene are associated with slower progression of HF (Sarzani, R. et al., J. Card. Fail., 13(7):521-529 (2007)). Importantly, while expression of APJ and apelin can be reduced or vary considerably with HF progression, the cardiovascular hemodynamic effects of apelin are sustained in patients with developed HF and receiving standard of care therapy (Japp, A. G. et al., Circulation, 121(16):1818-1827 (2010)).

In summary, there is a significant amount of evidence to indicate that APJ receptor agonism plays a cardioprotective role in HF and would be of potential benefit to HF patients. Apelin's very short half life in circulation limits its therapeutic utility, and consequently, there is a need for APJ receptor agonists with improved pharmacokinetic and signaling profile while maintaining or enhancing the beneficial effects of endogenous APJ agonist apelin.

SUMMARY OF THE INVENTION

The present invention provides 2,4-dihydroxy-nicotinamides, and their analogues thereof, which are useful as APJ agonists, including stereoisomers, tautomers, pharmaceutically acceptable salts, or solvates thereof.

The present invention also provides processes and intermediates for making the compounds of the present invention or stereoisomers, tautomers, pharmaceutically acceptable salts, or solvates thereof.

The present invention also provides pharmaceutical compositions comprising a pharmaceutically acceptable carrier and at least one of the compounds of the present invention or stereoisomers, tautomers, pharmaceutically acceptable salts, or solvates thereof.

The compounds of the invention may be used in the treatment and/or prophylaxis of multiple diseases or disorders associated with APJ, such as heart failure, coronary artery disease, cardiomyopathy, diabetes and related conditions including but not limited to acute coronary syndrome, myocardial ischemia, hypertension, pulmonary hypertension, coronary vasospasm, cerebral vasospasm, ischemia/reperfusion injury, angina, renal disease, metabolic syndrome and insulin resistance.

The compounds of the invention may be used in therapy.

The compounds of the invention may be used for the manufacture of a medicament for the treatment and/or prophylaxis of multiple diseases or disorders associated with APJ.

The compounds of the invention can be used alone, in combination with other compounds of the present invention, or in combination with one or more other agent(s).

Other features and advantages of the invention will be apparent from the following detailed description and claims.

DETAILED DESCRIPTION OF THE INVENTION

I. Compounds of the Invention

In a first aspect, the present disclosure provides, inter alia, a compound of Formula (I):

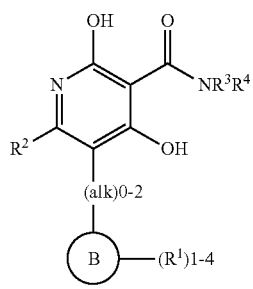

(I)

or a stereoisomer, an enantiomer, a diastereomer, a tautomer, a pharmaceutically acceptable salt, a prodrug, or a solvate thereof, wherein:

alk is $C_{1-6}$ alkyl substituted with 0-5 $R^e$;

ring B is independently selected from $C_{3-6}$ cycloalkyl, $C_{3-6}$ cycloalkenyl, aryl, bicyclic carbocyclyl, and 6-membered heteroaryl;

$R^1$ is independently selected from halogen, $NO_2$, —$(CH_2)_n$OR$^b$, $(CH_2)_nS(O)_pR_c$, —$(CH_2)_nC(=O)R^b$, —$(CH_2)_nNR^aR^a$, —$(CH_2)_nCN$, —$(CH_2)_nC(=O)NR^aR^a$, —$(CH_2)_nNR^aC(=O)R^b$, —$(CH_2)_nNR^aC(=O)NR^aR^a$, —$(CH_2)_nNR^aC(=O)OR^b$, —$(CH_2)_nOC(=O)NR^aR^a$, —$(CH_2)_nC(=O)OR^b$, —$(CH_2)_nS(O)_pNR^aR^a$, —$(CH_2)_nNR^aS(O)_pNR^aR^a$, —$(CH_2)_nNR^aS(O)_pR^c$, $C_{1-4}$ alkyl substituted with 0-3 $R^e$, —$(CH_2)_n$—$C_{3-6}$ carbocyclyl substituted with 0-3 $R^e$, and —$(CH_2)_n$-heterocyclyl substituted with 0-3 $R^e$;

$R^2$ is independently selected from $C_{1-5}$ alkyl substituted with 0-3 $R^e$; $C_{1-5}$ alkenyl substituted with 0-3 $R^e$, aryl substituted with 0-3 $R^e$, heterocyclyl substituted with 0-3 $R^e$, and $C_{3-6}$ cycloalkyl substituted with 0-3 $R^e$; provided when $R^2$ is $C_{1-5}$ alkyl, the carbon atom and the groups attached thereto except the one attached to the pyridine ring may be replaced by O, N, and S;

$R^3$ and $R^4$ are independently selected from $C_{1-5}$ alkyl substituted with 0-3 $R^6$; —$(CH_2)_n$—$C_{3-6}$ carbocyclyl substituted with 0-3 $R^6$, and —$(CH_2)_n$-heterocyclyl substituted with 0-3 $R^6$;

alternatively, $R^3$ and $R^4$ together with the nitrogen atom to which they are both attached form a heterocyclic ring or a spiro heterocyclic ring comprising carbon atoms and additional 1 to 4 heteroatoms selected from NR$^{5a}$, O, and S and substituted with 0-5 $R^5$;

$R^5$ is independently at each occurrence, selected from OH, halogen, —$(CR^7R^7)_n$—$C_{3-10}$ carbocycle, —$(CR^7R^7)_n$-heterocycle, and each substituted with 0-3 $R^6$;

$R^{5a}$ is independently at each occurrence, selected from —C(=O)OR$^b$, C(=O)NR$^aR^a$, —S(O)$_p$R$^c$, —$(CR^7R^7)_n$—$C_{3-10}$ carbocycle, —C(=O)—$C_{3-10}$ carbocycle, —$(CR^7R^7)_n$-heterocycle, each substituted with 0-3 $R^6$;

$R^6$ is independently selected from H, halogen, =O, —$(CH_2)_n$ OR$^b$, $(CH_2)_nS(O)_pR^c$, —$(CH_2)_nC(=O)R^b$, —$(CH_2)_n$ NR$^aR^a$, —$(CH_2)_nCN$, —$(CH_2)_nC(=O)NR^aR^a$, —$(CH_2)_n$ NR$^aC(=O)R^b$, —$(CH_2)_nNR^aC(=O)NR^aR^a$, —$(CH_2)_n$ NR$^aC(=O)OR^b$, —$(CH_2)_nOC(=O)NR^aR^a$, —$(CH_2)_nC(=O)OR^b$, —$(CH_2)_nS(O)_pNR^aR^a$, —$(CH_2)_n$ NR$^aS(O)_p$ NR$^aR^a$, —$(CH_2)_nNR^aS(O)_pR^c$, $C_{1-5}$ alkyl substituted with 0-3 $R^e$, $(CH_2)_n$—$C_{3-6}$ carbocyclyl substituted with 0-3 $R^e$, and —$(CH_2)_n$-heterocyclyl substituted with 0-3 $R^e$;

$R^7$ is, independently at each occurrence, selected from H, $C_{1-4}$ alkyl, and $(CH_2)_n$—$C_{3-12}$ carbocyclyl substituted with 0-3 $R^e$;

$R^a$, at each occurrence, is independently selected from H, $C_{1-6}$ alkyl substituted with 0-5 $R^e$, $C_{2-6}$ alkenyl substituted with 0-5 $R^e$, $C_{2-6}$ alkynyl substituted with 0-5 $R^e$, —$(CH_2)_n$—$C_{3-10}$carbocyclyl substituted with 0-5 $R^e$, and —$(CH_2)_n$-heterocyclyl substituted with 0-5 $R^e$; or $R^a$ and $R^a$ together with the nitrogen atom to which they are both attached form a heterocyclic ring substituted with 0-5 $R^e$;

$R^b$, at each occurrence, is independently selected from H, $C_{1-6}$ alkyl substituted with 0-5 $R^e$, $C_{2-6}$ alkenyl substituted with 0-5 $R^e$, $C_{2-6}$ alkynyl substituted with 0-5 $R^e$, —$(CH_2)_n$—$C_{3-10}$carbocyclyl substituted with 0-5 $R^e$, and —$(CH_2)_n$-heterocyclyl substituted with 0-5 $R^e$;

$R^c$, at each occurrence, is independently selected from $C_{1-6}$ alkyl substituted with 0-5 $R^e$, $C_{2-6}$alkenyl substituted with 0-5 $R^e$, $C_{2-6}$alkynyl substituted with 0-5 $R^e$, $C_{3-6}$carbocyclyl, and heterocyclyl;

$R^d$, at each occurrence, is independently selected from H and $C_{1-4}$alkyl substituted with 0-5 $R^e$;

$R^e$, at each occurrence, is independently selected from $C_{1-6}$ alkyl substituted with 0-5 $R_f$, $C_{2-6}$ alkenyl, $C_{2-6}$ alkynyl, —$(CH_2)_n$—$C_{3-6}$ cycloalkyl, —$(CH_2)_n$—$C_{4-6}$ heterocyclyl, —$(CH_2)_n$-aryl, —$(CH_2)_n$-heteroaryl, F, Cl, Br, CN, $NO_2$, =O, $CO_2H$, —$(CH_2)_nOR_f$, $S(O)_pR^f$, $C(=O)NR^fR^f$, $NR^fC(=O)R^f$, $S(O)_pNR^fR^f$, $NR^fS(O)_pR^f$, $NR^fC(=O)$ OR$^f$, OC(=O)NR$^fR^f$ and —$(CH_2)_nNR^fR^f$;

$R^f$, at each occurrence, is independently selected from H, F, Cl, Br, CN, OH, $C_{1-5}$alkyl (optimally substituted with halogen and OH), $C_{3-6}$ cycloalkyl, and phenyl, or $R^f$ and R$^f$ together with the nitrogen atom to which they are both attached form a heterocyclic ring optionally substituted with C$_{1-4}$alkyl;
n is independently selected from zero, 1, 2, 3, and 4; and
p, at each occurrence, is independently selected from zero, 1, and 2.

In a second aspect, the present disclosure provides a compound of Formula (II):

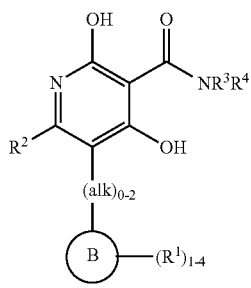

(II)

or a stereoisomer, an enantiomer, a diastereomer, a tautomer, a pharmaceutically acceptable salt, a prodrug, or a solvate thereof, within the scope of the first aspect, wherein:
ring B is independently selected from

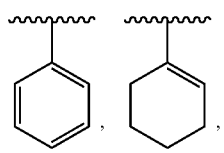

and 6-membered heteroaryl;
R$^1$ is independently selected from F, Cl, Br, NO$_2$, —(CH$_2$)$_n$OR$^b$, —(CH$_2$)$_n$C(=O)R$^b$, —(CH$_2$)$_n$NR$^a$R$^a$, —(CH$_2$)$_n$C(=O)NR$^a$R$^a$, —(CH$_2$)$_n$NR$^a$C(=O)R$^b$, C$_{1-4}$ alkyl substituted with 0-3 R$^e$ and C$_{3-6}$ cycloalkyl substituted with 0-3 R$^e$;
R$^2$ is independently selected from C$_{1-5}$ alkyl substituted with 0-3 R$^e$; C$_{1-5}$ alkenyl, aryl substituted with 0-3 R$^e$, heterocyclyl substituted with 0-3 R$^e$, and C$_{3-6}$ cycloalkyl; provided when R$^2$ is C$_{1-5}$ alkyl, the carbon atom and the groups attached thereto except the one attached to the pyridine ring may be replaced by O, N, and S;
R$^3$ and R$^4$ together with the nitrogen atom to which they are both attached form a heterocyclic ring or a spiro heterocyclic ring selected from

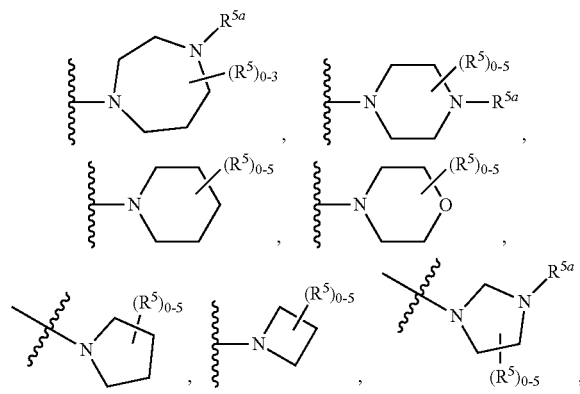

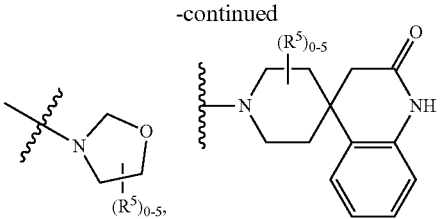

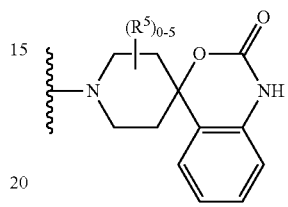

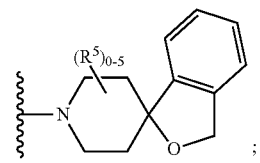

R$^5$ is independently at each occurrence, selected from OH, —(CH$_2$)$_n$-aryl, —(CH$_2$)$_n$—C$_{3-6}$ cycloalkyl and —(CH$_2$)$_n$-heterocycle, each substituted with 0-3 R$^6$;
R$^{5a}$ is independently at each occurrence, selected from —(CR$^7$R$^7$)$_n$—C$_{3-10}$ carbocycle and —(CR$^7$R$^7$)$_n$-heterocycle, —C(=O)—C$_{3-10}$ carbocycle, each substituted with 0-3 R$^6$;
R$^6$ is independently selected from H, F, Cl, Br, —OR$^b$, =O, —(CH$_2$)$_n$C(=O)R$^b$, —(CH$_2$)$_n$C(=O)OR$^b$, —(CH$_2$)$_n$NR$^a$R$^a$, CN, —(CH$_2$)$_n$C(=O)NR$^a$R$^a$, —NHC(=O)OR$^b$, C$_{1-4}$ alkyl substituted with 0-3 R$^e$, (CH$_2$)$_n$—C$_{3-6}$ carbocyclyl substituted with 0-3 R$^e$, and —(CH$_2$)$_n$-heterocyclyl substituted with 0-3 R$^e$;
R$^7$ is, independently at each occurrence, selected from H, C$_{1-4}$ alkyl, and (CH$_2$)$_n$—C$_{3-12}$ carbocyclyl substituted with 0-3 R$^e$;
R$^a$, at each occurrence, is independently selected from H, C$_{1-6}$ alkyl substituted with 0-5 R$^e$, —(CH$_2$)$_n$—C$_{3-10}$carbocyclyl substituted with 0-5 R$^e$, and —(CH$_2$)$_n$-heterocyclyl substituted with 0-5 R$^e$; or R$^a$ and R$^a$ together with the nitrogen atom to which they are both attached form a heterocyclic ring substituted with 0-5 R$^e$;
R$^b$, at each occurrence, is independently selected from H, C$_{1-6}$ alkyl substituted with 0-5 R$^e$, C$_{2-6}$ alkenyl substituted with 0-5 R$^e$, C$_{2-6}$ alkynyl substituted with 0-5 R$^e$, —(CH$_2$)$_n$—C$_{3-10}$carbocyclyl substituted with 0-5 R$^e$, and —(CH$_2$)$_n$-heterocyclyl substituted with 0-5 R$^e$;
R$^e$, at each occurrence, is independently selected from C$_{1-6}$ alkyl substituted with 0-5 R$^f$, C$_{2-6}$ alkenyl, C$_{2-6}$ alkynyl, —(CH$_2$)$_n$—C$_{3-6}$ cycloalkyl, —(CH$_2$)$_n$—C$_{4-6}$ heterocyclyl, —(CH$_2$)$_n$-aryl, —(CH$_2$)$_n$-heteroaryl, F, Cl, Br, CN, NO$_2$, =O, CO$_2$H, —(CH$_2$)$_n$OR$^f$, S(O)$_p$R$^f$, C(=O)NR$^f$R$^f$, NR$^f$C(=O)R$^f$, S(O)$_p$NR$^f$R$^f$, NR$^f$S(O)$_p$R$^f$, NR$^f$C(=O)OR$^f$, OC(=O)NR$^f$R$^f$ and —(CH$_2$)$_n$NR$^f$R$^f$;
R$^f$, at each occurrence, is independently selected from H, F, Cl, Br, CN, OH, C$_{1-5}$alkyl (optimally substituted with halogen and OH), C$_{3-6}$ cycloalkyl, and phenyl;
n is independently selected from zero, 1, 2, 3, and 4; and
p, at each occurrence, is independently selected from zero, 1, and 2.

In a third aspect, the present disclosure provides a compound of Formula (III):

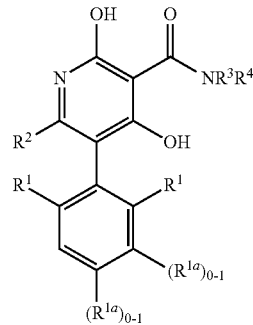

or a stereoisomer, an enantiomer, a diastereomer, a tautomer, a pharmaceutically acceptable salt, a prodrug, or a solvate thereof, within the scope of the first or second aspect, wherein:

$R^1$ is independently selected from F, Cl, OH, and $OC_{1-4}$ alkyl;

$R^{1a}$ is independently selected from F, Cl, and $C_{1-2}$ alkyl;

$R^2$ is independently selected from $C_{1-5}$ alkyl substituted with 0-3 $R^e$; $C_{1-5}$ alkenyl, aryl substituted with 0-3 $R^e$, heteroaryl substituted with 0-3 $R^e$, $C_{3-6}$ cycloalkyl and —$(CH_2)_{1-4}OC_{1-5}$alkyl, and —$(CH_2)_{1-3}OC_{3-6}$cycloalkyl;

$R^3$ and $R^4$ together with the nitrogen atom to which they are both attached form a heterocyclic ring or a spiro heterocyclic ring selected from

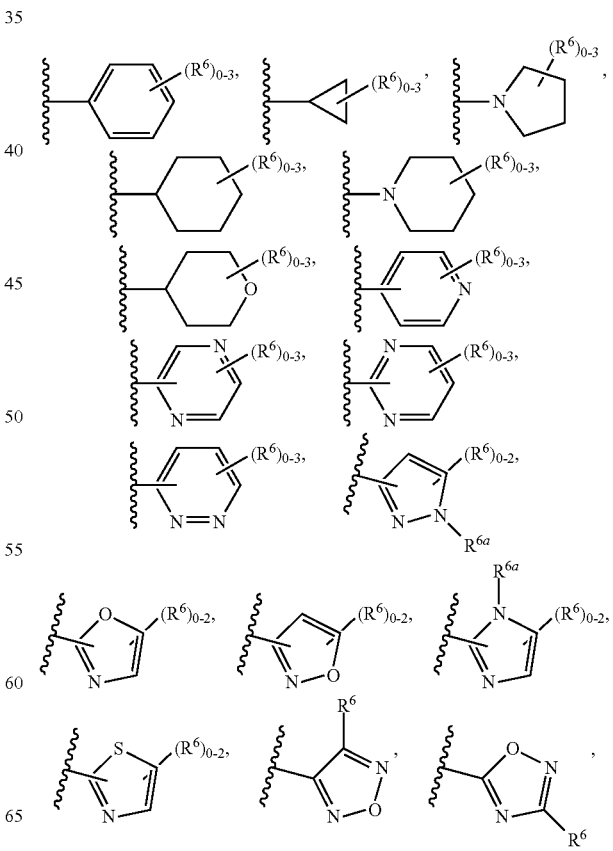

$R^5$ is independently at each occurrence, selected from OH, —$(CH_2)_n$-aryl, —$(CH_2)_n$—$C_{3-6}$ cycloalkyl and —$(CH_2)_n$-heterocycle, each substituted with 0-3 $R^6$;

$R^{5a}$ is independently at each occurrence, selected from —$(CR^7R^7)_n$—$C_{3-10}$ carbocycle and —$(CR^7R^7)_n$-heterocycle, —C(=O)—$C_{3-10}$ carbocycle, each substituted with 0-3 $R^6$;

$R^6$ is independently selected from H, F, Cl, Br, —$OR^b$, =O, —$(CH_2)_nC(=O)R^b$, —$(CH_2)_nC(=O)OR^b$, —$(CH_2)_n$ $NR^aR^a$, CN, —$(CH_2)_nC(=O)NR^aR^a$, $C_{1-4}$ alkyl substituted with 0-3 $R^e$, $(CH_2)_n$—$C_{3-6}$ carbocyclyl substituted with 0-3 $R^e$, and —$(CH_2)_n$-heterocyclyl substituted with 0-3 $R^e$;

$R^7$ is, independently at each occurrence, selected from H, $C_{1-4}$ alkyl, and $(CH_2)_n$—$C_{3-12}$ carbocyclyl substituted with 0-3 $R^e$;

$R^a$, at each occurrence, is independently selected from H, $C_{1-6}$ alkyl substituted with 0-5 $R^e$, —$(CH_2)_n$—$C_{3-10}$carbocyclyl substituted with 0-5 $R^e$, and —$(CH_2)_n$-heterocyclyl substituted with 0-5 $R^e$; or $R^a$ and $R^a$ together with the nitrogen atom to which they are both attached form a heterocyclic ring substituted with 0-5 $R^e$;

$R^b$, at each occurrence, is independently selected from H, $C_{1-6}$ alkyl substituted with 0-5 $R^e$, $C_{2-6}$ alkenyl substituted with 0-5 $R^e$, $C_{2-6}$ alkynyl substituted with 0-5 $R^e$, —$(CH_2)_n$—$C_{3-10}$carbocyclyl substituted with 0-5 $R^e$, and —$(CH_2)_n$-heterocyclyl substituted with 0-5 $R^e$;

$R^e$, at each occurrence, is independently selected from $C_{1-6}$ alkyl (optionally substituted with F and Cl), OH, $OCH_3$, $OCF_3$, —$(CH_2)_n$—$C_{3-6}$ cycloalkyl, —$(CH_2)_n$—$C_{4-6}$ heterocyclyl, —$(CH_2)_n$-aryl, —$(CH_2)_n$-heteroaryl, F, Cl, Br, CN, $NO_2$, =O, $CO_2H$; and n is independently selected from zero, 1, 2, 3, and 4.

In a fourth aspect, the present disclosure provides a compound of Formula (III), or a stereoisomer, an enantiomer, a diastereomer, a tautomer, a pharmaceutically acceptable salt, a prodrug, or a solvate thereof, within the scope of any of the first, second and third aspects, wherein:

$R^5$ is independently at each occurrence, selected from

-continued

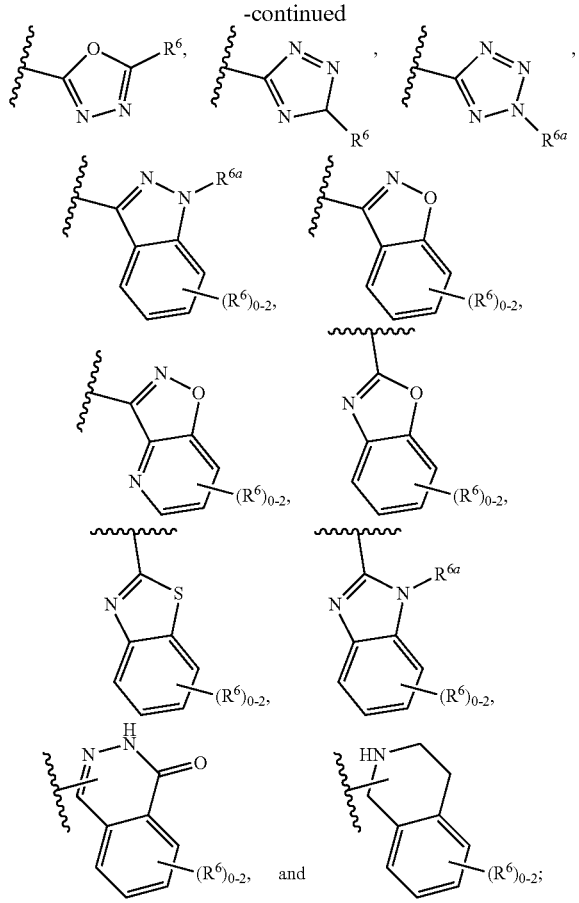

R⁶ is independently selected from H, F, Cl, Br, —OCH₃, —OCF₃, =O, CN, CH₃, CF₃—(CH₂)ₙ-aryl, —(CH₂)ₙ—C₃₋₆ cycloalkyl substituted with 0-3 Rᵉ, and —(CH₂)ₙ-heterocyclyl substituted with 0-3 Rᵉ;

R⁶ᵃ is independently selected from H, CH₃, aryl substituted with 0-3 Rᵉ, and heterocyclyl substituted with 0-3 Rᵉ;

Rᵃ, at each occurrence, is independently selected from H, C₁₋₆ alkyl substituted with 0-5 Rᵉ, —(CH₂)ₙ—C₃₋₁₀carbocyclyl substituted with 0-5 Rᵉ, and —(CH₂)ₙ-heterocyclyl substituted with 0-5 Rᵉ;

Rᵉ, at each occurrence, is independently selected from C₁₋₆ alkyl (optionally substituted with F and Cl), OH, OCH₃, OCF₃, —(CH₂)ₙ—C₃₋₆ cycloalkyl, —(CH₂)ₙ—C₄₋₆ heterocyclyl, —(CH₂)ₙ-aryl, —(CH₂)ₙ-heteroaryl, F, Cl, Br, CN, NO₂, =O, CO₂H; and n is independently selected from zero, 1, 2, and 3.

In a fifth aspect, the present disclosure provides a compound of Formula (III), or a stereoisomer, an enantiomer, a diastereomer, a tautomer, a pharmaceutically acceptable salt, a prodrug, or a solvate thereof, within the scope of any of the first, second and third aspects, wherein:

R³ and R⁴ together with the nitrogen atom to which they are both attached form a heterocyclic ring or a spiro heterocyclic ring selected from R⁵ᵃ is independently at each occurrence, selected from

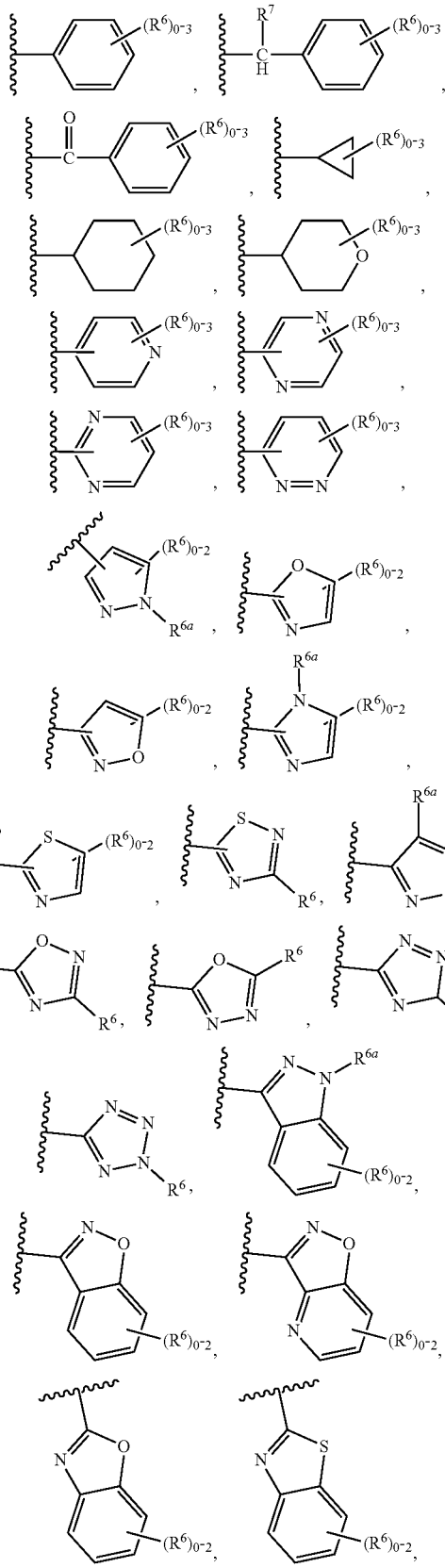

-continued

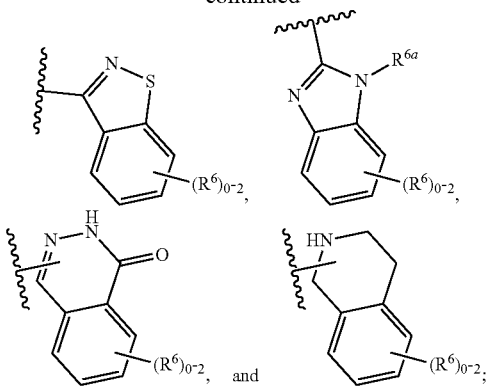

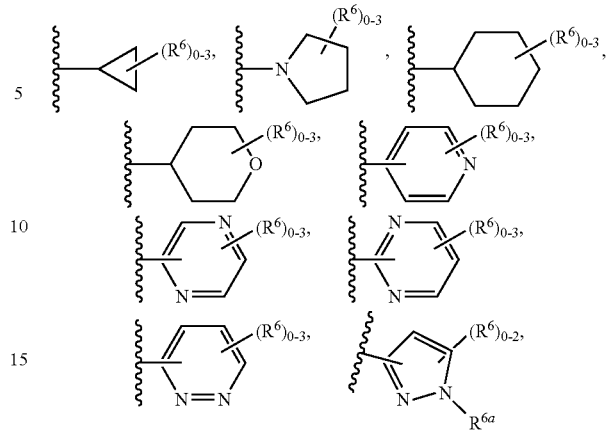

R⁶ is independently selected from H, F, Cl, Br, —OCH₃, —O(CH₂)₁₋₃OCH₃, —OCF₃, =O, CN, CH₃, CF₃— (CH₂)ₙ-aryl, —(CH₂)ₙ—C₃₋₆ cycloalkyl substituted with 0-3 Rᵉ, and —(CH₂)ₙ-heterocyclyl substituted with 0-3 Rᵉ;

R⁶ᵃ is independently selected from H, CH₃, aryl substituted with 0-3 Rᵉ, and heterocyclyl substituted with 0-3 Rᵉ;

Rᵉ, at each occurrence, is independently selected from C₁₋₆ alkyl (optionally substituted with F and Cl), OH, OCH₃, OCF₃, —(CH₂)ₙ—C₃₋₆ cycloalkyl, —(CH₂)ₙ—C₄₋₆ heterocyclyl, —(CH₂)ₙ-aryl, —(CH₂)ₙ-heteroaryl, F, Cl, Br, CN, NO₂, =O, CO₂H; and n is independently selected from zero, 1, 2, and 3.

In a sixth aspect, the present disclosures provides a compound of Formula (III), or a stereoisomer, an enantiomer, a diastereomer, a tautomer, a pharmaceutically acceptable salt, a prodrug, or a solvate thereof, within the scope of any of the first, second and third aspects, wherein:

R¹ is independently selected from F, Cl, OH, and OC₁₋₄ alkyl;

R¹ᵃ is independently selected from F, Cl, and C₁₋₂ alkyl;

R² is independently selected from C₁₋₅ alkyl substituted with 0-3 Rᵉ; C₁₋₅ alkenyl, phenyl substituted with 0-3 Rᵉ, 6-membered heteroaryl substituted with 0-3 Rᵉ, C₃₋₆ cycloalkyl and CH₂O(CH₂)₁₋₃CH₃;

R³ and R⁴ together with the nitrogen atom to which they are both attached form a heterocyclic ring or a spiro heterocyclic ring selected from

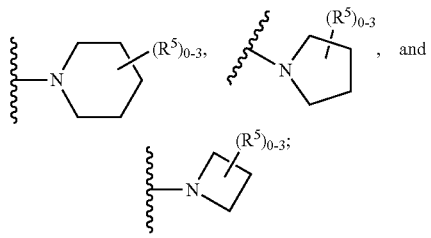

R⁵ is independently at each occurrence, selected from OH,

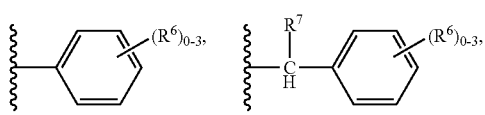

R⁶ is independently selected from H, F, Cl, Br, —OCH₃, —OCF₃, =O, CN, CH₃, CF₃, —C(=O)NH₂, —(CH₂)ₙ-aryl substituted with 0-3 Rᵉ, —(CH₂)ₙ—C₃₋₆ cycloalkyl substituted with 0-3 $R^e$, and —$(CH_2)_n$-heterocyclyl substituted with 0-3 $R^e$;

$R^{6a}$ is independently selected from H, $CH_3$, aryl substituted with 0-3 $R^e$, and heterocyclyl substituted with 0-3 $R^e$;

$R^a$, at each occurrence, is independently selected from H, $C_{1-6}$ alkyl substituted with 0-5 $R^e$, —$(CH_2)_n$—$C_{3-10}$carbocyclyl substituted with 0-5 $R^e$, and —$(CH_2)_n$-heterocyclyl substituted with 0-5 $R^e$;

$R^e$, at each occurrence, is independently selected from $C_{1-6}$ alkyl (optionally substituted with F and Cl), OH, $OCH_3$, $OCF_3$, —$(CH_2)_n$—$C_{3-6}$ cycloalkyl, —$(CH_2)_n$—$C_{4-6}$ heterocyclyl, —$(CH_2)_n$-aryl, —$(CH_2)_n$-heteroaryl, F, Cl, Br, CN, $NO_2$, =O, $CO_2H$; and n is independently selected from zero, 1, 2, and 3.

In a seventh aspect, the present disclosures provides a compound, or a stereoisomer, an enantiomer, a diastereomer, a tautomer, a pharmaceutically acceptable salt, a prodrug, or a solvate thereof, within the scope of the first, second, and third aspects, wherein:

$R^1$ is independently selected from —$CH_2OH$, —$OCH_3$, —$OCF_3$, $OCH_2Ph$, —$C(=O)NR^aR^a$, —$NR^aR^a$, $CH_3$, $CH_2CH_3$, $CH(CH_3)_2$, and cyclopropyl;

$R^2$ is independently selected from $C_{1-5}$ alkyl substituted with 0-3 $R^e$; $C_{1-5}$ alkenyl, phenyl substituted with 0-3 $R^e$, 6-membered heteroaryl substituted with 0-3 $R^e$, $C_{3-6}$ cycloalkyl and $CH_2O(CH_2)_{1-3}CH_3$;

$R^3$ and $R^4$ are independently selected from $C_{1-5}$ alkyl substituted with 0-3 $R^6$; —$(CH_2)_n$—$C_{3-6}$ carbocyclyl substituted with 0-3 $R^6$, and —$(CH_2)_n$-heterocyclyl substituted with 0-3 $R^6$;

$R^6$ is independently selected from H, halogen, —$(CH_2)_n$ $OR^b$, —$(CH_2)_nNR^aR^a$, —$(CH_2)_nC(=O)NR^aR^a$, —$(CH_2)_n$ $NR^aC(=O)R^b$, —$(CH_2)_nNR^aC(=O)OR^b$, $(CH_2)_nOC(=O)NR^aR^a$, —$(CH_2)_nC(=O)OR^b$, —$(CH_2)_n$ $S(O)_pNR^aR^a$, —$(CH_2)_nNR^aS(O)_pNR^aR^a$, $C_{1-5}$ alkyl substituted with 0-3 $R^e$, phenyl substituted with 0-3 $R^e$, and heterocyclyl substituted with 0-3 $R^e$;

$R^a$, at each occurrence, is independently selected from H, $C_{1-6}$ alkyl substituted with 0-5 $R^e$, —$(CH_2)_n$-phenyl substituted with 0-5 $R^e$, and —$(CH_2)_n$-heteroaryl substituted with 0-5 $R^e$;

$R^b$, at each occurrence, is independently selected from H, $C_{1-6}$ alkyl substituted with 0-5 $R^e$, —$(CH_2)_n$—$C_{3-10}$carbocyclyl substituted with 0-5 $R^e$, and —$(CH_2)_n$-heterocyclyl substituted with 0-5 $R^e$;

$R^e$, at each occurrence, is independently selected from $C_{1-6}$ alkyl (optionally substituted with F and Cl), OH, $OCH_3$, $OCF_3$, —$(CH_2)_n$—$C_{3-6}$ cycloalkyl, —$(CH_2)_n$—$C_{4-6}$ heterocyclyl, —$(CH_2)_n$-aryl, —$(CH_2)_n$-heteroaryl, F, Cl, Br, CN, $NO_2$, =O, $CO_2H$; and n is independently selected from zero, 1, 2, 3, and 4.

In an eighth aspect, the present invention provides a compound selected from the exemplified examples or stereoisomers, enantiomers, diastereomers, tautomers, pharmaceutically acceptable salts, prodrugs, or solvates thereof.

In another aspect, the present invention provides compounds of Formula (I), or stereoisomers, enantiomers, diastereomers, tautomers, pharmaceutically acceptable salts, solvates, or prodrugs thereof, wherein:

alk is $C_{1-6}$ alkyl substituted with 0-5 $R^e$;

ring B is independently selected from $C_{3-6}$ cycloalkyl, $C_{3-6}$ cycloalkenyl, aryl, bicyclic carbocyclyl, and 6-membered heteroaryl;

$R^1$ is independently selected from halogen, $NO_2$, —$(CH_2)_n$ $OR^b$, $(CH_2)_nS(O)_pR^c$, —$(CH_2)_nC(=O)R^b$, —$(CH_2)_nNR^aR^a$, —$(CH_2)_nCN$, —$(CH_2)_nC(=O)NR^aR^a$, —$(CH_2)_n$ $NR^aC(=O)R^b$, —$(CH_2)_nNR^aC(=O)NR^aR^a$, —$(CH_2)_n$ $NR^aC(=O)OR^b$, —$(CH_2)_n$ $OC(=O)NR^aR^a$, —$(CH_2)_nC(=O)OR^b$, —$(CH_2)_nS(O)_pNR^aR^a$, —$(CH_2)_nNR^aS(O)_p NR^aR^a$, —$(CH_2)_nNR^aS(O)_pR^c$, $C_{1-4}$ alkyl substituted with 0-3 $R^e$, —$(CH_2)_n$—$C_{3-6}$ carbocyclyl substituted with 0-3 $R^e$, and —$(CH_2)_n$-heterocyclyl substituted with 0-3 $R^e$;

$R^2$ is independently selected from $C_{1-5}$ alkyl substituted with 0-3 $R^e$; $C_{1-5}$ alkenyl substituted with 0-3 $R^e$, aryl substituted with 0-3 $R^e$, heterocyclyl substituted with 0-3 $R^e$, and $C_{3-6}$ cycloalkyl substituted with 0-3 $R^e$; provided when $R^2$ is $C_{1-5}$ alkyl, the methylene unit except the one attached to the pyridine ring may be replaced by O, N, and S;

$R^3$ and $R^4$ are independently selected from H, $C_{1-5}$ alkyl substituted with 0-3 $R^6$; —$(CH_2)_n$—$C_{3-6}$ carbocyclyl substituted with 0-3 $R^6$, and —$(CH_2)_n$-heterocyclyl substituted with 0-3 $R^6$; provided $R^3$ and $R^4$ are not both H;

alternatively, $R^3$ and $R^4$ together with the nitrogen atom to which they are both attached form a heterocyclic ring or a spiro heterocyclic ring comprising carbon atoms and 0 to 4 heteroatoms selected from N, $NR^5a$, O, and S and substituted with 0-5 $R^5$;

$R^5$ is independently at each occurrence, selected from OH, halogen, —$(CR^7R^7)_n$—$C_{3-10}$ carbocycle, —$(CR^7R^7)_n$-heterocycle, and each substituted with 0-3 $R^6$;

$R^{5a}$ is independently at each occurrence, selected from —$C(=O)OR^b$, $C(=O)NR^aR^a$, —$S(O)_pR^c$, —$(CR^7R^7)_n$ —$C_{3-10}$ carbocycle, —$C(=O)$—$C_{3-10}$ carbocycle, —$(CR^7R^7)_n$-heterocycle, —$C(=O)$-heterocycle, each substituted with 0-3 $R^6$;

$R^6$ is independently selected from H, halogen, =O, —$(CH_2)_n$ $OR^b$, $(CH_2)_nS(O)_pR^c$, —$(CH_2)_nC(=O)R^b$, —$(CH_2)_n$ $NR^aR^a$, —$(CH_2)_nCN$, —$(CH_2)_nC(=O)NR^aR^a$, —$(CH_2)_n$ $NR^aC(=O)R^b$, —$(CH_2)_nNR^aC(=O)NR^aR^a$, —$(CH_2)_n$ $NR^aC(=O)OR^b$, —$(CH_2)_n$ $OC(=O)NR^aR^a$, —$(CH_2)_nC(=O)OR^b$, —$(CH_2)_nS(O)_pNR^aR^a$, —$(CH_2)_n$ $NR^aS(O)_p NR^aR^a$, —$(CH_2)_nNR^aS(O)_pR^c$, $C_{1-5}$ alkyl substituted with 0-3 $R^e$, $(CH_2)_n$—$C_{3-6}$ carbocyclyl substituted with 0-3 $R^e$, and —$(CH_2)_n$-heterocyclyl substituted with 0-3 $R^e$;

$R^7$ is, independently at each occurrence, selected from H, $C_{1-4}$ alkyl, and $(CH_2)_n$—$C_{3-12}$ carbocyclyl substituted with 0-3 $R^e$;

$R^a$, at each occurrence, is independently selected from H, $C_{1-6}$ alkyl substituted with 0-5 $R^e$, $C_{2-6}$ alkenyl substituted with 0-5 $R^e$, $C_{2-6}$ alkynyl substituted with 0-5 $R^e$, —$(CH_2)_n$—$C_{3-10}$carbocyclyl substituted with 0-5 $R^e$, and —$(CH_2)_n$-heterocyclyl substituted with 0-5 $R^e$; or $R^a$ and $R^a$ together with the nitrogen atom to which they are both attached form a heterocyclic ring substituted with 0-5 $R^e$;

$R^b$, at each occurrence, is independently selected from H, $C_{1-6}$ alkyl substituted with 0-5 $R^e$, $C_{2-6}$ alkenyl substituted with 0-5 $R^e$, $C_{2-6}$ alkynyl substituted with 0-5 $R^e$, —$(CH_2)_n$—$C_{3-10}$carbocyclyl substituted with 0-5 $R^e$, and —$(CH_2)_n$-heterocyclyl substituted with 0-5 $R^e$;

$R^c$, at each occurrence, is independently selected from $C_{1-6}$ alkyl substituted with 0-5 $R^e$, $C_{2-6}$alkenyl substituted with 0-5 $R^e$, $C_{2-6}$alkynyl substituted with 0-5 $R^e C_{3-6}$carbocyclyl substituted with 0-5 $R^e$, and heterocyclyl substituted with 0-5 $R^e$;

$R^d$, at each occurrence, is independently selected from H and $C_{1-4}$alkyl substituted with 0-5 $R^e$;

$R^e$, at each occurrence, is independently selected from $C_{1-6}$ alkyl substituted with 0-5 $R^g$, $C_{2-6}$ alkenyl, $C_{2-6}$ alkynyl, —$(CH_2)_n$—$C_{3-6}$ cycloalkyl, —$(CH_2)_n$—$C_{4-6}$ heterocyclyl, —$(CH_2)_n$-aryl, —$(CH_2)_n$-heteroaryl, F, Cl, Br, CN, $NO_2$, =O, —$(CH_2)_nCO_2R^f$, —$(CH_2)_nOR^f$, —$(CH_2)_nS$ $(O)_pR^f$, $-(CH_2)_nC(=O)NR^fR^f$, $-(CH_2)_nNR^fC(=O)R^f$, $-(CH_2)_nS(O)_pNR^fR^f$, $-(CH_2)_nNR^fS(O)_pR^f$, $-(CH_2)_n NR^fC(=O)OR^f$, $-(CH_2)_nOC(=O)NR^fR^f$ and $-(CH_2)_n NR^fR^f$;

$R^f$, at each occurrence, is independently selected from H, $C_{1-5}$ alkyl (optimally substituted with halogen and OH), $C_{3-6}$ cycloalkyl, and phenyl, or $R^f$ and $R^f$ together with the nitrogen atom to which they are both attached form a heterocyclic ring optionally substituted with $C_{1-4}$ alkyl;

$R^g$, at each occurrence, is independently selected from H, F, Cl, Br, CN, OH, $C_{1-5}$ alkyl (optimally substituted with halogen and OH), $C_{3-6}$ cycloalkyl, and phenyl;

n is independently selected from zero, 1, 2, 3, and 4; and p, at each occurrence, is independently selected from zero, 1, and 2.

In another aspect, the present invention provides compounds of Formula (II), or stereoisomers, enantiomers, diastereomers, tautomers, pharmaceutically acceptable salts, solvates, or prodrugs thereof, wherein:

ring B is independently selected from

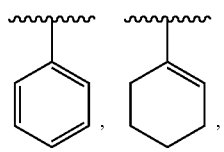

and 6-membered heteroaryl;

$R^1$ is independently selected from F, Cl, Br, NO$_2$, $-(CH_2)_n OR^b$, $-(CH_2)_nC(=O)R^b$, $-(CH_2)_nNR^aR^a$, $-(CH_2)_n CN$, $-(CH_2)_nC(=O)NR^aR^a$, $-(CH_2)_nNR^aC(=O)R^b$, $C_{1-4}$ alkyl substituted with 0-3 $R^e$ and $C_{3-6}$ cycloalkyl substituted with 0-3 $R^e$;

$R^2$ is independently selected from $C_{1-5}$ alkyl substituted with 0-3 $R^e$; $C_{1-5}$ alkenyl substituted with 0-3 $R^e$, aryl substituted with 0-3 $R^e$, heterocyclyl substituted with 0-3 $R^e$, and $C_{3-6}$ cycloalkyl substituted with 0-3 $R^e$; provided when $R^2$ is $C_{1-5}$ alkyl, the methylene unit except the one attached to the pyridine ring may be replaced by O, N, and S;

$R^3$ and $R^4$ are independently selected from H and $C_{1-5}$ alkyl substituted with 0-3 $R^6$; provided $R^3$ and $R^4$ are not both H;

alternatively, $R^3$ and $R^4$ together with the nitrogen atom to which they are both attached form a heterocyclic ring or a spiro heterocyclic ring selected from

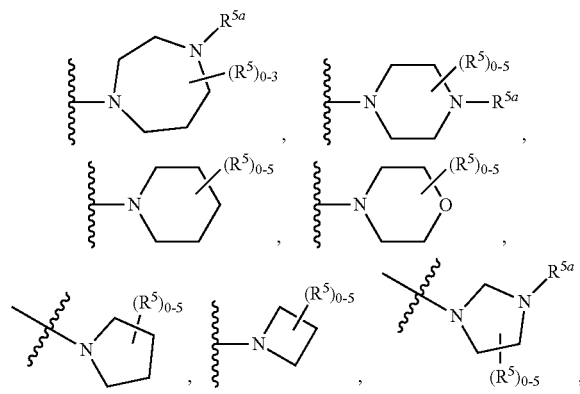

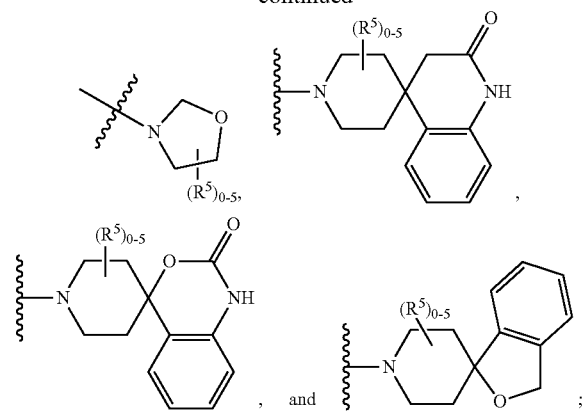

$R^5$ is independently at each occurrence, selected from OH, $-(CH_2)_n$-aryl, $-(CH_2)_n-C_{3-6}$ cycloalkyl and $-(CH_2)_n$-heterocycle, each substituted with 0-3 $R^6$;

$R^{5a}$ is independently at each occurrence, selected from $-(CR^7R^7)_n-C_{3-10}$ carbocycle and $-(CR^7R^7)_n$-heterocycle, $-C(=O)-C_{3-10}$ carbocycle, each substituted with 0-3 $R^6$;

$R^6$ is independently selected from H, F, Cl, Br, $-OR^b$, $=O$, $-(CH_2)_nC(=O)R^b$, $-(CH_2)_nC(=O)OR^b$, $-(CH_2)_n NR^aR^a$, CN, $-(CH_2)_nC(=O)NR^aR^a$, $-NHC(=O)OR^b$, $C_{1-4}$ alkyl substituted with 0-3 $R^e$, $(CH_2)_n-C_{3-6}$ carbocyclyl substituted with 0-3 $R^e$, and $-(CH_2)_n$-heterocyclyl substituted with 0-3 $R^e$;

$R^7$ is, independently at each occurrence, selected from H, $C_{1-4}$ alkyl, and $(CH_2)_n-C_{3-12}$ carbocyclyl substituted with 0-3 $R^e$;

$R^a$, at each occurrence, is independently selected from H, $C_{1-6}$ alkyl substituted with 0-5 $R^e$, $-(CH_2)_n-C_{3-10}$ carbocyclyl substituted with 0-5 $R^e$, and $-(CH_2)_n$-heterocyclyl substituted with 0-5 $R^e$; or $R^a$ and $R^a$ together with the nitrogen atom to which they are both attached form a heterocyclic ring substituted with 0-5 $R^e$;

$R^b$, at each occurrence, is independently selected from H, $C_{1-6}$ alkyl substituted with 0-5 $R^e$, $C_{2-6}$ alkenyl substituted with 0-5 $R^e$, $C_{2-6}$ alkynyl substituted with 0-5 $R^e$, $-(CH_2)_n-C_{3-10}$ carbocyclyl substituted with 0-5 $R^e$, and $-(CH_2)_n$-heterocyclyl substituted with 0-5 $R^e$;

$R^e$, at each occurrence, is independently selected from $C_{1-6}$ alkyl substituted with 0-5 $R^g$, $C_{2-6}$ alkenyl, $C_{2-6}$ alkynyl, $-(CH_2)_n-C_{3-6}$ cycloalkyl, $-(CH_2)_n-C_{4-6}$ heterocyclyl, $-(CH_2)_n$-aryl, $-(CH_2)_n$-heteroaryl, F, Cl, Br, CN, NO$_2$, $=O$, CO2R$^f$, $-(CH_2)_nOR^f$, S(O)$_pR^f$, C(=O) NR$^fR^f$, NR$^fC(=O)R^f$, S(O)$_pNR^fR^f$, NR$^fS(O)_pR^f$, NR$^fC(=O)OR^f$, OC(=O)NR$^fR^f$ and $-(CH_2)_nNR^fR^f$;

$R^f$, at each occurrence, is independently selected from H, $C_{1-5}$ alkyl (optimally substituted with halogen and OH), $C_{3-6}$ cycloalkyl, and phenyl;

$R^g$, at each occurrence, is independently selected from H, F, Cl, Br, CN, OH, $C_{1-5}$ alkyl (optimally substituted with halogen and OH);

n is independently selected from zero, 1, 2, 3, and 4; and p, at each occurrence, is independently selected from zero, 1, and 2.

In another aspect, the present invention provides compounds of Formula (IIIa):

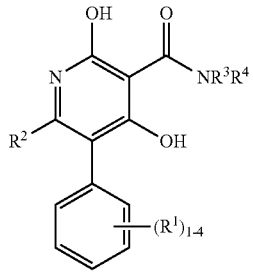

(IIIa)

or stereoisomers, enantiomers, diastereomers, tautomers, or pharmaceutically acceptable salts thereof, wherein:
$R^1$ is independently selected from F, Cl, —(CH$_2$)$_n$OH, C(=O)NR$^a$R$^a$, C$_{1-4}$ alkyl, and OC$_{1-4}$ alkyl;
$R^2$ is independently selected from C$_{1-5}$ alkyl substituted with 0-3 R$^e$; C$_{1-5}$ alkenyl, aryl substituted with 0-3 R$^e$, heteroaryl substituted with 0-3 R$^e$, C$_{3-6}$ cycloalkyl and —(CH$_2$)$_{1-4}$OC$_{1-5}$alkyl, and —(CH$_2$)$_{1-3}$OC$_{3-6}$cycloalkyl;
$R^3$ is independently selected from H and C$_{1-5}$ alkyl;
$R^4$ is independently selected from C$_{1-5}$ alkyl substituted with 0-3 R$^6$;
alternatively, $R^3$ and $R^4$ together with the nitrogen atom to which they are both attached form a heterocyclic ring or a spiro heterocyclic ring selected from

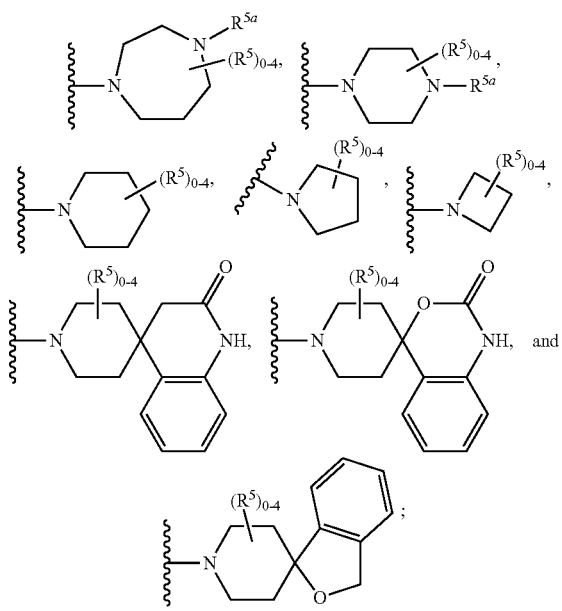

$R^5$ is independently at each occurrence, selected from OH, —(CH$_2$)$_n$-aryl, —(CH$_2$)$_n$—C$_{3-6}$ cycloalkyl and —(CH$_2$)$_n$-heterocycle, each substituted with 0-3 R$^6$;
$R^{5a}$ is independently at each occurrence, selected from —(CR$^7$R$^7$)$_n$—C$_{3-10}$ carbocycle and —(CR$^7$R$^7$)$_n$-heterocycle, —C(=O)—C$_{3-10}$ carbocycle, each substituted with 0-3 R$^6$;
$R^6$ is independently selected from H, F, Cl, Br, —OR$^b$, =O, —(CH$_2$)$_n$C(=O)R$^b$, —(CH$_2$)$_n$C(=O)OR$^b$, —(CH$_2$)$_n$NR$^a$R$^a$, CN, —(CH$_2$)$_n$C(=O)NR$^a$R$^a$, —(CH$_2$)$_n$NR$^a$C(=O)R$^b$, C$_{1-4}$ alkyl substituted with 0-3 R$^e$, (CH$_2$)$_n$—C$_{3-6}$ carbocyclyl substituted with 0-3 R$^e$, and —(CH$_2$)$_n$-heterocyclyl substituted with 0-3 R$^e$;
$R^7$ is, independently at each occurrence, selected from H, C$_{1-4}$ alkyl, and (CH$_2$)$_n$—C$_{3-12}$ carbocyclyl substituted with 0-3 R$^e$;
$R^a$, at each occurrence, is independently selected from H, C$_{1-6}$ alkyl substituted with 0-5 R$^e$, —(CH$_2$)$_n$—C$_{3-10}$carbocyclyl substituted with 0-5 R$^e$, and —(CH$_2$)$_n$-heterocyclyl substituted with 0-5 R$^e$; or R$^a$ and R$^a$ together with the nitrogen atom to which they are both attached form a heterocyclic ring substituted with 0-5 R$^e$;
$R^b$, at each occurrence, is independently selected from H, C$_{1-6}$ alkyl substituted with 0-5 R$^e$, C$_{2-6}$ alkenyl substituted with 0-5 R$^e$, C$_{2-6}$ alkynyl substituted with 0-5 R$^e$, —(CH$_2$)$_n$—C$_{3-10}$carbocyclyl substituted with 0-5 R$^e$, and —(CH$_2$)$_n$-heterocyclyl substituted with 0-5 R$^e$;
$R^e$, at each occurrence, is independently selected from C$_{1-6}$ alkyl (optionally substituted with F and Cl), OH, OCH$_3$, OCF$_3$, —(CH$_2$)$_n$—C$_{3-6}$ cycloalkyl, —(CH$_2$)$_n$—C$_{4-6}$ heterocyclyl, —(CH$_2$)$_n$-aryl, —(CH$_2$)$_n$-heteroaryl, F, Cl, Br, CN, NO$_2$, =O, CO$_2$H; and
n is independently selected from zero, 1, 2, 3, and 4.

In another aspect, the present invention provides compounds of Formula (IIIb):

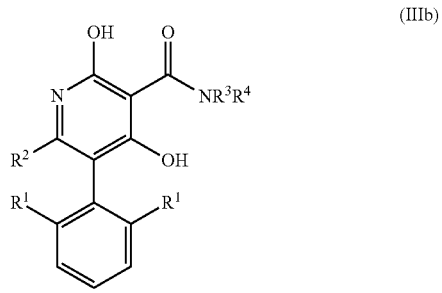

(IIIb)

or stereoisomers, enantiomers, diastereomers, tautomers, or pharmaceutically acceptable salts thereof, wherein:
$R^1$ is —OCH$_3$;
$R^2$ is independently selected from C$_{1-5}$ alkyl substituted with 0-3 R$^e$; C$_{1-5}$ alkenyl, phenyl substituted with 0-3 R$^e$, 6-membered heteroaryl substituted with 0-3 R$^e$, C$_{3-6}$ cycloalkyl and CH$_2$O(CH$_2$)$_{1-3}$CH$_3$;
$R^3$ is independently selected from H and C$_{1-5}$ alkyl;
$R^4$ is independently selected from C$_{1-5}$ alkyl substituted with 0-3 R$^6$;
alternatively, $R^3$ and $R^4$ together with the nitrogen atom to which they are both attached form a heterocyclic ring selected from

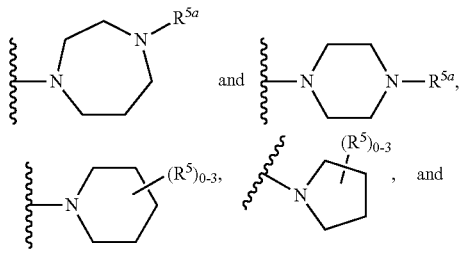

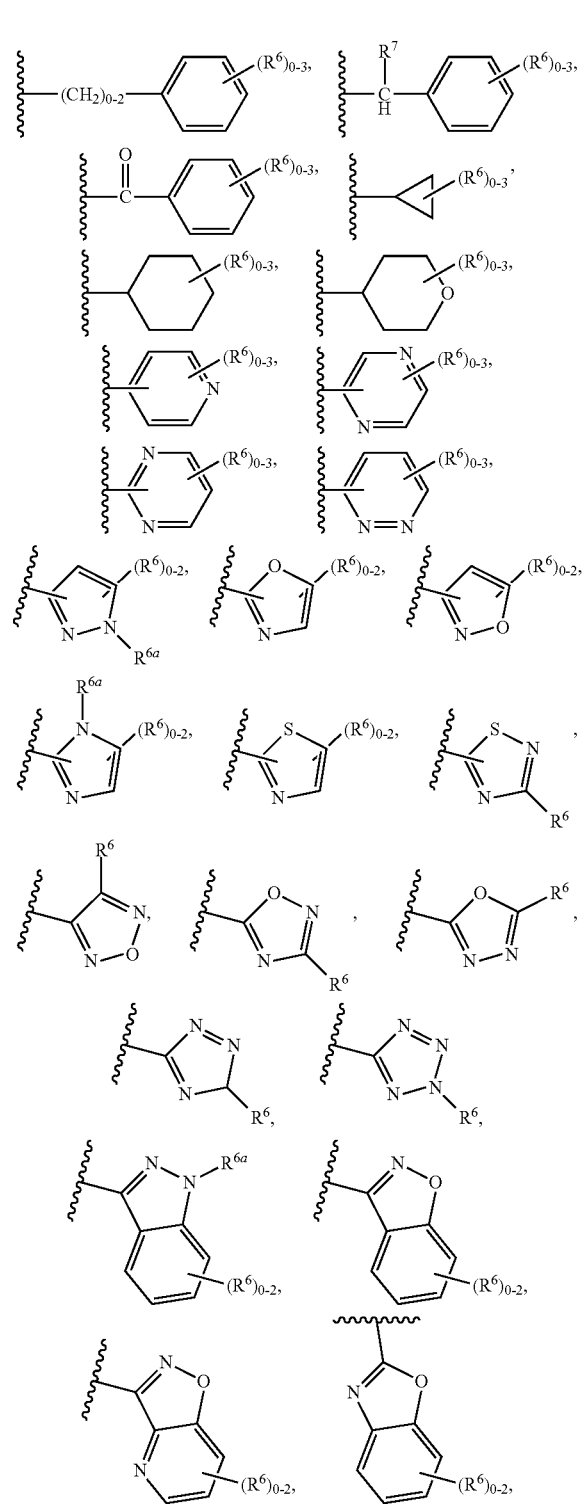
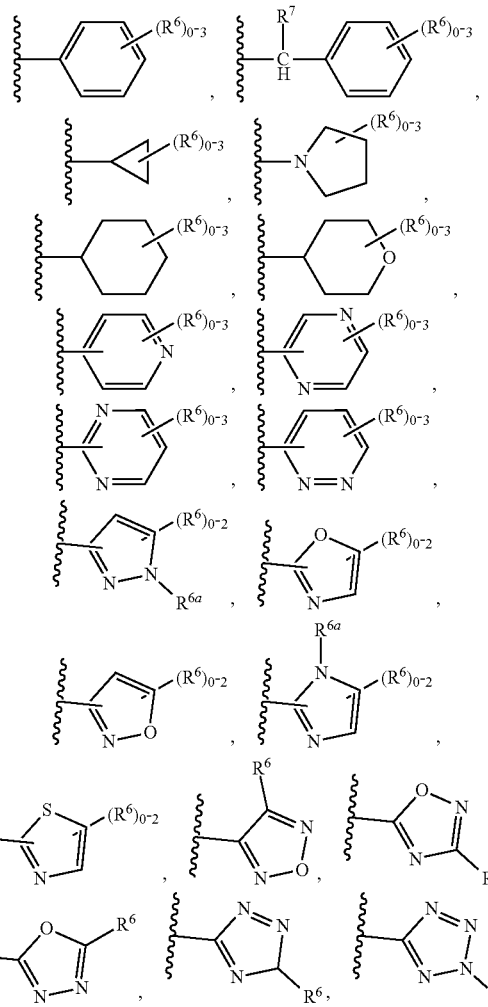

-continued

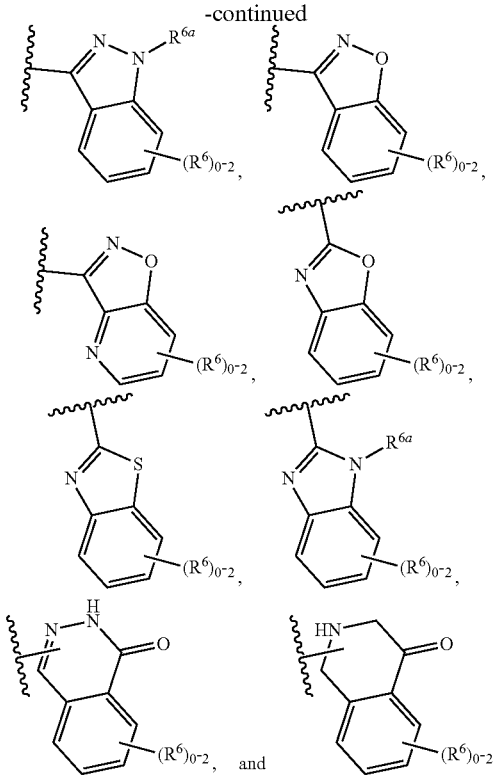

R⁶ is independently selected from H, F, Cl, Br, —OCH₃, —OCF₃, —OPh, =O, CN, CH₃, CF₃, —C(=O)NH₂, —NHC(=O)Ph, —(CH₂)$_n$-aryl substituted with 0-3 R$^e$, —(CH₂)$_n$-aryl substituted with 0-3 R$^e$, —(CH₂)$_n$—C$_{3-6}$ cycloalkyl substituted with 0-3 R$^e$, and —(CH₂)$_n$-heterocyclyl substituted with 0-3 R$^e$;

R$^{6a}$ is independently selected from H, CH₃, aryl substituted with 0-3 R$^e$, and heterocyclyl substituted with 0-3 R$^e$;

R$^a$, at each occurrence, is independently selected from H, C$_{1-6}$ alkyl substituted with 0-5 R$^e$, —(CH₂)$_n$—C$_{3-10}$carbocyclyl substituted with 0-5 R$^e$, and —(CH₂)$_n$-heterocyclyl substituted with 0-5 R$^e$;

R$^e$, at each occurrence, is independently selected from C$_{1-6}$ alkyl (optionally substituted with F and Cl), OH, OCH₃, OCF₃, —(CH₂)$_n$—C$_{3-6}$ cycloalkyl, —(CH₂)$_n$—C$_{4-6}$ heterocyclyl, —(CH₂)$_n$-aryl, —(CH₂)$_n$-heteroaryl, F, Cl, Br, CN, NO₂, =O, CO₂H; and n is independently selected from zero, 1, 2, and 3.

In another aspect, the present invention provides compounds of Formula (IIIa) or (IIIb), or stereoisomers, enantiomers, diastereomers, tautomers, pharmaceutically acceptable salts, solvates, or prodrugs thereof, wherein:

R³ and R⁴ together with the nitrogen atom to which they are both attached form a heterocyclic ring or a spiro heterocyclic ring selected from

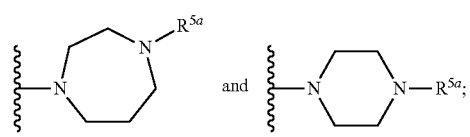

R$^{5a}$ is independently at each occurrence, selected from

-continued

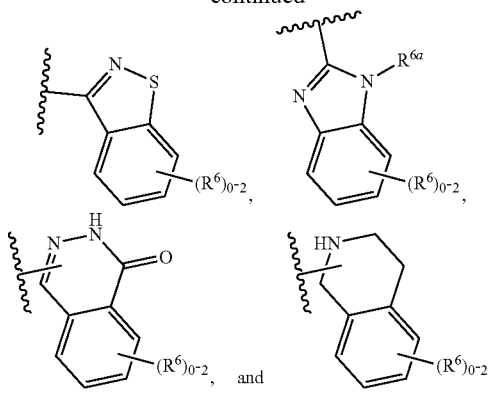

R$^6$ is independently selected from H, F, Cl, Br, —OCH$_3$, —O(CH$_2$)$_{1-3}$OCH$_3$, —OCF$_3$, =O, CN, CH$_3$, CF$_3$—(CH$_2$)$_n$-aryl, —(CH$_2$)$_n$—C$_{3-6}$ cycloalkyl substituted with 0-3 R$^e$, and —(CH$_2$)$_n$-heterocyclyl substituted with 0-3 R$^e$;

R$^{6a}$ is independently selected from H, CH$_3$, aryl substituted with 0-3 R$^e$, and heterocyclyl substituted with 0-3 R$^e$;

R$^e$, at each occurrence, is independently selected from C$_{1-6}$ alkyl (optionally substituted with F and Cl), OH, OCH$_3$, OCF$_3$, —(CH$_2$)$_n$—C$_{3-6}$ cycloalkyl, —(CH$_2$)$_n$—C$_{4-6}$ heterocyclyl, —(CH$_2$)$_n$-aryl, —(CH$_2$)$_n$-heteroaryl, F, Cl, Br, CN, NO$_2$, =O, CO$_2$H; and n is independently selected from zero, 1, 2, and 3.

In another aspect, the present invention provides compounds of Formula (IIIb), or stereoisomers, enantiomers, diastereomers, tautomers, or pharmaceutically acceptable salts thereof, wherein:

R$^1$ is —OCH$_3$;

R$^2$ is independently selected from C$_{1-5}$ alkyl substituted with 0-3 R$^e$; C$_{1-5}$ alkenyl, phenyl substituted with 0-3 R$^e$, 6-membered heteroaryl substituted with 0-3 R$^e$, C$_{3-6}$ cycloalkyl and CH$_2$O(CH$_2$)$_{1-3}$CH$_3$;

R$^3$ is independently selected from H and C$_{1-5}$ alkyl;

R$^4$ is independently selected from C$_{1-5}$ alkyl substituted with 0-3 R$^6$;

R$^6$ is independently selected from —OR$^b$, —C(=O)R$^b$, —C(=O)NR$^a$R$^a$, —NR$^a$C(=O)R$^b$, C$_{3-6}$cycloalkyl substituted with 0-3 R$^e$, aryl substituted with 0-3 R$^e$, and heteroaryl substituted with 0-3 R$^e$;

R$^a$, at each occurrence, is independently selected from H, C$_{1-6}$ alkyl substituted with 0-5 R$^e$, C$_{2-6}$ alkenyl substituted with 0-5 R$^e$, C$_{2-6}$ alkynyl substituted with 0-5 R$^e$, —(CH$_2$)$_n$—C$_{3-10}$carbocyclyl substituted with 0-5 R$^e$, and —(CH$_2$)$_n$-heterocyclyl substituted with 0-5 R$^e$; or R$^a$ and R$^a$ together with the nitrogen atom to which they are both attached form a heterocyclic ring substituted with 0-5 R$^e$;

R$^b$, at each occurrence, is independently selected from H, C$_{1-6}$ alkyl substituted with 0-5 R$^e$, —(CH$_2$)$_n$—C$_{3-10}$carbocyclyl substituted with 0-5 R$^e$, and —(CH$_2$)$_n$-heterocyclyl substituted with 0-5 R$^e$;

R$^e$, at each occurrence, is independently selected from C$_{1-6}$ alkyl substituted with 0-5 R$^g$, C$_{2-6}$ alkenyl, C$_{2-6}$ alkynyl, —(CH$_2$)$_n$—C$_{3-6}$ cycloalkyl, —(CH$_2$)$_n$—C$_{4-6}$ heterocyclyl, —(CH$_2$)$_n$-aryl, —(CH$_2$)$_n$-heteroaryl, F, Cl, Br, CN, NO$_2$, =O, CO$_2$R$^f$, —(CH$_2$)$_n$OR$^f$, S(O)$_p$R$^f$, C(=O)NR$^f$R$^f$, NR$^f$C(=O)R$^f$, S(O)$_p$NR$^f$R$^f$, NR$^f$S(O)$_p$R$^f$, NR$^f$C(=O)OR, OC(=O)NR$^f$R$^f$ and —(CH$_2$)$_n$NR$^f$R$^f$;

R$^f$, at each occurrence, is independently selected from H, C$_{1-5}$alkyl (optimally substituted with halogen and OH), C$_{3-6}$ cycloalkyl, and phenyl, or R$^f$ and R$^f$ together with the nitrogen atom to which they are both attached form a heterocyclic ring optionally substituted with C$_{1-4}$alkyl;

n is independently selected from zero, 1, 2, 3, and 4; and p, at each occurrence, is independently selected from zero, 1, and 2.

In another aspect, the present invention provides compounds of Formula (IV):

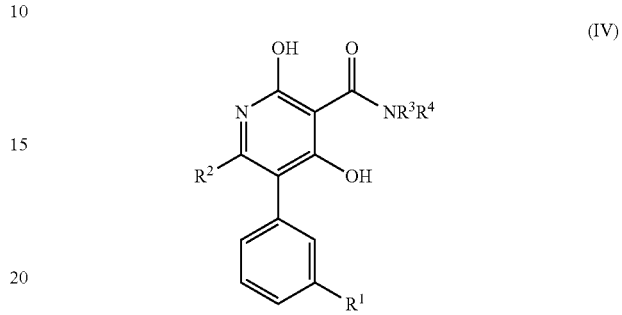

(IV)

or stereoisomers, enantiomers, diastereomers, tautomers, or pharmaceutically acceptable salts thereof, wherein:

R$^1$ is independently selected from —CH$_2$OH, —OCH$_3$, —OCF$_3$, OCH$_2$Ph, —C(=O)NR$^a$R$^a$, —NR$^a$R$^a$, CH$_3$, CH$_2$CH$_3$, CH(CH$_3$)$_2$, and cyclopropyl;

R$^2$ is independently selected from C$_{1-5}$ alkyl substituted with 0-3 R$^e$; C$_{1-5}$ alkenyl, phenyl substituted with 0-3 R$^e$, 6-membered heteroaryl substituted with 0-3 R$^e$, C$_{3-6}$ cycloalkyl and CH$_2$O(CH$_2$)$_{1-3}$CH$_3$;

R$^3$ and R$^4$ together with the nitrogen atom to which they are both attached form a heterocyclic ring selected from

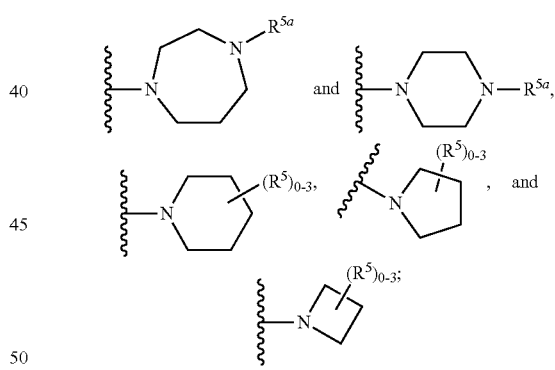

R$^{5a}$ is independently at each occurrence, selected from

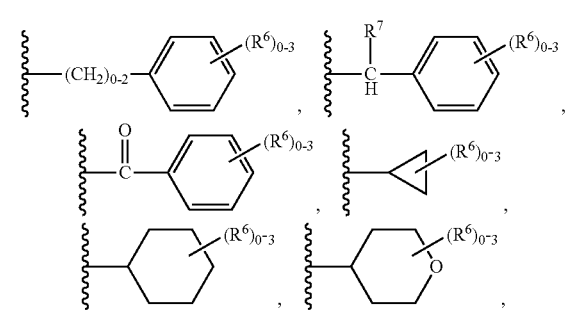

-continued
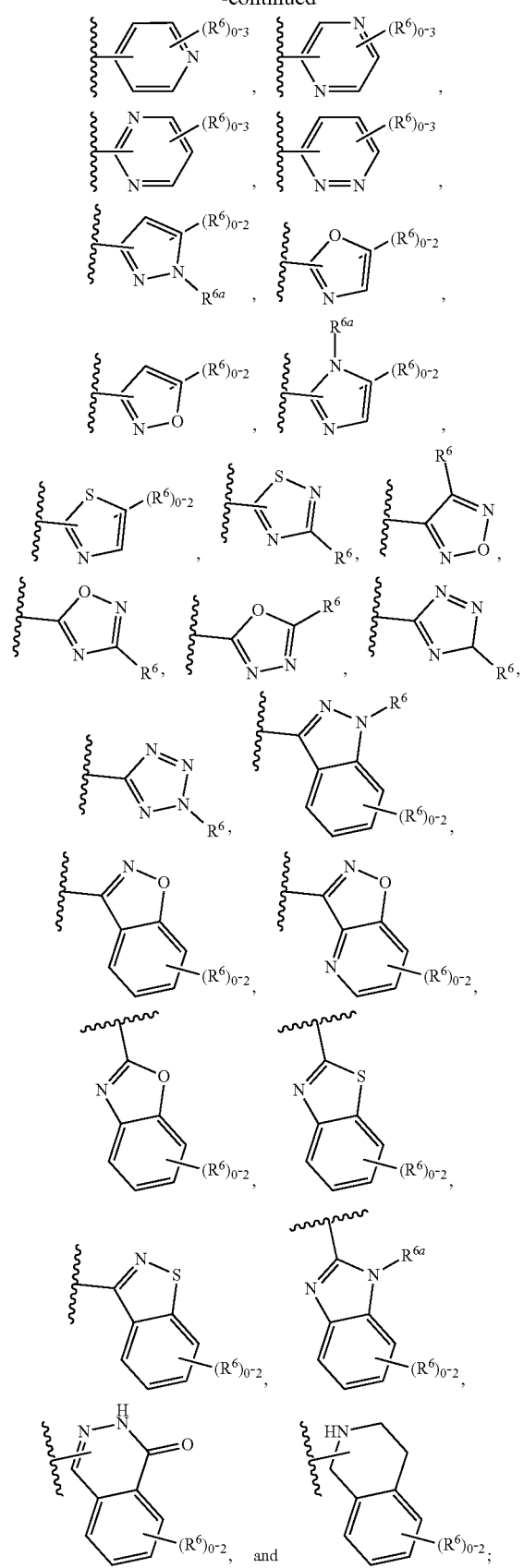
and
$R^5$ is independently at each occurrence, selected from OH,
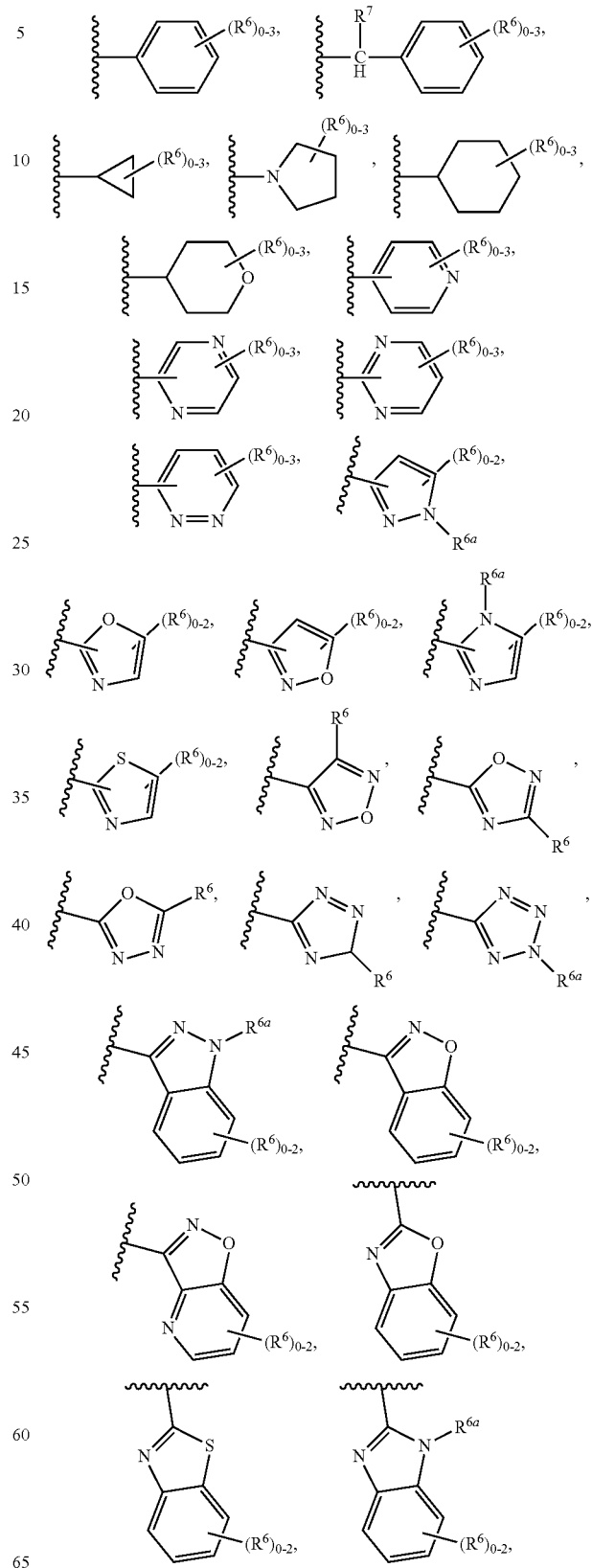

-continued

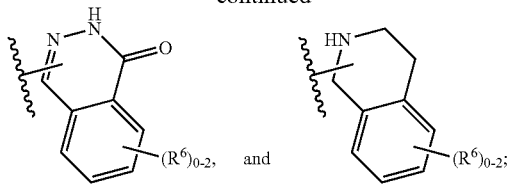

R⁶ is independently selected from H, F, Cl, Br, —OCH₃, —OCF₃, =O, CN, CH₃, CF₃, —C(=O)NH₂, —(CH₂)$_n$-aryl substituted with 0-3 R$^e$, —(CH₂)$_n$—C$_{3-6}$ cycloalkyl substituted with 0-3 R$^e$, and —(CH₂)$_n$-heterocyclyl substituted with 0-3 R$^e$;

R$^{6a}$ is independently selected from H, CH₃, aryl substituted with 0-3 R$^e$, and heterocyclyl substituted with 0-3 R$^e$;

R$^a$, at each occurrence, is independently selected from H, C$_{1-6}$ alkyl substituted with 0-5 R$^e$, —(CH₂)$_n$—C$_{3-10}$carbocyclyl substituted with 0-5 R$^e$, and —(CH₂)$_n$-heterocyclyl substituted with 0-5 R$^e$;

R$^e$, at each occurrence, is independently selected from C$_{1-6}$ alkyl (optionally substituted with F and Cl), OH, OCH₃, OCF₃, —(CH₂)$_n$—C$_{3-6}$ cycloalkyl, —(CH₂)$_n$—C$_{4-6}$ heterocyclyl, —(CH₂)$_n$-aryl, —(CH₂)$_n$-heteroaryl, F, Cl, Br, CN, NO₂, =O, CO₂H; and n is independently selected from zero, 1, 2, and 3.

In another aspect, the present invention provides compounds of Formula (IV), or stereoisomers, enantiomers, diastereomers, tautomers, pharmaceutically acceptable salts, solvates, or prodrugs thereof, wherein:

R¹ is independently selected from —CH₂OH, —C(=O)NHCH(CH₃)₂, CH₃, CH₂CH₃, and CH(CH₃)₂;

R² is independently selected from CH₂(CH₂)$_{1-3}$CH₃ and CH₂O(CH₂)$_{1-3}$CH₃;

R³ and R⁴ together with the nitrogen atom to which they are both attached form

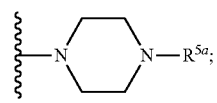

R$^{5a}$ is

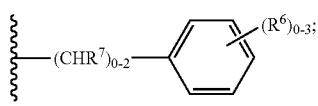

R⁶ is independently selected from H, F, Cl, Br, CH₃, and CF₃; and

R⁷ is independently selected from H, C$_{1-4}$alkyl, and phenyl.

In another aspect, the present invention provides compounds of Formula (IV), or stereoisomers, enantiomers, diastereomers, tautomers, pharmaceutically acceptable salts, solvates, or prodrugs thereof, wherein:

R¹ is independently selected from —CH₂OH, —C(=O)NHCH(CH₃)₂, CH₃, CH₂CH₃, and CH(CH₃)₂;

R² is independently selected from CH₂(CH₂)$_{1-3}$CH₃ and CH₂O(CH₂)$_{1-3}$CH₃;

R³ and R⁴ together with the nitrogen atom to which they are both attached form

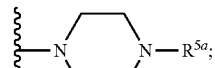

R$^{5a}$ is

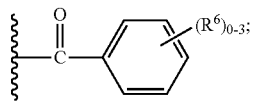

R⁶ is independently selected from H, F, Cl, Br, CH₃, and CF₃.

In another aspect, the present invention provides compounds of Formula (IV), or stereoisomers, enantiomers, diastereomers, tautomers, pharmaceutically acceptable salts, solvates, or prodrugs thereof, wherein:

R¹ is independently selected from —CH₂OH, —C(=O)NHCH(CH₃)₂, CH₃, CH₂CH₃, and CH(CH₃)₂;

R² is independently selected from CH₂(CH₂)$_{1-3}$CH₃ and CH₂O(CH₂)$_{1-3}$CH₃;

R³ and R⁴ together with the nitrogen atom to which they are both attached form

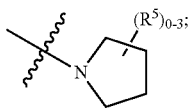

R⁵ is independently at each occurrence, selected from

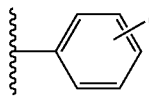 or 

R⁶ is independently selected from H, F, Cl, Br, CH₃, CF₃, aryl substituted with 0-3 R$^e$;

and R$^e$, at each occurrence, is independently selected from C$_{1-6}$ alkyl, OH, OCH₃, OCF₃.

In one non-limiting embodiment, ring B is

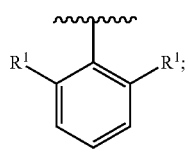

R¹ is OC$_{1-4}$ alkyl; R² is independently selected from C$_{1-5}$ alkyl substituted with 0-3 R$^e$; wherein the methylene unit of C$_{1-5}$ alkyl except the one attached directly to the pyridine ring may be replaced by O, N, and S; R³ and R⁴ together with the nitrogen atom to which they are both attached form

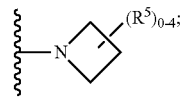

$R^5$ is independently at each occurrence, selected from

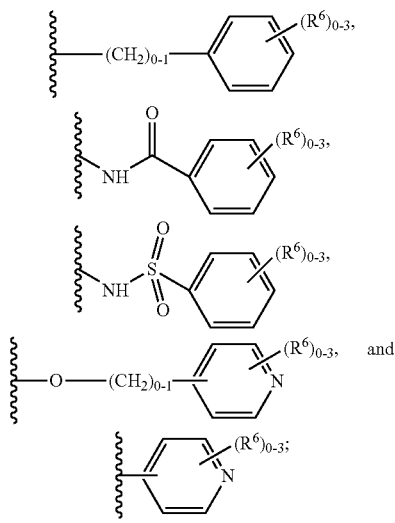

and
$R^6$ is independently selected from H, F, Cl, Br, $CH_3$, and $CF_3$.

In another non-limiting embodiment, Ring B is

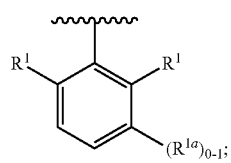

$R^1$ is independently selected from $OC_{1-4}$ alkyl; $R^{1a}$ is independently selected from F and Cl; $R^2$ is independently selected from $C_{1-5}$ alkyl substituted with 0-3 $R^e$; wherein the methylene unit of $C_{1-5}$ alkyl except the one attached directly to the pyridine ring may be replaced by O, N, and S; $R^3$ and $R^4$ together with the nitrogen atom to which they are both attached form

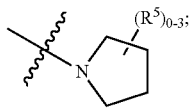

$R^5$ is independently at each occurrence, selected from

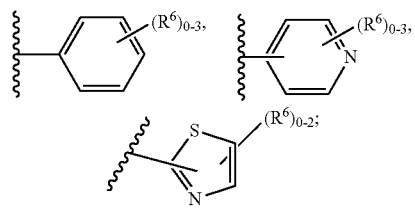

and
$R^6$ is independently selected from H, F, Cl, Br, $CH_3$, and $CF_3$.

In another non-limiting embodiment, ring B

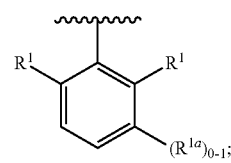

$R^1$ is independently selected from $OC_{1-4}$ alkyl; $R^{1a}$ is independently selected from F and Cl; $R^2$ is independently selected from $-CH_2CH_2CH_2CH_3$ am $-CH_2OCH_2CH_3$; $R^3$ and $R^4$ together with the nitrogen atom to which they are both attached form

$R^5$ is independently at each occurrence, selected from

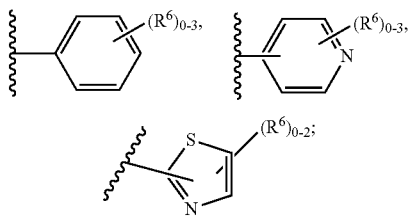

and
$R^6$ is independently selected from H, F, Cl, Br, $CH_3$, and $CF_3$.

In another non-limiting embodiment, ring B is

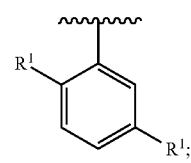

$R^1$ is independently selected from $OC_{1-4}$ alkyl; $R^2$ is independently selected from $C_{1-5}$ alkyl substituted with 0-3 $R^e$; wherein the methylene unit of $C_{1-5}$ alkyl except the one attached directly to the pyridine ring may be replaced by O, N, and S; $R^3$ and $R^4$ together with the nitrogen atom to which they are both attached form

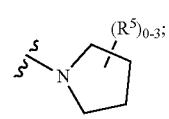

$R^5$ is independently at each occurrence, selected from

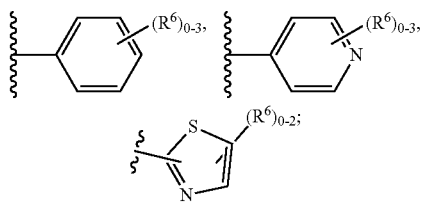

and
$R^6$ is independently selected from H, F, Cl, Br, CH$_3$, and CF$_3$.

In another non-limiting embodiment, ring B is

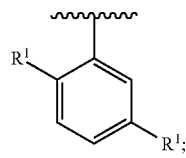

$R^1$ is independently selected from OC$_{1-4}$ alkyl; $R^2$ is independently selected from —CH$_2$CH$_2$CH$_2$CH$_3$ am —CH$_2$OCH$_2$CH$_3$; $R^3$ and $R^4$ together with the nitrogen atom to which they are both attached form

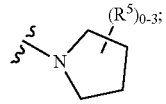

$R^5$ is independently at each occurrence, selected from

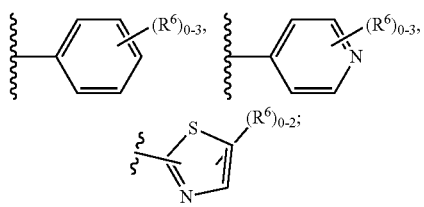

and
$R^6$ is independently selected from H, F, Cl, Br, CH$_3$, and CF$_3$.

In another non-limiting embodiment, ring B is

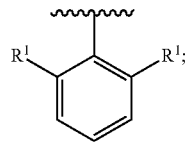

$R^1$ is OC$_{1-4}$ alkyl; $R^2$ is independently selected from C$_{1-5}$ alkyl substituted with 0-3 R$^e$; wherein the methylene unit of C$_{1-5}$ alkyl except the one attached directly to the pyridine ring may be replaced by O, N, and S; $R^3$ and $R^4$ together with the nitrogen atom to which they are both attached form

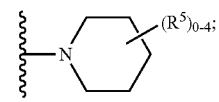

$R^5$ is independently at each occurrence, selected from

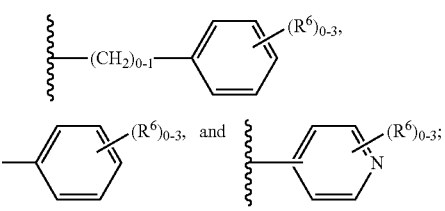

and
$R^6$ is independently selected from H, F, Cl, Br, CH$_3$, and CF$_3$.

In another non-limiting embodiment, ring B is

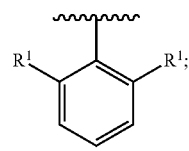

$R^1$ is OC$_{1-4}$ alkyl; $R^2$ is independently selected from —CH$_2$CH$_2$CH$_2$CH$_3$ am —CH$_2$OCH$_2$CH$_3$; $R^3$ and $R^4$ together with the nitrogen atom to which they are both attached form

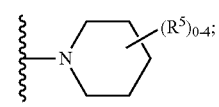

$R^5$ is independently at each occurrence, selected from

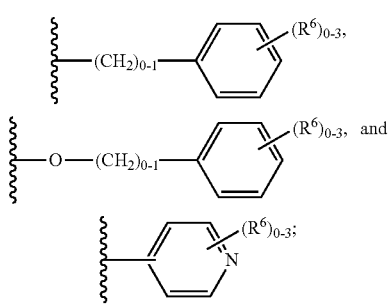

and
$R^6$ is independently selected from H, F, Cl, Br, CH$_3$, and CF$_3$.

In another non-limiting embodiment, ring B is

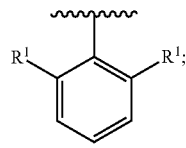

$R^1$ is $OC_{1-4}$ alkyl; $R^2$ is independently selected from $C_{1-5}$ alkyl substituted with 0-3 $R^e$; wherein the methylene unit of $C_{1-5}$ alkyl except the one attached directly to the pyridine ring may be replaced by O, N, and S; $R^3$ and $R^4$ together with the nitrogen atom to which they are both attached form

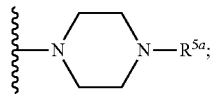

$R^{5a}$ is

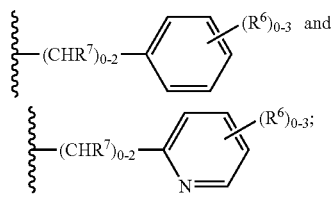

and
$R^6$ is independently selected from H, F, Cl, Br, $CH_3$, and $CF_3$; and
$R^7$ is independently selected from H, $C_{1-4}$alkyl, and phenyl.

In another non-limiting embodiment, ring B is

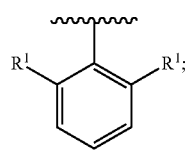

$R^1$ is $OC_{1-4}$ alkyl; $R^2$ is independently selected from $-CH_2CH_2CH_2CH_3$ am $-CH_2OCH_2CH_3$; $R^3$ and $R^4$ together with the nitrogen atom to which they are both attached form

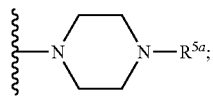

$R^{5a}$ is

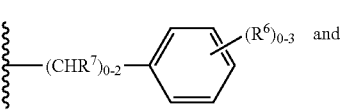

$R^6$ is independently selected from H, F, Cl, Br, $CH_3$, and $CF_3$; and
$R^7$ is independently selected from H, $C_{1-4}$alkyl, and phenyl.

In another non-limiting embodiment, ring B is

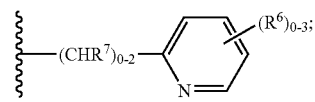

$R^1$ is $OC_{1-4}$ alkyl; $R^2$ is independently selected from $-CH_2CH_2CH_2CH_3$ am $-CH_2OCH_2CH_3$; $R^3$ and $R^4$ together with the nitrogen atom to which they are both attached form

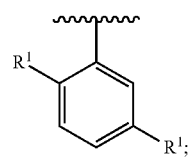

$R^{5a}$ is

$R^6$ is independently selected from H, F, Cl, Br, $CH_3$, and $CF_3$; and
$R^7$ is independently selected from H, $C_{1-4}$alkyl, and phenyl.

In another non-limiting embodiment, ring B is

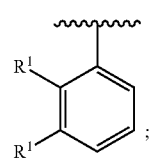

$R^1$ is $OC_{1-4}$ alkyl; $R^2$ is independently selected from $-CH_2CH_2CH_2CH_3$ am $-CH_2OCH_2CH_3$; $R^3$ and $R^4$ together with the nitrogen atom to which they are both attached form

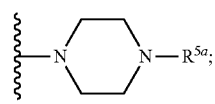

$R^{5a}$ is

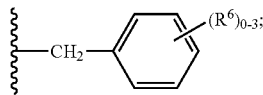

$R^6$ is independently selected from H, F, Cl, Br, $CH_3$, and $CF_3$; and.

In another non-limiting embodiment, ring B is

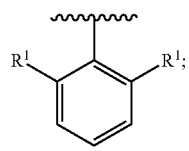

$R^1$ is $OC_{1-4}$ alkyl; $R^2$ is independently selected from $C_{1-5}$ alkyl substituted with 0-3 $R^e$; wherein the methylene unit of $C_{1-5}$ alkyl except the one attached directly to the pyridine ring may be replaced by O, N, and S; $R^3$ and $R^4$ together with the nitrogen atom to which they are both attached form

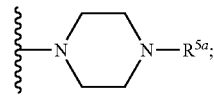

$R^{5a}$ is independently selected from

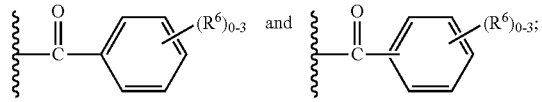

$R^6$ is independently selected from H, F, Cl, Br, $CH_3$, and $CF_3$.

In another non-limiting embodiment, ring B is

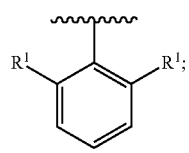

$R^1$ is $OC_{1-4}$ alkyl; $R^2$ is independently selected from $C_{1-5}$ alkyl substituted with 0-3 $R^e$; wherein the methylene unit of $C_{1-5}$ alkyl except the one attached directly to the pyridine ring may be replaced by O, N, and S; $R^3$ and $R^4$ together with the nitrogen atom to which they are both attached form

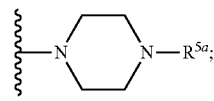

$R^{5a}$ is independently selected from

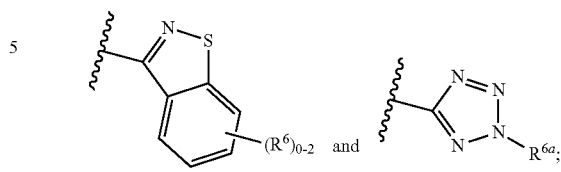

$R^6$ is independently selected from H, F, Cl, Br, $CH_3$, and $CF_3$; and
$R^{6a}$ is independently selected from H, $CH_3$, and phenyl In another non-limiting embodiment, ring B is

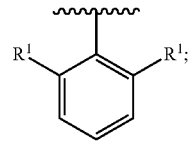

$R^1$ is $OC_{1-4}$ alkyl; $R^2$ is independently selected from $C_{1-5}$ alkyl wherein the methylene unit of $C_{1-5}$ alkyl except the one attached directly to the pyridine ring may be replaced by O, N, and S; $R^3$ is H; $R^4$ is $C_{1-3}$ alkyl substituted with 1-3 $R^6$; $R^6$ is independently selected from $C(=O)NHR^a$ and $-(CH_2)_n-C_{3-6}$ cycloalkyl; $R^a$ is $C_{1-3}$ alkyl substituted with 0-5 $R^e$, $R^e$ is $-(CH_2)_nCO_2R^f$; $R^f$ is independently selected from H and $C_{1-5}$alkyl; n is independently selected from zero, 1 and, 2.

In another non-limiting embodiment, ring B is

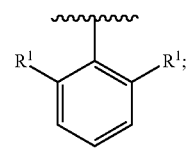

$R^1$ is $OC_{1-4}$ alkyl; $R^2$ is independently selected from $C_{1-5}$ alkyl wherein the methylene unit of $C_{1-5}$ alkyl except the one attached directly to the pyridine ring may be replaced by O, N, and S; $R^3$ is $C_{1-2}$ alkyl; $R^4$ is $C_{1-3}$ alkyl substituted with 1-3 $R^6$; $R^6$ is independently selected from $-OR^b$, NHC($=O)R^b$, aryl and heteroaryl; $R^b$ is independently selected from $-(CH_2)_n-C_{3-10}$ carbocyclyl and $-(CH_2)_n$-heterocyclyl; n is independently selected from zero, 1 and, 2.

In another aspect, the present invention provides a compound selected from the following list:
6-butyl-5-(2,6-dimethoxyphenyl)-3-[4-(4-methoxybenzoyl)piperazine-1-carbonyl]pyridine-2,4-diol (1);
6-butyl-5-(2,6-dimethoxyphenyl)-2,4-dihydroxy-N-methyl-N-(4-phenylbutyl)pyridine-3-carboxamide (2);
6-butyl-5-(2,6-dimethoxyphenyl)-3-[4-(1-methyl-1H-imidazol-2-yl)piperazine-1-carbonyl]pyridine-2,4-diol (3);
6-butyl-5-(2,6-dimethoxyphenyl)-3-[4-hydroxy-4-(pyridin-3-yl)piperidine-1-carbonyl]pyridine-2,4-diol (4);
6-butyl-5-(2,6-dimethoxyphenyl)-3-[4-(3-propyl-1,2,4-oxadiazol-5-yl)piperidine-1-carbonyl]pyridine-2,4-diol (5);
6-butyl-3-[4-(5-chloropyridin-2-yl)piperazine-1-carbonyl]-5-(2,6-dimethoxyphenyl)pyridine-2,4-diol (6);
6-butyl-5-(2,6-dimethoxyphenyl)-3-{4-[4-(2-methoxyethoxy)phenyl]piperazine-1-carbonyl}pyridine-2,4-diol (7);
6-butyl-5-(2,6-dimethoxyphenyl)-3-[2-(pyridin-2-yl)pyrrolidine-1-carbonyl]pyridine-2,4-diol (8);

6-butyl-3-{3-[4-(2-chloro-4-methoxy-5-methylphenyl)-5-methyl-1,3-thiazol-2-yl]pyrrolidine-1-carbonyl}-5-(2,6-dimethoxyphenyl)pyridine-2,4-diol (9);

methyl N-(4-{4-[6-butyl-5-(2,6-dimethoxyphenyl)-2,4-dihydroxypyridine-3-carbonyl]piperazin-1-yl}phenyl)carbamate (10);

6-butyl-5-(2,6-dimethoxyphenyl)-3-{4-[3-(trifluoromethyl)pyridin-2-yl]piperazine-1-carbonyl}pyridine-2,4-diol (11);

6-butyl-5-(2,6-dimethoxyphenyl)-3-[4-(2-methoxyphenyl)piperazine-1-carbonyl]pyridine-2,4-diol (12);

6-butyl-5-(2,6-dimethoxyphenyl)-3-{4-[4-(trifluoromethyl)pyrimidin-2-yl]piperazine-1-carbonyl}pyridine-2,4-diol (13);

3-(4-benzylpiperidine-1-carbonyl)-6-butyl-5-(2,6-dimethoxyphenyl)pyridine-2,4-diol (14);

6-butyl-5-(2,6-dimethoxyphenyl)-2,4-dihydroxy-N-methyl-N-[2-(pyridin-2-yl)ethyl]pyridine-3-carboxamide (15);

6-butyl-5-(2,6-dimethoxyphenyl)-3-[4-(diphenylmethyl)piperazine-1-carbonyl]pyridine-2,4-diol (16);

6-butyl-5-(2,6-dimethoxyphenyl)-3-[4-(4-methyl-1H-imidazol-5-yl)piperidine-1-carbonyl]pyridine-2,4-diol (17);

6-butyl-5-(2,6-dimethoxyphenyl)-3-[4-(4-methoxyphenyl)piperazine-1-carbonyl]pyridine-2,4-diol (18);

6-butyl-5-(2,6-dimethoxyphenyl)-3-[4-(2-methoxyphenyl)piperidine-1-carbonyl]pyridine-2,4-diol (19);

6-butyl-5-(2,6-dimethoxyphenyl)-3-{4-[3-(furan-2-yl)-1H-pyrazol-5-yl]piperidine-1-carbonyl}pyridine-2,4-diol (20);

6-butyl-5-(2,6-dimethoxyphenyl)-3-[4-(pyridazin-3-yl)piperazine-1-carbonyl]pyridine-2,4-diol (21);

6-butyl-5-(2,6-dimethoxyphenyl)-3-[4-(pyridin-4-yl)piperazine-1-carbonyl]pyridine-2,4-diol (22);

6-butyl-3-[4-(2-chlorophenyl)piperidine-1-carbonyl]-5-(2,6-dimethoxyphenyl)pyridine-2,4-diol (23);

4-{1-[6-butyl-5-(2,6-dimethoxyphenyl)-2,4-dihydroxypyridine-3-carbonyl]piperidin-4-yl}benzamide (24);

5-(2,6-dimethoxyphenyl)-6-(ethoxymethyl)-3-[(3S)-3-phenylpyrrolidine-1-carbonyl]pyridine-2,4-diol (25);

5-(2,6-dimethoxyphenyl)-6-(ethoxymethyl)-3-[(3R)-3-phenylpyrrolidine-1-carbonyl]pyridine-2,4-diol (26);

6-butyl-N-[2-(4-chlorophenyl)ethyl]-5-(2,6-dimethoxyphenyl)-2,4-dihydroxy-N-methylpyridine-3-carboxamide (27);

6-butyl-5-(2,6-dimethoxyphenyl)-3-[(3R)-3-phenylpyrrolidine-1-carbonyl]pyridine-2,4-diol (28);

6-butyl-5-(2,6-dimethoxyphenyl)-3-[(3S)-3-phenylpyrrolidine-1-carbonyl]pyridine-2,4-diol (29);

6-butyl-5-(2,6-dimethoxyphenyl)-3-(4-phenylpiperazine-1-carbonyl)pyridine-2,4-diol (30);

6-butyl-3-{4-[(4-chlorophenyl)methyl]piperazine-1-carbonyl}-5-(2,6-dimethoxyphenyl)pyridine-2,4-diol (31);

3-[4-(1,3-benzoxazol-2-yl)piperidine-1-carbonyl]-6-butyl-5-(2,6-dimethoxyphenyl)pyridine-2,4-diol (32);

N-benzyl-6-butyl-5-(2,6-dimethoxyphenyl)-2,4-dihydroxy-N-propylpyridine-3-carboxamide (33);

6-butyl-3-[3-(3-chlorophenyl)azetidine-1-carbonyl]-5-(2,6-dimethoxyphenyl)pyridine-2,4-diol (34);

6-butyl-3-[3-(2-chlorophenyl)pyrrolidine-1-carbonyl]-5-(2,6-dimethoxyphenyl)pyridine-2,4-diol (35);

6-butyl-3-[3-(3-chlorophenyl)pyrrolidine-1-carbonyl]-5-(2,6-dimethoxyphenyl)pyridine-2,4-diol (37);

6-butyl-3-[3-(3-chlorophenyl)pyrrolidine-1-carbonyl]-5-(2,6-dimethoxyphenyl)pyridine-2,4-diol (38);

6-butyl-5-(2,6-dimethoxyphenyl)-3-[3-(4-fluorophenyl)pyrrolidine-1-carbonyl]pyridine-2,4-diol (39);

6-butyl-5-(2,6-dimethoxyphenyl)-3-[3-(4-fluorophenyl)pyrrolidine-1-carbonyl]pyridine-2,4-diol (40);

3-(4-benzoylpiperazine-1-carbonyl)-6-butyl-5-(2,6-dimethoxyphenyl)pyridine-2,4-diol (41);

6-butyl-5-(2,6-dimethoxyphenyl)-3-[4-(3-fluorobenzoyl)piperazine-1-carbonyl]pyridine-2,4-diol (42);

6-butyl-5-(2,6-dimethoxyphenyl)-3-{4-[(4-fluorophenyl)methyl]piperazine-1-carbonyl}pyridine-2,4-diol (43);

6-butyl-5-(2,6-dimethoxyphenyl)-3-{4-[(2-fluorophenyl)methyl]piperazine-1-carbonyl}pyridine-2,4-diol (44);

6-butyl-5-(2,6-dimethoxyphenyl)-3-{4-[(3-fluorophenyl)methyl]piperazine-1-carbonyl}pyridine-2,4-diol (45);

6-butyl-5-(2,6-dimethoxyphenyl)-3-(4-hydroxy-4-phenylpiperidine-1-carbonyl)pyridine-2,4-diol (46);

6-butyl-3-[4-(4-chlorophenyl)-4-hydroxypiperidine-1-carbonyl]-5-(2,6-dimethoxyphenyl)pyridine-2,4-diol (47);

3-[4-(1,3-benzothiazol-2-yl)piperidine-1-carbonyl]-6-butyl-5-(2,6-dimethoxyphenyl)pyridine-2,4-diol (48);

3-[4-(1,2-benzothiazol-3-yl)piperazine-1-carbonyl]-6-butyl-5-(2,6-dimethoxyphenyl)pyridine-2,4-diol (49);

1'-[6-butyl-5-(2,6-dimethoxyphenyl)-2,4-dihydroxypyridine-3-carbonyl]-1,2-dihydrospiro[3,1-benzoxazine-4,4'-piperidine]-2-one (50);

3-[4-(1,3-benzoxazol-2-yl)piperazine-1-carbonyl]-6-butyl-5-(2,6-dimethoxyphenyl)pyridine-2,4-diol (51);

6-butyl-5-(2,6-dimethoxyphenyl)-3-[4-(1-phenyl-1H-1,2,3,4-tetrazol-5-yl)piperazine-1-carbonyl]pyridine-2,4-diol (52);

6-butyl-5-(2,6-dimethoxyphenyl)-3-[4-(1-phenyl-1H-1,2,3,4-tetrazol-5-yl)-1,4-diazepane-1-carbonyl]pyridine-2,4-diol (53);

3-[4-(1,3-benzothiazol-2-yl)piperazine-1-carbonyl]-6-butyl-5-(2,6-dimethoxyphenyl)pyridine-2,4-diol (54);

6-butyl-5-(2,6-dimethoxyphenyl)-3-[4-(1H-imidazol-4-yl)piperidine-1-carbonyl]pyridine-2,4-diol (55);

6-butyl-3-[4-(3-chlorophenyl)piperidine-1-carbonyl]-5-(2,6-dimethoxyphenyl)pyridine-2,4-diol (56);

6-butyl-3-[4-(2-chlorophenyl)piperazine-1-carbonyl]-5-(2,6-dimethoxyphenyl)pyridine-2,4-diol (57);

6-butyl-3-[4-(3-chlorophenyl)piperazine-1-carbonyl]-5-(2,6-dimethoxyphenyl)pyridine-2,4-diol (58);

6-butyl-5-(2,6-dimethoxyphenyl)-3-[4-(pyridin-2-yl)piperazine-1-carbonyl]pyridine-2,4-diol (59);

6-butyl-5-(2,6-dimethoxyphenyl)-3-[4-(3-phenyl-1,2,4-thiadiazol-5-yl)piperazine-1-carbonyl]pyridine-2,4-diol (60);

6-butyl-5-(2,6-dimethoxyphenyl)-3-[4-(pyrrolidin-1-yl)piperidine-1-carbonyl]pyridine-2,4-diol (61);

6-butyl-5-(2,6-dimethoxyphenyl)-3-(4-phenylpiperidine-1-carbonyl)pyridine-2,4-diol (62);

6-butyl-3-(4-cyclohexylpiperazine-1-carbonyl)-5-(2,6-dimethoxyphenyl)pyridine-2,4-diol (63);

6-butyl-5-(2,6-dimethoxyphenyl)-3-({3H-spiro[2-benzofuran-1,4'-piperidine]-1'-yl}carbonyl)pyridine-2,4-diol (64);

6-butyl-5-(2,6-dimethoxyphenyl)-3-[4-(6-fluoro-1,2-benzoxazol-3-yl)piperidine-1-carbonyl]pyridine-2,4-diol (65);

1-[6-butyl-5-(2,6-dimethoxyphenyl)-2,4-dihydroxypyridine-3-carbonyl]-2',3'-dihydro-1'H-spiro[piperidine-4,4'-quinoline]-2'-one (66);

6-butyl-5-(2,6-dimethoxyphenyl)-3-[4-(5-phenyl-1H-pyrazol-3-yl)piperidine-1-carbonyl]pyridine-2,4-diol (67);

6-butyl-3-[4-(4-chlorophenyl)piperazine-1-carbonyl]-5-(2,6-dimethoxyphenyl)pyridine-2,4-diol (68);

6-butyl-5-(2,6-dimethoxyphenyl)-3-{4-[3-(pyridin-3-yl)-1,2,4-oxadiazol-5-yl]piperidine-1-carbonyl}pyridine-2,4-diol (69);

6-(Ethoxymethyl)-5-(4-fluoro-2,6-dimethoxyphenyl)-3-[(3R)-3-phenylpyrrolidine-1-carbonyl]pyridine-2,4-diol (70);

6-butyl-5-(3-fluoro-2,6-dimethoxyphenyl)-3-[(3R)-3-phenylpyrrolidine-1-carbonyl]pyridine-2,4-diol (71);

6-butyl-3-[3-(2-chlorophenyl)pyrrolidine-1-carbonyl]-5-(2,6-dimethoxyphenyl)pyridine-2,4-diol (72);

(6-butyl-5-(2,6-dimethoxyphenyl)-2,4-dihydroxypyridin-3-yl)(3-(5-chloropyridin-2-yl)pyrrolidin-1-yl)methanone (74);

6-butyl-3-[3-(5-chloropyridin-2-yl)pyrrolidine-1-carbonyl]-5-(2,6-dimethoxyphenyl)pyridine-2,4-diol (75);

3-[3-(5-chloropyridin-2-yl)pyrrolidine-1-carbonyl]-5-(2,6-dimethoxyphenyl)-6-(ethoxymethyl)pyridine-2,4-diol (76);

3-[3-(5-chloropyridin-2-yl)pyrrolidine-1-carbonyl]-5-(2,6-dimethoxyphenyl)-6-(ethoxymethyl)pyridine-2,4-diol (77);

6-butyl-5-(2,6-dimethoxyphenyl)-3-[3-(3-fluoropyridin-2-yl)pyrrolidine-1-carbonyl]pyridine-2,4-diol (78);

6-butyl-5-(2,6-dimethoxyphenyl)-3-[3-(5-fluoropyridin-2-yl)pyrrolidine-1-carbonyl]pyridine-2,4-diol (79);

6-butyl-5-(2,6-dimethoxyphenyl)-3-[3-(5-fluoropyridin-2-yl)pyrrolidine-1-carbonyl]pyridine-2,4-diol (80);

6-butyl-5-(2,6-dimethoxyphenyl)-3-[3-(3-fluoropyridin-2-yl)pyrrolidine-1-carbonyl]pyridine-2,4-diol (81);

6-butyl-3-[3-(3,5-difluoropyridin-2-yl)pyrrolidine-1-carbonyl]-5-(2,6-dimethoxyphenyl)pyridine-2,4-diol (82);

6-butyl-3-[3-(3,5-difluoropyridin-2-yl)pyrrolidine-1-carbonyl]-5-(2,6-dimethoxyphenyl)pyridine-2,4-diol (83);

3-[3-(3,5-difluoropyridin-2-yl)pyrrolidine-1-carbonyl]-5-(2,6-dimethoxyphenyl)-6-(ethoxymethyl)pyridine-2,4-diol (84);

3-[3-(3,5-difluoropyridin-2-yl)pyrrolidine-1-carbonyl]-5-(2,6-dimethoxyphenyl)-6-(ethoxymethyl)pyridine-2,4-diol (85);

(5-(2,6-dimethoxyphenyl)-6-(4-fluorophenyl)-2,4-dihydroxypyridin-3-yl)(3-(2-fluorophenyl)pyrrolidin-1-yl)methanone (86);

(3-(3,5-difluoropyridin-2-yl)pyrrolidin-1-yl)(5-(2,6-dimethoxyphenyl)-6-(4-fluorophenyl)-2,4-dihydroxypyridin-3-yl)methanone (87);

5-(2,6-dimethoxyphenyl)-3-{4-[(3-fluorophenyl)methyl]piperazine-1-carbonyl}-6-(2-methoxyethyl)pyridine-2,4-diol (88);

5-(2,6-dimethoxyphenyl)-6-(ethoxymethyl)-3-{4-[(2-fluorophenyl)methyl]piperazine-1-carbonyl}pyridine-2,4-diol (89);

5-(2,6-dimethoxyphenyl)-6-(ethoxymethyl)-3-{4-[(3-fluorophenyl)methyl]piperazine-1-carbonyl}pyridine-2,4-diol (90);

6-(ethoxymethyl)-3-{4-[(3-fluorophenyl)methyl]piperazine-1-carbonyl}-5-(2-methoxyphenyl)pyridine-2,4-diol (91);

6-butyl-5-(2,6-dimethoxyphenyl)-3-(4-phenoxypiperidine-1-carbonyl)pyridine-2,4-diol (92);

6-butyl-3-{4-[(2,4-dichlorophenyl)methyl]piperazine-1-carbonyl}-5-(2,6-dimethoxyphenyl)pyridine-2,4-diol (93);

6-butyl-3-{4-[(2,3-dichlorophenyl)methyl]piperazine-1-carbonyl}-5-(2,6-dimethoxyphenyl)pyridine-2,4-diol (94);

N-(2-{1-[6-butyl-5-(2,6-dimethoxyphenyl)-2,4-dihydroxypyridin-3-yl]-N-methylformamido}ethyl)benzamide (95);

6-butyl-5-(2,5-dimethoxyphenyl)-3-[(3S)-3-phenylpyrrolidine-1-carbonyl]pyridine-2,4-diol (96);

6-butyl-5-(2,5-dimethoxyphenyl)-3-[(3R)-3-phenylpyrrolidine-1-carbonyl]pyridine-2,4-diol (97);

N-{1-[6-butyl-5-(2,6-dimethoxyphenyl)-2,4-dihydroxypyridine-3-carbonyl]azetidin-3-yl}benzamide (98);

6-butyl-5-(2,6-dimethoxyphenyl)-2,4-dihydroxy-N-methyl-N-(2-phenoxyethyl)pyridine-3-carboxamide (99);

6-butyl-3-{4-[(5-chloropyridin-2-yl)oxy]piperidine-1-carbonyl}-5-(2,6-dimethoxyphenyl)pyridine-2,4-diol (100);

6-butyl-5-(2,6-dimethoxyphenyl)-3-[4-(pyridin-2-ylmethyl)piperazine-1-carbonyl]pyridine-2,4-diol (101);

6-butyl-N-{2-[(5-chloro-3-fluoropyridin-2-yl)amino]ethyl}-5-(2,6-dimethoxyphenyl)-2,4-dihydroxy-N-methylpyridine-3-carboxamide (102);

6-butyl-3-{4-[(2,3-dichlorophenyl)methyl]piperazine-1-carbonyl}-5-(2,5-dimethoxyphenyl)pyridine-2,4-diol (103);

3-{4-[(2,3-dichlorophenyl)methyl]piperazine-1-carbonyl}-5-(2,6-dimethoxyphenyl)-6-(ethoxymethyl)pyridine-2,4-diol (104);

6-butyl-3-[4-(5-chloropyridine-2-carbonyl)piperazine-1-carbonyl]-5-(2,6-dimethoxyphenyl)pyridine-2,4-diol (105);

6-butyl-5-(2,6-dimethoxyphenyl)-3-{4-[(2-methylphenyl)methyl]piperidine-1-carbonyl}pyridine-2,4-diol (106);

6-butyl-5-(2,6-dimethoxyphenyl)-3-(4-{[3-(trifluoromethyl)phenyl]methyl}piperazine-1-carbonyl)pyridine-2,4-diol (107);

6-butyl-3-{4-[(2,3-difluorophenyl)methyl]piperazine-1-carbonyl}-5-(2,6-dimethoxyphenyl)pyridine-2,4-diol (108);

6-butyl-3-[4-(cyclohexylmethyl)piperazine-1-carbonyl]-5-(2,6-dimethoxyphenyl)pyridine-2,4-diol (109);

6-butyl-3-{4-[(2,3-difluorophenyl)methyl]piperazine-1-carbonyl}-5-(2,5-dimethoxyphenyl)pyridine-2,4-diol (110);

6-butyl-3-[4-(cyclopropylmethyl)piperazine-1-carbonyl]-5-(2,6-dimethoxyphenyl)pyridine-2,4-diol (111);

6-butyl-3-{4-[(2,3-dichlorophenyl)methyl]piperazine-1-carbonyl}-5-(2,3-dimethoxyphenyl)pyridine-2,4-diol (112);

3-{4-[(2-bromo-5-fluorophenyl)methyl]piperidine-1-carbonyl}-6-butyl-5-(2,6-dimethoxyphenyl)pyridine-2,4-diol (113);

3-{4-[(2,3-difluorophenyl)methyl]piperazine-1-carbonyl}-5-(2,6-dimethoxyphenyl)-6-(ethoxymethyl)pyridine-2,4-diol (114);

6-butyl-5-(2,6-dimethoxyphenyl)-3-{3-[(3-fluoropyridin-2-yl)oxy]azetidine-1-carbonyl}pyridine-2,4-diol (115);

6-butyl-3-{3-[(2,3-difluorophenyl)methoxy]azetidine-1-carbonyl}-5-(2,6-dimethoxyphenyl)pyridine-2,4-diol (116);

6-butyl-5-(2,6-dimethoxyphenyl)-N-[2-(2-fluorophenyl)ethyl]-2,4-dihydroxy-N-propylpyridine-3-carboxamide (117);

N-{1-[6-butyl-5-(2,6-dimethoxyphenyl)-2,4-dihydroxypyridine-3-carbonyl]azetidin-3-yl}-2,3-difluorobenzene-1-sulfonamide (118);

6-butyl-3-[4-(2,3-difluorobenzoyl)piperazine-1-carbonyl]-5-(2,6-dimethoxyphenyl)pyridine-2,4-diol (119);

6-butyl-5-(2,6-dimethoxyphenyl)-3-{4-[(3-fluoropyridin-2-yl)methyl]piperazine-1-carbonyl}pyridine-2,4-diol (120);

6-butyl-5-(2,6-dimethoxyphenyl)-3-{4-[(2-fluoro-3-methylphenyl)methyl]piperazine-1-carbonyl}pyridine-2,4-diol (121);

6-butyl-3-{4-[(2,5-difluorophenyl)methyl]piperazine-1-carbonyl}-5-(2,6-dimethoxyphenyl)pyridine-2,4-diol (122);

6-butyl-3-{4-[(6-chloropyridin-2-yl)methyl]piperazine-1-carbonyl}-5-(2,6-dimethoxyphenyl)pyridine-2,4-diol (123);

5-(2,6-dimethoxyphenyl)-6-(ethoxymethyl)-3-[3-(3-fluorophenyl)pyrrolidine-1-carbonyl]pyridine-2,4-diol (124);
6-cyclopentyl-5-(2,6-dimethoxyphenyl)-3-[3-(3-fluorophenyl)pyrrolidine-1-carbonyl]pyridine-2,4-diol (125);
5-(2,6-dimethoxyphenyl)-6-(ethoxymethyl)-3-[3-(2-fluorophenyl)pyrrolidine-1-carbonyl]pyridine-2,4-diol (126);
5-(2,6-dimethoxyphenyl)-6-(ethoxymethyl)-3-[3-(2-fluorophenyl)pyrrolidine-1-carbonyl]pyridine-2,4-diol (127);
3-[3-(3,5-difluoropyridin-2-yl)pyrrolidine-1-carbonyl]-5-(3-methoxyphenyl)-6-(2-methyl-1,3-thiazol-4-yl)pyridine-2,4-diol (128);
3-[3-(3,5-difluoropyridin-2-yl)pyrrolidine-1-carbonyl]-5-(3-methoxyphenyl)-6-(2-methyl-1,3-thiazol-4-yl)pyridine-2,4-diol (129);
6-butyl-3-[3-(5-chloro-3-fluoropyridin-2-yl)pyrrolidine-1-carbonyl]-5-(2,6-dimethoxyphenyl)-4-hydroxy-1,2-dihydropyridin-2-one (130);
3-[3-(2,4-difluorophenyl)pyrrolidine-1-carbonyl]-5-(2,6-dimethoxyphenyl)-6-(ethoxymethyl)-4-hydroxy-1,2-dihydropyridin-2-one (131);
3-[3-(2,4-difluorophenyl)pyrrolidine-1-carbonyl]-5-(2,6-dimethoxyphenyl)-6-(ethoxymethyl)-4-hydroxy-1,2-dihydropyridin-2-one (132);
3-[3-(2,6-difluorophenyl)pyrrolidine-1-carbonyl]-5-(2,6-dimethoxyphenyl)-6-(ethoxymethyl)-4-hydroxy-1,2-dihydropyridin-2-one (133);
3-[3-(2,6-difluorophenyl)pyrrolidine-1-carbonyl]-5-(2,6-dimethoxyphenyl)-6-(ethoxymethyl)-4-hydroxy-1,2-dihydropyridin-2-one (134);
6-butyl-3-[3-(5-chloro-3-fluoropyridin-2-yl)pyrrolidine-1-carbonyl]-5-(2,6-dimethoxyphenyl)-4-hydroxy-1,2-dihydropyridin-2-one (135);
3-[(3S)-3-(benzyloxy)pyrrolidine-1-carbonyl]-6-butyl-5-(2,6-dimethoxyphenyl)pyridine-2,4-diol (136);
3-[(3S)-3-(benzyloxy)pyrrolidine-1-carbonyl]-5-(2,6-dimethoxyphenyl)-6-(ethoxymethyl)pyridine-2,4-diol (137);
6-butyl-5-(3-ethylphenyl)-4-hydroxy-3-{5-[(2-methyl-1,3-thiazol-4-yl)methyl]-1,3,4-oxadiazol-2-yl}-1,2-dihydropyridin-2-one (138);
2-[3-(2-butyl-5-{4-[(2,3-difluorophenyl)methyl]piperazine-1-carbonyl}-4,6-dihydroxypyridin-3-yl)phenyl]acetonitrile (139);
6-butyl-3-[3-(3,5-difluoropyridin-2-yl)pyrrolidine-1-carbonyl]-5-[3-(propan-2-yl)phenyl]pyridine-2,4-diol (140);
6-butyl-3-[3-(3,5-difluoropyridin-2-yl)pyrrolidine-1-carbonyl]-5-[3-(propan-2-yl)phenyl]pyridine-2,4-diol (141);
6-butyl-3-[3-(3,5-difluoropyridin-2-yl)pyrrolidine-1-carbonyl]-5-(3-methoxyphenyl)pyridine-2,4-diol (142);
6-butyl-3-[3-(3,5-difluoropyridin-2-yl)pyrrolidine-1-carbonyl]-5-(3-methoxyphenyl)pyridine-2,4-diol (143);
6-butyl-3-[3-(3,5-difluoropyridin-2-yl)pyrrolidine-1-carbonyl]-5-[3-(hydroxymethyl)phenyl]pyridine-2,4-diol (144);
3-{2-butyl-5-[3-(3,5-difluoropyridin-2-yl)pyrrolidine-1-carbonyl]-4,6-dihydroxypyridin-3-yl}-N-(propan-2-yl)benzamide (145);
3-{2-butyl-5-[3-(3,5-difluoropyridin-2-yl)pyrrolidine-1-carbonyl]-4,6-dihydroxypyridin-3-yl}-N-(propan-2-yl)benzamide (146);
6-butyl-3-[3-(3,5-difluoropyridin-2-yl)pyrrolidine-1-carbonyl]-5-[3-(hydroxymethyl)phenyl]pyridine-2,4-diol (147);
6-butyl-3-[(3R)-3-phenylpyrrolidine-1-carbonyl]-5-[3-(propan-2-yl)phenyl]pyridine-2,4-diol (148);
5-(2,6-dimethoxyphenyl)-6-[(ethylamino)methyl]-3-[3-(3-fluorophenyl)pyrrolidine-1-carbonyl]pyridine-2,4-diol (149);
5-(2,6-dimethoxyphenyl)-6-[(ethylamino)methyl]-3-[3-(2-fluorophenyl)pyrrolidine-1-carbonyl]pyridine-2,4-diol (150);
5-(2,6-dimethoxyphenyl)-6-[(ethylamino)methyl]-3-[3-(2-fluorophenyl)pyrrolidine-1-carbonyl]pyridine-2,4-diol (151);
methyl (S)-(2-(6-butyl-5-(2,6-dimethoxyphenyl)-4-hydroxy-2-oxo-1,2-dihydropyridine-3-carboxamido)-3-cyclohexylpropanoyl)glycinate (152);
6-butyl-3-[4-(2,3-dichlorobenzoyl)piperazine-1-carbonyl]-5-(2,6-dimethoxyphenyl)pyridine-2,4-diol (153);
6-butyl-3-{4-[(2,3-difluorophenyl)methyl]piperazine-1-carbonyl}-5-(2,3-dimethoxyphenyl)pyridine-2,4-diol (154).

The invention may be embodied in other specific forms without departing from the spirit or essential attributes thereof. This invention also encompasses all combinations of alternative aspects of the invention noted herein. It is understood that any and all embodiments of the present invention may be taken in conjunction with any other embodiment to describe additional embodiments of the present invention. Furthermore, any elements (including individual variable definitions) of an embodiment are meant to be combined with any and all other elements from any of the embodiments to describe additional embodiments. The present invention also provides a pharmaceutical composition comprising a compound of formula I, or an enantiomer, diastereomer, or a pharmaceutically-acceptable salt, and a pharmaceutically acceptable carrier therefore.

In another embodiment, the compounds of the present invention have $EC_{50}$ values ≤10 μM, using the APJ hcAMP assay disclosed herein, preferably, $EC_{50}$ values ≤5 μM, more preferably, $EC_{50}$ values ≤1 μM, even more preferably, $EC_{50}$ values ≤0.5 μM, even more preferably, $EC_{50}$ values ≤0.1 μM, even more preferably, $EC_{50}$ values ≤0.01 μM.

In another aspect, the present invention provides compounds selected from any subset list of compounds exemplified in the present application.

In another aspect, the present invention provides compounds selected from the subset in which the APJ hcAMP $EC_{50}$ potency range is A.

In another aspect, the present invention provides compounds selected from the subset in which the APJ hcAMP $EC_{50}$ potency range is B.

In another aspect, the present invention provides compounds selected from the subset in which the APJ hcAMP $EC_{50}$ potency range is C.

II. Other Embodiments of the Invention

In another embodiment, the present invention provides a composition comprising at least one of the compounds of the present invention or a stereoisomer, a tautomer, a pharmaceutically acceptable salt, or a solvate thereof.

In another embodiment, the present invention provides a pharmaceutical composition comprising a pharmaceutically acceptable carrier and at least one of the compounds of the present invention or a stereoisomer, a tautomer, a pharmaceutically acceptable salt, or a solvate thereof.

In another embodiment, the present invention provides a pharmaceutical composition, comprising a pharmaceutically acceptable carrier and a therapeutically effective amount of at least one of the compounds of the present invention or a stereoisomer, a tautomer, a pharmaceutically acceptable salt, or a solvate thereof.

In another embodiment, the present invention provides a process for making a compound of the present invention or a stereoisomer, a tautomer, a pharmaceutically acceptable salt, or a solvate thereof.

In another embodiment, the present invention provides an intermediate for making a compound of the present invention or a stereoisomer, a tautomer, a pharmaceutically acceptable salt, or a solvate thereof.

The present invention provides a pharmaceutical composition further comprising additional therapeutic agent(s). In a preferred embodiment, the present invention provides pharmaceutical composition, wherein the additional therapeutic agent is, for example, angiotensin converting enzyme (ACE) inhibitor, β-adrenergic receptor blocker, angiotensin II receptor blocker, diuretic, aldosterone antagonist and digitalis compound.

In another embodiment, the present invention provides a method for the treatment and/or prophylaxis of multiple diseases or disorders associated with APJ or apelin activity, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

Examples of diseases or disorders associated with the activity of the APJ and apelin that can be prevented, modulated, or treated according to the present invention include, but are not limited to heart failure such as acute decompensated heart failure (ADHF), atrial fibrillation, coronary artery disease, peripheral vascular disease, atherosclerosis, diabetes, metabolic syndrome, hypertension, pulmonary hypertension, cerebrovascular disorders and the sequelae thereof, cardiovascular disorders, angina, ischemia, stroke, myocardial infarction, acute coronary syndrome, reperfusion injury, angioplastic restenosis, vascular complications of diabetes and obesity.

In another embodiment, the present invention provides a method for the treatment and/or prophylaxis of heart failure, coronary artery disease, peripheral vascular disease, atherosclerosis, diabetes, metabolic syndrome, hypertension, pulmonary hypertension, atrial fibrillation, angina, ischemia, stroke, myocardial infarction, acute coronary syndrome, reperfusion injury, angioplastic restenosis, vascular complications of diabetes, obesity, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a method for the treatment and/or prophylaxis of heart failure such as ADHF, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a method for the treatment and/or prophylaxis of diabetes and obesity, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a method for the treatment and/or prophylaxis of hypertension, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a method for the treatment and/or prophylaxis of pulmonary hypertension, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a method for the treatment and/or prophylaxis of acute coronary syndrome and cardiac ischemia, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a compound of the present invention for use in therapy.

In another embodiment, the present invention provides a compound of the present invention for use in therapy for the treatment and/or prophylaxis of multiple diseases or disorders associated with APJ and apelin.

In another embodiment, the present invention also provides the use of a compound of the present invention for the manufacture of a medicament for the treatment and/or prophylaxis of multiple diseases or disorders associated with APJ and apelin.

In another embodiment, the present invention provides a method for the treatment and/or prophylaxis of multiple diseases or disorders associated with APJ and apelin, comprising administering to a patient in need thereof a therapeutically effective amount of a first and second therapeutic agent, wherein the first therapeutic agent is a compound of the present invention. Preferably, the second therapeutic agent, for example selected inotropic agent such as β-adrenergic agonist (for example dobutamine).

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in the treatment and/or prophylaxis of multiple diseases or disorders associated with APJ and apelin.

Where desired, the compound of the present invention may be used in combination with one or more other types of cardiovascular agents and/or one or more other types of therapeutic agents which may be administered orally in the same dosage form, in a separate oral dosage form or by injection. The other type of cardiovascular agents that may be optionally employed in combination with the APJ agonist of the present invention may be one, two, three or more cardiovascular agents administered orally in the same dosage form, in a separate oral dosage form, or by injection to produce an additional pharmacological benefit.

The compounds of the present invention may be employed in combination with additional therapeutic agent (s) selected from one or more, preferably one to three, of the following therapeutic agents: anti-hypertensive agents, ACE inhibitors, mineralocorticoid receptor antagonists, angiotensin receptor blockers, calcium channel blockers, β-adrenergic receptor blockers, diuretics, vasorelaxation agents such as nitrates, anti-atherosclerotic agents, anti-dyslipidemic agents, anti-diabetic agents, anti-hyperglycemic agents, anti-hyperinsulinemic agents, anti-thrombotic agents, anti-retinopathic agents, anti-neuropathic agents, anti-nephropathic agents, anti-ischemic agents, calcium channel blockers, anti-obesity agents, anti-hyperlipidemic agents, anti-hypertriglyceridemic agents, anti-hypercholesterolemic agents, anti-restenotic agents, anti-pancreatic agents, lipid lowering agents, anorectic agents, memory enhancing agents, anti-dementia agents, cognition promoting agents, appetite suppressants, agents for treating heart failure, agents for treating peripheral arterial disease, agents for treating malignant tumors, and anti-inflammatory agents.

In another embodiment, additional therapeutic agent(s) used in combined pharmaceutical compositions or combined methods or combined uses, are selected from one or more, preferably one to three, of the following therapeutic agents in treating heart failure: ACE inhibitors, β-blockers, diuretics, mineralocorticoid receptor antagonists, renin inhibitors, calcium channel blockers, angiotensin II receptor antagonists, nitrates, digitalis compounds, inotropic agents.

The present invention may be embodied in other specific forms without parting from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans-(or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

As used herein, the term "alkyl" or "alkylene" is intended to include both branched and straight-chain saturated aliphatic hydrocarbon groups having the specified number of carbon atoms. For examples, "$C_1$ to $C_{12}$ alkyl" or "$C_{1-12}$ alkyl" (or alkylene), is intended to include $C_1$, $C_2$, $C_3$, $C_4$, $C_5$, $C_6$, $C_7$, $C_8$, $C_9$, $C_{10}$, $C_{11}$ and $C_{12}$ alkyl groups; "$C_4$ to $C_{18}$ alkyl" or "$C_{4-18}$ alkyl" (or alkylene), is intended to include $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, and $C_{18}$ alkyl groups. Additionally, for example, "$C_1$ to $C_6$ alkyl" or "$C_{1-6}$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "$C_0$ alkyl" or "$C_0$ alkylene" is used, it is intended to denote a direct bond.

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, and 4-methyl-3-pentenyl.

"Alkynyl" or "alkynylene" is intended to include hydrocarbon chains of either straight or branched configuration having one or more, preferably one to three, carbon-carbon triple bonds that may occur in any stable point along the chain. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

When the term "hydrocarbon chain" is used, it is intended to include "alkyl", "alkenyl" and "alkynyl", unless otherwise specified.

The term "alkoxy" or "alkyloxy" refers to an —O-alkyl group. For example, "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "cycloalkyl" refers to cyclized alkyl groups, including mono-, bi- or poly-cyclic ring systems. For example, "$C_3$ to $C_6$ cycloalkyl" or "$C_{3-6}$ cycloalkyl" is intended to include $C_3$, $C_4$, $C_5$, and $C_6$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl". The term "cycloalkenyl" refers to cyclized alkenyl groups. $C_{4-6}$ cycloalkenyl is intended to include $C_4$, $C_5$, and $C_6$ cycloalkenyl groups. Example cycloalkenyl groups include, but are not limited to, cyclobutenyl, cyclopentenyl, and cyclohexenyl.

As used herein, "carbocycle", "carbocyclyl", or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic hydrocarbon ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, indanyl, and tetrahydronaphthyl. When the term "carbocycle" is used, it is intended to include "aryl." A bridged ring occurs when one or more, preferably one to three, carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocycle" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable.

Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or bicyclic aromatic hydrocarbons, including, for example, phenyl, and naphthyl. Aryl moieties are well known and described, for example, in Lewis, R. J., ed., *Hawley's Condensed Chemical Dictionary*, 15th Edition, John Wiley & Sons, Inc., New York (2007). "$C_{6-10}$ aryl" refers to phenyl and naphthyl.

The term "benzyl", as used herein, refers to a methyl group on which one of the hydrogen atoms is replaced by a phenyl group.

As used herein, the term "heterocycle", "heterocyclyl", or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and S(O)$_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydrobenzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Examples of 5- to 6-membered heteroaryls include, but are not limited to, pyridinyl, furanyl, thienyl, pyrrolyl, pyrazolyl, pyrazinyl, imidazolyl, imidazolidinyl, tetrazolyl, isoxazolyl, oxazolyl, oxadiazolyl, oxazolidinyl, thiadiazinyl, thiadiazolyl, thiazolyl, triazinyl, and triazolyl.

Bridged rings are also included in the definition of heterocycle. A bridged ring occurs when one or more, preferably one to three, atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counter ion" is used to represent a negatively charged species such as chloride, bromide, hydroxide, acetate, and sulfate or a positively charged species such as sodium (Na+), potassium (K+), ammonium ($R_nNH_m+$ where n=0-4 and m=0-4) and the like.

When a dotted ring is used within a ring structure, this indicates that the ring structure may be saturated, partially saturated or unsaturated.

As used herein, the term "amine protecting group" means any group known in the art of organic synthesis for the protection of amine groups which is stable to an ester reducing agent, a disubstituted hydrazine, R4-M and R7-M, a nucleophile, a hydrazine reducing agent, an activator, a strong base, a hindered amine base and a cyclizing agent. Such amine protecting groups fitting these criteria include those listed in Wuts, P. G. M. et al., *Protecting Groups in Organic Synthesis*, 4th Edition, Wiley (2007) and *The Peptides: Analysis, Synthesis, Biology*, Vol. 3, Academic Press, New York (1981), the disclosure of which is hereby incorporated by reference. Examples of amine protecting groups include, but are not limited to, the following: (1) acyl types such as formyl, trifluoroacetyl, phthalyl, and p-toluenesulfonyl; (2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); (3) aliphatic carbamate types such as tert-butyloxycarbonyl (Boc), ethoxycarbonyl, diisopropylmethoxycarbonyl, and allyloxycarbonyl; (4) cyclic alkyl carbamate types such as cyclopentyloxycarbonyl and adamantyloxycarbonyl; (5) alkyl types such as triphenylmethyl and benzyl; (6) trialkylsilane such as trimethylsilane; (7) thiol containing types such as phenylthiocarbonyl and dithiasuccinoyl; and (8) alkyl types such as triphenylmethyl, methyl, and benzyl; and substituted alkyl types such as 2,2,2-trichloroethyl, 2-phenylethyl, and t-butyl; and trialkylsilane types such as trimethylsilane.

As referred to herein, the term "substituted" means that at least one hydrogen atom is replaced with a non-hydrogen group, provided that normal valencies are maintained and that the substitution results in a stable compound. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R, then said group may optionally be substituted with up to three R groups, and at each occurrence R is selected independently from the definition of R.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent.

Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Allen, Jr., L. V., ed., *Remington: The Science and Practice of Pharmacy*, 22nd Edition, Pharmaceutical Press, London, UK (2012), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology*, 112:309-396, Academic Press (1985);

b) Bundgaard, H., Chapter 5, "Design and Application of Prodrugs", Krosgaard-Larsen, P. et al., eds., *A Textbook of Drug Design and Development*, pp. 113-191, Harwood Academic Publishers (1991);

c) Bundgaard, H., *Adv. Drug Deliv. Rev.*, 8:1-38 (1992);

d) Bundgaard, H. et al., *J. Pharm. Sci.*, 77:285 (1988);

e) Kakeya, N. et al., *Chem. Pharm. Bull.*, 32:692 (1984); and f) Rautio, J., ed., *Prodrugs and Targeted Delivery (Methods and Principles in Medicinal Chemistry)*, Vol. 47, Wiley-VCH (2011).

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (2nd Edition, reproduced (2006)); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, 3rd Edition, Academic Press, San Diego, Calif. (2008).

The present invention is intended to include all isotopes of atoms occurring in the present compounds. Isotopes include those atoms having the same atomic number but different mass numbers. By way of general example and without limitation, isotopes of hydrogen include deuterium and tritium. Deuterium has one proton and one neutron in its nucleus and that has twice the mass of ordinary hydrogen. Deuterium can be represented by symbols such as "$^{2}H$" or "D". The term "deuterated" herein, by itself or used to modify a compound or group, refers to replacement of one or more hydrogen atom(s), which is attached to carbon(s), with a deuterium atom. Isotopes of carbon include $^{13}C$ and $^{14}C$.

Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or min, "h" for hour or h, "rt" for room temperature, "RT" for retention time, "atm" for atmosphere, "psi" for pounds per square inch, "conc." for concentrate, "aq" for "aqueous", "sat" or "sat'd" for saturated, "MW" for molecular weight, "mp" for melting point, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", "Z" and "ee" are stereochemical designations familiar to one skilled in the art.

| | |
|---|---|
| AcOH or HOAc | acetic acid |
| ACN | acetonitrile |
| Alk | alkyl |
| BBr$_3$ | boron tribromide |
| Bn | benzyl |
| Boc | tert-butyloxycarbonyl |
| BOP reagent | benzotriazol-1-yloxytris(dimethylamino)phosphonium hexafluorophosphate |
| Bu | butyl |
| i-Bu | isobutyl |
| t-Bu | tert-butyl |
| t-BuOH | tert-butanol |
| nBuLi | nButyllithium |
| Cbz | carbobenzyloxy |
| CDCl$_3$ | deutero-chloroform |
| CD$_3$OD | deutero-methanol |
| CH$_2$Cl$_2$ | dichloromethane |
| CH$_3$CN | acetonitrile |
| CHCl$_3$ | chloroform |
| CO$_2$ | carbon dioxide |
| DCM | dichloromethane |
| DIEA, DIPEA or Hunig's base | diisopropylethylamine |
| DMF | dimethyl formamide |
| DMSO | dimethyl sulfoxide |
| EDC | 1-ethyl-3-(3-dimethylaminopropyl)carbodiimide |
| Et | ethyl |
| Et$_3$N or TEA | triethylamine |
| Et$_2$O | diethyl ether |
| EtOAc | ethyl acetate |
| EtOH | ethanol |
| HCl | hydrochloric acid |
| HOAT | 1-hydroxy-7-azabenzotriazole |
| HPLC | high-performance liquid chromatography |
| K$_2$CO$_3$ | potassium carbonate |
| K$_2$HPO$_4$ | potassium hydrogenphosphate |
| LCMS | liquid chromatography mass spectrometry |
| LiHMDS | lithium bis(trimethylsilyl)amide |
| LG | leaving group |
| Me | methyl |
| MeOH | methanol |
| MgSO$_4$ | magnesium sulfate |
| MsOH or MSA | methylsulfonic acid |
| NBS | N-bromosuccinimide |
| NaCl | sodium chloride |
| Na$_2$CO$_3$ | sodium carbonate |
| NaHCO$_3$ | sodium bicarbonate |
| NaOH | sodium hydroxide |
| Na$_2$SO$_4$ | sodium sulfate |
| NH$_3$ | ammonia |
| NH$_4$Cl | ammonium chloride |
| NH$_4$OAc | ammonium acetate |
| PdCl$_2$(dppf) | [1,1'-Bis(diphenylphosphino)ferrocene]dichloropalladium (II) |
| Pd(OAc)$_2$ | palladium(II) acetate |
| Pd(PPh$_3$)$_4$ | tetrakis(triphenylphosphine)palladium(0) |
| PG | protecting group |
| Ph | phenyl |
| Pr | propyl |
| i-Pr | isopropyl |
| i-PrOH or IPA | isopropanol |
| Rt | retention time |
| SiO$_2$ | silica oxide |
| SFC | supercritical fluid chromatography |
| TEA | triethylamine |
| TFA | trifluoroacetic acid |
| THF | tetrahydrofuran |
| TiCl$_4$ | titanium tetrachloride |
| T3P ® | 1-propanephosphonic acid cyclic anhydride |

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

The novel compounds of this invention may be prepared using the reactions and techniques described in this section. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. Restrictions to the substituents that are compatible with the reaction conditions will be readily apparent to one skilled in the art and alternate methods must then be used.

Synthesis

The compounds of Formula (I) may be prepared by the exemplary processes described in the following schemes and working examples, as well as relevant published literature procedures that are used by one skilled in the art. Exemplary reagents and procedures for these reactions appear hereinafter and in the working examples. Protection and de-protection in the processes below may be carried out by procedures generally known in the art (see, for example, Wuts, P. G. M. et al., *Protecting Groups in Organic Synthesis*, 4th Edition, Wiley (2007)). General methods of organic synthesis and functional group transformations are found in: Trost, B. M. et al., eds., *Comprehensive Organic Synthesis: Selectivity, Strategy & Efficiency in Modern Organic Chemistry*, Pergamon Press, New York, N.Y. (1991); Smith, M. B. et al., *March's Advanced Organic Chemistry: Reactions, Mechanisms, and Structure*. 6th Edition, Wiley & Sons, New York, N.Y. (2007); Katritzky, A. R. et al, eds., *Comprehensive Organic Functional Groups Transformations II*, 2nd Edition, Elsevier Science Inc., Tarrytown, N.Y. (2004); Larock, R. C., *Comprehensive Organic Transformations*, VCH Publishers, Inc., New York, N.Y. (1999), and references therein.

Compounds of Formula (I) can be prepared as described in Scheme 1.

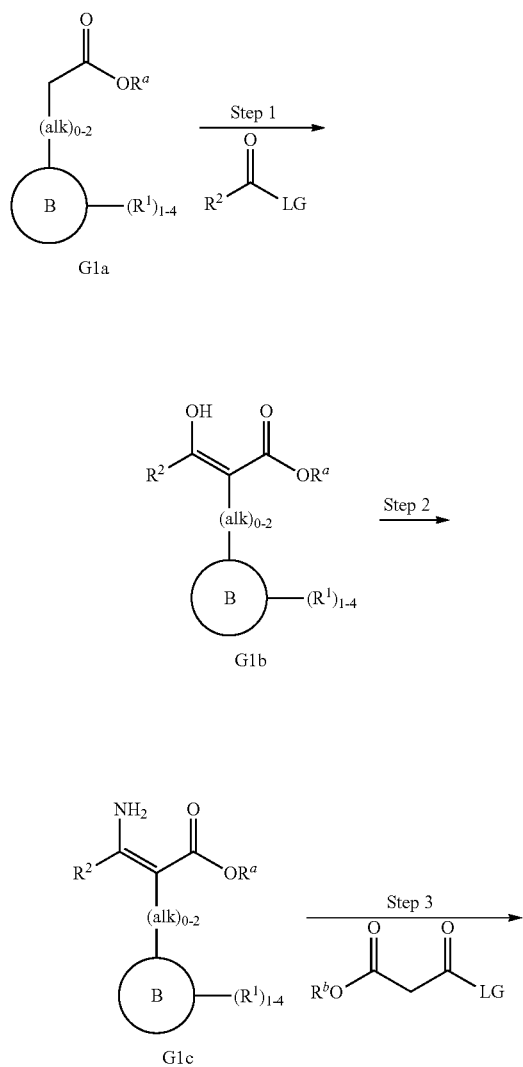

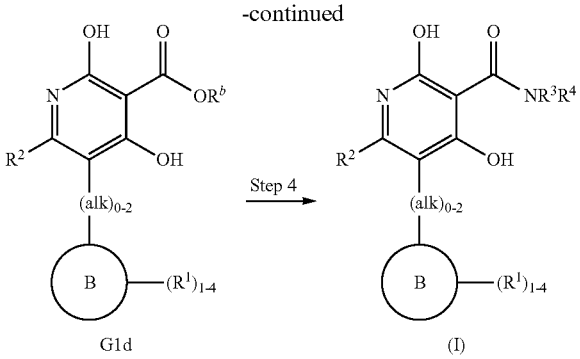

Step 1 describes the preparation of compounds of Formula G1b by condensing an ester of Formula G1a with an acid $R^2CO$-LG, where LG represents a leaving group (such as halogens and the like). Preferred solvents are ethers (such as tetrahydrofuran, dioxane and the like) and polar aprotic solvents (such as N,N-dimethylformamide). Preferred bases are metal amides (such as lithium bis(trimethylsilyl)amide and lithium diisopropylamide and the like) and metal hydrides (such as sodium hydride and the like).

Step 2 describes the preparation of compounds of Formula G1c by condensation of compounds of Formula G1b with ammonia. Preferred sources of ammonia are ammonia (gas) or salts thereof (such as ammonium acetate, ammonium formate and the like). Preferred solvents are alcohols (such as methanol, ethanol and the like).

Step 3 describes the preparation of pyridine compounds of Formula G1d from compounds of formula G1c by condensation with malonate derivatives $R^bOCOCH_2CO$-LG, where LG represents a leaving group (such as halogens or alkoxides such as ethoxide and the like) in the presence of base. The process can be performed in a single step, or stepwise. Preferred solvents for the first step of the two step process are halogenated solvents (such as DCM and the like), ethers (such as tetrahydrofuran, dioxane and the like) and water. Preferred bases for the first step of the two step process are tertiary amines (such as TEA, DIEA and the like) and alkaline metal-carbonates, -bicarbonates, -hydroxides (such as sodium carbonate, sodium bicarbonate, sodium hydroxide and the like). Preferred solvents for the second step and for the single step process are alcohols (such as MeOH and EtOH and the like). Preferred bases for the second step and for the single step process are alkaline metal alkoxides (such as sodium ethoxide and the like).

Step 4 describes the preparation of compounds of Formula (I) from the corresponding esters of Formula G1d with amines of $NHR^3R^4$. A preferred reaction condition is heating at elevated temperature (such as 100° C. to 160° C.) with the aid of a microwave reactor and preferred solvents are ethanol and DMF. Alternatively, compounds of Formula (I) can be prepared from the corresponding esters of Formula G1d and amines of $NHR^3R^4$ using catalysts. Preferred catalysts are 1-hydroxy-7-azabenzotriazole (HOAT) and zirconium (IV) tert butoxide ($Zr(OtBu)_4$) and a preferred solvent is toluene.

Alternatively compounds of Formula G1d in Scheme 1 can be prepared as described in Scheme 2.

Scheme 2

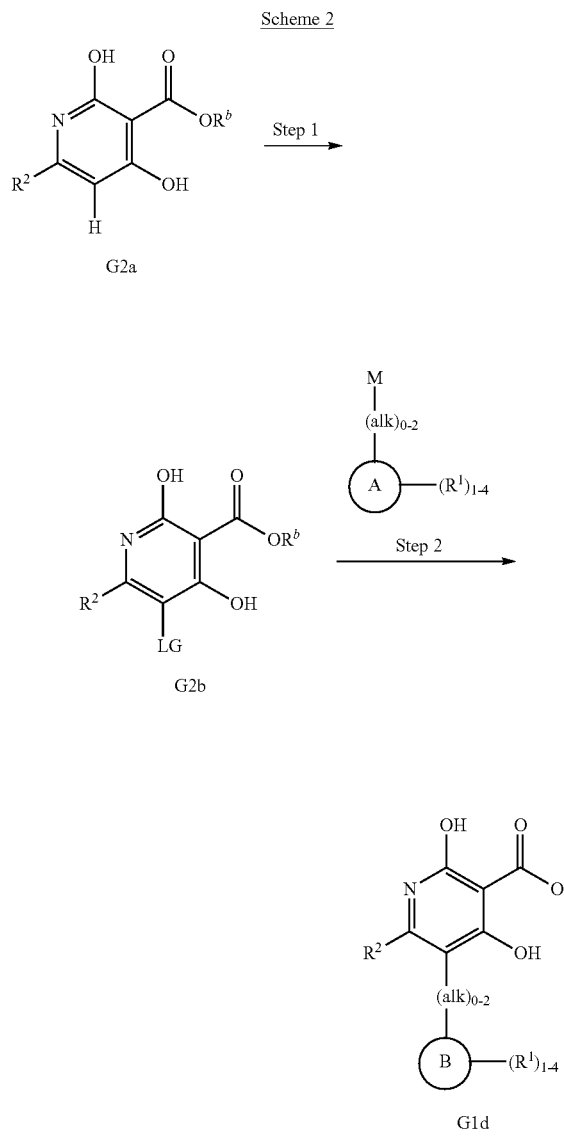

Scheme 3

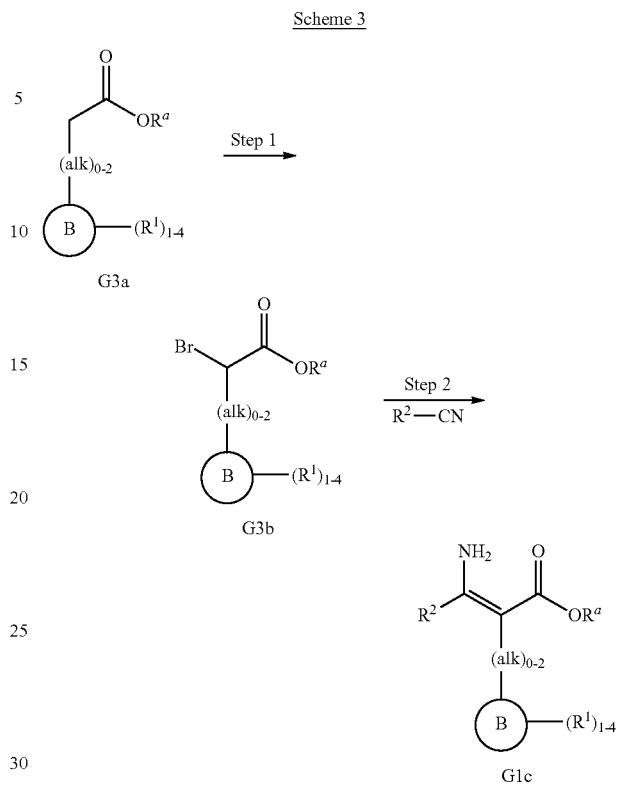

Step 1 describes the preparation of compounds of Formula G2b from a compound of Formula G2a (prepared as described in W2007/197478), where LG represents a leaving group (such as halogens, preferably bromine). Preferred reagents for incorporating the leaving group are sources of bromine (such as elemental bromine and NBS and the like). Preferred solvents are halogenated solvents (such as DCM and the like).

Step 2 describes the preparation of compounds of Formula G1d by coupling an organometallic reagent M-(alk)$_{0-2}$-Ⓑ-(R$^1$)$_{1-4}$ with a compound of Formula G2b. The organometallic reagent M-(alk)$_{0-2}$-Ⓑ-(R$^1$)$_{1-4}$ is preferably generated by reaction of a alkylboronic acid or ester B(OR)$_2$-(alk)$_{0-2}$-Ⓑ-(R$^1$)$_{1-4}$, R=H or alkyl, with a transition metal catalyst (such as Pd(PPh$_3$)$_4$ and Pd(OAc)$_2$ and the like). Preferred solvents are ethers (such as tetrahydrofuran, dioxane and the like), aprotic solvents (such as toluene and the like) and water. Preferred bases are alkaline metal-carbonates, -bicarbonates (such as sodium carbonate, sodium bicarbonate and the like).

Alternatively compounds of Formula G1c in Scheme 1 can be prepared as described in Scheme 3.

Step 1 describes the preparation of compounds of Formula G3b by bromination of an ester of Formula G3a. Preferred sources of bromine are elemental bromine and NBS and the like. Preferred solvents are ethers (such as tetrahydrofuran, dioxane and the like). Preferred bases are metal amides (such as lithium bis(trimethylsilyl)amide and lithium diisopropylamide and the like) and metal hydrides (such as sodium hydride and the like).

Step 2 describes the preparation of compounds of Formula G1c from compounds of Formula G3b via condensation with nitrile R$^2$—CN in the presence of a transition metal. The preferred transition metal is zinc, and a co-catalyst (zinc oxide, alkyl sulfonic acids and the like) can be used. Inert solvents such as ethers (such as tetrahydrofuran, dioxane and the like) and aprotic solvents (such as toluene and the like) can be used, preferably the reaction is run under neat conditions.

IV. Biology

APJ receptor was discovered in 1993 as an orphan G protein-coupled receptor (GPCR) and was subsequently found to recognize apelin peptide as its endogenous ligand. It belongs to class A of GPCRs and has a classical 7-transmembrane domain structure, exhibiting greatest sequence homology to angiotensin AT1 receptor (for review see Pitkin, S. L. et al., *Pharmacol. Rev.*, 62(3):331-342 (2010)). APJ is expressed in wide variety of peripheral tissues and the CNS, and has relatively high expression in placenta, myocardium, vascular endothelial cells, smooth muscle cells as well as cardiac myocytes (Kleinz, J. M. et al., *Pharmacol. Ther.*, 107(2): 198-211(2005)). Apelin peptide was originally identified in bovine stomach extract and remains to date the only known endogenous ligand and agonist of APJ receptor (Tatemoto, K. et al., *Biochem. Biophys. Res. Com-*

*mun.*, 255:471-476 (1998)). Tissue expression of apelin gene mirrors closely the APJ expression pattern and has been postulated to act in an autocrine or paracrine manner, often exemplified by reference to "apelin-APJ system". Apelin gene encodes 77 amino acid precursor peptide that is cleaved to form mature secreted peptide undergoing further proteolytic cleavage forming shorter C-terminal fragments. Apelin-36, -17 and -13 represent the major active forms with the pyroglutamated form of apelin-13 being the most stable and the most abundant form present in the cardiac tissue (Maguire, J. J. et al., *Hypertension,* 54(3):598-604 (2009)). Apelin has very short half life in circulation, estimated to be less than 5 minutes (Japp, A. G. et al., *Circulation,* 121(16): 1818-1827 (2010)).

Activation of APJ receptor is known to inhibit forskolin-stimulated cyclic AMP (cAMP) levels in pertussis toxin-sensitive manner, indicating coupling to the Gi proteins. The binding affinity of apelin and the $EC_{50}$ values in the cAMP assay are reported to be in the sub-nanomolar range (for review see Pitkin, S. L. et al., *Pharmacol. Rev.,* 62(3):331-342(2010)). In addition to cAMP inhibition, APJ receptor activation also leads to 3-arrestin recruitment, receptor internalization and activation of extracellular-regulated kinases (ERKs) (for review see Kleinz, J. M. et al., *Pharmacol. Ther.,* 107(2):198-211 (2005)). Which of these signaling mechanisms contribute to modulation of downstream physiological effects of apelin is not clear at present. APJ receptor has been shown to interact with the AT1 receptor. While apelin does not bind AT1 and angiotensin II does not bind APJ, it has been postulated that certain physiological actions of apelin are mediated, at least in part, via functional antagonism of the angiotensin II and AT1 receptor pathway (Chun, A. J. et al., *J. Clin. Invest.,* 118(10):3343-3354 (2008)).

It is also desirable and preferable to find compounds with advantageous and improved characteristics compared with known HF treatment agents, in one or more of the following categories that are given as examples, and are not intended to be limiting: (a) pharmacokinetic properties, including oral bioavailability, half life, and clearance; (b) pharmaceutical properties; (c) dosage requirements; (d) factors that decrease blood drug concentration peak-to-trough characteristics; (e) factors that increase the concentration of active drug at the receptor; (f) factors that decrease the liability for clinical drug-drug interactions; (g) factors that decrease the potential for adverse side-effects, including selectivity versus other biological targets; and (h) improved therapeutic index.

As used herein, the term "patient" encompasses all mammalian species.

As used herein, the term "subject" refers to any human or non-human organism that could potentially benefit from treatment with an APJ agonist. Exemplary subjects include human beings of any age with risk factors for development of heart failure and the sequelae thereof, angina, ischemia, cardiac ischemia, myocardial infarction, reperfusion injury, angioplastic restenosis, hypertension, vascular complications of diabetes, obesity or endotoxemia, stroke, as well as atherosclerosis, coronary artery disease, acute coronary syndrome, and/or dyslipidemias.

As used herein, "treating" or "treatment" cover a treatment of a disease-state in a mammal, particularly in a human, and include: (a) inhibiting a disease-state, i.e., arresting it development; and/or (b) relieving a disease-state, i.e., causing regression of a disease state.

As used herein, "prophylaxis" is the protective treatment of a disease state to reduce and/or minimize the risk and/or reduction in the risk of recurrence of a disease state by administering to a patient a therapeutically effective amount of at least one of the compounds of the present invention or a or a stereoisomer, a tautomer, a pharmaceutically acceptable salt, or a solvate thereof. Patients may be selected for prophylaxis therapy based on factors that are known to increase risk of suffering a clinical disease state compared to the general population. For prophylaxis treatment, conditions of the clinical disease state may or may not be presented yet. "Prophylaxis" treatment can be divided into (a) primary prophylaxis and (b) secondary prophylaxis. Primary prophylaxis is defined as treatment to reduce or minimize the risk of a disease state in a patient that has not yet presented with a clinical disease state, whereas secondary prophylaxis is defined as minimizing or reducing the risk of a recurrence or second occurrence of the same or similar clinical disease state.

As used herein, "prevention" cover the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population.

"Therapeutically effective amount" is intended to include an amount of a compound of the present invention that is effective when administered alone or in combination to modulate APJ and/or to prevent or treat the disorders listed herein. When applied to a combination, the term refers to combined amounts of the active ingredients that result in the preventive or therapeutic effect, whether administered in combination, serially, or simultaneously.

Assay Methods
Intracellular cAMP Accumulation Assay

HEK293 cells stably expressing human APJ receptor were used to assess the activity of compounds. Cultured cells were detached and resuspended in the cAMP Homogeneous Time-Resolved Fluorescence (HTRF) assay buffer (Cisbio cat; #62AM4PEJ). The assay was performed in 384-well assay plates (Perkin-Elmer; cat #6008289) according to assay protocol provided by the manufacturer. Serial dilutions of a compound together with assay buffer containing 0.2 nM IBMX and 2 µM forskolin were added to each well containing 5,000 cells and incubated for 30 minutes at room temperature. Subsequently, cAMP D2 reagent was added in the lysis buffer followed by the EuK antibody (Cisbio; cat #62AM4PEJ) and incubated for 60 min. The fluorescence emission ratio was measured using fluorometer. The intracellular cAMP concentrations (compound-stimulated inhibition of forskolin-mediated cAMP production) were calculated by extrapolation from a standard curve using known cAMP concentrations. The $EC_{50}$ values were obtained by fitting the data to a sigmoidal concentration-response curve with variable slope. The maximal achievable inhibition of forskolin-induced cAMP levels ($Y_{max}$) for each compound was expressed as relative percentage of inhibition attained using pyroglutamated apelin-13 ((Pyr1)apelin-13) peptide, which was set to 100%.

The examples disclosed below were tested in the APJ in vitro assays described above and were found having human APJ cyclic AMP (hcAMP) activity. The $EC_{50}$ value of each compound is presented at the end of the example description.

The compounds of the present invention possess activity as agonists of APJ receptor, and, therefore, may be used in the treatment of diseases associated with APJ activity. Accordingly, the compounds of the present invention can be administered to mammals, preferably humans, for the treatment of a variety of conditions and disorders, including, but not limited to, treating, preventing, or slowing the progression of heart failure, coronary artery disease, peripheral vascular disease, atherosclerosis, diabetes, metabolic syndrome and the sequelae of thereof, hypertension, pulmonary hypertension, cerebrovascular disorders, atrial fibrillation, angina, ischemia, stroke, myocardial infarction, acute coronary syndrome, reperfusion injury, angioplastic restenosis, vascular complications of diabetes and obesity.

The biological activity of the exemplified compounds of this invention determined by the assay described above is shown at the end of each example. The APJ cAMP $EC_{50}$ potency ranges are as follows: A=0.01-10 nM; B=10.01-100 nM; C=100.01-300 nM.

V. Pharmaceutical Compositions, Formulations and Combinations

The compounds of this invention can be administered for any of the uses described herein by any suitable means, for example, orally, such as tablets, capsules (each of which includes sustained release or timed release formulations), pills, powders, granules, elixirs, tinctures, suspensions (including nanosuspensions, microsuspensions, spray-dried dispersions), syrups, and emulsions; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms.

Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Allen, Jr., L. V. et al., *Remington: The Science and Practice of Pharmacy* (2 Volumes), 22nd Edition, Pharmaceutical Press (2012), The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.001 to about 5000 mg per day, preferably between about 0.01 to about 1000 mg per day, and most preferably between about 0.1 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more other therapeutic agent(s), e.g., agents used in treatment of heart failure or other pharmaceutically active material.

The compounds of the present invention may be employed in combination with other APJ agonists or one or more other suitable therapeutic agents useful in the treatment of the aforementioned disorders including: agents for treating heart failure, anti-hypertensive agents, anti-atherosclerotic agents, anti-dyslipidemic agents, anti-diabetic agents, anti-hyperglycemic agents, anti-hyperinsulinemic agents, anti-thrombotic agents, anti-retinopathic agents, anti-neuropathic agents, anti-nephropathic agents, anti-ischemic agents, anti-obesity agents, anti-hyperlipidemic agents, anti-hypertriglyceridemic agents, anti-hypercholesterolemic agents, anti-restenotic agents, anti-pancreatic agents, lipid lowering agents, anorectic agents, memory enhancing agents, anti-dementia agents, cognition promoting agents, appetite suppressants, and agents for treating peripheral arterial disease.

The compounds of the present invention may be employed in combination with additional therapeutic agent(s) selected from one or more, preferably one to three, of the following therapeutic agents in treating heart failure and coronary artery disease: ACE inhibitors, β-blockers, diuretics, mineralocorticoid receptor antagonists, renin inhibitors, calcium channel blockers, angiotensin II receptor antagonists, nitrates, digitalis compounds, inotropic agents and β-receptor agonists, anti-hyperlipidemic agents, plasma HDL-raising agents, anti-hypercholesterolemic agents, cholesterol biosynthesis inhibitors (such as HMG CoA reductase inhibitors), LXR agonist, probucol, raloxifene, nicotinic acid, niacinamide, cholesterol absorption inhibitors, bile acid sequestrants (such as anion exchange resins, or quaternary amines (e.g., cholestyramine or colestipol), low density lipoprotein receptor inducers, clofibrate, fenofibrate, benzofibrate, cipofibrate, gemfibrizol, vitamin $B_6$, vitamin $B_{12}$, anti-oxidant vitamins, anti-diabetes agents, platelet aggregation inhibitors, fibrinogen receptor antagonists, aspirin and fibric acid derivatives.

The compounds of the invention may be used in combination with one or more, preferably one to three, of the following anti-diabetic agents depending on the desired target therapy. Studies indicate that diabetes and hyperlipidemia modulation can be further improved by the addition of a second agent to the therapeutic regimen. Examples of anti-diabetic agents include, but are not limited to, sulfonylureas (such as chlorpropamide, tolbutamide, acetohexamide, tolazamide, glyburide, gliclazide, glynase, glimepiride, and glipizide), biguanides (such as metformin), thiazolidinediones (such as ciglitazone, pioglitazone, troglitazone, and rosiglitazone), and related insulin sensitizers, such as selective and non-selective activators of PPARα, PPARPβ and PPARγ; dehydroepiandrosterone (also referred to as DHEA or its conjugated sulphate ester, DHEA-$SO_4$); anti-glucocorticoids; TNFα inhibitors; dipeptidyl peptidase IV (DPP4) inhibitor (such as sitagliptin, saxagliptin), GLP-1 agonists or analogs (such as exenatide), α-glucosidase inhibitors (such as acarbose, miglitol, and voglibose), pramlintide (a synthetic analog of the human hormone amylin), other insulin secretagogues (such as repaglinide, gliquidone, and nateglinide), insulin, as well as the therapeutic agents discussed above for treating heart failure and atherosclerosis.

The compounds of the invention may be used in combination with one or more, preferably one to three, of the following anti-obesity agents selected from phenylpropanolamine, phentermine, diethylpropion, mazindol, fenfluramine, dexfenfluramine, phentiramine, $β_3$-adrenergic receptor agonist agents; sibutramine, gastrointestinal lipase inhibitors (such as orlistat), and leptins. Other agents used in treating obesity or obesity-related disorders include neuropeptide Y, enterostatin, cholecytokinin, bombesin, amylin, histamine $H_3$ receptors, dopamine $D_2$ receptor modulators, melanocyte stimulating hormone, corticotrophin releasing factor, galanin and gamma amino butyric acid (GABA).

The above other therapeutic agents, when employed in combination with the compounds of the present invention may be used, for example, in those amounts indicated in the *Physicians' Desk Reference*, as in the patents set out above, or as otherwise determined by one of ordinary skill in the art.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients but also to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The compounds of the present invention can be administered alone or in combination with one or more additional therapeutic agents. By "administered in combination" or "combination therapy" it is meant that the compound of the present invention and one or more additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

The compounds of the present invention are also useful as standard or reference compounds, for example as a quality standard or control, in tests or assays involving the APJ receptor and apelin activity. Such compounds may be provided in a commercial kit, for example, for use in pharmaceutical research involving APJ and apelin or anti-heart failure activity. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving APJ and apelin.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises a first therapeutic agent, comprising a compound of the present invention or a pharmaceutically acceptable salt form thereof; and, (c) a package insert stating that the pharmaceutical composition can be used for the treatment and/or prophylaxis of multiple diseases or disorders associated with APJ and apelin (as defined previously). In another embodiment, the package insert states that the pharmaceutical composition can be used in combination (as defined previously) with a second therapeutic agent for the treatment and/or prophylaxis of multiple diseases or disorders associated with APJ and apelin. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Other features of the invention will become apparent in the course of the following descriptions of exemplary embodiments that are given for illustration of the invention and are not intended to be limiting thereof.

VI. Examples

The following Examples are offered as illustrative, as a partial scope and particular embodiments of the invention and are not meant to be limiting of the scope of the invention. Abbreviations and chemical symbols have their usual and customary meanings unless otherwise indicated. Unless otherwise indicated, the compounds described herein have been prepared, isolated and characterized using the schemes and other methods disclosed herein or may be prepared using the same.

As a person of ordinary skill in the art would be able to understand that a pyridone in a molecule may tautomerize to its keto and enol forms as shown in the following equation, wherein $R^1$, $R^2$, $R^3$ and $R^4$ are as defined above, this disclosure is intended to cover all possible tautomers even when a structure depicts only one of them.

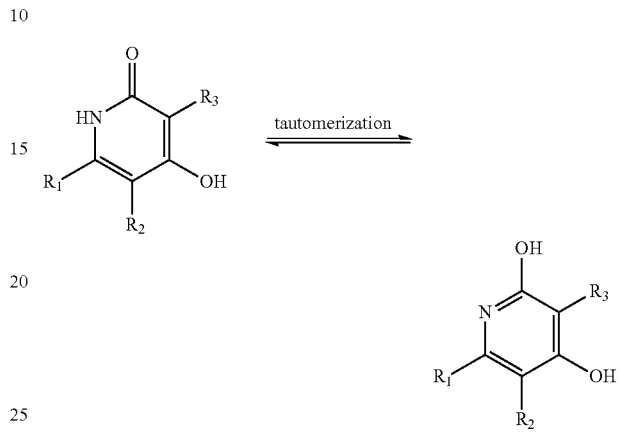

Description of Analytical LCMS Methods:

Method A: Column: Waters Acquity UPLC BEH C18, 2.1×50 mm, 1.7 μm particles; Mobile Phase A: 5:95 ACN:water with 10 mM NH4OAc; Mobile Phase B: 95:5 ACN:water with 10 mM NH4OAc; Temperature: 50° C.; Gradient: 0-100% B over 3 minutes, then a 0.75 minute hold at 100% B; Flow: 1.11 mL/min; Detection: UV at 220 nm.

Method B: Column: Waters Acquity UPLC BEH C18, 2.1×50 mm, 1.7 μm particles; Mobile Phase A: 5:95 ACN:water with 0.1% TFA; Mobile Phase B: 95:5 ACN:water with 0.1% TFA; Temperature: 50° C.; Gradient: 0-100% B over 3 minutes, then a 0.75 minute hold at 100% B; Flow: 1.11 mL/min; Detection: UV at 220 nm.

Method C: Column: PHENOMENEX® Luna 3 Lm C18 (2.0×30 mm); Mobile Phase A: 10:90 MeOH:water with 0.1% TFA; Mobile Phase B: 90:10 MeOH:water with 0.1% TFA; Gradient: 0-100% B over 2 minutes, then a 1 minute hold at 100% B; Flow: 1 mL/min; Detection: UV at 220 nm.

Method D: Waters Acquity UPLC BEH C18, 2.1×50 mm, 1.7 μm particles; Mobile Phase A: water with 0.1% TFA; Mobile Phase B: ACN with 0.1% TFA; Gradient: 2-98% B over 1 minute, then a 0.5 minute hold at 98% B; Flow: 0.8 mL/min; Detection: UV at 220 nm.

Method E: Column: Phenomenex Luna 3u C18(2) 2.0×30 mm; Mobile Phase A: 10:90 MeOH:water with 10 mM NH4OAc; Mobile Phase B: 90:10 MeOH:water with 10 mM NH4OAc; Gradient: 0-100% B over 2 minutes; Flow: 1.11 mL/min; Detection: UV at 220 nm.

Example 1

6-butyl-5-(2,6-dimethoxyphenyl)-3-[4-(4-methoxybenzoyl)piperazine-1-carbonyl]pyridine-2,4-diol

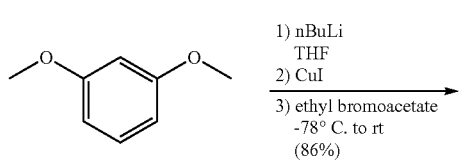

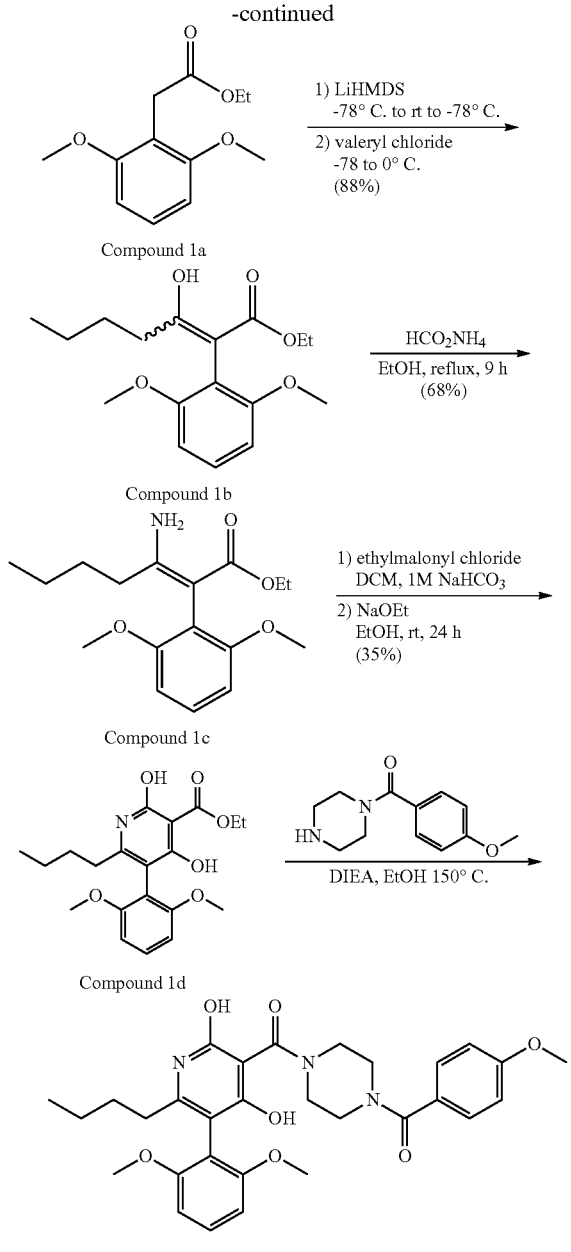

Compound 1a. Ethyl 2-(2,6-dimethoxyphenyl)acetate

To a solution of 1,3-dimethoxybenzene (3.3 mL, 25 mmol) in THF (40 mL) was added dropwise 2.5M nBuLi in hexanes (10 mL, 25 mmol) over a 10 min period then the mixture stirred for 2 h. Crushed copper(I) iodide (2.38 g, 12.5 mmol) was added slowly then the reaction mixture stirred for 1 h, turning homogeneous. The mixture was cooled to −78° C. then ethyl bromoacetate (2.8 mL, 25 mmol) was added dropwise over 20 min. The cold bath was removed and the mixture allowed to warm to room temperature. The mixture was quenched by the addition of water then Et$_2$O added and the mixture filtered through celite. The filtrate was diluted with 1.5N K$_2$HPO$_4$ and extracted with Et$_2$O (2×). The combined organic extracts were washed with brine, dried (MgSO$_4$) filtered and concentrated under reduced pressure. The residue was purified by silica gel chromatography eluting with 0 to 15% EtOAc/hexanes to give Compound 1a (4.8 g, 86% yield) as a light brown oil which solidified upon standing. LCMS (Method E) Rt=1.90. MS m/z=225.1 (M+H). $^1$H NMR (500 MHz, CDCl$_3$) δ 7.23 (t, J=8.4 Hz, 1H), 6.58 (d, J=8.3 Hz, 2H), 4.17 (q, J=7.2 Hz, 2H), 3.83 (s, 6H), 3.71 (s, 2H), 1.27 (t, J=7.2 Hz, 3H).

Compound 1b. Ethyl 2-(2,6-dimethoxyphenyl)-3-hydroxyhept-2-enoate

To a solution of Compound 1a (1.50 g, 6.7 mmol) in THF (14 mL) at −78° C. was added dropwise 1.0M LHMDS in THF (16.7 mL, 16.7 mmol) and the mixture was stirred for 10 min. The cold bath was removed and the reaction mixture stirred at room temperature for 1 h. The mixture was cooled to −78° C. then valeryl chloride (1.34 mL, 11.0 mmol) was added dropwise and the mixture allowed to warm to 0° C. and stirred for 15 min. The mixture was quenched by the addition of saturated NH$_4$Cl and extracted with EtOAc (3×). The combined extracts were washed with brine, dried (Na$_2$SO$_4$) filtered and concentrated under reduced pressure. The residue was purified by silica gel chromatography eluting with 0 to 30% EtOAc/hexanes to give an isomeric mixture of Compound 1b (1.80 g, 88% yield) as a clear colorless oil. LCMS (Method C) Rt=2.21. MS m/z=309.1 (M+H). $^1$H NMR of major isomer (400 MHz, CDCl$_3$) δ 13.22 (s, 1H), 7.26-7.22 (m, 1H), 6.56 (d, J=8.6 Hz, 2H), 4.14 (q, J=7.0 Hz, 2H), 3.75 (s, 5H), 2.05-1.96 (m, 2H), 1.51-1.42 (m, 2H), 1.22-1.17 (m, 2H), 1.14 (t, J=7.2 Hz, 3H), 0.77 (t, J=7.3 Hz, 3H).

Compound 1c. Ethyl 3-amino-2-(2,6-dimethoxyphenyl)hept-2-enoate

To a mixture of Compound 1b (1.8 g, 5.9 mmol) and ammonium formate (1. g, 29 mmol) in absolute ethanol (35 mL) was added molecular sieves then the mixture heated at reflux for 10 h. The mixture was allowed to cool to room temperature then filtered and concentrated under reduced pressure. The residue was dissolved in water and extracted with EtOAc (3×). The extracts were dried (Na$_2$SO$_4$) filtered and concentrated under reduced pressure. The residue was purified by silica gel chromatography eluting with 0 to 35% EtOAc/hexanes to give Compound 1c (1.2 g, 68% yield) as a clear colorless oil. LCMS (Method C) Rt=1.84 min. MS m/z=308.1 (M+H). $^1$H NMR (400 MHz, CDCl$_3$) δ 7.21 (t, J=8.4 Hz, 1H), 6.55 (d, J=8.4 Hz, 2H), 4.05 (q, J=7.0 Hz, 2H), 3.75 (s, 6H), 1.98-1.88 (m, 2H), 1.43-1.31 (m, 2H), 1.18 (dt, J=15.0, 7.5 Hz, 2H), 1.09 (t, J=7.0 Hz, 3H), 0.73 (t, J=7.4 Hz, 3H).

Compound 1d. Ethyl 6-butyl-5-(2,6-dimethoxyphenyl)-2,4-dihydroxynicotinate

To a solution of Compound 1c (1.20 g, 4.0 mmol) in a mixture of DCM (20 mL) and 1N NaHCO$_3$ (24 mL, 24 mmol) was added dropwise a solution of ethyl malonyl chloride (1.5 mL, 12 mmol) in DCM (5 mL) and the mixture stirred for 10 min. The mixture was diluted with DCM, the layers separated, and the aqueous layer extracted with DCM (2×). The combined organic extracts were washed with saturated NH$_4$Cl and brine, dried (Na$_2$SO$_4$), filtered and concentrated under reduced pressure. The residue was dissolved in absolute EtOH (20 mL) then 2.5M sodium ethoxide in ethanol (6.4 mL, 16 mmol) added and the mixture stirred for 24 h, generating a precipitate. The mixture was evaporated to dryness under reduced pressure then diluted with saturated $NH_4Cl$ and the aqueous portion extracted with DCM (3×). The combined extracts were washed with brine, dried ($Na_2SO_4$), decanted and concentrated under reduced pressure onto celite. The residue was purified by silica gel chromatography eluting with 5 to 75% EtOAc/DCM to give Compound 1d (0.52 g, 35% yield) as a white solid. LCMS (Method C) Rt=1.95 min. MS m/z=376.1 (M+H). $^1$H NMR (400 MHz, DMSO-$d_6$) δ 7.33 (t, J=8.4 Hz, 1H), 6.70 (d, J=8.4 Hz, 2H), 4.30 (q, J=6.8 Hz, 2H), 3.68 (s, 6H), 2.09 (t, J=7.2 Hz, 2H), 1.37-1.23 (m, 5H), 1.12-0.99 (m, 2H), 0.65 (t, J=7.4 Hz, 3H).

Example 1. 6-butyl-5-(2,6-dimethoxyphenyl)-3-[4-(4-methoxybenzoyl)piperazine-1-carbonyl]pyridine-2,4-diol To a suspension of Compound 1d (25 mg, 0.067 mmol) in ethanol (0.5 mL) was added (4-methoxyphenyl)(piperazin-1-yl)methanone, HCl (21 mg, 0.080 mmol). The resulting mixture was heated under microwave irradiation at 150° C. for 3 hours. The mixture was concentrated under reduced pressure and purified by reverse phase HPLC to give Example 1 (28 mg, 77% yield). LCMS (Method C) Rt=1.79 min, m/z=550.1 (M+H). $^1$H NMR (500 MHz, DMSO-d6) δ 7.42 (d, J=8.3 Hz, 2H), 7.33 (t, J=8.3 Hz, 1H), 7.00 (d, J=8.5 Hz, 2H), 6.70 (d, J=8.3 Hz, 2H), 3.81 (s, 3H), 3.69 (s, 6H), 3.57 (br. s., 8H), 2.10-2.04 (m, 2H), 1.31 (d, J=6.1 Hz, 2H), 1.09-0.99 (m, 2H), 0.65 (t, J=7.3 Hz, 3H). Human APJ cAMP $EC_{50}$ Potency range C.

The following compounds, Examples 2 to 7, 10 to 34, and 41 to 69, were prepared by the general procedures described for Example

TABLE 1

| Ex# | Structure | Name | NMR | Rt(min) method M + H | AP J cAMP EC$_{50}$ (nM) |
|---|---|---|---|---|---|
| 2 | 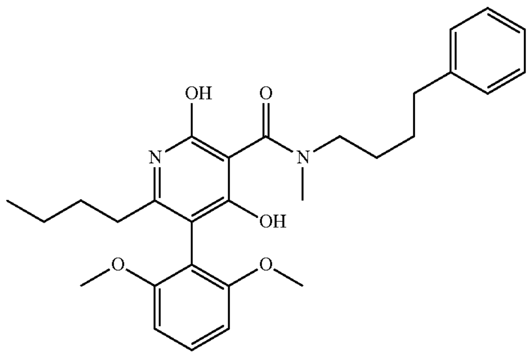 [SMILES: CCCCc1nc(O)c(C(=O)N(C)CCCCc2ccccc2)c(O)c1-c1c(OC)cccc1OC] | 6-butyl-5-(2,6-dimethoxyphenyl)-2,4-dihydroxy-N-methyl-N-(4-phenylbutyl)pyridine-3-carboxamide | $^1$H NMR (500 MHz, DMSO-d6) δ 7.31 (t, J = 8.4 Hz, 1H), 7.24 (d, J = 7.3 Hz, 2H), 7.16 (br. s., 3H), 6.68 (d, J = 8.5 Hz, 2H), 3.64 (s, 4H), 3.44 (d, J = 4.3 Hz, 2H), 2.87 (s, 3H), 2.10-1.98 (m, 2H), 1.53 (br. s., 4H), 1.28 (d, J = 6.1 Hz, 2H), 1.04 (d, J = 6.7 Hz, 2H), 0.62 (t, J = 7.0 Hz, 3H) | 1.93 A 493.1 | C |
| 3 | 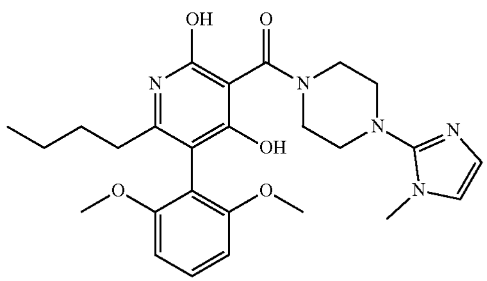 [SMILES: CCCCc1nc(O)c(C(=O)N2CCN(c3nccn3C)CC2)c(O)c1-c1c(OC)cccc1OC] | 6-butyl-5-(2,6-dimethoxyphenyl)-3-[4-(1-methyl-1H-imidazol-2-yl)piperazine-1-carbonyl]pyridine-2,4-diol | $^1$H NMR (500 MHz, DMSO-d6) δ 7.32 (t, J = 8.4 hz, 1H), 7.14 (d, J = 14.6 Hz, 2H), 6.69 (d, J = 8.2 Hz, 2H), 3.67 (s, 6H), 3.57 (s, 3H), 3.47-3.38 (m, 6H), 3.21 (br. s., 2H), 2.12-2.00 (m, 2H), 1.29 (t, J = 7.2 Hz, 2H), 1.10-0.97 (m, 2H), 0.63 (t, J = 7.3 Hz, 3H) | 1.27 A 496.1 | C |
| 4 | 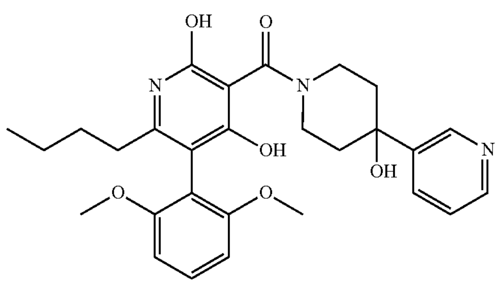 [SMILES: CCCCc1nc(O)c(C(=O)N2CCC(O)(c3cccnc3)CC2)c(O)c1-c1c(OC)cccc1OC] | 6-butyl-5-(2,6-dimethoxyphenyl)-3-[4-hydroxy-4-(pyridin-3-yl)piperidine-1-carbonyl]pyridine-2,4-diol | $^1$H NMR (500 MHz, DMSO-6) δ 8.86 (s, 1H), 8.71 (d, J = 5.2 Hz, 1H), 8.40 (d, J = 8.2 Hz, 1H), 7.90-7.79 (m, 1H), 7.34 (t, J = 8.2 Hz, 1H), 6.71 (d, J = 8.5 Hz, 2H), 3.68 (s, 9H), 3.49 (br. s., 1H), 2.17-1.99 (m, 4H), 1.74 (d, J = 12.5 Hz, 2H), 1.37-1.21 (m, 2H), 1.15-0.97 (m, 2H), 0.65 (t, J = 7.3 Hz, 3H) | 1.24 A 508.4 | C |

TABLE 1-continued

| Ex# | Structure | Name | NMR | Rt(min) method M + H | API cAMP EC$_{50}$ (nM) |
|---|---|---|---|---|---|
| 5 | 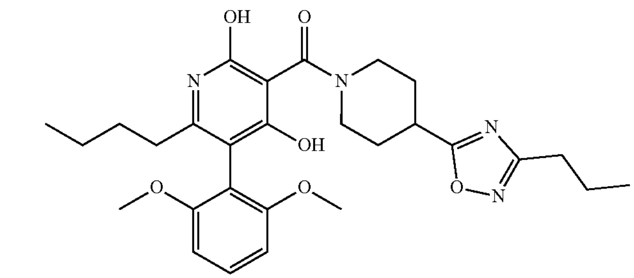 [SMILES: CCCCc1nc(O)c(C(=O)N2CCC(c3nc(CCC)no3)CC2)c(O)c1-c1c(OC)cccc1OC] | 6-butyl-5-(2,6-dimethoxyphenyl)-3-[4-(3-propyl-1,2,4-oxadiazol-5-yl)piperidine-1-carbonyl]pyridine-2,4-diol | $^1$H NMR (500 MHz, DMSO-d6) δ 7.33 (t, J = 8.4 Hz, 1H), 6.70 (d, J = 8.5 Hz, 2H), 3.69 (s, 6H), 3.45-3.28 (m, 2H), 3.09 (br. s., 2H), 2.66 (t, J = 7.3 Hz, 2H), 2.11-2.00 (m, 4H), 1.83-1.65 (m, 4H), 1.38-1.25 (m, 2H), 1.10-1.02 (m, 2H), 0.93 (t, J = 7.5 Hz, 3H), 0.66 (t, J = 7.3 Hz, 3H) | 1.61 A 525.5 | B |
| 6 | 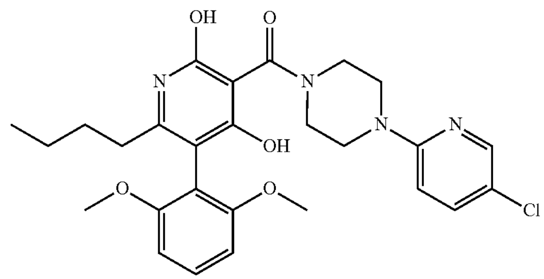 [SMILES: CCCCc1nc(O)c(C(=O)N2CCN(c3ccc(Cl)cn3)CC2)c(O)c1-c1c(OC)cccc1OC] | 6-butyl-3-[4-(5-chloropyridin-2-yl)piperazine-1-carbonyl]-5-(2,6-dimethoxyphenyl)pyridine-2,4-diol | $^1$H NMR (500 MHz, DMSO-d6) δ 8.12 (d, J = 2.4 Hz, 1H), 7.62 (dd, J = 9.2, 2.4 Hz, 1H), 7.31 (t, J = 8.4 Hz, 1H), 6.89 (d, J = 9.2 Hz, 2H), 6.69 (d, J = 8.5 Hz, 2H), 3.68 (s, 6H), 3.57 (br. s., 4H), 3.44 (br. s., 4H), 2.12-2.00 (m, 2H), 1.37-1.22 (m, 2H), 1.12-0.95 (m, 2H), 0.64 (t, J = 7.3 Hz, 3H) | 1.65 A 527.4 | B |
| 7 | 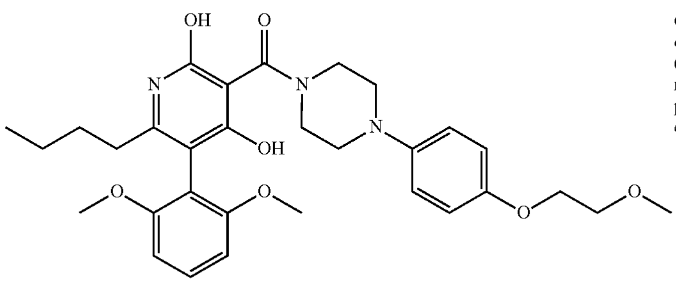 [SMILES: CCCCc1nc(O)c(C(=O)N2CCN(c3ccc(OCCOC)cc3)CC2)c(O)c1-c1c(OC)cccc1OC] | 6-butyl-5-(2,6-dimethoxyphenyl)-3-{4-[4-(2-methoxyethoxy)phenyl]piperazine-1-carbonyl}pyridine-2,4-diol | $^1$H NMR (500 MHz, DMSO-d6) δ 7.33 (t, J = 8.4 Hz, 1H), 6.98 (d, J = 8.9 Hz, 2H), 6.88 (d, J = 8.9 Hz, 2H), 6.71 (d, J = 8.2 Hz, 2H), 4.03 (d, J = 4.3 Hz, 2H), 3.70 (s, 6H), 3.64 (d, J = 4.3 Hz, 4H), 3.45 (br. s., 4H), 3.31 (s, 2H), 3.22-3.06 (m, 3H), 2.08 (t, J = 7.6 Hz, 2H), 1.38-1.25 (m, 2H), 1.13-1.03 (m, 2H), 0.66 (t, J = 7.2 Hz, 3H) | 1.54 A 566.3 | C |

TABLE 1-continued

| Ex# | Structure | Name | NMR | Rt(min) method M + H | API cAMP EC$_{50}$ (nM) |
|---|---|---|---|---|---|
| 10 | 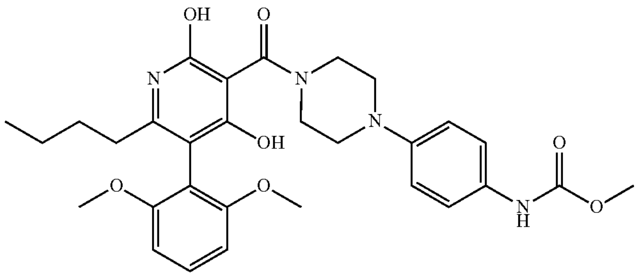 [SMILES: CCCCc1nc(O)c(C(=O)N2CCN(c3ccc(NC(=O)OC)cc3)CC2)c(O)c1-c1c(OC)cccc1OC] | methyl N-(4-{4-[6-butyl-5-(2,6-dimethoxyphenyl)-2,4-dihydroxypyridine-3-carbonyl]piperazin-1-yl}phenyl)carbamate | $^1$H NMR (500 MHz, DMSO-d6) δ 7.37-7.24 (m, 3H), 6.91 (d, J = 8.2 Hz, 2H), 6.70 (d, J = 8.2 Hz, 2H), 3.69 (s, 6H), 3.64 (s, 3H), 3.55-3.40 (m, 4H), 3.23-3.07 (m, 4H), 2.08 (br. s., 2H), 1.37-1.24 (m, 2H), 1.13-1.02 (m, 2H), 0.65 (t, J = 7.3 Hz, 3H) | 1.42 565.3 | B |
| 11 | 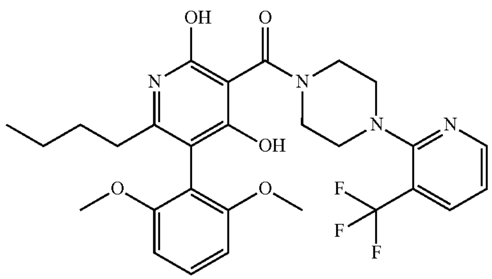 [SMILES: CCCCc1nc(O)c(C(=O)N2CCN(c3ncccc3C(F)(F)F)CC2)c(O)c1-c1c(OC)cccc1OC] | 6-butyl-5-(2,6-dimethoxyphenyl)-3-{4-[3-(trifluoromethyl)pyridin-2-yl]piperazine-1-carbonyl}pyridine-2,4-diol | $^1$H NMR (500 MHz, DMSO-d6) δ 8.55 (br. s., 1H), 8.10 (d, J = 7.0 Hz, 1H), 7.33 (t, J = 8.2 Hz, 1H), 7.24 (br. s., 1H), 6.71 (d, J = 8.5 Hz, 2H), 3.69 (s, 6H), 3.51-3.39 (m, 4H), 3.24 (br. s., 4H), 2.08 (t, J = 7.5 Hz, 2H), 1.30 (d, J = 7.0 Hz, 2H), 1.12-0.98 (m, 2H), 0.65 (t, J = 7.2 Hz, 3H) | 1.77 B 562.3 | B |
| 12 | 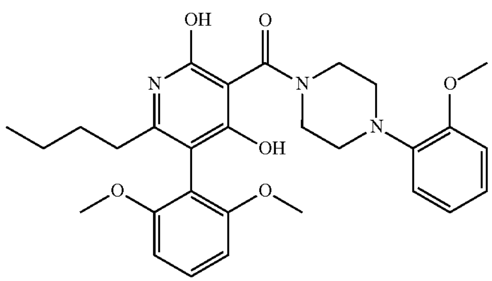 [SMILES: CCCCc1nc(O)c(C(=O)N2CCN(c3ccccc3OC)CC2)c(O)c1-c1c(OC)cccc1OC] | 6-butyl-5-(2,6-dimethoxyphenyl)-3-[4-(2-methoxyphenyl)piperazine-1-carbonyl]pyridine-2,4-diol | $^1$H NMR (500 MHz, DMSO-d6) δ 7.33 (t, J = 8.4 Hz, 1H), 7.04-6.94 (m, 2H), 6.90 (br. s., 2H), 6.71 (d, J = 8.5 Hz, 2H), 3.80 (s, 3H), 3.69 (s, 6H), 3.51-3.29 (m, 4H), 3.00 (br. s., 4H), 2.08 (t, J = 7.6 Hz, 2H), 1.36-1.22 (m, 2H), 1.11-1.01 (m, 2H), 0.65 (t, J = 7.3 Hz, 3H) | 1.61 A 522.5 | A |

TABLE 1-continued

| Ex# | Structure | Name | NMR | Rt(min) method M + H | API cAMP EC$_{50}$ (nM) |
|---|---|---|---|---|---|
| 13 | 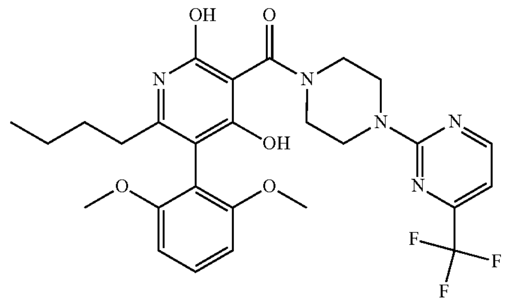 [SMILES: CCCCc1nc(O)c(C(=O)N2CCN(c3nccc(C(F)(F)F)n3)CC2)c(O)c1-c1c(OC)cccc1OC] | 6-butyl-5-(2,6-dimethoxyphenyl)-3-{4-[4-(trifluoromethyl)pyrimidin-2-yl]piperazine-1-carbonyl}pyridine-2,4-diol | $^1$H NMR (500 MHz, DMSO-d6) δ 8.70 (d, J = 4.9 Hz, 1H), 7.32 (t, J = 8.2 Hz, 1H), 7.08-7.00 (m, 1H), 6.69 (d, J = 8.2 Hz, 2H), 3.85 (br. s., 6H), 3.68 (s, 6H), 3.48-3.33 (m, 2H), 2.13-2.02 (m, 2H), 1.36-1.24 (m, 2H), 1.11-0.95 (m, 2H), 0.64 (t, J = 7.2 Hz, 3H) | 1.76 A 562.4 | B |
| 14 | 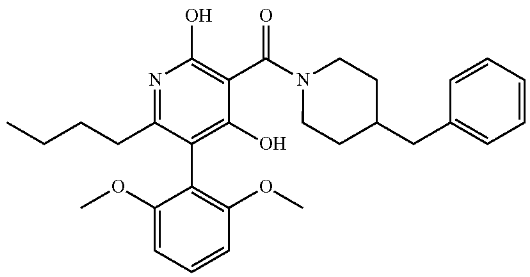 [SMILES: CCCCc1nc(O)c(C(=O)N2CCC(Cc3ccccc3)CC2)c(O)c1-c1c(OC)cccc1OC] | 3-(4-benzylpiperidine-1-carbonyl)-6-butyl-5-(2,6-dimethoxyphenyl)pyridine-2,4-diol | $^1$H NMR (500 MHz, DMSO-d6) δ 7.36-7.23 (m, 3H), 7.21-7.11 (m, 3H), 6.74-6.64 (m, 2H), 3.66 (s, 6H), 3.51-3.34 (m, 5H), 2.78 (br. s., 1H), 2.08-1.99 (m, 2H), 1.75 (br. s., 1H), 1.58 (d, J = 11.3 Hz, 2H), 1.28 (t, J = 7.0 Hz, 2H), 1.18 (d, J = 12.2 Hz, 2H), 1.09-1.01 (m, 2H), 0.63 (t, J = 7.3 Hz, 3H) | 1.91 A 505.4 | A |
| 15 | 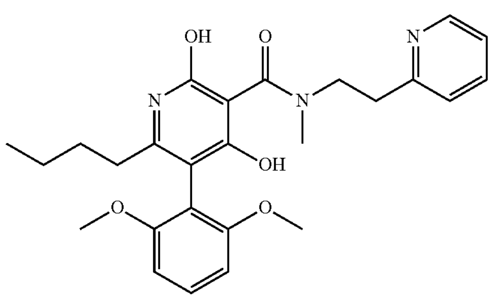 [SMILES: CCCCc1nc(O)c(C(=O)N(C)CCc2ccccn2)c(O)c1-c1c(OC)cccc1OC] | 6-butyl-5-(2,6-dimethoxyphenyl)-2,4-dihydroxy-N-methyl-N-[2-(pyridin-2-yl)ethyl]pyridine-3-carboxamide | $^1$H NMR (500 MHz, DMSO-d6) δ 8.61 (br. s., 1H), 8.18 (br. s., 1H), 7.81 (br. s., 1H), 7.66 (br. s., 1H), 7.34 (t, J = 8.2 Hz, 1H), 6.71 (d, J = 8.2 Hz, 2H), 3.67 (br. s., 6H), 3.57-3.42 (m, 2H), 3.24-3.02 (m, 2H), 2.89 (br. s., 2H), 2.13-1.99 (m, 2H), 1.38-1.19 (m, 2H), 1.14-0.99 (m, 2H), 0.65 (t, J = 7.2 Hz, 3H) | 1.37 A 466.4 | A |

TABLE 1-continued

| Ex# | Structure | Name | NMR | Rt(min) method M + H | API cAMP EC$_{50}$ (nM) |
|---|---|---|---|---|---|
| 16 | 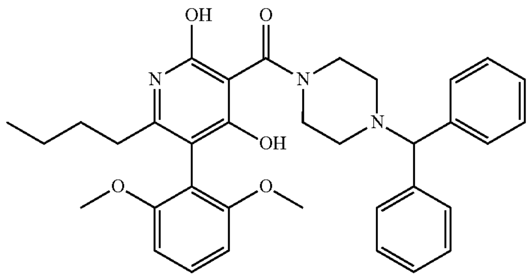 [SMILES: CCCCc1nc(O)c(C(=O)N2CCN(C(c3ccccc3)c3ccccc3)CC2)c(O)c1-c1c(OC)cccc1OC] | 6-butyl-5-(2,6-dimethoxyphenyl)-3-[4-(diphenylmethyl)piperazine-1-carbonyl]pyridine-2,4-diol | $^1$H NMR (500 MHz, DMSO-d6) δ 7.45 (d, J = 7.0 Hz, 4H), 7.32 (t, J = 7.3 Hz, 5H), 7.24-7.18 (m, 2H), 6.69 (d, J = 8.2 Hz, 2H), 4.38 (br. s., 1H), 3.65 (s, 6H), 3.48 (br. s., 4H), 2.38 (br. s., 4H), 2.11-2.00 (m, 2H), 1.35-1.21 (m, 2H), 1.06-0.99 (m, 2H), 0.63 (t, J = 7.2 Hz, 3H) | 2.04 A 582.4 | A |
| 17 | 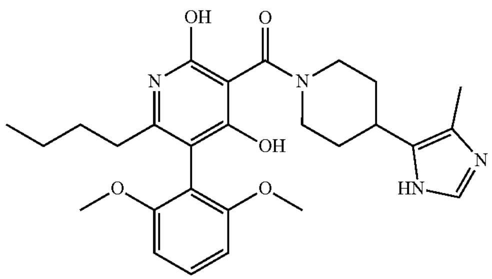 [SMILES: CCCCc1nc(O)c(C(=O)N2CCC(c3[nH]cnc3C)CC2)c(O)c1-c1c(OC)cccc1OC] | 6-butyl-5-(2,6-dimethoxyphenyl)-3-[4-(4-methyl-1H-imidazol-5-yl)piperidine-1-carbonyl]pyridine-2,4-diol | $^1$H NMR (500 MHz, DMSO-d6) δ 8.89 (s, 1H), 7.40-7.27 (m, 1H), 6.71 (d, J = 8.2 Hz, 2H), 3.69 (s, 6H), 3.18-2.88 (m, 4H), 2.28 (s, 3H), 2.12-2.00 (m, 2H), 1.96-1.68 (m, 4H), 1.35-1.20 (m, 2H), 1.14-1.01 (m, 2H), 0.66 (t, J = 7.2 Hz, 3H) | 1.20 A 495.3 | B |
| 18 | 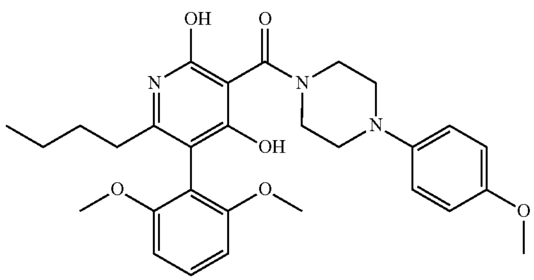 [SMILES: CCCCc1nc(O)c(C(=O)N2CCN(c3ccc(OC)cc3)CC2)c(O)c1-c1c(OC)cccc1OC] | 6-butyl-5-(2,6-dimethoxyphenyl)-3-[4-(4-methoxyphenyl)piperazine-1-carbonyl]pyridine-2,4-diol | $^1$H NMR (500 MHz, DMSO-d6) δ 7.33 (t, J = 8.4 Hz, 1H), 7.05 (d, J = 8.5 Hz, 2H), 6.89 (d, J = 8.5 Hz, 2H), 6.71 (d, J = 8.2 Hz, 2H), 3.77-3.57 (m, 10H), 3.15 (br. s, 4H), 2.09 (t, J = 7.3 Hz, 2H), 1.38-1.26 (m, 2H), 1.14-1.00 (m, 2H), 0.65 (t, J = 7.3 Hz, 3H) | 1.60 A 522.3 | B |

TABLE 1-continued

| Ex# | Structure | Name | NMR | Rt(min) method M + H | API cAMP EC$_{50}$ (nM) |
|---|---|---|---|---|---|
| 19 | 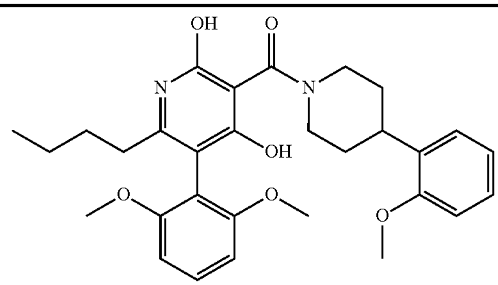 | 6-butyl-5-(2,6-dimethoxyphenyl)-3-{4-(2-methoxyphenyl)piperidine-1-carbonyl]pyridine-2,4-diol | $^1$H NMR (500 MHz, DMSO-d6) δ 7.31 (t, J = 8.2 Hz, 1H), 7.20-7.17 (m, 1H), 7.13 (d, J = 7.6 Hz, 1H), 6.95 (d, J = 8.2 Hz, 1H), 6.89 (t, J = 7.5 Hz, 1H), 6.69 (d, J = 8.5 Hz, 2H), 3.78 (s, 3H), 3.67 (s, 6H), 3.19-3.10 (m, 2H), 3.01-2.84 (m, 2H), 2.06 (t, J = 7.6 Hz, 2H), 1.72 (d, J = 12.5 Hz, 2H), 1.61 (d, J = 11.6 Hz, 2H), 1.29 (t, J = 7.3 Hz, 2H), 1.10-0.99 (m, 2H), 0.63 (t, J = 7.3 Hz, 3H) | 1.86 A 521.3 | B |
| 20 | 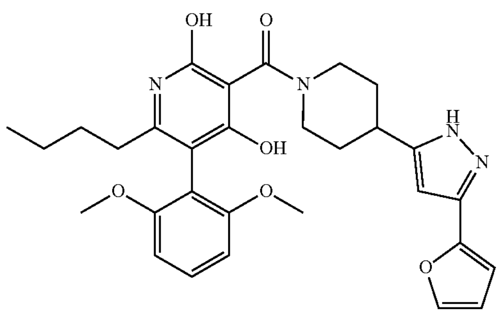 [SMILES: CCCCc1nc(O)c(C(=O)N2CCC(c3cc(-c4ccco4)n[nH]3)CC2)c(O)c1-c1c(OC)cccc1OC] | 6-butyl-5-(2,6-dimethoxyphenyl)-3-{4-[3-(furan-2-yl)-1H-pyrazol-5-yl]piperidine-1-carbonyl}pyridine-2,4-diol | $^1$H NMR (500 MHz, DMSO-d6) δ 7.67 (s, 1H), 7.33 (t, J = 8.4 Hz, 1H), 6.76-6.63 (m, 3H), 6.55 (br. s., 1H), 6.32 (s, 1H), 3.69 (s, 6H), 3.52 (br. s., 1H), 3.08-2.85 (m, 4H), 2.08 (t, J = 7.8 Hz, 2H), 1.97 (d, J = 11.9 Hz, 2H), 1.66 (d, J = 11.6 Hz, 2H), 1.38-1.26 (m, 2H), 1.11-0.97 (m, 2H), 0.65 (t, J = 7.3 Hz, 3H) | 1.58 A 547.2 | B |
| 21 | 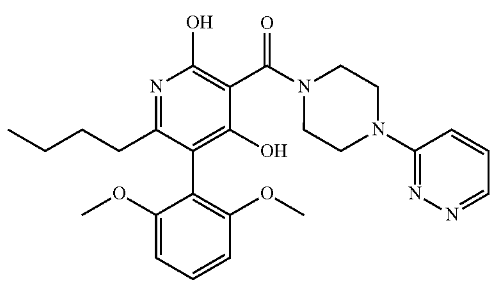 [SMILES: CCCCc1nc(O)c(C(=O)N2CCN(c3cccnn3)CC2)c(O)c1-c1c(OC)cccc1OC] | 6-butyl-5-(2,6-dimethoxyphenyl)-3-[4-(pyridazin-3-yl)piperazine-1-carbonyl]pyridine-2,4-diol | $^1$H NMR (500 MHz, DMSO-d6) δ 8.65 (d, J = 4.3 Hz, 1H), 7.69-7.63 (m, 1H), 7.59-7.53 (m, 1H), 7.34 (t, J = 8.4 Hz, 1H), 6.71 (d, J = 8.5 Hz, 2H), 3.74 (br. s., 6H), 3.50 (br. s., 8H), 2.15-1.96 (m, 2H), 1.36-1.26 (m, 2H), 1.12-1.02 (m, 2H), 0.66 (t, J = 7.3 Hz, 3H) | 1.26 A 494.0 | C |

TABLE 1-continued

| Ex# | Structure | Name | NMR | Rt(min) method M + H | API cAMP EC$_{50}$ (nM) |
|---|---|---|---|---|---|
| 22 | 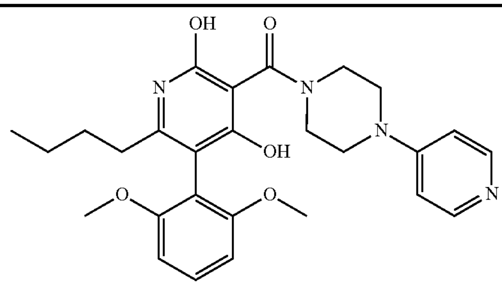 | 6-butyl-5-(2,6-dimethoxyphenyl)-3-[4-(pyridin-4-yl)piperazine-1-carbonyl]pyridine-2,4-diol | $^1$H NMR (500 MHz, DMSO-d6) δ 8.27 (d, J = 7.0 Hz, 2H), 7.34 (t, J = 8.4 Hz, 1H), 7.22-7.15 (m, 2H), 6.71 (d, J = 8.5 Hz, 2H), 3.80 (br. s., 4H), 3.69 (s, 6H), 3.62-3.42 (m, 4H), 2.18-2.03 (m, 2H), 1.38-1.23 (m, 2H), 1.13-0.97 (m, 2H), 0.65 (t, J = 7.3 Hz, 3H) | 1.10 A 493.2 | C |
| 23 | 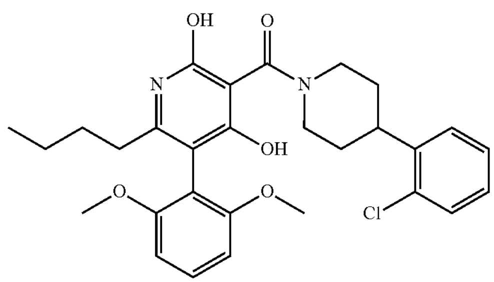 [SMILES: CCCCc1nc(O)c(C(=O)N2CCC(c3ccccc3Cl)CC2)c(O)c1-c1c(OC)cccc1OC] | 6-butyl-3-[4-(2-chlorophenyl)piperidine-1-carbonyl]-5-(2,6-dimethoxyphenyl)pyridine-2,4-diol | $^1$H NMR (500 MHz, DMSO-d6) δ 7.43 (d, J = 7.9 Hz, 1H), 7.33 (br. s., 2H), 7.23 (d, J = 8.2 Hz, 2H), 6.63 (d, J = 8.2 Hz, 2H), 3.71-3.57 (m, 6H), 3.33 (br. s., 2H), 3.18 (br. s., 2H), 1.97 (br. s., 2H), 1.81-1.53 (m, 4H), 1.36-1.19 (m, 3H), 1.12-0.98 (m, 2H), 0.66 (t, J = 7.3 Hz, 3H) | 1.90 A 525.1 | B |
| 24 | 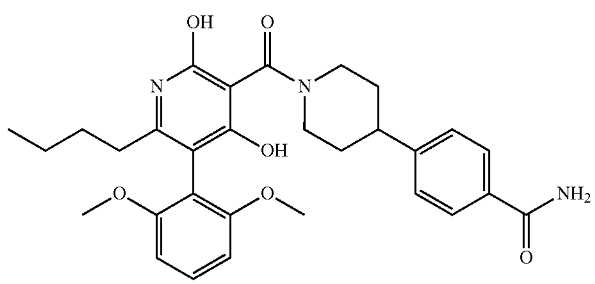 [SMILES: CCCCc1nc(O)c(C(=O)N2CCC(c3ccc(C(N)=O)cc3)CC2)c(O)c1-c1c(OC)cccc1OC] | 4-{1-[6-butyl-5-(2,6-dimethoxyphenyl)-2,4-dihydroxypyridine-3-carbonyl]piperidin-4-yl}benzamide | $^1$H NMR (500 MHz, DMSO-d6) δ 7.40-7.29 (m, 4H), 7.24 (br. s., 1H), 6.69 (d, J = 8.2 Hz, 2H), 3.67 (s, 6H), 3.41 (br. s., 4H), 3.32 (br. s., 1H), 2.38-2.22 (m, 2H), 2.07 (br. s., 2H), 1.30 (br. s., 2H), 1.05 (br. s., 2H), 0.64 (br. s., 3H) | 1.37 A 534.1 | B |

TABLE 1-continued

| Ex# | Structure | Name | NMR | Rt(min) method M + H | API cAMP EC$_{50}$ (nM) |
|---|---|---|---|---|---|
| 25 | 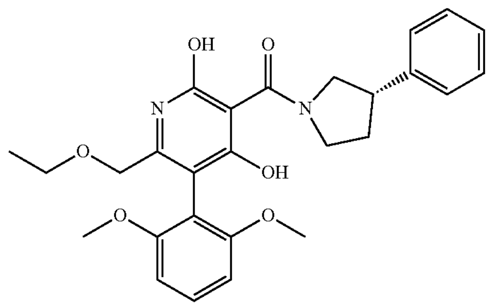 [SMILES: CCOCc1nc(O)c(C(=O)N2CC[C@@H](c3ccccc3)C2)c(O)c1-c1c(OC)cccc1OC] | 5-(2,6-dimethoxyphenyl)-6-(ethoxymethyl)-3-[(3S)-3-phenylpyrrolidine-1-carbonyl]pyridine-2,4-diol | $^1$H NMR (500 MHz, DMSO-d6) δ 7.34 (d, J = 7.9 Hz, 5H), 7.26 (br. s., 1H), 6.72 (d, J = 8.2 Hz, 2H), 3.91 (br. s., 2H), 3.69 (br. s., 6H), 3.43 (br. s., 5H), 3.26 (br. s., 2H), 2.28 (br. s., 1H), 2.12-1.95 (m, 1H), 0.98 (br. s., 3H) | 1.46 A 479.2 | B |
| 26 | 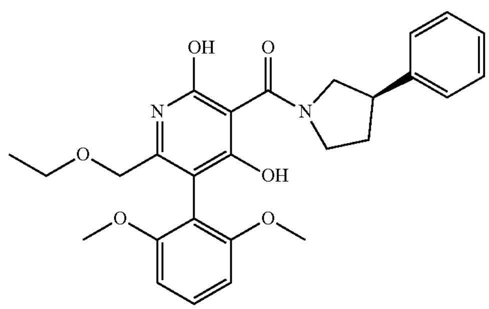 [SMILES: CCOCc1nc(O)c(C(=O)N2CC[C@H](c3ccccc3)C2)c(O)c1-c1c(OC)cccc1OC] | 5-(2,6-dimethoxyphenyl)-6-(ethoxymethyl)-3-[(3R)-3-phenylpyrrolidine-1-carbonyl]pyridine-2,4-diol | $^1$H NMR (500 MHz, DMSO-d6) δ 7.34 (d, J = 7.9 Hz, 5H), 7.26 (d, J = 4.6 Hz, 1H), 6.71 (d, J = 8.2 Hz, 2H), 3.91 (br. s., 3H), 3.68 (s, 7H), 3.48 (br. s., 3H), 3.26 (br. s., 2H), 2.28 (br. s., 1H), 2.07 (s, 1H), 0.98 (br. s., 3H) | 1.53 A 479.1 | B |
| 27 | 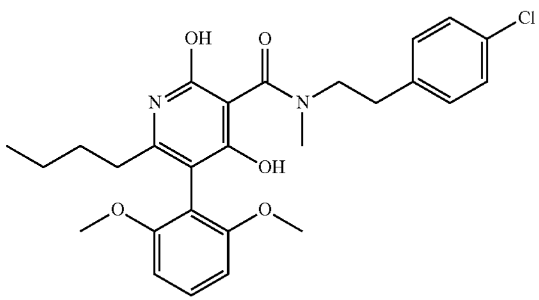 [SMILES: CCCCc1nc(O)c(C(=O)N(C)CCc2ccc(Cl)cc2)c(O)c1-c1c(OC)cccc1OC] | 6-butyl-N-[2-(4-chlorophenyl)ethyl]-5-(2,6-dimethoxyphenyl)-2,4-dihydroxy-N-methylpyridine-3-carboxamide | $^1$H NMR (500 MHz, DMSO-d6) δ 7.36-6.99 (m, 7H), 6.70 (d, J = 8.2 Hz, 2H), 3.65 (br. s., 6H), 2.91 (s, 2H), 2.83 (br. s., 2H), 2.55 (s, 3H), 2.08 (t, J = 7.0 Hz, 2H), 1.37-1.26 (m, 2H), 1.14-0.97 (m, 2H), 0.67 (t, J = 6.9 Hz, 3H) | 2.08 C 499.2 | B |

TABLE 1-continued

| Ex# | Structure | Name | NMR | Rt(min) method M + H | API cAMP EC$_{50}$ (nM) |
|---|---|---|---|---|---|
| 28 | 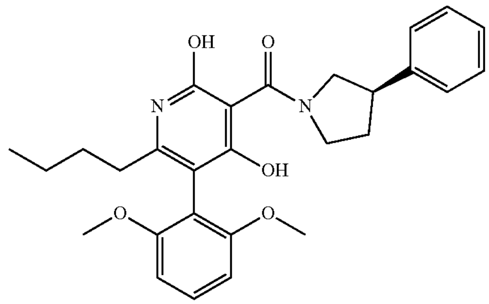 [SMILES: CCCCc1nc(O)c(C(=O)N2CC[C@H](c3ccccc3)C2)c(O)c1-c1c(OC)cccc1OC] | 6-butyl-5-(2,6-dimethoxyphenyl)-3-[(3R)-3-phenylpyrrolidine-1-carbonyl]pyridine-2,4-diol | $^1$H NMR (400 MHz, DMSO-d6) δ 7.40-7.21 (m, 6H), 6.70 (d, J = 8.4 Hz, 2H), 3.68 (s, 6H), 3.53-3.18 (m, 6H), 2.26 (br. s., 6H), 2.07 (d, J = 7.3 Hz, 2H), 1.34-1.21 (m, 2H), 1.07 (br. s., 2H), 0.65 (d, J = 2.6 Hz, 3H). | 2.01 C 477.2 | A |
| 29 | 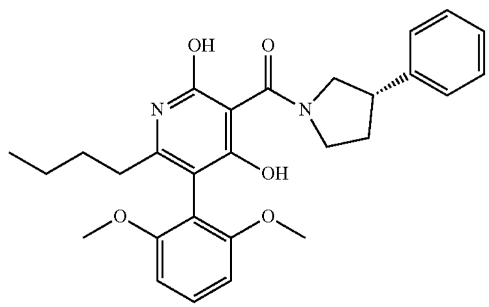 [SMILES: CCCCc1nc(O)c(C(=O)N2CC[C@@H](c3ccccc3)C2)c(O)c1-c1c(OC)cccc1OC] | 6-butyl-5-(2,6-dimethoxyphenyl)-3-[(3S)-3-phenylpyrrolidine-1-carbonyl]pyridine-2,4-diol | $^1$H NMR (500 MHz, DMSO-d6) δ 7.42-7.18 (m, 6H), 6.70 (d, J = 8.5 Hz, 2H), 4.35-3.74 (m, 4H), 3.68 (s, 6H), 3.43 (br. s., 2H), 2.27 (br. s., 1H), 2.08 (d, J = 6.1 Hz, 2H), 1.37-1.25 (m, 2H), 1.06 (d, J = 7.0 Hz, 2H), 0.65 (br. s., 3H). | 2.00 C 477.2 | A |
| 30 | 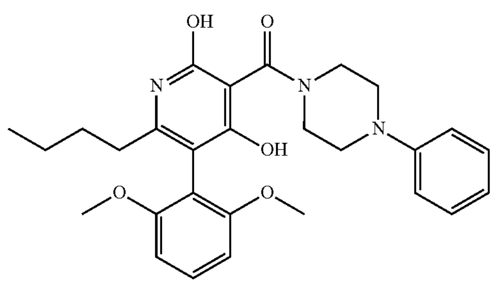 [SMILES: CCCCc1nc(O)c(C(=O)N2CCN(c3ccccc3)CC2)c(O)c1-c1c(OC)cccc1OC] | 6-butyl-5-(2,6-dimethoxyphenyl)-3-(4-phenylpiperazine-1-carbonyl)pyridine-2,4-diol | $^1$H NMR (500 MHz, DMSO-d6) δ 7.32 (t, J = 8.2 Hz, 1H), 7.27-7.20 (m, 2H), 7.04-6.93 (m, 2H), 6.81 (t, J = 7.2 Hz, 1H), 6.70 (d, J = 8.5 Hz, 2H), 3.69 (s, 6H), 3.25-3.18 (m, 8H), 2.08 (t, J = 7.6 Hz, 2H), 1.31 (quin, J = 7.6 Hz, 2H), 1.12-1.02 (m, 2H), 0.65 (t, J = 7.3 Hz, 3H). | 1.79 C 492.2 | B |

TABLE 1-continued

| Ex# | Structure | Name | NMR | Rt(min) method M + H | API cAMP EC$_{50}$ (nM) |
|---|---|---|---|---|---|
| 31 | 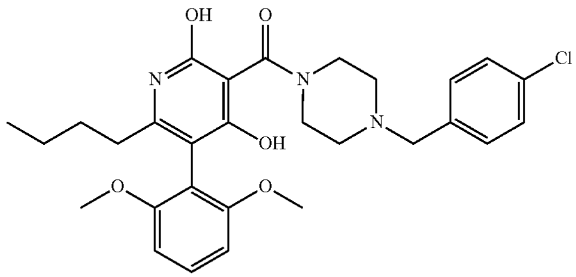 [SMILES: CCCCc1nc(O)c(C(=O)N2CCN(Cc3ccc(Cl)cc3)CC2)c(O)c1-c1c(OC)cccc1OC] | 6-butyl-3-{4-[(4-chlorophenyl)methyl]piperazine-1-carbonyl}-5-(2,6-dimethoxyphenyl)pyridine-2,4-diol | $^1$H NMR (500 MHz, DMSO-d6) δ 7.52 (br. s., 5H), 7.32 (t, J = 8.4 Hz, 1H), 6.69 (d, J = 8.2 Hz, 2H), 4.25 (br. s., 4H), 3.67 (s, 6H), 3.42 (br. s., 4H), 2.06 (t, J = 7.6 Hz, 2H), 1.32-1.19 (m, 2H), 1.11-0.96 (m, 2H), 0.63 (t, J = 7.2 Hz, 3H) | 0.73 D 540.6 | A |
| 32 | 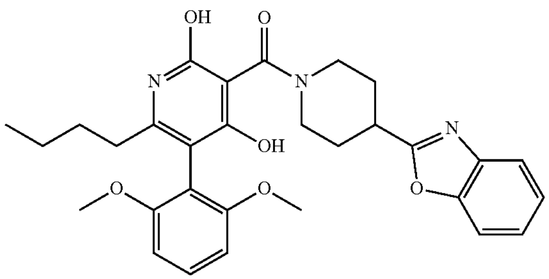 [SMILES: CCCCc1nc(O)c(C(=O)N2CCC(c3nc4ccccc4o3)CC2)c(O)c1-c1c(OC)cccc1OC] | 3-[4-(1,3-benzoxazol-2-yl)piperidine-1-carbonyl]-6-butyl-5-(2,6-dimethoxyphenyl)pyridine-2,4-diol | $^1$H NMR (500 MHz, DMSO-d6) δ 7.70 (t, J = 8.7 Hz, 2H), 7.42-7.23 (m, 3H), 6.69 (d, J = 8.2 Hz, 2H), 3.68 (s, 6H), 3.46-3.30 (m, 2H), 3.12 (br. s., 2H), 2.56 (s, 1H), 2.14 (d, J = 11.3 Hz, 2H), 2.06 (t, J = 7.5 Hz, 2H), 1.87 (br. s., 2H), 1.38-1.24 (m, 2H), 1.12-1.01 (m, 2H), 0.66 (t, J = 7.3 Hz, 3H) | 1.95 C 532.2 | B |
| 33 | 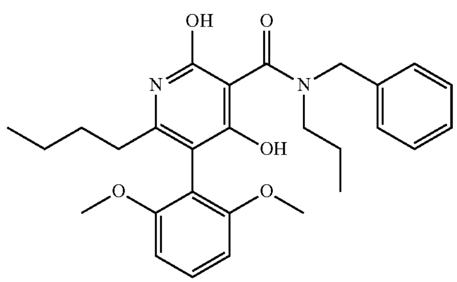 [SMILES: CCCCc1nc(O)c(C(=O)N(CCC)Cc2ccccc2)c(O)c1-c1c(OC)cccc1OC] | N-benzyl-6-butyl-5-(2,6-dimethoxyphenyl)-2,4-dihydroxy-N-propylpyridine-3-carboxamide | $^1$H NMR (500 MHz, DMSO-d6) δ 7.49-7.21 (m, 6H), 6.71 (d, J = 8.5 Hz, 2H), 4.73-4.42 (m, 2H), 3.67 (br. s., 6H), 3.13 (br. s., 2H), 2.07 (br. s., 2H), 1.51-1.43 (m, 2H), 1.37-1.21 (m, 2H), 1.06 (d, J = 6.4 Hz, 2H), 0.72 (br. s., 3H), 0.65 (br. s., 3H) | 0.92 D 479.6 | C |

TABLE 1-continued

| Ex# | Structure | Name | NMR | Rt(min) method M + H | API cAMP EC$_{50}$ (nM) |
|---|---|---|---|---|---|
| 34 | 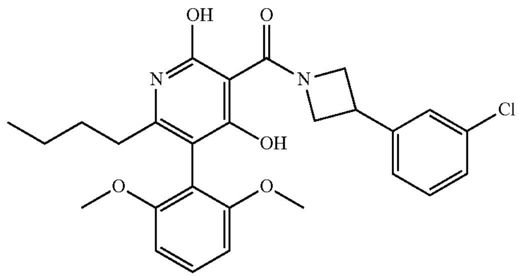 [SMILES: CCCCc1nc(O)c(C(=O)N2CC(c3cccc(Cl)c3)C2)c(O)c1-c1c(OC)cccc1OC] | 6-butyl-3-[3-(3-chlorophenyl)azetidine-1-carbonyl]-5-(2,6-dimethoxyphenyl)pyridine-2,4-diol | $^1$H NMR (500 MHz, DMSO-d6) δ 7.52-7.29 (m, 5H), 6.71 (d, J = 8.5 Hz, 2H), 4.75-4.35 (m, 2H), 4.09-3.86 (m, 2H), 3.69 (s, 6H), 3.49-3.39 (m, 1H), 2.10 (t, J = 7.6 Hz, 2H), 1.37-1.21 (m, 2H), 1.15-1.03 (m, 2H), 0.65 (t, J = 7.2 Hz, 3H) | 2.10 A 497.2 | A |
| 41 | 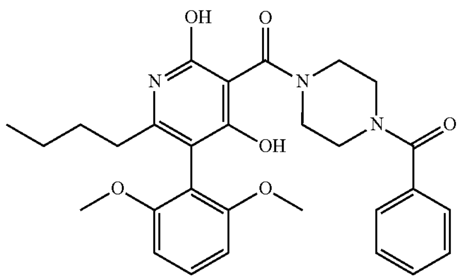 [SMILES: CCCCc1nc(O)c(C(=O)N2CCN(C(=O)c3ccccc3)CC2)c(O)c1-c1c(OC)cccc1OC] | 3-(4-benzoylpiperazine-1-carbonyl)-6-butyl-5-(2,6-dimethoxyphenyl)pyridine-2,4-diol | $^1$H NMR (500 MHz, DMSO-d6) δ 7.52-7.42 (m, 5H), 7.33 (t, J = 8.2 Hz, 1H), 6.70 (d, J = 8.2 Hz, 2H), 3.68 (s, 6H), 3.44-3.29 (m, 8H), 2.07 (br. s., 2H), 1.38-1.22 (m, 2H), 1.15-0.95 (m, 2H), 0.65 (t, J = 7.0 Hz, 3H) | 1.78 C 520.1 | A |
| 42 | 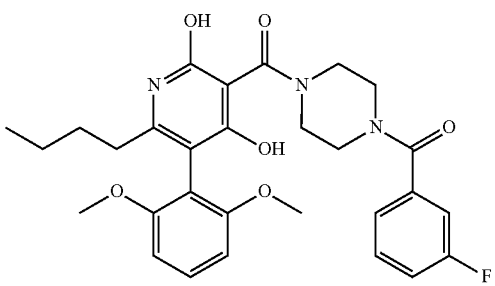 [SMILES: CCCCc1nc(O)c(C(=O)N2CCN(C(=O)c3cccc(F)c3)CC2)c(O)c1-c1c(OC)cccc1OC] | 6-butyl-5-(2,6-dimethoxyphenyl)-3-[4-(3-fluorobenzoyl)piperazine-1-carbonyl]pyridine-2,4-diol | $^1$H NMR (500 MHz, DMSO-d6) δ 7.52 (d, J = 7.2 Hz, 1H), 7.37-7.24 (m, 4H), 6.70 (d, J = 8.3 Hz, 2H), 3.68 (s, 6H), 2.06 (br. s., 2H), 1.31 (br. s., 2H), 1.12-0.99 (m, 2H), 0.65 (t, J = 7.3 Hz, 3H). | 1.81 C 538.1 | A |

TABLE 1-continued

| Ex# | Structure | Name | NMR | Rt(min) method M + H | API cAMP EC$_{50}$ (nM) |
|---|---|---|---|---|---|
| 43 | 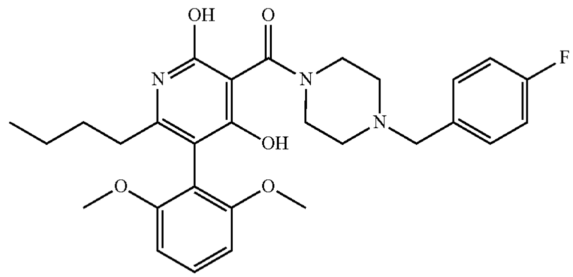 [SMILES: CCCCc1nc(O)c(C(=O)N2CCN(Cc3ccc(F)cc3)CC2)c(O)c1-c1c(OC)cccc1OC] | 6-butyl-5-(2,6-dimethoxyphenyl)-3-{4-[(4-fluorophenyl)methyl]piperazine-1-carbonyl}pyridine-2,4-diol | $^1$H NMR (500 MHz, DMSO-d6) δ 7.40-7.28 (m, 3H), 7.15 (br. s., 2H), 6.69 (d, J = 8.3 Hz, 2H), 3.67 (s, 6H), 3.48 (br. s., 6H), 2.39 (br. s., 4H), 2.08-1.99 (m, 2H), 1.28 (d, J = 7.7 Hz, 2H), 1.07-1.00 (m, 2H), 0.63 (t, J = 7.3 Hz, 3H) | 0.72 D 524.4 | A |
| 44 | 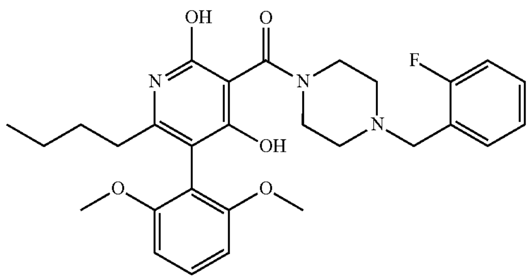 [SMILES: CCCCc1nc(O)c(C(=O)N2CCN(Cc3ccccc3F)CC2)c(O)c1-c1c(OC)cccc1OC] | 6-butyl-5-(2,6-dimethoxyphenyl)-3-{4-[(2-fluorophenyl)methyl]piperazine-1-carbonyl}pyridine-2,4-diol | $^1$H NMR (500 MHz, DMSO-d6) δ 7.42 (t, J = 7.2 Hz, 1H), 7.36-7.25 (m, 2H), 7.22-7.08 (m, 2H), 6.68 (d, J = 8.5 Hz, 2H), 3.67 (s, 6H), 3.56 (s, 2H), 3.44 (br. s., 4H), 2.43 (br. s., 4H), 2.05 (t, J = 7.6 Hz, 2H), 1.29 (t, J = 7.2 Hz, 2H), 1.10-10.98 (m, 2H), 0.63 (t, J = 7.2 Hz, 3H) | 0.71 D 524.4 | A |
| 45 | 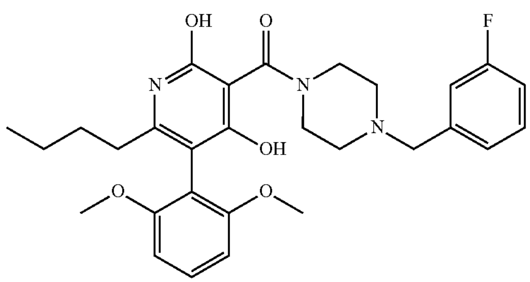 | 6-butyl-5-(2,6-dimethoxyphenyl)-3-{4-[(3-fluorophenyl)methyl]piperazine-1-carbonyl}pyridine-2,4-diol | $^1$H NMR (500 MHz, DMSO-d6) δ 7.42-7.28 (m, 2H), 7.19-7.13 (m, 2H), 7.08 (t, J = 8.4 Hz, 1H), 6.68 (d, J = 8.5 Hz, 2H), 3.67 (s, 6H), 3.52 (s, 2H), 3.46 (br. s., 4H), 2.41 (br. s., 4H), 2.05 (t, J = 7.4 Hz, 2H), 1.35-1.23 (m, 2H), 1.09-0.98 (m, 2H), 0.63 (t, J = 7.2 Hz, 3H) | 0.72 D 524.4 | A |

| Ex# | Structure | Name | NMR | Rt(min) method M + H | API cAMP EC$_{50}$ (nM) |
|---|---|---|---|---|---|
| 46 | 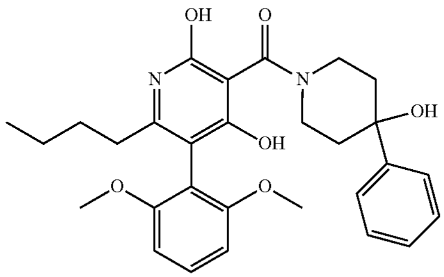 [SMILES: CCCCc1nc(O)c(C(=O)N2CCC(O)(c3ccccc3)CC2)c(O)c1-c1c(OC)cccc1OC] | 6-butyl-5-(2,6-dimethoxyphenyl)-3-(4-hydroxy-4-phenylpiperidine-1-carbonyl)pyridine-2,4-diol | $^{1}$H NMR (500 MHz, DMSO-d6) δ 7.46 (d, J = 7.6 Hz, 2H), 7.31 (t, J = 7.6 Hz, 3H), 7.24-7.15 (m, 1H), 6.68 (d, J = 8.2 Hz, 2H), 3.66 (s, 6H), 3.54-3.44 (m, 4H), 2.09-1.92 (m, 4H), 1.62 (d, J = 13.1 Hz, 2H), 1.35-1.24 (m, 2H), 1.08-0.96 (m, 2H), 0.63 (t, J = 7.2 Hz, 3H) | 1.60 B 507.2 | B |
| 47 | 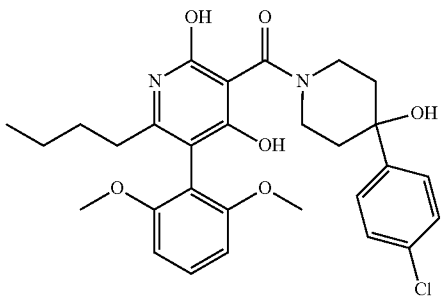 [SMILES: CCCCc1nc(O)c(C(=O)N2CCC(O)(c3ccc(Cl)cc3)CC2)c(O)c1-c1c(OC)cccc1OC] | 6-butyl-3-[4-(4-chlorophenyl)-4-hydroxypiperidine-1-carbonyl]-5-(2,6-dimethoxyphenyl)pyridine-2,4-diol | $^{1}$H NMR (500 MHz, DMSO-d6) δ 7.47 (d, J = 8.4 Hz, 2H), 7.36 (d, J = 8.4 Hz, 2H), 7.30 (t, J = 8.3 Hz, 1H), 6.68 (d, J = 8.3 Hz, 2H), 3.65 (s, 6H), 3.53 (br. s., 4H), 2.10-1.90 (m, 4H), 1.59 (d, J = 12.5 Hz, 2H), 1.33-1.22 (m, 2H), 1.12-0.96 (m, 2H), 0.62 (t, J = 7.3 Hz, 3H) | 1.53 A 541.3 | B |
| 48 | 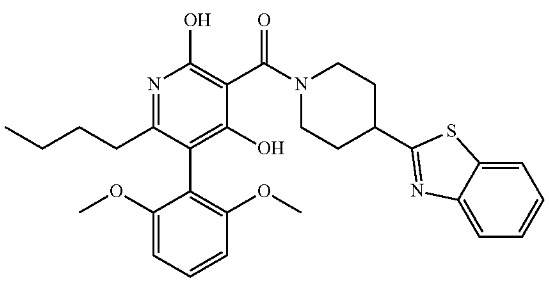 [SMILES: CCCCc1nc(O)c(C(=O)N2CCC(c3nc4ccccc4s3)CC2)c(O)c1-c1c(OC)cccc1OC] | 3-[4-(1,3-benzothiazol-2-yl)piperidine-1-carbonyl]-6-butyl-5-(2,6-dimethoxyphenyl)pyridine-2,4-diol | $^{1}$H NMR (500 MHz, DMSO-d6) δ 8.07 (d, J = 7.9 Hz, 1H), 7.95 (d, J = 7.9 Hz, 1H), 7.52-7.47 (m, 1H), 7.45-7.38 (m, 1H), 7.31 (t, J = 8.4 Hz, 1H), 6.69 (d, J = 8.5 Hz, 2H), 3.68 (s, 6H), 3.49-3.29 (m, 4H), 3.07 (br. s., 1H), 2.15 (d, J = 11.3 Hz, 2H), 2.06 (t, J = 7.8 Hz, 2H), 1.83 (br. s., 2H), 1.38-1.24 (m, 2H), 1.13-0.97 (m, 2H), 0.64 (t, J = 7.3 Hz, 3H) | 1.73 A 549.2 | B |

TABLE 1-continued

| Ex# | Structure | Name | NMR | Rt(min) method M + H | API cAMP EC$_{50}$ (nM) |
|---|---|---|---|---|---|
| 49 | 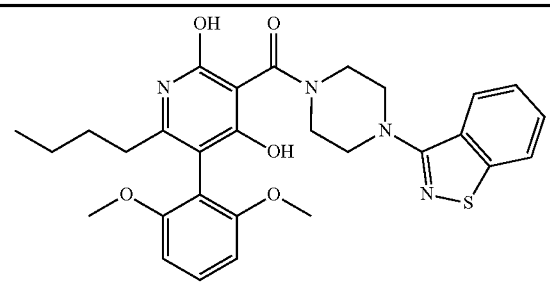 | 3-[4-(1,2-benzothiazol-3-yl)piperazine-1-carbonyl]-6-butyl-5-(2,6-dimethoxyphenyl)pyridine-2,4-diol | $^1$H NMR (500 MHz, DMSO-d6) δ 8.14 (d, J = 8.2 Hz, 1H), 8.08 (d, J = 7.9 Hz, 1H), 7.59 (t, J = 7.5 Hz, 1H), 7.47 (t, J = 7.5 Hz, 1H), 7.33 (t, J = 8.2 Hz, 1H), 6.71 (d, J = 8.5 Hz, 2H), 3.70 (s, 6H), 3.52 (br. s., 4H), 3.42 (br. s., 4H), 2.13-2.01 (m, 2H), 1.42-1.28 (m, 2H), 1.14-1.01 (m, 2H), 0.66 (t, J = 7.3 Hz, 3H) | 1.73 A 549.4 | A |
| 50 | 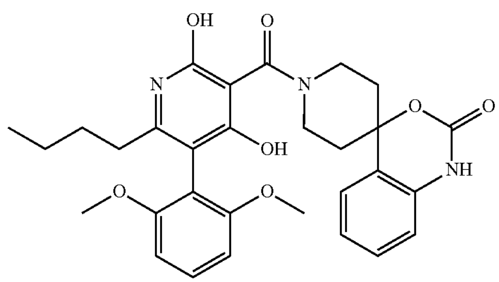 [SMILES: CCCCc1nc(O)c(C(=O)N2CCC3(CC2)OC(=O)Nc2ccccc23)c(O)c1-c1c(OC)cccc1OC] | 3'-[6-butyl-5-(2,6-dimethoxyphenyl)-2,4-dihydroxypyridine-3-carbonyl]-1,2-dihydrospiro[3,1-benzoxazine-4,4'-piperidine]-2-one | $^1$H NMR (500 MHz, DMSO-d6) δ 7.40-7.18 (m, 3H), 7.05 (t, J = 7.5 Hz, 1H), 6.92 (d, J = 7.6 Hz, 1H), 6.71 (d, J = 8.2 Hz, 2H), 3.68 (s, 6H), 3.53-3.42 (m, 4H), 2.16-1.97 (m, 6H), 1.39-1.23 (m, 2H), 1.12-0.98 (m, 2H), 0.65 (t, J = 7.3 Hz, 3H) | 1.44 A 548.2 | B |
| 51 | 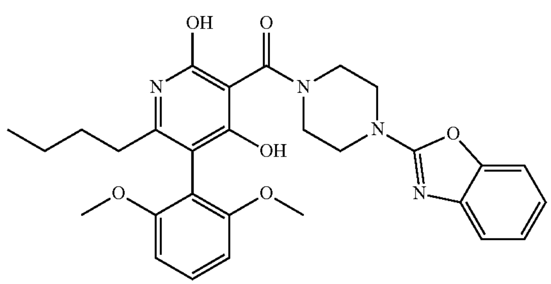 [SMILES: CCCCc1nc(O)c(C(=O)N2CCN(c3nc4ccccc4o3)CC2)c(O)c1-c1c(OC)cccc1OC] | 3-[4-(1,3-benzoxazol-2-yl)piperazine-1-carbonyl]-6-butyl-5-(2,6-dimethoxyphenyl)pyridine-2,4-diol | $^1$H NMR (500 MHz, DMSO-d6) δ 7.43 (d, J = 7.9 Hz, 1H), 7.37-7.27 (m, 2H), 7.18 (t, J = 7.6 Hz, 1H), 7.10-6.97 (m, 1H), 6.71 (d, J = 8.5 Hz, 2H), 3.70 (s, 12H), 3.55-3.41 (m, 2H), 2.15-2.04 (m, 2H), 1.37-1.24 (m, 2H), 1.13-1.01 (m, 2H), 0.66 (t, J = 7.3 Hz, 3H) | 1.57 A 533.4 | B |

| Ex# | Structure | Name | NMR | Rt(min) method M + H | API cAMP EC$_{50}$ (nM) |
|---|---|---|---|---|---|
| 52 | 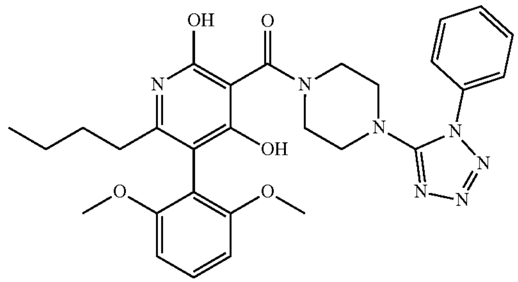 [SMILES: CCCCc1nc(O)c(C(=O)N2CCN(c3nnnn3-c3ccccc3)CC2)c(O)c1-c1c(OC)cccc1OC] | 6-butyl-5-(2,6-dimethoxyphenyl)-3-[4-(1-phenyl-1H-1,2,3,4-tetrazol-5-yl)piperazine-1-carbonyl]pyridine-2,4-diol | $^1$H NMR (500 MHz, DMSO-d6) δ 7.72-7.54 (m, 5H), 7.30 (t, J = 8.4 Hz, 1H), 6.67 (d, J = 8.5 Hz, 2H), 3.64 (s, 6H), 3.53-3.41 (m, 4H), 3.22 (br. s., 4H), 2.03 (t, J = 7.6 Hz, 2H), 1.32-1.18 (m, 2H), 1.08-0.95 (m, 2H), 0.62 (t, J = 7.3 Hz, 3H) | 1.50 A 560.2 | A |
| 53 | 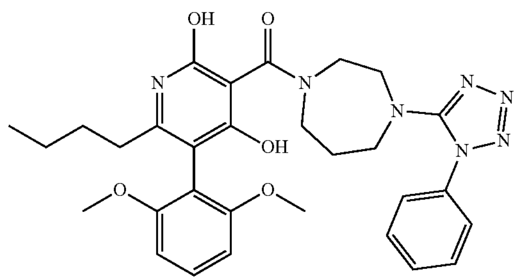 [SMILES: CCCCc1nc(O)c(C(=O)N2CCCN(c3nnnn3-c3ccccc3)CC2)c(O)c1-c1c(OC)cccc1OC] | 6-butyl-5-(2,6-dimethoxyphenyl)-3-[4-(1-phenyl-1H-1,2,3,4-tetrazol-5-yl)-1,4-diazepane-1-carbonyl]pyridine-2,4-diol | $^1$H NMR (500 MHz, DMSO-d6) δ 7.59 (d, J = 17.7 Hz, 5H), 7.42-7.28 (m, 1H), 6.70 (d, J = 8.5 Hz, 2H), 3.65 (s, 6H), 3.54-3.28 (m, 6H), (2.07 (m, 2H), 1.74 (2H), 1.55 (m, 2H), 1.33 (m, 2H), 1.07 (m, 2H), 0.65 (t, 3H) | 1.52 A 574.4 | B |
| 54 | 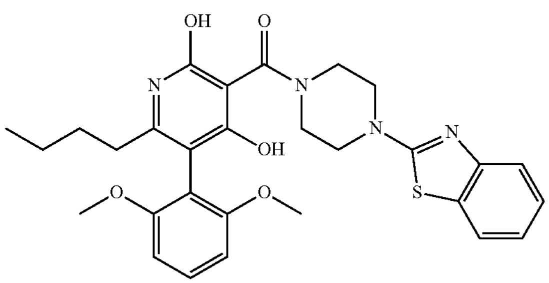 [SMILES: CCCCc1nc(O)c(C(=O)N2CCN(c3nc4ccccc4s3)CC2)c(O)c1-c1c(OC)cccc1OC] | 3-[4-(1,3-benzothiazol-2-yl)piperazine-1-carbonyl]-6-butyl-5-(2,6-dimethoxyphenyl)pyridine-2,4-diol | $^1$H NMR (500 MHz, DMSO-d6) δ 7.79 (d, J = 7.9 Hz, 1H), 7.49 (d, J = 8.2 Hz, 1H), 7.39-7.24 (m, 2H), 7.10 (t, J = 7.5 Hz, 1H), 6.71 (d, J = 8.5 Hz, 2H), 3.78-3.60 (m, 12H), 3.50 (d, J = 7.6 Hz, 2H), 2.14-2.04 (m, 2H), 1.32 (quin, J = 7.5 Hz, 2H), 1.12-0.99 (m, 2H), 0.66 (t, J = 7.3 Hz, 3H) | 1.55 B 549.4 | B |

TABLE 1-continued

| Ex# | Structure | Name | Rt(min) method M + H | API cAMP EC$_{50}$ (nM) |
|---|---|---|---|---|
| 55 | 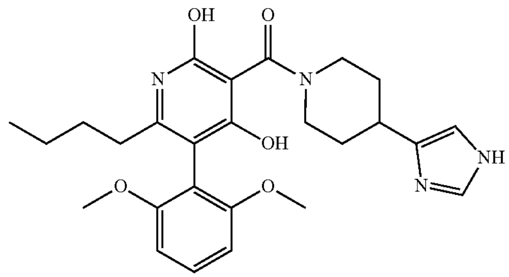 [SMILES: CCCCc1nc(O)c(C(=O)N2CCC(c3c[nH]cn3)CC2)c(O)c1-c1c(OC)cccc1OC] | 6-butyl-5-(2,6-dimethoxyphenyl)-3-[4-(1H-imidazol-4-yl)piperidine-1-carbonyl]pyridine-2,4-diol | 1.19 A 481.3 ¹H NMR (500 MHz, DMSO-d6) δ 7.56 (s, 1H), 7.31 (t, J = 8.2 Hz, 1H), 6.76 (s, 1H), 6.68 (d, J = 8.2 Hz, 2H), 3.66 (s, 6H), 3.50 (br. s., 1H), 2.98 (m, 2H), 2.77 (m, 2H), 2.05 (t, J = 7.6 Hz, 2H), 1.95-1.84 (m, 2H), 1.54 (d, J = 10.4 Hz, 2H), 1.34-1.22 (m, 2H), 1.09-0.94 (m, 2H), 0.63 (t, J = 7.3 Hz, 3H) | B |
| 56 | 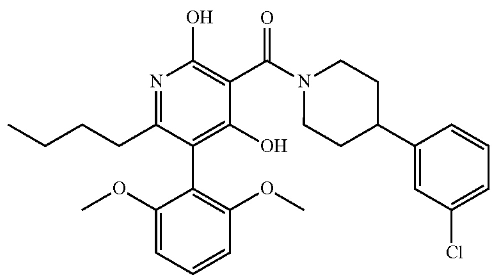 [SMILES: CCCCc1nc(O)c(C(=O)N2CCC(c3cccc(Cl)c3)CC2)c(O)c1-c1c(OC)cccc1OC] | 6-butyl-3-[4-(3-chlorophenyl)piperidine-1-carbonyl]-5-(2,6-dimethoxyphenyl)pyridine-2,4-diol | 2.00 B 525.2 ¹H NMR (500 MHz, DMSO-d6) δ 7.40-7.17 (m, 5H), 6.69 (d, J = 8.2 Hz, 2H), 3.67 (s, 6H), 3.50 (br. s., 1H), 3.06-2.76 (m, 4H), 2.05 (t, J = 7.6 Hz, 2H), 1.79 (d, J = 11.3 Hz, 2H), 1.65 (d, J = 10.4 Hz, 2H), 1.36-1.20 (m, 2H), 1.13-0.97 (m, 2H), 0.65 (t, J = 7.3 Hz, 3H) | B |
| 57 | 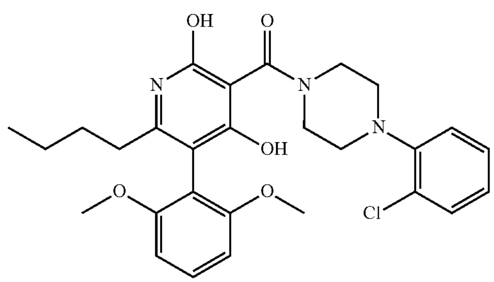 [SMILES: CCCCc1nc(O)c(C(=O)N2CCN(c3ccccc3Cl)CC2)c(O)c1-c1c(OC)cccc1OC] | 6-butyl-3-[4-(2-chlorophenyl)piperazine-1-carbonyl]-5-(2,6-dimethoxyphenyl)pyridine-2,4-diol | 1.90 B 526.3 ¹H NMR (500 MHz, DMSO-d6) δ 7.44 (d, J = 7.6 Hz, 1H), 7.37-7.24 (m, 2H), 7.16 (d, J = 7.9 Hz, 1H), 7.07 (t, J = 7.6 Hz, 1H), 6.70 (d, J = 8.5 Hz, 2H), 3.69 (s, 6H), 3.49 (4H), 3.07-2.95 (m, 14H), 2.07 (t, J = 7.6 Hz, 2H), 1.38-1.24 (m, 2H), 1.14-0.98 (m, 2H), 0.65 (t, J = 7.3 Hz, 3H) | B |

TABLE 1-continued

| Ex# | Structure | Name | NMR | Rt(min) method M + H | API cAMP EC$_{50}$ (nM) |
|---|---|---|---|---|---|
| 58 | 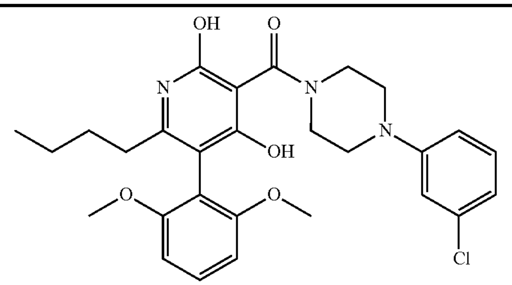 | 6-butyl-3-[4-(3-chlorophenyl)piperazine-1-carbonyl]-5-(2,6-dimethoxyphenyl)pyridine-2,4-diol | $^1$H NMR (500 MHz, DMSO-d6) δ 7.33 (t, J = 8.2 Hz, 1H), 7.24 (t, J = 8.2 Hz, 1H), 7.01-6.89 (m, 2H), 6.82 (d, J = 6.7 Hz, 1H), 6.71 (d, J = 8.2 Hz, 2H), 3.70 (s, 6H), 3.40 (4H), 3.26 (4H), 2.09 (t, J = 7.6 Hz, 2H), 1.36-1.25 (m, 2H), 1.12-1.01 (m, 2H), 0.66 (t, J = 7.3 Hz, 3H) | 1.90 B 526.2 | B |
| 59 | 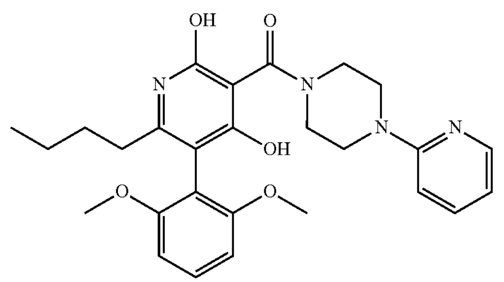 [SMILES: CCCCc1nc(O)c(C(=O)N2CCN(c3ccccn3)CC2)c(O)c1-c1c(OC)cccc1OC] | 6-butyl-5-(2,6-dimethoxyphenyl)-3-[4-(4-pyridin-2-yl)piperazine-1-carbonyl]pyridine-2,4-diol | $^1$H NMR (500 MHz, DMSO-d6) δ 8.13 (d, J = 3.4 Hz, 1H), 7.63-7.49 (m, 1H), 7.33 (t, J = 8.2 Hz, 1H), 6.86 (d, J = 8.5 Hz, 1H), 6.74-6.66 (m, 3H), 3.69 (s, 6H), 3.63-3.41 (m, 8H), 2.13-1.99 (m, 2H), 1.32 (quin, J = 7.5 Hz, 2H), 1.15-1.00 (m, 2H), 0.66 (t, J = 7.3 Hz, 3H) | 1.45 A 493.3 | B |
| 60 | 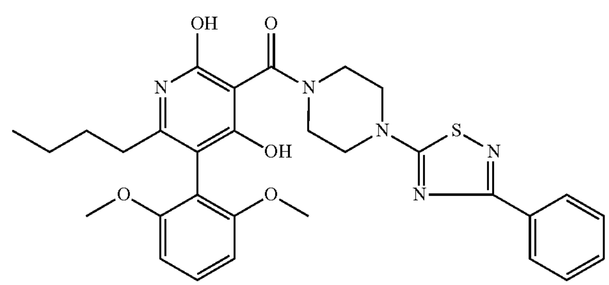 [SMILES: CCCCc1nc(O)c(C(=O)N2CCN(c3nc(-c4ccccc4)ns3)CC2)c(O)c1-c1c(OC)cccc1OC] | 6-butyl-5-(2,6-dimethoxyphenyl)-3-[4-(3-phenyl-1,2,4-thiadiazol-5-yl)piperazine-1-carbonyl]pyridine-2,4-diol | $^1$H NMR (500 MHz, DMSO-d6) δ 8.17-8.03 (m, 2H), 7.53-7.43 (m, 3H), 7.34 (t, J = 8.2 Hz, 1H), 6.71 (d, J = 8.5 Hz, 2H), 3.70 (s, 10H), 3.53-3.43 (m, 4H), 2.14-2.04 (m, 2H), 1.39-1.24 (m, 2H), 1.13-1.01 (m, 2H), 0.66 (t, J = 7.3 Hz, 3H) | 1.78 A 576.4 | B |

| Ex# | Structure | Name | NMR | Rt(min) method M + H | API cAMP EC$_{50}$ (nM) |
|---|---|---|---|---|---|
| 61 | 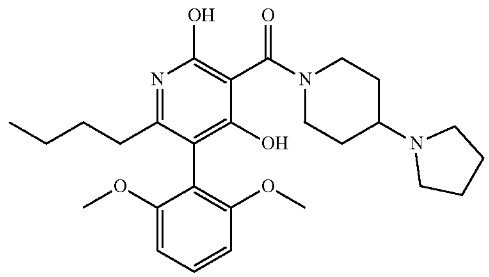 [SMILES: CCCCc1nc(O)c(C(=O)N2CCC(N3CCCC3)CC2)c(O)c1-c1c(OC)cccc1OC] | 6-butyl-5-(2,6-dimethoxyphenyl)-3-[4-(pyrrolidin-1-yl)piperidine-1-carbonyl]pyridine-2,4-diol | $^1$H NMR (500 MHz, DMSO-d6) δ 7.33 (t, J = 8.2 Hz, 1H), 6.70 (d, J = 8.2 Hz, 2H), 3.69 (s, 5H), 3.49 (br. s., 1H), 3.05-2.85 (m, 2H), 2.65 (br. s., 3H), 2.11-2.00 (m, 2H), 1.93-1.82 (m, 3H), 1.73 (br. s., 4H), 1.47 (d, J = 9.8 Hz, 2H), 1.31 (quin, J = 7.5 Hz, 2H), 1.12-1.01 (m, 2H), 0.65 (t, J = 7.3 Hz, 3H) | 1.13 A 484.5 | B |
| 62 | 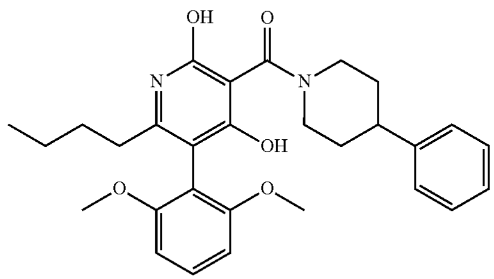 [SMILES: CCCCc1nc(O)c(C(=O)N2CCC(c3ccccc3)CC2)c(O)c1-c1c(OC)cccc1OC] | 6-butyl-5-(2,6-dimethoxyphenyl)-3-(4-phenylpiperidine-1-carbonyl)pyridine-2,4-diol | $^1$H NMR (500 MHz, DMSO-d6) δ 7.37-7.09 (m, 6H), 6.67 (d, J = 8.5 Hz, 2H), 3.66 (s, 6H), 3.47 (br. s., 1H), 3.02-2.69 (m, 4H), 2.02 (t, J = 7.5 Hz, 2H), 1.81-1.71 (m, 2H), 1.66 (d, J = 11.6 Hz, 2H), 1.36-1.24 (m, 2H), 1.13-1.00 (m, 2H), 0.65 (t, J = 7.3 Hz, 3H) | 1.81 A 491.4 | B |
| 63 | 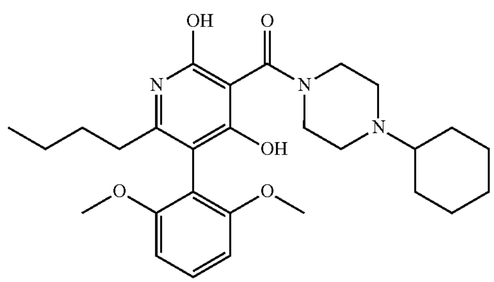 [SMILES: CCCCc1nc(O)c(C(=O)N2CCN(C3CCCCC3)CC2)c(O)c1-c1c(OC)cccc1OC] | 6-butyl-3-(4-cyclohexylpiperazine-1-carbonyl)-5-(2,6-dimethoxyphenyl)pyridine-2,4-diol | $^1$H NMR (500 MHz, DMSO-d6) δ 7.33 (t, J = 8.4 Hz, 1H), 6.71 (d, J = 8.2 Hz, 2H), 3.68 (s, 6H), 3.59-3.09 (m, 10H), 2.09-2.02 (m, 2H), 1.94 (br. s., 2H), 1.80 (br. s., 2H), 1.60 (d, J = 12.2 Hz, 1H), 1.38-1.19 (m, 6H), 1.13-1.03 (m, 3H), 0.65 (t, J = 7.3 Hz, 3H) | 1.29 A 498.5 | B |

TABLE 1-continued

| Ex# | Structure | Name | NMR | Rt(min) method M + H | API cAMP EC$_{50}$ (nM) |
|---|---|---|---|---|---|
| 64 | 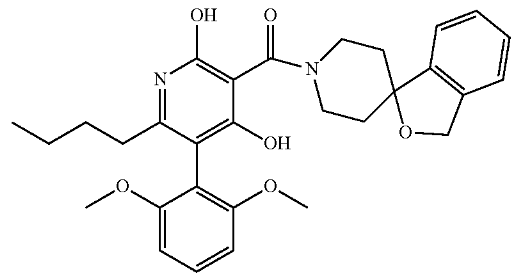 [SMILES: CCCCc1nc(O)c(C(=O)N2CCC3(CC2)OCc2ccccc23)c(O)c1-c1c(OC)cccc1OC] | 6-butyl-5-(2,6-dimethoxyphenyl)-3-({3H-spiro[2-benzofuran-1,4'-piperidine]-1'-yl}carbonyl)pyridine-2,4-diol | $^1$H NMR (500 MHz, DMSO-d6) δ 7.39-7.26 (m, 4H), 7.23 (d, J = 4.6 Hz, 1H), 6.71 (d, J = 8.5 Hz, 2H), 5.04 (s, 2H), 3.69 (s, 6H), 3.50-3.37 (m, 4H), 2.13-1.92 (m, 4H), 1.69 (d, J = 12.8 Hz, 2H), 1.31 (quin, J = 7.5 Hz, 2H), 1.12-0.98 (m, 2H), 0.65 (t, J = 7.2 Hz, 3H) | 1.69 A 519.2 | B |
| 65 | 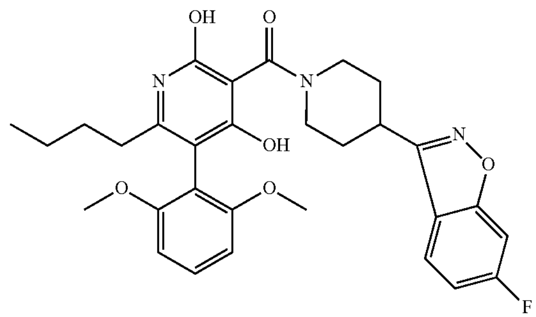 [SMILES: CCCCc1nc(O)c(C(=O)N2CCC(c3noc4cc(F)ccc34)CC2)c(O)c1-c1c(OC)cccc1OC] | 6-butyl-5-(2,6-dimethoxyphenyl)-3-[4-(6-fluoro-1,2-benzoxazol-3-yl)piperidine-1-carbonyl]pyridine-2,4-diol | $^1$H NMR (500 MHz, DMSO-d6) δ 8.07 (dd, J = 8.7, 5.3 Hz, 1H), 7.69 (d, J = 7.0 Hz, 1H), 7.38-7.23 (m, 2H), 6.70 (d, J = 8.2 Hz, 2H), 3.68 (s, 6H), 3.52-3.33 (m, 4H), 3.10 (br. s., 1H), 2.06 (d, J = 7.9 Hz, 4H), 1.91 (br. s., 2H), 1.31 (t, J = 7.2 Hz, 2H), 1.11-0.99 (m, 2H), 0.65 (t, J = 7.3 Hz, 3H) | 1.45 A 550.2 | B |
| 66 | 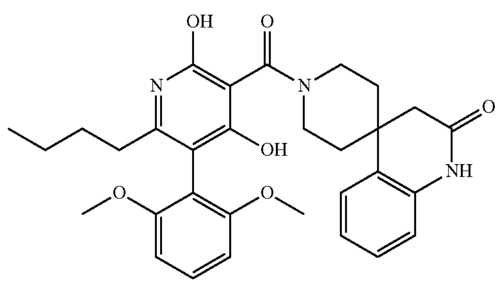 [SMILES: CCCCc1nc(O)c(C(=O)N2CCC3(CC2)CC(=O)Nc2ccccc23)c(O)c1-c1c(OC)cccc1OC] | 1-[6-butyl-5-(2,6-dimethoxyphenyl)-2,4-dihydroxypyridine-3-carbonyl]-2',3'-dihydro-1'H-spiro[piperidine-4,4'-quinoline]-2'-one | $^1$H NMR (500 MHz, DMSO-d6) δ 7.37-7.29 (m, 2H), 7.22-7.13 (m, 1H), 7.01 (t, J = 7.5 Hz, 1H), 6.91 (d, J = 7.6 Hz, 1H), 6.71 (d, J = 8.2 Hz, 2H), 3.68 (s, 6H), 3.53-3.39 (m, 7H), 2.67 (s, 2H), 2.09-2.01 (m, 2H), 1.92 (m, 2H), 1.62 (d, J = 12.5 Hz, 2H), 1.31 (t, J = 7.3 Hz, 2H), 1.13-1.02 (m, 2H), 0.65 (t, J = 7.3 Hz, 3H) | 1.45 A 546.3 | B |

TABLE 1-continued

| Ex# | Structure | Name | NMR | Rt(min) method M + H | API cAMP EC$_{50}$ (nM) |
|---|---|---|---|---|---|
| 67 | 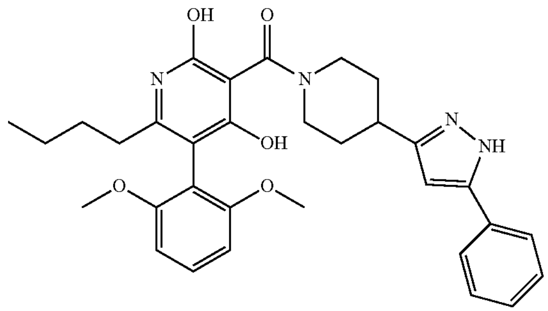 [SMILES: CCCCc1nc(O)c(C(=O)N2CCC(c3cc(-c4ccccc4)[nH]n3)CC2)c(O)c1-c1c(OC)cccc1OC] | 6-butyl-5-(2,6-dimethoxyphenyl)-3-[4-(5-phenyl-1H-pyrazol-3-yl)piperidine-1-carbonyl]pyridine-2,4-diol | $^1$H NMR (500 MHz, DMSO-d6) δ 7.75 (d, J = 7.3 Hz, 2H), 7.46-7.27 (m, 4H), 6.71 (d, J =8.2 Hz, 2H), 6.52 (s, 1H), 3.69 (s, 6H), 3.57-3.33 (m, 2H), 3.08-2.84 (m, 3H), 2.16-1.93 (m, 4H), 1.68 (d, J = 10.1 Hz 2H), 1.43-1.24 (m, 2H), 1.12-0.98 (m, 2H), 0.65 (t, J = 7.3 Hz, 3H) | 1.64 A 555.1 | C |
| 68 | 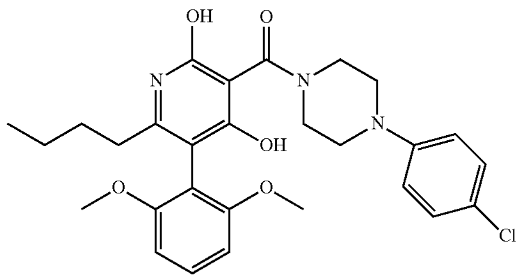 [SMILES: CCCCc1nc(O)c(C(=O)N2CCN(c3ccc(Cl)cc3)CC2)c(O)c1-c1c(OC)cccc1OC] | 6-butyl-3-[4-(4-chlorophenyl)piperazine-1-carbonyl]-5-(2,6-dimethoxyphenyl)pyridine-2,4-diol | $^1$H NMR (500 MHz, DMSO-d6) δ 7.33 (t, J = 8.4 Hz, 1H), 7.26 (d, J = 9.2 Hz, 2H), 6.98 (d, J = 8.9 Hz, 2H), 6.71 (d, J = 8.5 Hz, 2H), 3.69 (s, 5H), 3.57-3.40 (m, 7H), 3.21 (br. s., 4H), 2.13-2.00 (m, 2H), 1.39-1.25 (m, 2H), 1.13-1.00 (m, 2H), 0.65 (t, J = 7.3 Hz, 3H) | 1.78 A 526.2 | B |
| 69 | 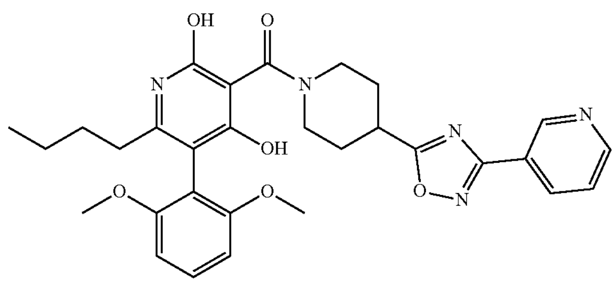 [SMILES: CCCCc1nc(O)c(C(=O)N2CCC(c3nc(-c4cccnc4)no3)CC2)c(O)c1-c1c(OC)cccc1OC] | 6-butyl-5-(2,6-dimethoxyphenyl)-3-{4-[3-(pyridin-3-yl)-1,2,4-oxadiazol-5-yl]piperidine-1-carbonyl}pyridine-2,4-diol | $^1$H NMR (500 MHz, DMSO-d6) δ 9.18 (s, 1H), 8.79 (d, J = 3.7 Hz, 1H), 8 38 (d, J = 7.9 Hz, 1H), 7.69-7.55 (m, 1H), 7.40-7.18 (m, 1H), 6.74-6.60 (m, 2H), 3.75-3.65 (m, 5H), 3.56-3.05 (m, 3H), 2.16 (d, J = 13.1 Hz, 2H), 2.10-2.01 (m, 2H), 1.91 (s, 11H), 1.42-1.22 (m, 3H), 1.16-1.01 (m, 2H), 0.66 (t, J = 7.3 Hz, 3H) | 1.50 A 561.2 | B |

Example 70. 6-(Ethoxymethyl)-5-(4-fluoro-2,6-dimethoxyphenyl)-3-[(3R)-3-phenylpyrrolidine-1-carbonyl]pyridine-2,4-diol)

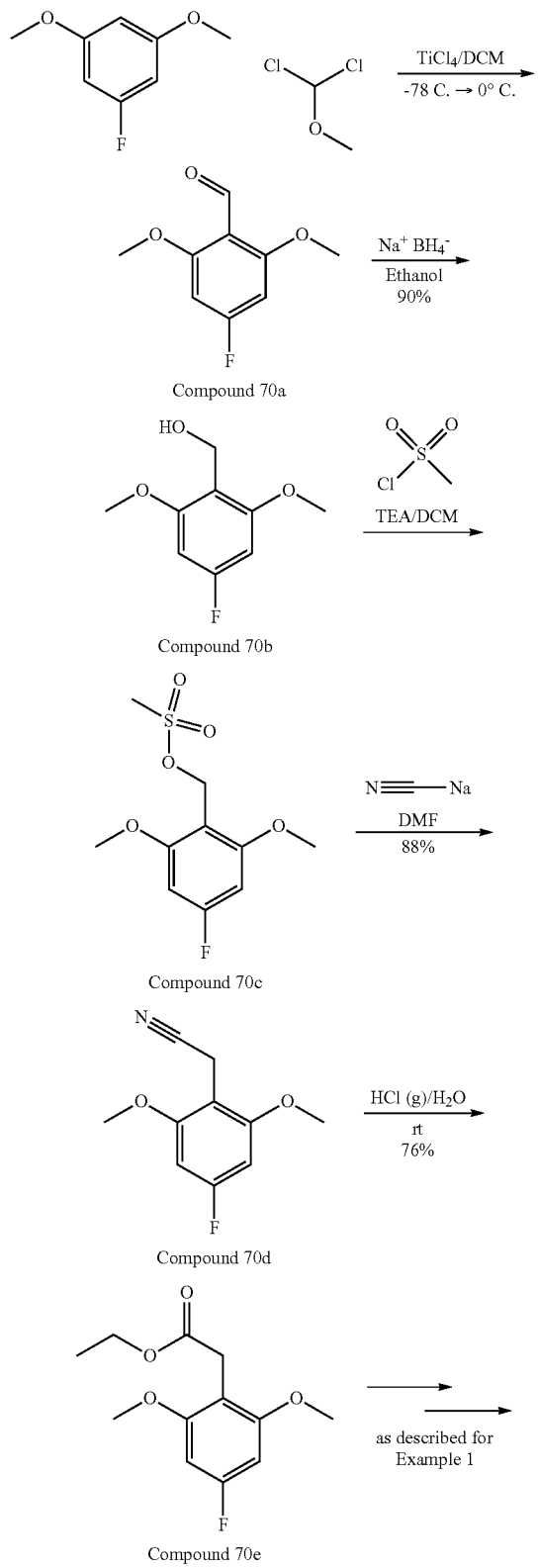

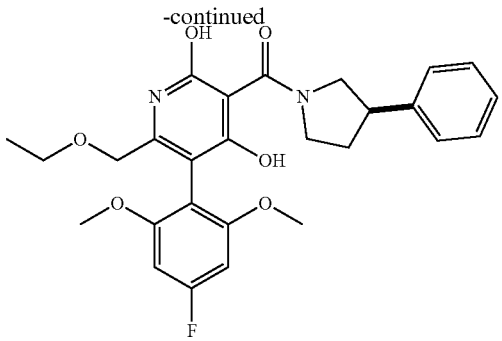

Example 70

Compound 70a. 4-Fluoro-2,6-dimethoxybenzaldehyde

To a stirred solution of 1-fluoro-3,5-dimethoxybenzene (3.00 g, 19.2 mmol) in dichloromethane (45 mL) was slowly added a 1.0 M solution of $TiCl_4$ in dichloromethane (38.4 mL, 38.4 mmol) at 0° C. over 15 min. The mixture was cooled to −78° C. and treated with dichloro(methoxy)methane (2.26 mL, 25.0 mmol) dropwise. The reaction mixture was stirred at −78° C. for 30 min and allowed to warm to 0° C. After 1 hour, the mixture was poured into cold dilute HCl solution, and the aqueous phase was extracted with ethyl acetate (2×). The organic fractions were combined, dried over $Na_2SO_4$, filtered and concentrated under reduced pressure. The residue was purified on silica gel chromatography eluting with 0% to 30% ACN/DCM to afford Compound 70a (1.60 g, 45%) as a white solid. MS m/z=184.9 (M+H). $^1$H NMR (400 MHz, $CDCl_3$) δ 10.42 (s, 1H), 6.34 (s, 1H), 6.31 (s, 1H), 3.91 (s, 6H)

Compound 70b. (4-Fluoro-2,6-dimethoxyphenyl)methanol

To a suspension of Compound 70a (2.52 g, 13.7 mmol) in ethanol (60 mL) at 0° C. was added sodium borohydride (0.35 g, 9.1 mmol). The ice bath was removed and stirring continued for 20 min. The mixture was cooled to 0° C. then quenched by the addition of saturated ammonium chloride solution. The resulting suspension was concentrated and redissolved in EtOAc/water mixture. The layers were separated and the organic fraction was washed with brine, dried over $Na_2SO_4$, and concentrated to give Compound 70b (2.3 g, 90%) as a white solid which was used without further purification. LCMS (Method C) Rt=1.38 min. $^1$H NMR (400 MHz, $CDCl_3$) δ 6.33 (s, 1H), 6.31 (s, 1H), 4.74 (m, 2H), 3.85 (s, 6H)

Compound 70c. 4-Fluoro-2,6-dimethoxybenzyl methanesulfonate

To a solution of Compound 70b (2.3 g, 13 mmol) in dichloromethane (80 mL) was added TEA (3.5 mL, 25 mmol). The mixture was cooled to 0° C. and treated with mesyl chloride (7.4 mL, 0.095 mol) in dichloromethane (25 mL). After 30 min, the mixture was diluted with dichloromethane (100 mL) and the organic phase washed with water (3×50 mL). The organic layer was dried over $Na_2SO_4$ and concentrated under reduced pressure to give Compound 70c (2.7 g, 82%) which was used without further purifica-

Compound 70d. 2-(4-Fluoro-2,6-dimethoxyphenyl)acetonitrile

To a solution of Compound 70c (2.7 g, 10 mmol) in DMF (40 mL) was added sodium cyanide (1.0 g, 20 mmol) and the mixture was stirred for 30 min. The mixture was diluted with water (800 mL) and extracted with 30% ethyl acetate in hexane (3×200 mL). The combined organic layers were dried over $Na_2SO_4$ and concentrated under reduced pressure. The residue was purified by silica gel chromatography eluting with 0% to 5% ethyl acetate in hexane to give Compound 70d (1.8 g, 88%). LCMS (Method C) Rt=1.57, MS m/z=196.0 (M+H). $^1$H NMR (400 MHz, DMSO-$d_6$) δ 6.67 (s, 1H), 6.64 (s, 1H), 3.85 (s, 6H), 3.65 (s, 2H)

Compound 70e. Ethyl 2-(4-fluoro-2,6-dimethoxyphenyl)acetate

To a solution of Compound 70d (1.75 g, 8.97 mmol) in EtOH (40 mL) was bubbled HCl gas for a 2 h period. The mixture was concentrated under reduced pressure and the residue was diluted with water (50 mL) and heated at 40° C. overnight. After allowing to cool to rt, the reaction mixture was extracted with ethyl acetate (3×50 mL). The combined organic layers were dried over $Na_2SO_4$ and concentrated under reduced pressure to give Compound 70e (1.6 g, 76%). LCMS (Method C) Rt=1.86. MS m/z=243.1 (M+H). $^1$H NMR (400 MHz, DMSO-$d_6$) δ 6.58 (s, 1H), 6.55 (s, 1H), 4.05 (q, J=7.0 Hz, 2H), 3.76 (s, 6H), 3.49 (s, 2H), 1.17 (t, J=7.2 Hz, 3H)

Example 70. 1-({5-[6-(ethoxymethyl)-5-(4-fluoro-2,6-dimethoxyphenyl)-2,4-dihydroxypyridin-3-yl]-1,3,4-oxadiazol-2-yl}methyl)-1,2-dihydropyridin-2-one Example 70 was prepared from Compound 70e using the method described for Example 1 (12%). LCMS (Method C) Rt=1.86 min, m/z=497.1 (M+H). $^1$H NMR (400 MHz, CHLOROFORM-d) δ 7.33 (m, 5H), 6.38 (m, 2H), 4.16 (s, 2H), 3.87-3.77 (m, 2H), 3.74 (s, 6H), 3.71-3.64 (m, 2H), 3.54 (m, 3H), 2.44-2.28 (m, 2H), 1.24 (t, J=6.8 Hz, 3H). Human APJ cAMP $EC_{50}$ Potency range B.

Example 71. 6-butyl-5-(3-fluoro-2,6-dimethoxyphenyl)-3-[(3R)-3-phenylpyrrolidine-1-carbonyl]pyridine-2,4-diol

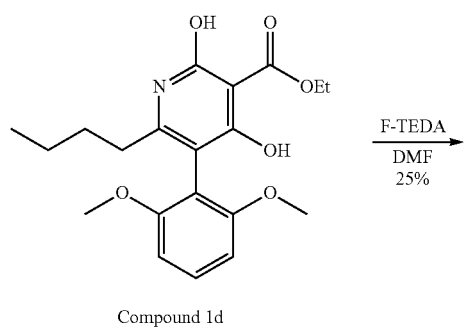

Compound 1d

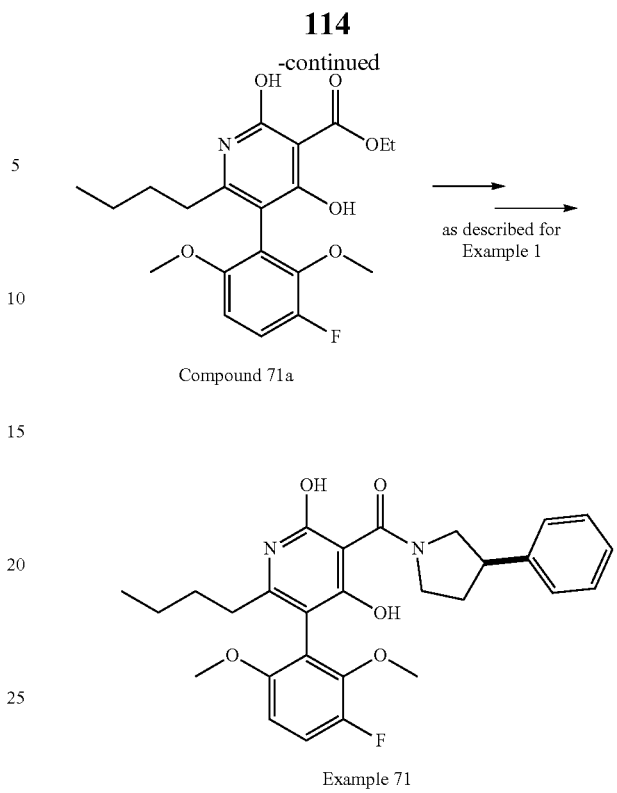

Compound 71a

Example 71

Compound 71a. Ethyl 6-butyl-5-(3-fluoro-2,6-dimethoxyphenyl)-2,4-dihydroxynicotinate To a solution of Compound 1d (650 mg, 1.73 mmol) in DMF (7.5 mL) at 0° C. was slowly added 1-Chloromethyl-4-fluoro-1,4-diazoniabicyclo[2.2.2]octane bis(tetrafluoroborate), N-Chloromethyl-N'-fluorotriethylenediammonium bis(tetrafluoroborate) (F-TEDA, 613 mg, 1.73 mmol). After stirring for one minute at 0° C., the ice bath was removed and stirring continued at rt for 16 h. The mixture was diluted with EtOAc, the organic phase washed with water (3×), then brine, dried over $Na_2SO_4$, filtered and concentrated under reduced pressure. The resulting solid was triturated with EtOAc (3×). The triturate was evaporated under reduced pressure and the residue purified by silica gel chromatography eluting with 0-100% ethyl acetate in hexane to give Compound 71a (170 mg, 25%) as a white solid. LCMS (Method C) Rt=1.75. MS m/z=394.1.0 (M+H). $^1$H NMR (400 MHz, CDCl$_3$) δ 7.10 (dd, J=11.2, 9.2 Hz, 1H), 6.69-6.54 (m, 1H), 4.41 (q, J=7.0 Hz, 2H), 3.82 (m, 3H), 3.72 (s, 3H), 2.35 (t, J=7.8 Hz, 2H), 1.52 (td, J=7.5, 2.5 Hz, 2H), 1.40 (t, J=7.0 Hz, 3H), 0.78 (t, J=7.3 Hz, 3H)

Example 71. 6-butyl-5-(3-fluoro-2,6-dimethoxyphenyl)-3-[(3R)-3-phenylpyrrolidine-1-carbonyl]pyridine-2,4-diol Example 71 was prepared from Compound 71a using the method described for Example 1 (13%). LCMS (Method C) Rt=2.04 min, m/z=495.1 (M+H). $^1$H NMR (400 MHz, CHLOROFORM-d) δ 7.33 (m, 5H), 6.38 (m, 2H), 4.16 (s, 2H), 3.87-3.77 (m, 2H), 3.74 (s, 6H), 3.71-3.64 (m, 2H), 3.54 (m, 3H), 2.44-2.28 (m, 2H), 1.24 (t, J=6.8 Hz, 3H). Human APJ cAMP $EC_{50}$ Potency range A.

Example 72. 6-butyl-3-[3-(2-chlorophenyl)pyrrolidine-1-carbonyl]-5-(2,6-dimethoxyphenyl)pyridine-2,4-diol

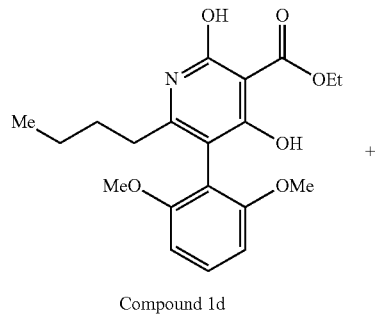

Compound 1d

+

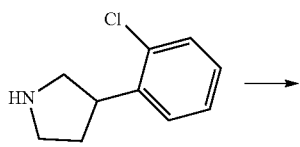

→

-continued

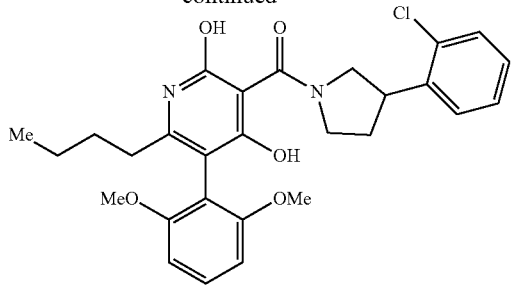

Example 72

Example 72 was prepared from compound 1d and 3-(2-chlorophenyl)pyrrolidine by the general procedures described for Example 1. The racemic material was separated using chiral SFC chromatography (Column: Chiralpak OD-H, 30×250 mm, 5 micron, Column: Chiralpak OD-H, 30×250 mm, 5 micron, Mobile Phase: 35% MeOH/65% $CO_2$, Flow Conditions: 85 mL/min, 150 Bar, 40° C., Detector Wavelength: 220 nm, Injection: 0.5 mL of ~6.5 mg/mL in MeOH:ACN (1:1)). Two peaks were isolated. Example 72 (42% yield) was designated as peak 2 (peak 2 retention time=13.6, Chiral analytical HPLC: Column: Chiralpak OD-H, 4.6×250 mm, 5 micron, Mobile Phase: 35% MeOH/65% $CO_2$, Flow Conditions: 2.0 mL/min, 150 Bar, 40° C., Detector Wavelength: 220 nm, Injection: 10 μL of ~1 mg/mL in MeOH). LCMS (Method C) Rt=2.07 min, m/z=511.1 (M+H). $^1$H NMR (500 MHz, DMSO-d6) δ 7.50 (br. s., 2H), 7.34 (dd, J=14.3, 6.9 Hz, 3H), 6.71 (d, J=8.0 Hz, 2H), 3.91 (br. s., 1H), 3.69 (br. s., 6H), 2.26 (br. s., 1H), 2.08 (br. s., 3H), 1.50 (br. s., 2H), 1.38-1.21 (m, 2H), 1.07 (br. s., 2H), 1.00-0.84 (m, 2H), 0.65 (br. s., 3H). Human APJ cAMP $EC_{50}$ Potency range A.

The following compounds, Examples 8, 9, 35, and Examples 37 to 40, were prepared by the general procedures described for Example 72.

TABLE 2

| Ex# | Structure | Name | Chiral HPLC retention time (min) | NMR | Rt(min) method M + H | APJ cAMP EC$_{50}$ (nM) |
|---|---|---|---|---|---|---|
| 8 | 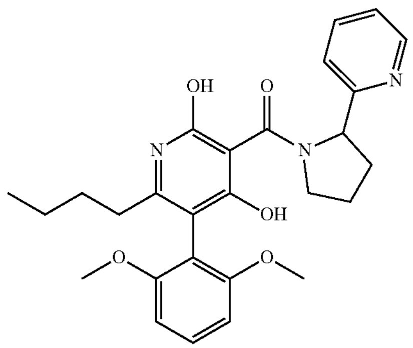 [SMILES: CCCCc1nc(O)c(C(=O)N2CCCC2c2ccccn2)c(O)c1-c1c(OC)cccc1OC] | 6-butyl-5-(2,6-dimethoxyphenyl)-3-[2-(pyridin-2-yl)pyrrolidine-1-carbonyl]pyridine-2,4-diol | Racemic | $^1$H NMR (500 MHz, DMSO-d6) δ 7.44-7.24 (m, 5H), 6.71 (d, J = 8.2 Hz, 2H), 3.93-3.79 (m, 1H), 3.69 (s, 6H), 3.43 (br. s., 1H), 3.34 (br. s., 1H), 2.27 (br. s., 2H), 2.15-1.92 (m, 4H), 1.33-1.20 (m, 2H), 1.07 (br. s., 2H), 0.66 (br. s., 3H) | 1.74 A 477.4 | A |
| 9 | 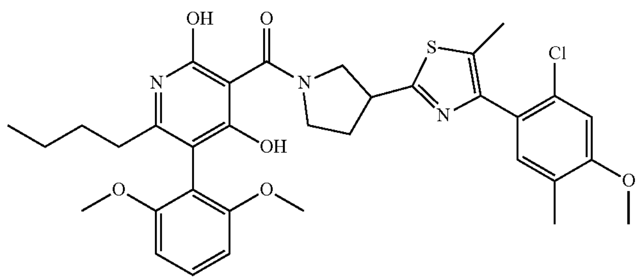 [SMILES: CCCCc1nc(O)c(C(=O)N2CCC(c3nc(-c4cc(C)c(OC)cc4Cl)c(C)s3)C2)c(O)c1-c1c(OC)cccc1OC] | 6-butyl-3-[3-[4-(2-chloro-4-methoxy-5-methylphenyl)-5-methyl-1,3-thiazol-2-yl]pyrrolidine-1-carbonyl]-5-(2,6-dimethoxyphenyl)pyridine-2,4-diol | racemic | $^1$H NMR (500 MHz, DMSO-d6) δ 7.32 (d, J = 8.5 Hz, 1H), 7.22 (s, 2H), 6.71 (d, J = 8.2 Hz, 2H), 3.95-3.79 (m, 6H), 3.73-3.58 (m, 6H), 3.39-3.22 (m, 1H), 2.26 (br. s., 3H), 2.15 (br. s., 3H), 2.09 (br. s., 2H), 1.32 (br. s., 2H), 1.09 (br. s., 2H), 0.66 (br. s., 3H) | 2.20 A 652.4 | A |
| 35 | 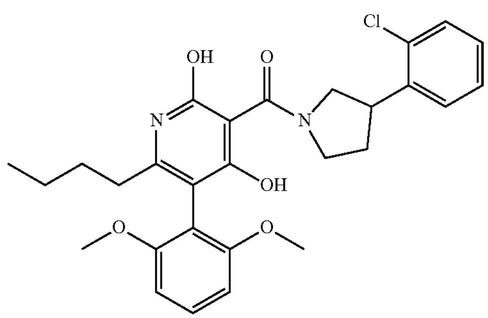 [SMILES: CCCCc1nc(O)c(C(=O)N2CCC(c3ccccc3Cl)C2)c(O)c1-c1c(OC)cccc1OC] | 6-butyl-3-[3-(2-chlorophenyl)pyrrolidine-1-carbonyl]-5-(2,6-dimethoxyphenyl)pyridine-2,4-diol | Rt = 10.05 (peak 1) Chiralpak OD-H, 4.6 x 250 mm, 5 micron, Mobile Phase: 35% MeOH/65% CO$_2$, Flow Conditions: 2.0 mL/min, 150 Bar, 40° C., Detector Wavelength: 220 | $^1$H NMR (500 MHz, DMSO-d6) δ 7.51 (d, J = 7.4 Hz, 2H), 7.40-7.26 (m, 3H), 6.71 (d, J = 8.3 Hz, 2H), 3.93 (br. s., 1H), 3.69 (br. s., 6H), 2.26 (br. s., 1H), 2.09 (br. s., 3H), 1.50 (br. s., 2H), 1.31 (br. s., 2H), 1.07 (br. s., 2H), 0.96 (br. s., 2H), 0.65 (br. s., 3H) | 2.07 C 511.1 | A |

TABLE 2-continued

| Ex# | Structure | Name | Chiral HPLC retention time (min) | NMR | Rt(min) method M + H | APJ cAMP EC$_{50}$ (nM) |
|---|---|---|---|---|---|---|
| 37 | 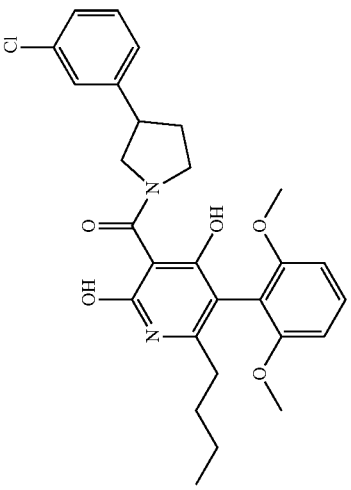 | 6-butyl-3-[3-(3-chlorophenyl)pyrrolidine-1-carbonyl]-5-(2,6-dimethoxyphenyl)pyridine-2,4-diol | Rt = 19.39 (peak 1) Chiralpak OD-H, 4.6 × 250 mm, 5 micron, Mobile Phase: 35% MeOH/65% CO$_2$, Flow Conditions: 2.0 mL/min, 150 Bar, 40° C., Detector Wavelength: 220 | $^1$H NMR (500 MHz, DMSO-d6) δ 7.47-7.24 (m, 5H), 6.70 (d, J = 8.0 Hz, 2H), 3.90 (br. s., 1H), 3.68 (br. s., 13H), 2.27 (br. s., 1H), 2.09 (br. s., 2H), 1.31 (br. s., 2H), 1.07 (br. s., 2H), 0.64 (br. s., 3H) | 2.09 C 511.1 | A |
| 38 | 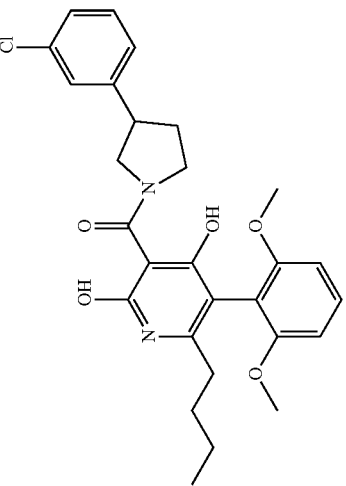 | 6-butyl-3-[3-(3-chlorophenyl)pyrrolidine-1-carbonyl]-5-(2,6-dimethoxyphenyl)pyridine-2,4-diol | Rt = 21.82 (peak 2) Chiralpak OD-H, 4.6 × 100 mm, 3 micron, Mobile Phase: 35% MeOH/65% CO$_2$, Flow Conditions: 0.8 mL/min, 2000 PSI, 45° C., wavelength: 220 nm | $^1$H NMR (500 MHz, DMSO-d6) δ 7.44-7.26 (m, 5H), 6.71 (d, J = 7.2 Hz, 2H), 3.90 (br. s., 1H), 3.68 (br. s., 6H), 2.28 (br. s., 1H), 2.09 (br. s., 2H), 1.31 (br. s., 2H), 1.07 (br. s., 2H), 0.65 (br. s., 3H) | 2.09 C 511.1 | A |

TABLE 2-continued

| Ex# | Structure | Name | Chiral HPLC retention time (min) | NMR | Rt(min) method M + H | APJ cAMP EC$_{50}$ (nM) |
|---|---|---|---|---|---|---|
| 39 | 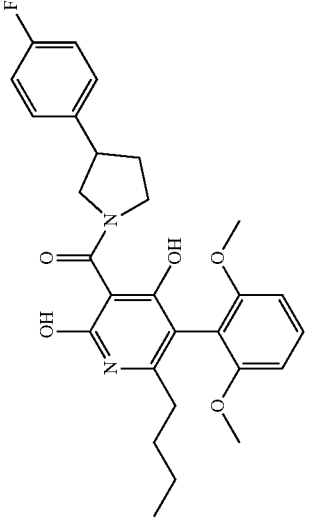 | 6-butyl-5-(2,6-dimethoxyphenyl)-3-[3-(4-fluorophenyl)pyrrolidine-1-carbonyl]pyridine-2,4-diol | Rt = 21.82 (peak 1) Chiralpak OD-H, 4.6 × 100 mm, 3 micron, Mobile Phase: 35% MeOH/65% CO$_2$, Flow Conditions: 0.8 mL/min, 2000 PSI, 45° C., wavelength: 220 nm | $^1$H NMR (500 MHz, DMSO-d6) δ 7.39 (br. s., 3H), 7.16 (br. s., 2H), 6.70 (br. s., 2H), 3.94-3.86 (m, 1H), 3.68 (br. s., 6H), 2.26 (br. s., 1H), 2.08 (br. s., 3H), 1.38-1.20 (m, 5H), 1.07 (br. s., 2H), 0.87 (br. s., 1H), 0.65 (br. s., 3H) | 1.99 C 495.1 | A |
| 40 | 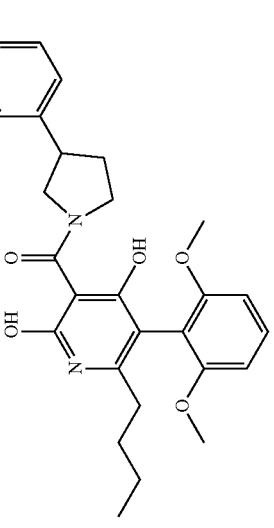 | 6-butyl-5-(2,6-dimethoxyphenyl)-3-[3-(4-fluorophenyl)pyrrolidine-1-carbonyl]pyridine-2,4-diol | Rt = 15.66 (peak 2) Chiralpak OD-H, 4.6 × 100 mm, 3 micron, Mobile Phase: 35% MeOH/65% CO$_2$, Flow Conditions: 0.8 mL/min, 2000 PSI, 45° C., wavelength: 220 nm | 1H NMR (500 MHz, DMSO-d6) δ 7.44-7.26 (m, 3H), 7.17 (br. s., 2H), 6.71 (2H), 3.92 (br. s., 1H), 3.69 (br. s., 6H), 2.27 (br. s., 1H), 2.09 (br. s., 3H) 1.36-1.21 (m, 5H), 1.08 (br. s., 2H), 0.88 (br. s., 1H), 0.66 (br. s., 3H) | 1.99 C 495.1 | A |

Example 74. (6-butyl-5-(2,6-dimethoxyphenyl)-2,4-dihydroxypyridin-3-yl)(3-(5-chloropyridin-2-yl)pyrrolidin-1-yl)methanone

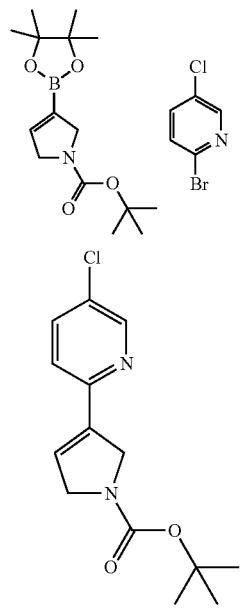

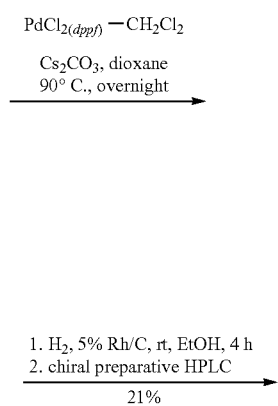

Compound 74a

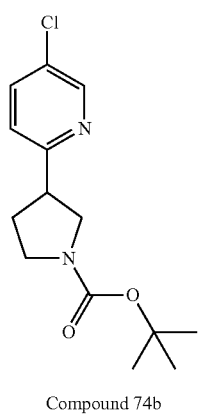

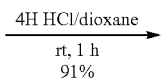

Compound 74b

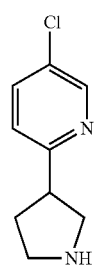

Compound 74c

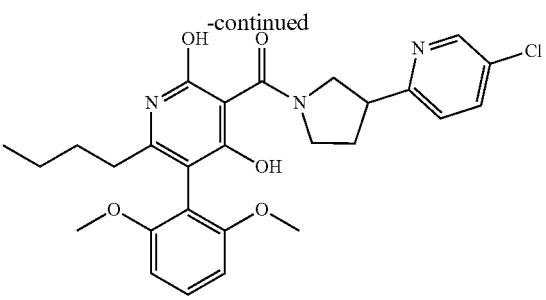

Example 74

Compound 74a. tert-butyl 3-(5-chloropyridin-2-yl)-2,5-dihydro-1H-pyrrole-1-carboxylate A mixture of tert-butyl 3-(4,4,5,5-tetramethyl-1,3,2-dioxaborolan-2-yl)-2,5-dihydro-1H-pyrrole-1-carboxylate (106 mg, 0.360 mmol), 2-bromo-5-chloropyridine (76 mg, 0.40 mmol), cesium carbonate (350 mg, 1.10 mmol) and PdCl$_2$(dppf)-CH$_2$Cl$_2$ (18 mg, 0.022 mmol) in dioxane (2.4 mL) and water (0.5 mL) was degassed and heated at 90° C. for 14 h. The mixture was diluted with EtOAc, washed with brine, dried over sodium sulfate, filtered and concentrated under reduced pressure. The residue was subjected to silica gel chromatography eluting with 0-100% EtOAc/hexane to give 74a (50 mg, 0.18 mmol, 50% yield) as a yellow solid. $^1$H NMR (400 MHz, CHLOROFORM-d) δ 8.62-8.41 (m, 1H), 7.82-7.57 (m, 1H), 7.40-7.16 (m, 1H), 6.60-6.32 (m, 1H), 4.60-4.49 (m, 2H), 4.41-4.27 (m, 2H), 1.52-1.45 (m, 9H).

Compound 74b. tert-butyl 3-(5-chloropyridin-2-yl)pyrrolidine-1-carboxylate

A mixture of 74a (530 mg, 1.90 mmol) and 5% Rh/C (390 mg, 0.190 mmol) in EtOH (8 mL) was stirred under hydrogen atmosphere (ballon) for 4 h. The mixture was filtered through Celite and concentrated under reduced pressure. The residue was purified using silica gel chromatography eluting with 0-100% EtOAc/hexane, followed by chiral SFC preparative HPLC (column: Chiralpak IC, 30×250 mm, 5 micron; mobile phase: 10% IPA/0.1% DEA/90% CO$_2$; flow condition: 85 mL/min, 150 bar, 40° C.; wavelength: 220 nm) to give compound 74b (designated as peak 1, 110 mg, 21% yield). Peak 1 retention time=11.87 min (Chiralpak IC, 4.6×250 mm, 5 micron; mobile phase: 10% IPA/0.1% DEA/90% CO$_2$; flow condition: 2.0 mL/min, 150 bar, 40° C.; wavelength: 220 nm. LCMS (Method B) Rt=0.96 min, m/z=283.2 (M+H). $^1$H NMR (400 MHz, CHLOROFORM-d) δ 8.52 (d, J=2.2 Hz, 1H), 7.64-7.56 (m, 1H), 7.14 (d, J=8.4 Hz, 1H), 3.97-3.29 (m, 5H), 2.34-2.05 (m, 2H), 1.50-1.44 (m, 9H).

Compound 74c. tert-butyl 3-(5-chloropyridin-2-yl)-2,5-dihydro-1H-pyrrole-1-carboxylate Compound 74b (110 mg, 0.38 mmol) and 4N HCl/dioxane (1.0 mL, 4.0 mmol) was stirred at rt for 5 h. The mixture was diluted with diethyl ether, and the precipitate was collected by filtration to give compound 74c (89 mg, 0.35 mmol, 91% yield) as a white solid. LCMS (Method B) Rt=0.47 min, m/z=183.1 (M+H). $^1$H NMR (500 MHz, DMSO-d6) δ 7.79 (d, J=2.5 Hz, 1H), 7.24-6.97 (m, 1H), 6.83-6.56 (m, 1H), 3.01 (s, 1H), 2.83 (s, 2H), 2.77-2.67 (m, 1H), 2.54 (br. s., 2H), 1.85-1.57 (m, 1H), 1.53-1.14 (m, 1H).

Example 74. (6-butyl-5-(2,6-dimethoxyphenyl)-2,4-dihydroxypyridin-3-yl)(3-(5-chloropyridin-2-yl)pyrrolidin-1-yl)methanone Example 74 was prepared (35% yield) from Compound 1d and Compound 74c using the method described for Example 1. LCMS (Method B) Rt=0.89 min, m/z=512.3 (M+H). $^1$H NMR (500 MHz, DMSO-d6) δ 8.56 (br. s., 1H), 7.92-7.83 (m, 1H), 7.51-7.38 (m, 1H), 7.32 (s, 1H), 6.69 (d, J=8.3 Hz, 2H), 3.66 (br. s., 10H), 2.89 (s, 1H), 2.35-2.17 (m, 1H), 2.08 (br. s., 3H), 1.37-1.22 (m, 2H), 1.08-0.98 (m, 2H), 0.69-0.50 (m, 3H). Human APJ cAMP $EC_{50}$ Potency range A.

The following compounds, Example 75 to Example 87, were prepared by the general procedures described for Example 74.

TABLE 3

| Ex# | Structure | Name | Chiral Amine intermediate with Retention time (min) | NMR | Rt(min) method M + H | APJ cAMP EC$_{50}$ (nM) |
|---|---|---|---|---|---|---|
| 75 | 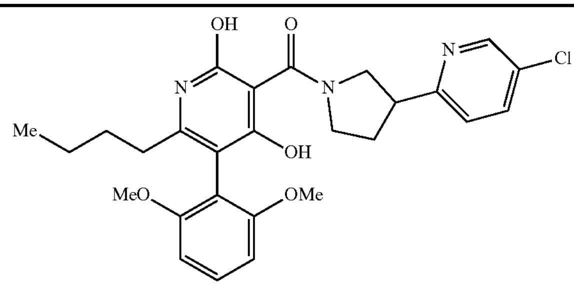 | 6-butyl-3-[3-(5-chloropyridin-2-yl)pyrrolidine-1-carbonyl]-5-(2,6-dimethoxyphenyl)pyridine-2,4-diol | Rt = 2.84, isomer 2) Whelko (4.6 × 250 mm, 5 micron; mobile phase: 10% IPA/90% CO$_2$; flow condition: 3.0 mL/min, 140 bar, 40° C.; wavelength: 220 nm. | $^1$H NMR (500 MHz, DMSO-d6) δ 8.56 (br. s., 1H), 7.92-7.83 (m, 1H), 7.51-7.38 (m, 1H), 7.32 (s, 1H), 6.69 (d, J = 8.3 Hz, 2H), 3.66 (br. s., 10H), 2.89 (s, 1H), 2.35-2.17 (m, 1H), 2.08 (br. s., 3H), 1.37-1.22 (m, 2H), 1.08-0.98 (m, 2H), 0.69-0.50 (m, 3H) | 0.89 A 512.3 | A |
| 76 | 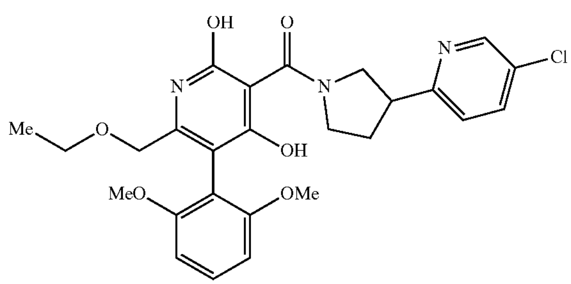 [SMILES: CCOCc1nc(O)c(C(=O)N2CCC(c3ccc(Cl)cn3)C2)c(O)c1-c1c(OC)cccc1OC] | 3-[3-(5-chloropyridin-2-yl)pyrrolidine-1-carbonyl]-5-(2,6-dimethoxyphenyl)-6-(ethoxymethyl)pyridine-2,4-diol | Rt = 3.85, isomer 1) Whelko (4.6 × 250 mm, 5 micron; mobile phase: 10% IPA/90% CO$_2$; flow condition: 3.0 mL/min, 140 bar, 40° C.; wavelength: 220 nm. | $^1$H NMR (500 MHz, DMSO-d6) δ 8.57 (br. s., 1H), 7.88 (d, J = 6.7 Hz, 1H), 7.50-7.39 (m, 1H), 7.33 (s, 1H), 6.70 (d, J = 8.3 Hz, 2H), 3.89 (br. s., 2H), 3.67 (br. s., 6H), 3.33-3.19 (m, 2H), 2.55 (s, 6H), 2.34-2.23 (m, 1H), 2.16-1.92 (m, 1H), 0.97 (br. s., 3H) | 0.81 A 514.3 | A |

TABLE 3-continued

| Ex# | Structure | Name | Chiral Amine intermediate with Retention time (min) | NMR | Rt(min) method M + H | APJ cAMP EC$_{50}$ (nM) |
|---|---|---|---|---|---|---|
| 77 | 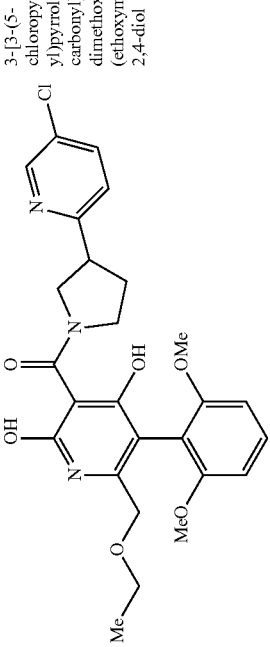 | 3-[3-(5-chloropyridin-2-yl)pyrrolidine-1-carbonyl]-5-(2,6-dimethoxyphenyl)-6-(ethoxymethyl)pyridine-2,4-diol | 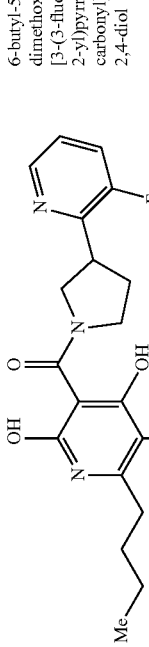 Rt = 2.84, (isomer 2) Whelko (4.6 × 250 mm, 5 micron; mobile phase: 10% IPA/90% CO$_2$; flow condition: 3.0 mL/min, 140 bar, 40° C.; wavelength: 220 nm. | $^1$H NMR (500 MHz, DMSO-d6) δ 8.57 (br. s., 1H), 7.88 (d, J = 6.7 Hz, 1H), 7.50-7.39 (m, 1H), 7.33 (s, 1H), 6.70 (d, J = 8.3 Hz, 2H), 3.89 (br. s., 2H), 3.67 (br. s., 6H), 3.33-3.19 (m, 2H), 2.55 (s, 6H), 2.34-2.23 (m, 1H), 2.16-1.92 (m, 1H), 0.97 (br. s., 3H) | 0.81 A 514.3 | A |
| 78 | 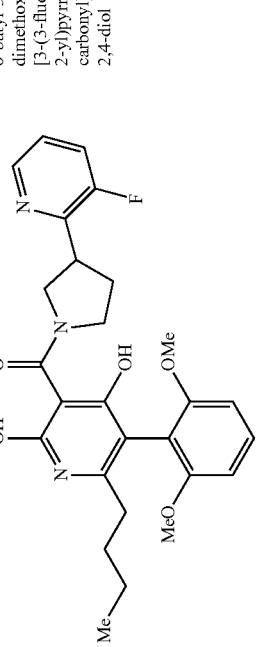 | 6-butyl-5-(2,6-dimethoxyphenyl)-3-[3-(3-fluoropyridin-2-yl)pyrrolidine-1-carbonyl]pyridine-2,4-diol | 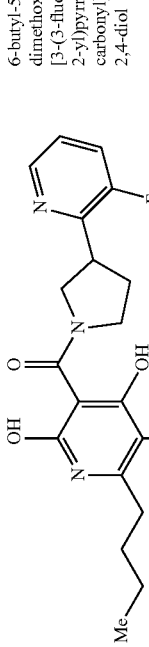 Rt = 5.15, (isomer 2) Whelko (4.6 × 250 mm, 5 micron; mobile phase: 10% IPA/90% CO$_2$; flow condition: 3.0 mL/min, 140 bar, 40° C.; wavelength: 220 nm. | $^1$H NMR (500 MHz, DMSO-d6) δ 8.41 (d, J = 3.3 Hz, 1H), 7.71 (br. s., 1H), 7.47-7.37 (m, 1H), 7.33 (t, J = 8.4 Hz, 1H), 6.71 (s, 1H), 6.70 (s, 1H), 3.68 (s, 11H), 3.58 (s, 1H), 2.32-2.02 (m, 4H), 1.37-1.22 (m, 2H), 1.14-0.94 (m, 2H), 0.65 (t, J = 7.0 Hz, 3H) | 0.87 A 496.3 | A |

TABLE 3-continued

| Ex# | Structure | Name | Chiral Amine intermediate with Retention time (min) | NMR | Rt(min) method M + H | APJ cAMP EC₅₀ (nM) |
|---|---|---|---|---|---|---|
| 79 | 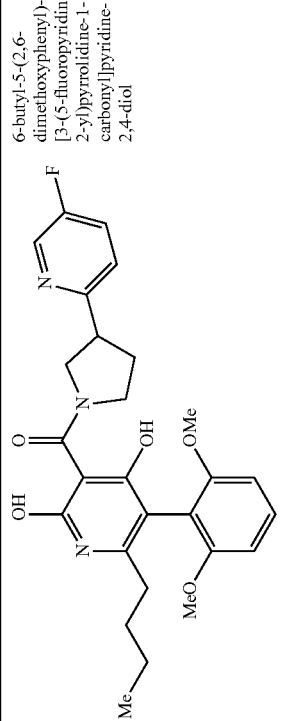 | 6-butyl-5-(2,6-dimethoxyphenyl)-3-[3-(5-fluoropyridin-2-yl)pyrrolidin-1-carbonyl]pyridine-2,4-diol | 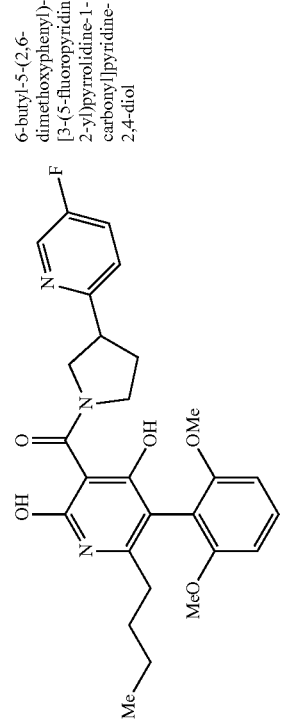 Rt: 4.37, (isomer 1) Whelko (4.6 × 250 mm, 5 micron; mobile phase: 10% IPA/90% CO₂; flow condition: 3.0 mL/min, 140 bar, 40° C.; wavelength: 220 nm. | ¹H NMR (400 MHz, DMSO-d6) δ 12.27 (br. s., 1H), 11.64-10.86 (m, 1H), 8.52 (d, J = 2.9 Hz, 1H), 7.87-7.59 (m, 1H), 7.54-7.41 (m, 1H), 7.31 (t, J = 8.4 Hz, 1H), 6.69 (d, J = 8.4 Hz, 2H), 3.67 (s, 6H), 3.90-3.31 (m, 5H), 2.31-2.19 (m, 1H), 2.07 (br. s., 3H), 1.39-1.22 (m, 2H), 1.14-0.92 (m, 2H), 0.63 (t, J = 7.3 Hz, 3H) | 0.86 A 496.3 | A |
| 80 | 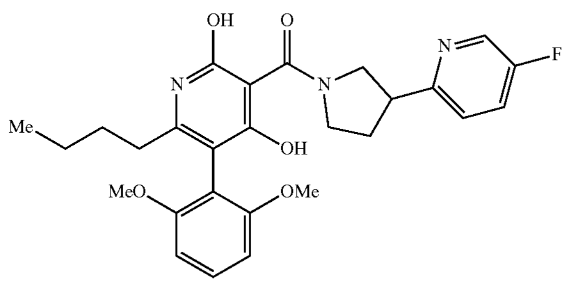 [SMILES: CCCCc1nc(O)c(C(=O)N2CCC(c3ccc(F)cn3)C2)c(O)c1-c1c(OC)cccc1OC] | 6-butyl-5-(2,6-dimethoxyphenyl)-3-[3-(5-fluoropyridin-2-yl)pyrrolidin-1-carbonyl]pyridine-2,4-diol | Rt: 4.89, (isomer 1) Whelko (4.6 × 250 mm, 5 micron; mobile phase: 10% IPA/90% CO₂; flow condition: 3.0 mL/min, 140 bar, 40° C.; wavelength: 220 nm. | ¹H NMR (400 MHz, DMSO-d6) δ 12.27 (br. s., 1H), 11.64-10.86 (m, 1H), 8.52 (d, J = 2.9 Hz, 1H), 7.87-7.59 (m, 1H), 7.54-7.41 (m, 1H), 7.31 (t, J = 8.4 Hz, 1H), 6.69 (d, J = 8.4 Hz, 2H), 3.67 (s, 6H), 3.90-3.31 (m, 5H), 2.31-2.19 (m, 1H), 2.07 (br. s., 3H), 1.39-1.22 (m, 2H), 1.14-0.92 (m, 2H), 0.63 (t, J = 7.3 Hz, 3H) | 0.86 A 496.3 | A |

TABLE 3-continued

| Ex# | Structure | Name | Chiral Amine intermediate with Retention time (min) | NMR | Rt(min) method M + H | APJ cAMP EC$_{50}$ (nM) |
|---|---|---|---|---|---|---|
| 81 | 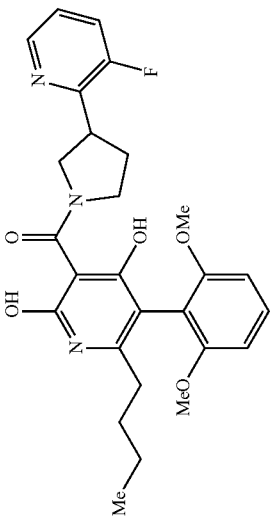 | 6-butyl-5-(2,6-dimethoxyphenyl)-3-[3-(3-fluoropyridin-2-yl)pyrrolidine-1-carbonyl]pyridine-2,4-diol | Rt = 4.80, (isomer 1) Whelko (4.6 × 250 mm, 5 micron; mobile phase: 10% IPA/90% CO$_2$; flow condition: 3.0 mL/min, 140 bar, 40° C.; wavelength: 220 nm. | $^1$H NMR (500 MHz, DMSO-d6) δ 8.41 (d, J = 3.3 Hz, 1H), 7.71 (br. s., 1H), 7.47-7.37 (m, 1H), 7.33 (t, J = 8.4 Hz, 1H), 6.71 (s, 1H), 6.70 (s, 1H), 3.68 (s, 11H), 3.58 (s, 1H), 2.32-2.02 (m, 4H), 1.37-1.22 (m, 2H), 1.14-0.94 (m, 2H), 0.65 (t, J = 7.0 Hz, 3H) | 0.87 A 496.3 | A |
| 82 | 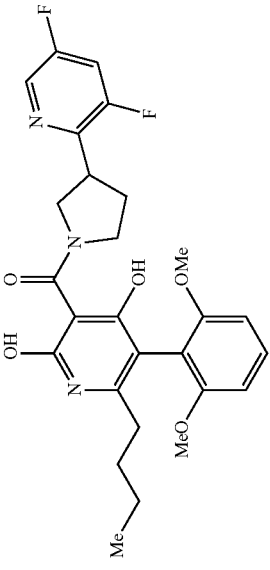 | 6-butyl-3-[3-(3,5-difluoropyridin-2-yl)pyrrolidine-1-carbonyl]-5-(2,6-dimethoxyphenyl)pyridine-2,4-diol | Rt = 4.80, (isomer 1) Whelko (4.6 × 250 mm, 5 micron; mobile phase: 10% IPA/90% CO$_2$; flow condition: 3.0 mL/min, 140 bar, 40° C.; wavelength: 220 nm. | $^1$H NMR (500 MHz, DMSO-d6) δ 8.78-8.23 (m, 1H), 7.90 (br. s., 1H), 7.31 (t, J = 8.4 Hz, 1H), 6.69 (d, J = 7.9 Hz, 2H), 3.67 (br. s., 11H), 2.32-2.20 (m, 1H), 2.07 (br. s., 3H), 1.30 (br. s., 2H), 1.06 (d, J = 7.0 Hz, 2H), 0.82-0.56 (m, 3H) | 0.89 A 514.3 | A |

TABLE 3-continued

| Ex# | Structure | Name | Chiral Amine intermediate with Retention time (min) | NMR | Rt(min) method M + H | APJ cAMP EC$_{50}$ (nM) |
|---|---|---|---|---|---|---|
| 83 | (structure) | 6-butyl-3-[3-(3,5-difluoropyridin-2-yl)pyrrolidine-1-carbonyl]-5-(2,6-dimethoxyphenyl)pyridine-2,4-diol | (structure) Rt = 3.86, (isomer 2) Whelko (4.6 × 250 mm, 5 micron; mobile phase: 10% IPA/90% CO$_2$; flow condition: 3.0 mL/min, 140 bar, 40° C.; wavelength: 220 nm. | $^1$H NMR (500 MHz, DMSO-d6) δ 8.78-8.23 (m, 1H), 7.90 (br. s., 1H), 7.31 (t, J = 8.4 Hz, 1H), 6.69 (d, J = 7.9 Hz, 2H), 3.67 (br. s., 11H), 2.32-2.20 (m, 1H), 2.07 (br. s., 3H), 1.30 (br. s., 2H), 1.06 (d, J = 7.0 Hz, 2H), 0.82-0.56 (m, 3H) | 0.89 A 514.3 | A |
| 84 | (structure) | 3-[3-(3,5-difluoropyridin-2-yl)pyrrolidine-1-carbonyl]-5-(2,6-dimethoxyphenyl)-6-(ethoxymethyl)pyridine-2,4-diol | (structure) Rt = 4.80, (isomer 1) Whelko (4.6 × 250 mm, 5 micron; mobile phase: 10% IPA/90% CO$_2$; flow condition: 3.0 mL/min, 140 bar, 40° C.; wavelength: 220 nm. | $^1$H NMR (500 MHz, DMSO-d6) δ 8.46 (br. s., 1H), 7.87 (br. s., 1H), 7.33 (t, J = 8.4 Hz, 1H), 6.70 (d, J = 8.2 Hz, 2H), 3.98-3.46 (m, 10H), 3.31-3.19 (m, 2H), 2.55 (s, 4H), 2.32-2.23 (m, 1H), 2.19-2.05 (m, 0.97 (t, J = 6.6 Hz, 3H) | 0.83 A 516.0 | A |

TABLE 3-continued

| Ex# | Structure | Name | Chiral Amine intermediate with Retention time (min) | NMR | Rt(min) method M + H | APJ cAMP EC$_{50}$ (nM) |
|---|---|---|---|---|---|---|
| 85 | (structure) | 3-[3-(3,5-difluoropyridin-2-yl)pyrrolidine-1-carbonyl]-5-(2,6-dimethoxyphenyl)-6-(ethoxymethyl)pyridine-2,4-diol | (structure with Boc) Rt = 3.86, (isomer 2) Whelko (4.6 × 250 mm, 5 micron; mobile phase: 10% IPA/90% CO$_2$; flow condition: 3.0 mL/min, 140 bar, 40° C.; wavelength: 220 nm. | $^1$H NMR (500 MHz, DMSO-d6) δ 8.46 (br. s., 1H), 7.87 (br. s., 1H), 7.33 (t, J = 8.4 Hz, 1H), 6.70 (d, J = 8.2 Hz, 2H), 3.98-3.46 (m, 10H), 3.31-3.19 (m, 2H), 2.55 (s, 4H), 2.32-2.23 (m, 1H), 2.19-2.05 (m, 1H), 0.97 (t, J = 6.6 Hz, 3H) | 0.83 A 516.0 | A |
| 86 | (structure) | (5-(2,6-dimethoxyphenyl)-6-(4-fluorophenyl)-2,4-dihydroxypyridin-3-yl)(3-(2-fluorophenyl)pyrrolidin-1-yl)methanone | (structure with Cbz) Rt = 10.65, (isomer 1) Chiralpak IF, 4.6 × 250 mm, 5 micron; mobile phase: 15% IPA/90% CO$_2$; Flow Conditions: 2.0 mL/min, 150 bar, 40° C.; wavelength: 220 nm. | $^1$H NMR (500 MHz, DMSO-d6) δ 7.45 (t, J = 7.0 Hz, 1H), 7.28-7.34 (m, 1H), 7.12-7.22 (m, 5H), 7.00-7.05 (m, 2H), 6.53 (t, J = 8.2 Hz, 2H), 3.92 (br s, 1H), 3.77 (br s, 1H), 3.64 (br s, 2H), 3.56 (s, 6H), 3.40-3.45 (m, 1H), 2.27 (br s, 1H), 2.07 (br s, 1H) | 1.62 A 532.9 | A |

TABLE 3-continued

| Ex# | Structure | Name | Chiral Amine intermediate with Retention time (min) | NMR | Rt(min) method M + H | APJ cAMP EC$_{50}$ (nM) |
|---|---|---|---|---|---|---|
| 87 | 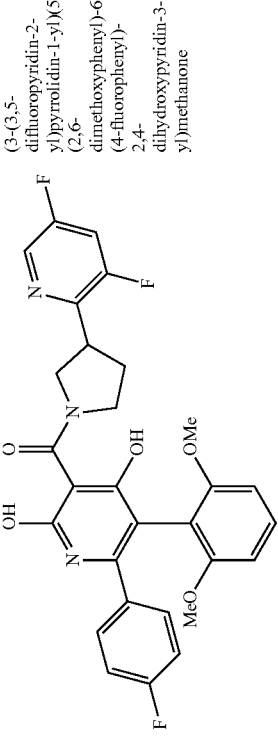 | (3-(3,5-difluoropyridin-2-yl)pyrrolidin-1-yl)(5-(2,6-dimethoxyphenyl)-6-(4-fluorophenyl)-2,4-dihydroxypyridin-3-yl)methanone | 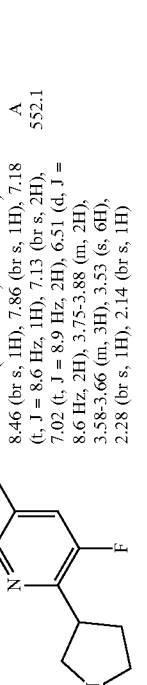 Rt = 3.86, isomer 2) Whelko (4.6 × 250 mm, 5 micron; mobile phase: 10% IPA/90% CO$_2$; flow condition: 3.0 mL/min, 140 bar, 40° C.; wavelength: 220 nm. | $^1$H NMR (500 MHz, DMSO-d6) δ 8.46 (br s, 1H), 7.86 (br s, 1H), 7.18 (t, J = 8.6 Hz, 1H), 7.13 (br s, 2H), 7.02 (t, J = 8.9 Hz, 2H), 6.51 (d, J = 8.6 Hz, 2H), 3.75-3.88 (m, 2H), 3.58-3.66 (m, 3H), 3.53 (s, 6H), 2.28 (br s, 1H), 2.14 (br s, 1H) | 1.53 A 552.1 | A |

The following compounds, Example 88 to Example 123, and Examples 153-154 were prepared by the general procedures described for Example 1.

TABLE 4

| Ex# | Structure | Name | NMR | Rt(min) method M + H | Human cAMP $EC_{50}$ |
|---|---|---|---|---|---|
| 88 | 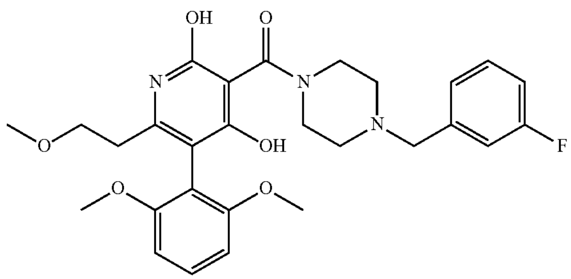 [SMILES: COCCc1nc(O)c(C(=O)N2CCN(Cc3cccc(F)c3)CC2)c(O)c1-c1c(OC)cccc1OC] | 5-(2,6-dimethoxyphenyl)-3-{4-[(3-fluorophenyl)methyl]piperazine-1-carbonyl}-6-(2-methoxyethyl)pyridine-2,4-diol | $^1$H NMR (500 MHz, DMSO-d6) δ 7.46-7.29 (m, 2H), 7.23-7.13 (m, 2H), 7.10 (t, J = 8.4 Hz, 1H), 6.72 (d, J = 8.5 Hz, 2H), 3.70 (s, 6H), 3.54 (s, 2H), 3.30-3.24 (m, 2H), 3.06 (s, 3H), 2.58-2.54 (m, 3H), 2.43 (br. s., 4H), 2.39 (br s, 1H), 2.35 (t, J = 7.2 Hz, 2H) | 1.39 A 526.3 | C |
| 89 | 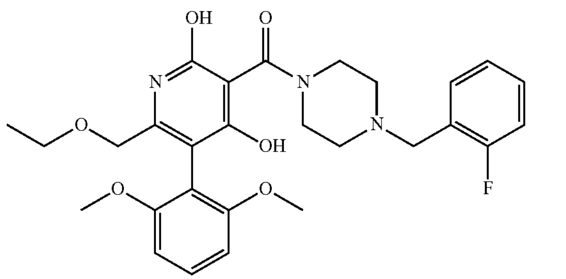 [SMILES: CCOCc1nc(O)c(C(=O)N2CCN(Cc3ccccc3F)CC2)c(O)c1-c1c(OC)cccc1OC] | 5-(2,6-dimethoxyphenyl)-6-(ethoxymethyl)-3-{4-[(2-fluorophenyl)methyl]piperazine-1-carbonyl}pyridine-2,4-diol | $^1$H NMR (500 MHz, DMSO-d6) δ 7.44 (t, J = 6.9 Hz, 1H), 7.33 (t, J = 8.3 Hz, 2H), 7.25-7.15 (m, 2H), 6.70 (d, J = 8.5 Hz, 2H), 3.87 (s, 2H), 3.68 (s, 6H), 3.58 (s, 2H), 3.26-3.21 (m, 4H), 2.45 (br. s., 4H), 1.92 (s, 2H), 0.99 (t, J = 6.9 Hz, 3H) | 1.47 A 526.1 | A |
| 90 | 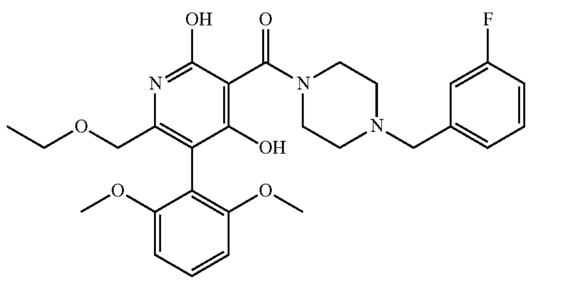 [SMILES: CCOCc1nc(O)c(C(=O)N2CCN(Cc3cccc(F)c3)CC2)c(O)c1-c1c(OC)cccc1OC] | 5-(2,6-dimethoxyphenyl)-6-(ethoxymethyl)-3-{4-[(3-fluorophenyl)methyl]piperazine-1-carbonyl}pyridine-2,4-diol | $^1$H NMR (500 MHz, DMSO-d6) δ 7.42-7.35 (m, 1H), 7.31 (t, J = 8.4 Hz, 1H), 7.21-7.13 (m, 2H), 7.10-7.03 (m, 1H), 6.68 (d, J = 8.5 Hz, 2H), 3.86 (s, 2H), 3.67 (s, 6H), 3.57-3.52 (m, 2H), 3.29-3.19 (m, 4H), 2.41 (br. s., 4H), 1.91 (s, 2H), 0.99 (t, J = 7.0 Hz, 3H) | 1.82 A 526.1 | B |

TABLE 4-continued

| Ex# | Structure | Name | NMR | Rt(min) method M + H | Human cAMP EC$_{50}$ |
|---|---|---|---|---|---|
| 91 | 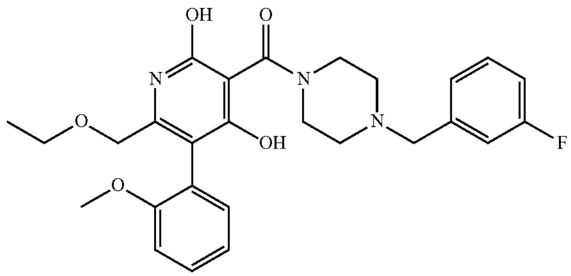 [SMILES: CCOCc1nc(O)c(C(=O)N2CCN(Cc3cccc(F)c3)CC2)c(O)c1-c1ccccc1OC] | 6-(ethoxymethyl)-3-{4-[(3-fluorophenyl)methyl]piperazine-1-carbonyl}-5-(2-methoxyphenyl)pyridine-2,4-diol | $^1$H NMR (500 MHz, DMSO-d6) δ 7.46-7.26 (m, 2H), 7.21-6.90 (m, 7H), 4.02-3.81 (m, 2H), 3.69 (s, 3H), 3.52 (s, 2H), 3.30-3.16 (m, 2H), 2.45-2.34 (m, 4H), 1.90 (s, 4H), 0.98 (t, J = 6.9 Hz, 3H) | 1.39 A 496.1 | B |
| 92 | 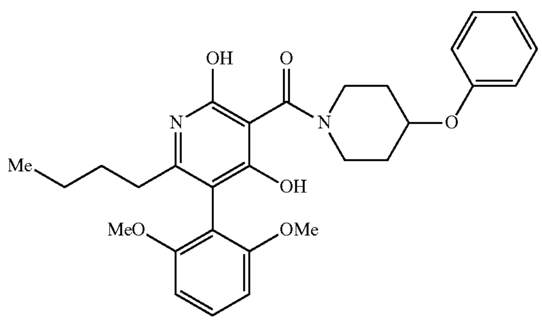 [SMILES: CCCCc1nc(O)c(C(=O)N2CCC(Oc3ccccc3)CC2)c(O)c1-c1c(OC)cccc1OC] | 6-butyl-5-(2,6-dimethoxyphenyl)-3-(4-phenoxypiperidine-1-carbonyl)pyridine-2,4-diol | $^1$H NMR (500 MHz, DMSO-d6) δ 7.56-7.20 (m, 3H), 7.11-6.84 (m, 3H), 6.68 (d, J = 8.2 Hz, 2H), 4.62 (br. s., 1H), 3.74-3.45 (m, 6H), 2.54 (s, 4H), 2.10-1.91 (m, 4H), 1.64 (br. s., 2H), 1.27 (d, J = 7.0 Hz, 2H), 1.09-0.94 (m, 2H), 0.62 (t, J = 7.1 Hz, 3H) | 0.94 D 507.4 | A |
| 93 | 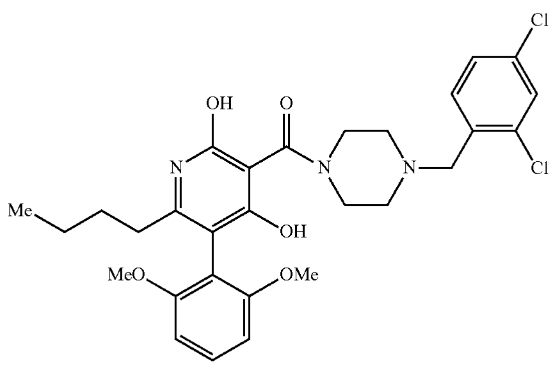 [SMILES: CCCCc1nc(O)c(C(=O)N2CCN(Cc3ccc(Cl)cc3Cl)CC2)c(O)c1-c1c(OC)cccc1OC] | 6-butyl-3-{4-[(2,4-dichlorophenyl)methyl]piperazine-1-carbonyl}-5-(2,6-dimethoxyphenyl)pyridine-2,4-diol | $^1$H NMR (500 MHz, DMSO-d6) δ 7.59 (s, 1H), 7.54 (d, J = 8.3 Hz, 1H), 7.42 (d, J = 7.2 Hz, 1H), 7.32 (t, J = 8.4 Hz, 1H), 6.69 (d, J = 8.3 Hz, 2H), 3.66 (s, 6H), 3.49 (m, 2H), 2.53-2.39 (m, 8H), 2.05 (t, J = 7.7 Hz, 2H), 1.38-1.20 (m, 2H), 1.13-0.96 (m, 2H), 0.63 (t, J = 7.3 Hz, 3H) | 1.66 A 574.0 | A |

TABLE 4-continued

| Ex# | Structure | Name | NMR | Rt(min) method M + H | Human cAMP EC$_{50}$ |
|---|---|---|---|---|---|
| 94 | 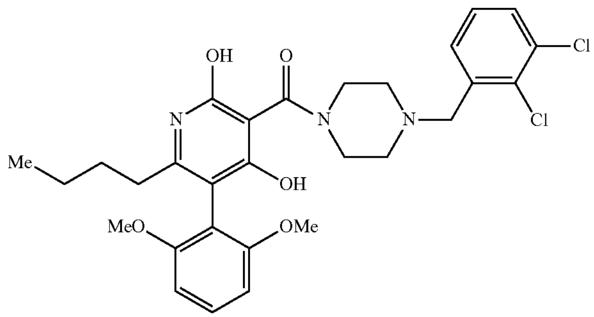 [SMILES: CCCCc1nc(O)c(C(=O)N2CCN(Cc3cccc(Cl)c3Cl)CC2)c(O)c1-c1c(OC)cccc1OC] | 6-butyl-3-{4-[(2,3-dichlorophenyl)methyl]piperazine-1-carbonyl}-5-(2,6-dimethoxyphenyl)pyridine-2,4-diol | $^1$H NMR (500 MHz, DMSO-d6) δ 7.62-7.42 (m, 2H), 7.40-7.15 (m, 2H), 6.68 (d, J = 8.4 Hz, 2H), 3.77-3.66 (m, 1H), 3.65 (s, 6H), 3.63-3.49 (m, 1H), 2.59- 2.38 (m, 8H), 2.04 (t, J = 7.5 Hz, 2H), 1.38-1.21 (m, 2H), 1.10-0.96 (m, 2H), 0.62 (t, J = 7.3 Hz, 3H) | 0.94 A 574.0 | A |
| 95 | 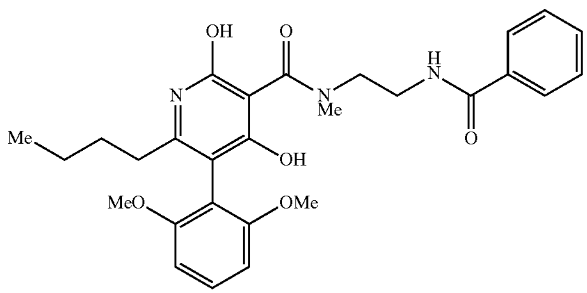 [SMILES: CCCCc1nc(O)c(C(=O)N(C)CCNC(=O)c2ccccc2)c(O)c1-c1c(OC)cccc1OC] | N-(2-{1-[6-butyl-5-(2,6-dimethoxyphenyl)-2,4-dihydroxypyridin-3-yl]-N-methylformamido}ethyl)benzamide | $^1$H NMR (500 MHz, DMSO-d6) δ 7.85 (d, J = 6.7 Hz, 2H), 7.56-7.47 (m, 1H), 7.47-7.39 (m, 2H), 7.32 (t, J = 8.3 Hz, 1H), 6.69 (d, J = 8.4 Hz, 2H), 3.67-3.45 (br s, 6H), 2.93 (br. s., 3H), 2.55 (s, 2H), 2.07 (t, J = 7.7 Hz, 2H), 1.35-1.25 (m, 2H), 1.22 (s, 2H), 1.11-0.98 (m, 2H), 0.63 (t, J = 7.3 Hz, 3H) | 1.42 A 508.2 | B |
| 96 | 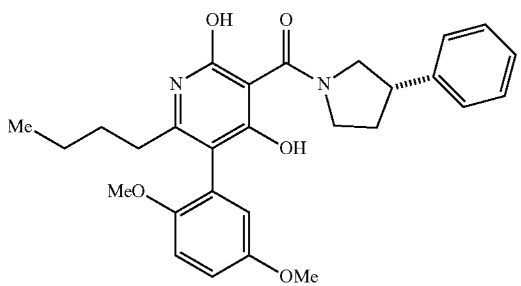 [SMILES: CCCCc1nc(O)c(C(=O)N2CC[C@@H](c3ccccc3)C2)c(O)c1-c1cc(OC)ccc1OC] | 6-butyl-5-(2,5-dimethoxyphenyl)-3-[(3S)-3-phenylpyrrolidine-1-carbonyl]pyridine-2,4-diol | $^1$H NMR (500 MHz, DMSO-d6) δ 7.33 (d, J = 6.6 Hz, 4H), 7.24 (br. s., 1H), 7.03-6.85 (m, 2H), 6.66 (d, J = 6.5 Hz, 1H), 3.69 (s, 3H), 3.64 (br. s., 3H), 2.55 (s, 4H), 2.36-1.92 (m, 4H), 1.35 (br. s., 2H), 1.23 (s, 1H), 1.09 (br. s., 2H), 0.66 (br. s., 3H) | 1.76 A 477.4 | A |

TABLE 4-continued

| Ex# | Structure | Name | NMR | Rt(min) method M + H | Human cAMP EC$_{50}$ |
|---|---|---|---|---|---|
| 97 | 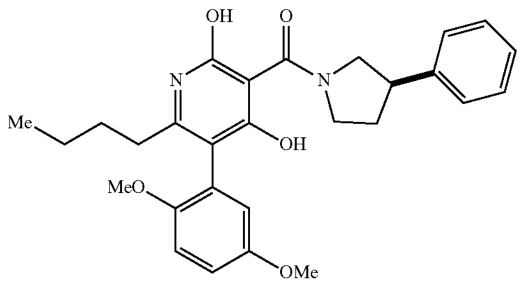 [SMILES: CCCCc1nc(O)c(C(=O)N2CC[C@H](c3ccccc3)C2)c(O)c1-c1cc(OC)ccc1OC] | 6-butyl-5-(2,5-dimethoxyphenyl)-3-[(3R)-3-phenylpyrrolidine-1-carbonyl]pyridine-2,4-diol | $^1$H NMR (500 MHz, DMSO-d6) δ 7.33 (d, J = 6.6 Hz, 4H), 7.24 (br. s., 1H), 7.03-6.85 (m, 2H), 6.66 (d, J = 6.5 Hz, 1H), 3.69 (s, 3H), 3.64 (br. s., 3H), 2.55 (s, 4H), 2.36-1.92 (m, 4H), 1.35 (br. s., 2H), 1.23 (s, 1H), 1.09 (br. s., 2H), 0.66 (br. s., 3H) | 1.76 A 477.4 | A |
| 98 | 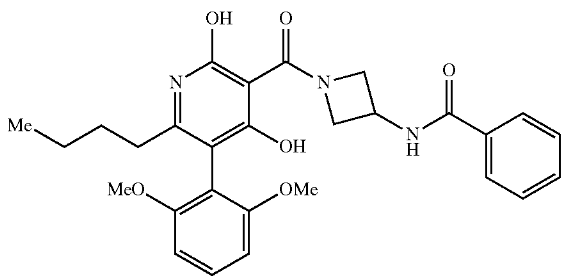 [SMILES: CCCCc1nc(O)c(C(=O)N2CC(NC(=O)c3ccccc3)C2)c(O)c1-c1c(OC)cccc1OC] | N-[1-[6-butyl-5-(2,6-dimethoxyphenyl)-2,4-dihydroxypyridine-3-carbonyl]azetidin-3-yl]benzamide | $^1$H NMR (500 MHz, DMSO-d6) δ 14.94-14.57 (m, 1H), 11.81-10.94 (m, 1H), 9.25-8.85 (m, 1H), 8.05-7.81 (m, 2H), 7.62-7.45 (m, 3H), 7.41-7.22 (m, 1H), 6.71 (d, J = 8.5 Hz, 2H), 4.81-4.57 (m, 2H), 4.47-4.26 (m, 2H), 4.13-3.95 (m, 1H), 3.69 (s, 6H), 2.17-1.99 (m, 2H), 1.41-1.24 (m, 2H), 1.14-0.98 (m, 2H), 0.66 (s, 3H) | 0.88 D 506.3 | A |
| 99 | 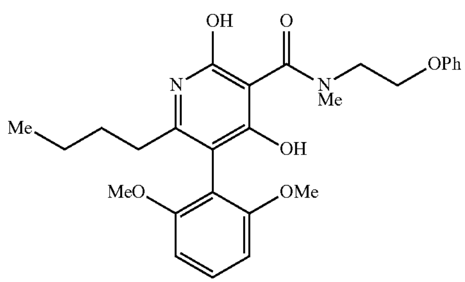 [SMILES: CCCCc1nc(O)c(C(=O)N(C)CCOc2ccccc2)c(O)c1-c1c(OC)cccc1OC] | 6-butyl-5-(2,6-dimethoxyphenyl)-2,4-dihydroxy-N-methyl-N-(2-phenoxyethyl)pyridine-3-carboxamide | $^1$H NMR (500 MHz, DMSO-d6) δ 7.37-7.22 (m, 3H), 6.92 (t, J = 7.2 Hz, 3H), 6.69 (d, J = 8.4 Hz, 2H), 4.13 (br. s., 2H), 3.64 (br. s., 6H), 3.02 (s, 3H), 2.55 (s, 2H), 2.06 (t, J = 7.6 Hz, 2H), 1.36-1.25 (m, 2H), 1.12-0.98 (m, 2H), 0.64 (t, J = 7.3 Hz, 3H) | 1.64 A 481.0 | B |

TABLE 4-continued

| Ex# | Structure | Name | NMR | Rt(min) method M + H | Human cAMP EC$_{50}$ |
|---|---|---|---|---|---|
| 100 | 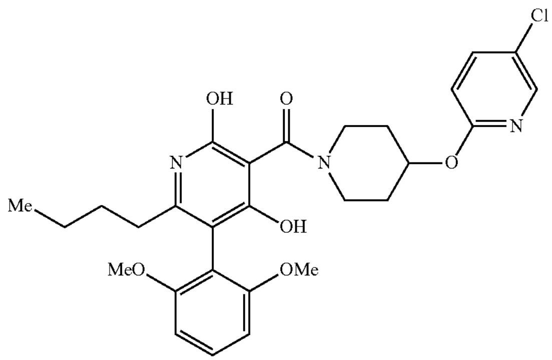 [SMILES: CCCCc1nc(O)c(C(=O)N2CCC(Oc3ccc(Cl)cn3)CC2)c(O)c1-c1c(OC)cccc1OC] | 6-butyl-3-{4-[(5-chloropyridin-2-yl)oxy]piperidine-1-carbonyl}-5-(2,6-dimethoxyphenyl)pyridine-2,4-diol | $^1$H NMR (500 MHz, DMSO-d6) δ 8.18 (br. s., 1H), 7.78 (d, J = 6.9 Hz, 1H), 7.29 (t, J = 8.2 Hz, 1H), 6.85 (d, J = 8.8 Hz, 1H), 6.67 (d, J = 8.2 Hz, 2H), 3.65 (s, 6H), 3.29 (br. s., 1H), 2.55 (s, 4H), 2.13-1.94 (m, 4H), 1.69 br. s., 2H), 1.33-1.27 (m, 2H), 1.10 0.98 (m, 2H), 0.63 (t, J = 7.2 Hz, 3H) | 1.78 A 542.1 | A |
| 101 | 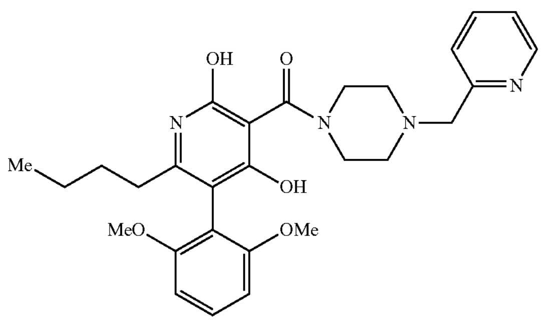 [SMILES: CCCCc1nc(O)c(C(=O)N2CCN(Cc3ccccn3)CC2)c(O)c1-c1c(OC)cccc1OC] | 6-butyl-5-(2,6-dimethoxyphenyl)-3-[4-(pyridin-2-ylmethyl)piperazine-1-carbonyl]pyridine-2,4-diol | $^1$H NMR (500 MHz, DMSO-d6) δ 8.47 (d, J = 4.3 Hz, 1H), 7.77 (t, J = 7.0 Hz, 1H), 7.46 (d, J = 7.9 Hz, 1H), 7.38-7.19 (m, 2H), 6.68 (d, J = 8.4 Hz, 2H), 3.79-3.66 (m, 1H), 3.65 (s, 6H), 3.63-3.39 (m, 1H), 2.55 (s, 4H), 2.45 br. s., 4H), 2.13-1.99 (m, 2H), 1.32-1.24 (m, 2H), 1.11-0.94 (m, 2H), 0.62 (t, J = 7.3 Hz, 3H) | 1.23 A 507.0 | A |
| 102 | 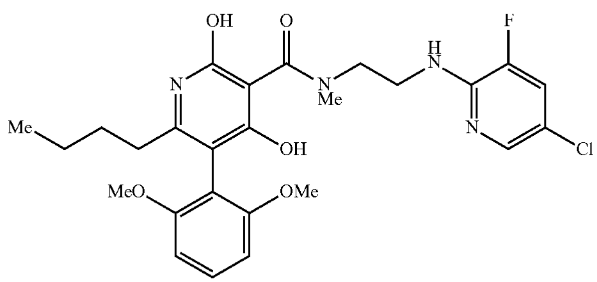 [SMILES: CCCCc1nc(O)c(C(=O)N(C)CCNc2ncc(Cl)cc2F)c(O)c1-c1c(OC)cccc1OC] | 6-butyl-N-{2-[(5-chloro-3-fluoropyridin-2-yl)amino]ethyl}-5-(2,6-dimethoxyphenyl)-2,4-dihydroxy-N-methylpyridine-3-carboxamide | $^1$H NMR (500 MHz, DMSO-d6) δ 7.89-7.74 (m, 1H), 7.56 (d, J = 10.7 Hz, 1H), 7.29 (t, J = 8.1 Hz, 1H), 6.67 (d, J = 8.2 Hz, 2H), 3.64 (br. s., 6H), 3.48 (br. s., 2H), 2.91 (br. s., 3H), 2.55 (s, 2H), 2.03 (d, J = 7.5 Hz, 2H), 1.35- 1.26 (m, 2H), 1.12-0.99 (m, 2H), 0.64 (t, J = 7.3 Hz, 3H) | 1.65 A 533.1 | B |

TABLE 4-continued

| Ex# | Structure | Name | NMR | Rt(min) method M + H | Human cAMP EC$_{50}$ |
|---|---|---|---|---|---|
| 103 | 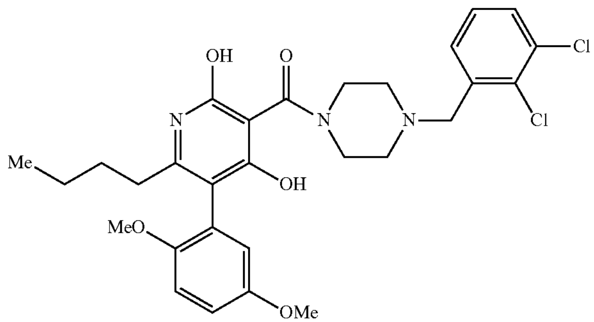 [SMILES: CCCCc1nc(O)c(C(=O)N2CCN(Cc3cccc(Cl)c3Cl)CC2)c(O)c1-c1cc(OC)ccc1OC] | 6-butyl-3-{4-[(2,3-dichlorophenyl)methyl]piperazine-1-carbonyl}-5-(2,5-dimethoxyphenyl)pyridine-2,4-diol | $^1$H NMR (500 MHz, DMSO-d6) δ 7.65-7.44 (m, 2H), 7.40-7.25 (m, 1H), 7.05-6.80 (m, 2H), 6.62 (d, J = 2.6 Hz, 1H), 3.74-3.70 (m, 2H), 3.68 (br s, 3H), 3.62 (s, 3H), 2.55 (s, 4H), 2.46 (br. s., 4H), 2.23-2.02 (m, 2H), 1.42-1.27 (m, 2H), 1.12-0.99 (m, 2H), 0.65 (t, J = 7.3 Hz, 3H) | 1.93 A 574.4 | A |
| 104 | 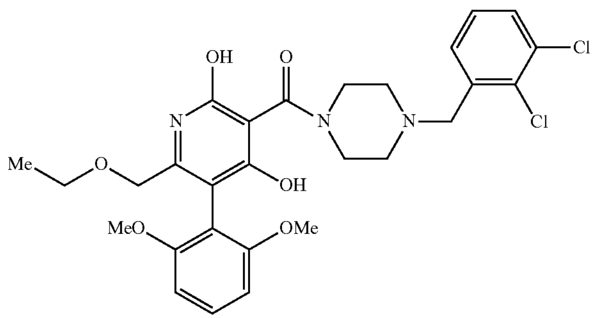 | 3-{4-[(2,3-dichlorophenyl)methyl]piperazine-1-carbonyl}-5-(2,6-dimethoxyphenyl)-6-(ethoxymethyl)pyridine-2,4-diol | $^1$H NMR (500 MHz, DMSO-d6) δ 7.67 (d, J = 7.9 Hz, 1H), 7.58 (d, J = 7.6 Hz, 1H), 7.43 (t, J = 7.8 Hz, 1H), 7.34 (t, J = 8.4 Hz, 1H), 6.70 (d, J = 8.4 Hz, 2H), 3.80-3.53 (m, 8H), 3.23 (q, J = 6.9 Hz, 2H), 3.05-2.85 (m, 4H), 2.55 (s, 4H), 1.15 (t, J = 7.3 Hz, 2H), 0.96 (t, J = 7.0 Hz, 3H) | 1.65 A 576.3 | A |
| 105 | 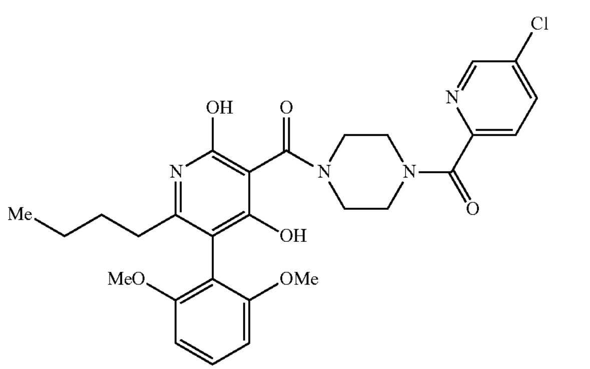 [SMILES: CCCCc1nc(O)c(C(=O)N2CCN(C(=O)c3ccc(Cl)cn3)CC2)c(O)c1-c1c(OC)cccc1OC] | 6-butyl-3-{4-(5-chloropyridine-2-carbonyl)piperazine-1-carbonyl}-5-(2,6-dimethoxyphenyl)pyridine-2,4-diol | $^1$H NMR (500 MHz, DMSO-d6) δ 8.85-8.53 (m, 1H), 8.15-7.95 (m, 1H), 7.75-7.59 (m, 1H), 7.42-7.22 (m, 1H), 6.69 (d, J = 8.3 Hz, 2H), 3.63 (br. s., 6H), 2.55 (br. s, 8H), 2.16-2.00 (m, 2H), 1.32-1.24 (m, 2H), 1.12-0.98 (m, 2H), 0.62 (t, J = 7.0 Hz, 3H) | 1.43 A 555.1 | A |

TABLE 4-continued

| Ex# | Structure | Name | NMR | Rt(min) method M + H | Human cAMP EC$_{50}$ |
|---|---|---|---|---|---|
| 106 | 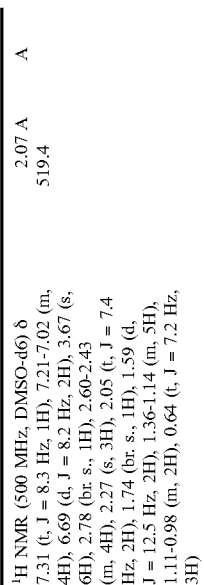 | 6-butyl-5-(2,6-dimethoxyphenyl)-3-{4-[(2-methylphenyl)methyl]piperidine-1-carbonyl}pyridine-2,4-diol | $^1$H NMR (500 MHz, DMSO-d6) δ 7.31 (t, J = 8.3 Hz, 1H), 7.21-7.02 (m, 4H), 6.69 (d, J = 8.2 Hz, 2H), 3.67 (s, 6H), 2.78 (br. s., 1H), 2.60-2.43 (m, 4H), 2.27 (s, 3H), 2.05 (t, J = 7.4 Hz, 2H), 1.74 (br. s., 1H), 1.59 (d, J = 12.5 Hz, 2H), 1.36-1.14 (m, 5H), 1.11-0.98 (m, 2H), 0.64 (t, J = 7.2 Hz, 3H) | 2.07 A 519.4 | A |
| 107 | 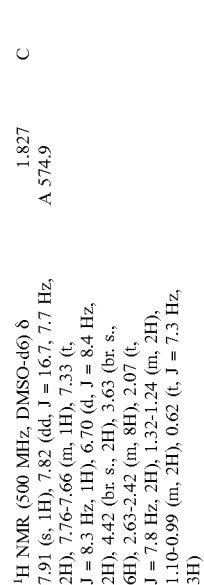 | 6-butyl-5-(2,6-dimethoxyphenyl)-3-(4-{[3-(trifluoromethyl)phenyl]methyl}piperazine-1-carbonyl)pyridine-2,4-diol | $^1$H NMR (500 MHz, DMSO-d6) δ 7.91 (s, 1H), 7.82 (dd, J = 16.7, 7.7 Hz, 2H), 7.76-7.66 (m, 1H), 7.33 (t, J = 8.3 Hz, 1H), 6.70 (d, J = 8.4 Hz, 2H), 4.42 (br. s., 2H), 3.63 (br. s., 6H), 2.63-2.42 (m, 8H), 2.07 (t, J = 7.8 Hz, 2H), 1.32-1.24 (m, 2H), 1.10-0.99 (m, 2H), 0.62 (t, J = 7.3 Hz, 3H) | 1.827 A 574.9 | C |
| 108 | 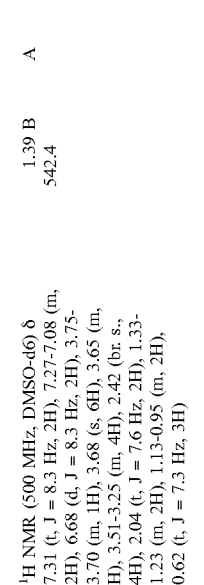 | 6-butyl-3-{4-[(2,3-difluorophenyl)methyl]piperazine-1-carbonyl}-5-(2,6-dimethoxyphenyl)pyridine-2,4-diol | $^1$H NMR (500 MHz, DMSO-d6) δ 7.31 (t, J = 8.3 Hz, 2H), 7.27-7.08 (m, 2H), 6.68 (d, J = 8.3 Hz, 2H), 3.75-3.70 (m, 1H), 3.68 (s, 6H), 3.65 (m, 1H), 3.51-3.25 (m, 4H), 2.42 (br. s., 4H), 2.04 (t, J = 7.6 Hz, 2H), 1.33-1.23 (m, 2H), 1.13-0.95 (m, 2H), 0.62 (t, J = 7.3 Hz, 3H) | 1.39 B 542.4 | A |

TABLE 4-continued

| Ex# | Structure | Name | NMR | Rt(min) method M + H | Human cAMP EC$_{50}$ |
|---|---|---|---|---|---|
| 109 | 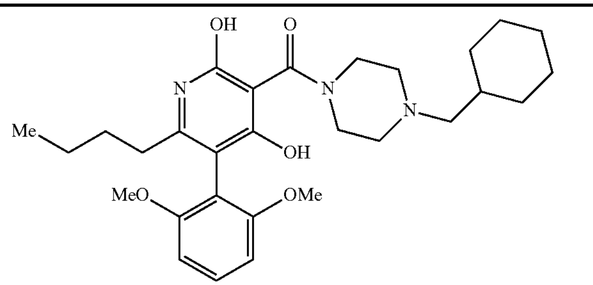 | 6-butyl-3-[4-(cyclohexylmethyl)piperazine-1-carbonyl]-5-(2,6-dimethoxyphenyl)pyridine-2,4-diol | $^1$H NMR (500 MHz, DMSO-d6) δ 7.32 (t, J = 8.3 Hz, 1H), 6.69 (d, J = 8.4 Hz, 2H), 3.67 (s, 6H), 2.55 (s, 4H), 2.34 (br. s., 4H), 2.14-1.97 (m, 4H), 1.73 (d, J = 12.3 Hz, 2H), 1.69-1.55 (m, 3H), 1.48 (br. s., 1H), 1.34-1.25 (m, 2H), 1.24-1.10 (m, 3H), 1.10-0.99 (m, 2H), 0.83 (q, J = 11.0 Hz, 2H), 0.64 (t, J = 7.3 Hz, 3H) | 1.40 B 512.2 | B |
| 110 | 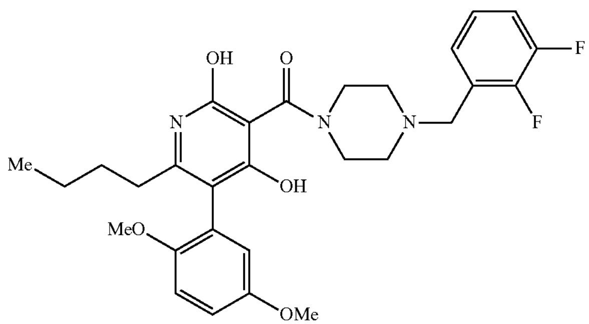 [SMILES: CCCCc1nc(O)c(C(=O)N2CCN(Cc3cccc(F)c3F)CC2)c(O)c1-c1cc(OC)ccc1OC] | 6-butyl-3-{4-[(2,3-difluorophenyl)methyl]piperazine-1-carbonyl}-5-(2,5-dimethoxyphenyl)pyridine-2,4-diol | $^1$H NMR (500 MHz, DMSO-d6) δ 7.34 (q, J = 8.3 Hz, 1H), 7.28-7.13 (m, 2H), 7.04-6.86 (m, 2H), 6.65 (d, J = 2.9 Hz, 1H), 3.69 (s, 3H), 3.63 (s, 3H), 3.62-3.57 (m, 2H), 2.55 (s, 4H), 2.43 (br. s., 4H), 2.24-2.02 (m, 2H), 1.34 (quin, J = 7.4 Hz, 2H), 1.13-0.99 (m, 2H), 0.66 (t, J = 7.3 Hz, 3H) | 1.59 A 542.1 | A |
| 111 | 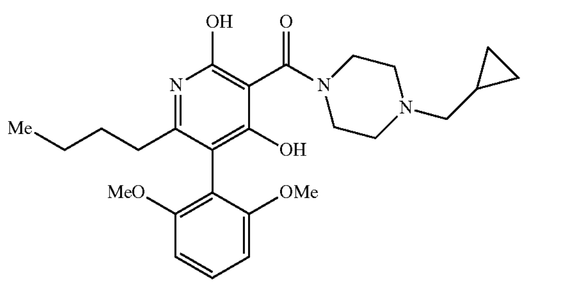 [SMILES: CCCCc1nc(O)c(C(=O)N2CCN(CC3CC3)CC2)c(O)c1-c1c(OC)cccc1OC] | 6-butyl-3-[4-cyclopropylmethyl)piperazine-1-carbonyl]-5-(2,6-dimethoxyphenyl)pyridine-2,4-diol | $^1$H NMR (500 MHz, DMSO-d6) δ 7.33 (t, J = 8.3 Hz, 1H), 6.71 (d, J = 8.3 Hz, 2H), 3.68 (s, 6H), 3.08 (d, J = 6.3 Hz, 2H), 2.53 (d, J = 19.7 Hz, 8H), 2.08 (t, J = 7.5 Hz, 2H), 1.44-1.23 (m, 2H), 1.15-0.96 (m, 3H), 0.75-0.58 (m, 5H), 0.38 (d, J = 3.8 Hz, 2H) | 1.13 A 470.0 | B |

TABLE 4-continued

| Ex# | Structure | Name | NMR | Rt(min) method M + H | Human cAMP EC$_{50}$ |
|---|---|---|---|---|---|
| 112 | (structure) | 6-butyl-3-{4-[(2,3-dichlorophenyl)methyl]piperazine-1-carbonyl}-5-(2,3-dimethoxyphenyl)pyridine-2,4-diol | $^1$H NMR (500 MHz, DMSO-d6) δ 7.72-7.53 (m, 2H), 7.43 (br. s., 1H), 7.12-7.00 (m, 2H), 6.68 (d, J = 6.7 Hz, 1H), 3.82 (s, 3H), 3.57 (s, 3H), 3.42 (br. s., 2H), 2.56-2.43 (m, 8H), 2.07 (br. s., 2H), 1.44-1.30 (m, 2H), 1.14-1.00 (m, 2H), 0.67 (t, J = 7.3 Hz, 3H) | 1.82 A 574.14 | A |
| 113 | (structure) | 3-{4-[(2-bromo-5-fluorophenyl]methyl]piperidine-1-carbonyl}-6-butyl-5-(2,6-dimethoxyphenyl)pyridine-2,4-diol | $^1$H NMR (500 MHz, DMSO-d6) δ 7.62 (dd, J = 8.7, 5.6 Hz, 1H), 7.32 (t, J = 8.3 Hz, 1H), 7.24 (dd, J = 9.6, 2.7 Hz, 1H), 7.10-6.97 (m, 1H), 6.69 (d, J = 8.4 Hz, 2H), 3.67 (s, 6H), 2.66 (d, J = 7.0 Hz, 2H), 2.55 (s, 2H), 2.05 (t, J = 7.7 Hz, 2H), 1.89 (d, J = 18.3 Hz, 1H), 1.58 (d, J = 12.2 Hz, 2H), 1.28 (d, J = 7.2 Hz, 4H), 1.13-0.98 (m, 2H), 0.64 (t, J = 7.3 Hz, 3H) | 2.05 A 602.9 | A |
| 114 | (structure) | 3-{4-[(2,3-difluorophenyl)methyl]piperazine-1-carbonyl}-5-(2,6-dimethoxyphenyl)-6-(ethoxymethyl)pyridine-2,4-diol | $^1$H NMR (500 MHz, DMSO-d6) δ 7.63-7.49 (m, 1H), 7.46-7.30 (m, 3H), 6.70 (d, J = 8.3 Hz, 2H), 4.33 (br. s., 2H), 3.67 (br s, 6H), 3.28-3.18 (m, 2H), 2.61-2.42 (m, 8H), 0.97 (t, J = 6.9 Hz, 3H) | 1.19 B 544.1 | A |

TABLE 4-continued

| Ex# | Structure | Name | NMR | Rt(min) method M + H | Human cAMP EC$_{50}$ |
|---|---|---|---|---|---|
| 115 | 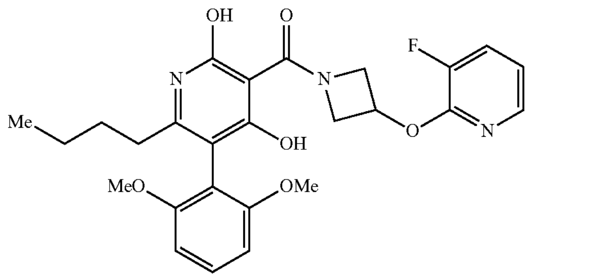 [SMILES: CCCCc1nc(O)c(C(=O)N2CC(Oc3ncccc3F)C2)c(O)c1-c1c(OC)cccc1OC] | 6-butyl-5-(2,6-dimethoxyphenyl)-3-{3-[(3-fluoropyridin-2-yl)oxy]azetidine-1-carbonyl}pyridine-2,4-diol | $^1$H NMR (500 MHz, DMSO-d6) δ 7.96 (d, J = 4.0 Hz, 1H), 7.72 (t, J = 9.1 Hz, 1H), 7.31 (t, J = 7.7 Hz, 1H), 7.08 (br. s., 1H), 6.69 (d, J = 7.9 Hz, 2H), 5.40 (br. s., 1H), 4.66 (br. s., 1H), 4.50 (br. s., 1H), 4.39 (br. s., 1H), 4.02 (br. s., 1H), 3.71-3.45 (m, 6H), 2.08 (br. s., 2H), 1.29 (d, J = 7.1 Hz, 2H), 1.14-0.96 (m, 2H), 0.63 (t, J = 6.8 Hz, 3H) | 2.0 A 498.0 | A |
| 116 | 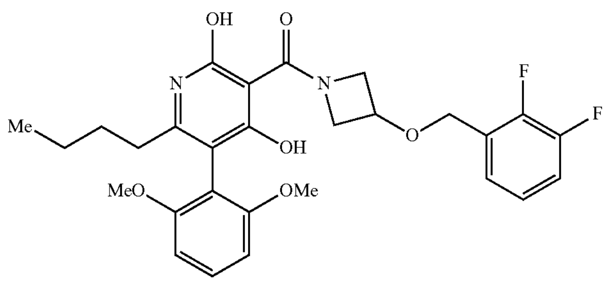 [SMILES: CCCCc1nc(O)c(C(=O)N2CC(OCc3cccc(F)c3F)C2)c(O)c1-c1c(OC)cccc1OC] | 6-butyl-3-{3-[(2,3-difluorophenyl)methoxy]azetidine-1-carbonyl]-5-(2,6-dimethoxyphenyl)pyridine-2,4-diol | $^1$H NMR (500 MHz, DMSO-d6) δ 7.41 (q, J = 8.8 Hz, 1H), 7.36-7.27 (m, 2H), 7.28-7.15 (m, 1H), 6.69 (d, J = 8.3 Hz, 2H), 4.57 (s, 2H), 4.42 (br. s., 2H), 4.26 (br. s., 2H), 3.81 (br. s., 1H), 3.66 (s, 6H), 2.08 (t, J = 7.5 Hz, 2H), 1.39-1.22 (m, 2H), 1.12-0.97 (m, 2H), 0.64 (t, J = 7.3 Hz, 3H) | 2.03 B 529.1 | A |
| 117 | 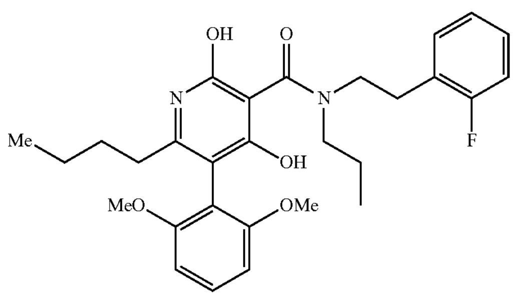 [SMILES: CCCCc1nc(O)c(C(=O)N(CCC)CCc2ccccc2F)c(O)c1-c1c(OC)cccc1OC] | 6-butyl-5-(2,6-dimethoxyphenyl)-N-[2-(2-fluorophenyl)ethyl]-2,4-dihydroxy-N-propylpyridine-3-carboxamide | $^1$H NMR (500 MHz, DMSO-d6) δ 7.38-7.21 (m, 2H), 7.10 (br. s., 3H), 6.66 (d, J = 8.2 Hz, 2H), 3.60 (br. s., 6H), 3.32 (br. s., 2H), 2.93-2.72 (m, 2H), 2.55 (s, 2H), 2.05 (d, J = 6.6 Hz, 2H), 1.52 (br. s., 2H), 1.29 (br. s., 2H), 1.06 (d, J = 6.4 Hz, 2H), 0.93-0.70 (m, 3H), 0.65 (t, J = 6.7 Hz, 3H) | 1.93 A 511.0 | C |

TABLE 4-continued

| Ex# | Structure | Name | NMR | Rt(min) method M + H | Human cAMP EC$_{50}$ |
|---|---|---|---|---|---|
| 118 | 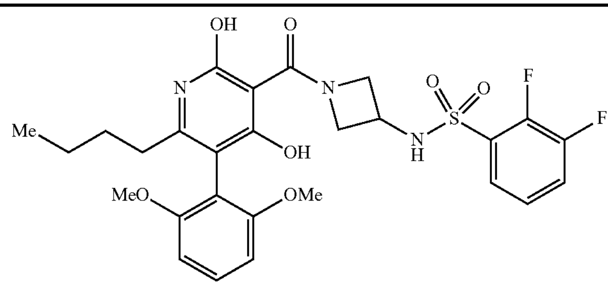 | N-{1-[6-butyl-5-(2,6-dimethoxyphenyl)-2,4-dihydroxypyridine-3-carbonyl]azetidin-3-yl}-2,3-difluorobenzene-1-sulfonamide | $^1$H NMR (500 MHz, DMSO-d6) δ 7.96-7.74 (m, 1H), 7.62 (br. s., 1H), 7.43 (d, J = 4.5 Hz, 1H), 7.31 (t, J = 8.3 Hz, 1H), 6.68 (d, J = 8.4 Hz, 2H), 4.19 (br. s., 3H), 3.82-3.70 (m, 1H), 3.65 (s, 6H), 3.47 (br. s., 1H), 2.06 (t, J = 7.6 Hz, 2H), 1.38-1.22 (m, 2H), 1.11-0.97 (m, 2H), 0.63 (t, J = 7.3 Hz, 3H) | 1.86 B 578.1 | A |
| 119 | 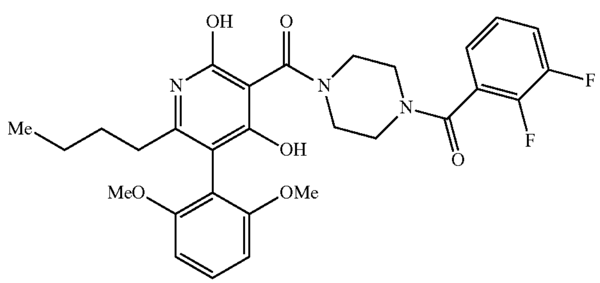 [SMILES: CCCCc1nc(O)c(C(=O)N2CCN(C(=O)c3cccc(F)c3F)CC2)c(O)c1-c1c(OC)cccc1OC] | 6-butyl-3-[4-(2,3-difluorobenzoyl)piperazine-1-carbonyl]-5-(2,6-dimethoxyphenyl)pyridine-2,4-diol | $^1$H NMR (500 MHz, DMSO-d6) δ 7.64-7.44 (m, 1H), 7.31 (d, J = 7.9 Hz, 3H), 6.69 (d, J = 8.3 Hz, 2H), 3.59 (br s, 6H), 2.55 (s, 8H), 2.06 (br. s., 2H), 1.27 (br. s., 2H), 1.04 (br. s.., 2H), 0.71-0.53 (m, 3H) | 1.57 B 556.4 | A |
| 120 | 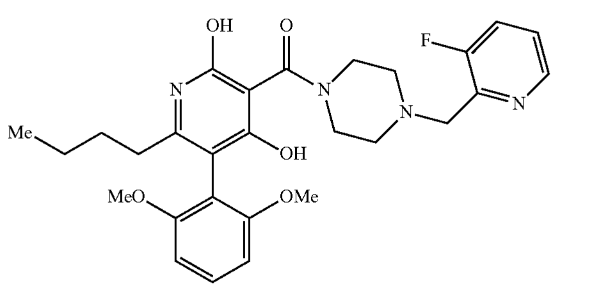 [SMILES: CCCCc1nc(O)c(C(=O)N2CCN(Cc3ncccc3F)CC2)c(O)c1-c1c(OC)cccc1OC] | 6-butyl-5-(2,6-dimethoxyphenyl)-3-{4-[(3-fluoropyridin-2-yl)methyl]piperazine-1-carbonyl}pyridine-2,4-diol | $^1$H NMR (500 MHz, DMSO-d6) δ 8.37 (d, J = 4.2 Hz, 1H), 7.67 (s, 1H), 7.50-7.36 (m, 1H), 7.35-7.25 (m, 1H), 6.68 (d, J = 8.4 Hz, 2H), 3.79 (br. s.., 2H), 3.64 (br s, 6H), 2.55 (s, 4H), 2.46 (br. s., 4H), 2.04 (t, J = 7.5 Hz, 2H), 1.37-1.18 (m, 2H), 1.10-0.95 (m, 2H), 0.61 (t, J = 7.3 Hz, 3H) | 0.68 D 525.08 | A |

TABLE 4-continued

| Ex# | Structure | Name | NMR | Rt(min) method M + H | Human cAMP EC$_{50}$ |
|---|---|---|---|---|---|
| 121 | 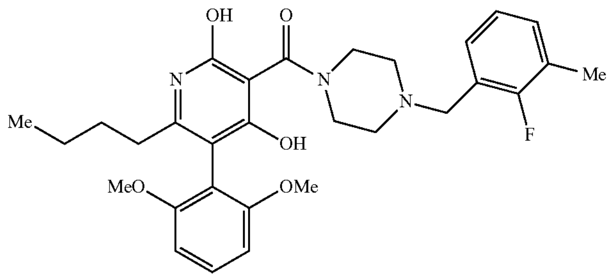 [SMILES: CCCCc1nc(O)c(C(=O)N2CCN(Cc3cccc(C)c3F)CC2)c(O)c1-c1c(OC)cccc1OC] | 6-butyl-5-(2,6-dimethoxyphenyl)-3-{4-[(2-fluoro-3-methylphenyl)methyl]piperazine-1-carbonyl}pyridine-2,4-diol | $^1$H NMR (500 MHz, DMSO-d6) δ 7.32 (t, J = 8.3 Hz, 1H), 7.26-7.14 (m, 2H), 7.12-7.01 (m, 1H), 6.69 (d, J = 8.4 Hz, 2H), 3.67 (s, 6H), 3.55 (br. s., 2H), 2.55 (s, 4H), 2.43 (br. s., 4H), 2.23 (s, 3H), 2.05 (t, J = 7.5 Hz, 2H), 1.41-1.20 (m, 2H), 1.11-0.96 (m, 2H), 0.64 (t, J = 7.2 Hz, 3H) | 1.66 A 538.4 | A |
| 122 | 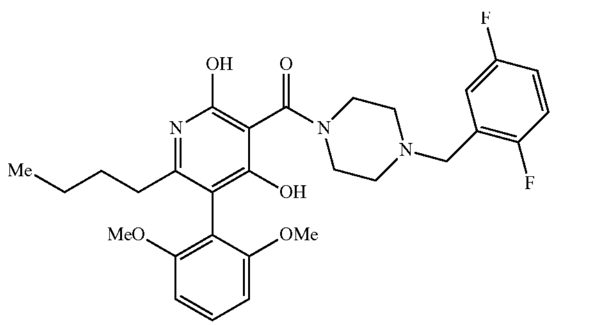 [SMILES: CCCCc1nc(O)c(C(=O)N2CCN(Cc3cc(F)ccc3F)CC2)c(O)c1-c1c(OC)cccc1OC] | 6-butyl-3-{4-[(2,5-difluorophenyl)methyl]piperazine-1-carbonyl}-5-(2,6-dimethoxyphenyl)pyridine-2,4-diol | $^1$H NMR (500 MHz, DMSO-d6) δ 7.49-7.06 (m, 4H), 6.69 (d, J = 8.4 Hz, 2H), 3.75-3.68 (m, 2H), 3.67 (br s, 6H), 2.55 (s, 4H), 2.45 (br. s., 4H), 2.05 (t, J = 7.5 Hz, 2H), 1.38-1.21 (m, 2H), 1.15-0.94 (m, 2H), 0.64 (t, J = 7.2 Hz, 3H) | 1.60 A 542.4 | A |
| 123 | 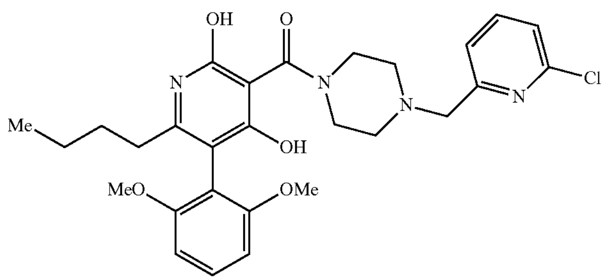 [SMILES: CCCCc1nc(O)c(C(=O)N2CCN(Cc3cccc(Cl)n3)CC2)c(O)c1-c1c(OC)cccc1OC] | 6-butyl-3-{4-[(6-chloropyridin-2-yl)methyl]piperazine-1-carbonyl}-5-(2,6-dimethoxyphenyl)pyridine-2,4-diol | $^1$H NMR (500 MHz, DMSO-d6) δ 7.84 (t, J = 7.7 Hz, 1H), 7.48 (d, J = 7.5 Hz, 1H), 7.39 (d, J = 7.9 Hz, 1H), 7.31 (t, J = 8.2 Hz, 1H), 6.68 (d, J = 8.3 Hz, 2H), 3.75-3.68 (m, 2H), 3.66 (s, 6H), 2.55 (s, 4H), 2.46 (br. s., 4H), 2.04 (d, J = 7.7 Hz, 2H), 1.42-1.18 (m, 2H), 1.13-0.94 (m, 2H), 0.62 (t, J = 7.2 Hz, 3H) | 1.46 A 541.3 | A |

TABLE 4-continued

| Ex# | Structure | Name | NMR | Rt(min) method M + H | Human cAMP EC$_{50}$ |
|---|---|---|---|---|---|
| 153 | 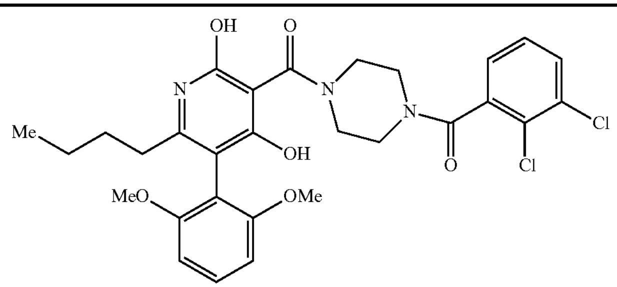 | 6-butyl-3-[4-(2,3-dichlorobenzoyl)piperazine-1-carbonyl]-5-(2,6-dimethoxyphenyl)pyridine-2,4-diol | $^1$H NMR (500 MHz, DMSO-d6) δ 7.69 (d, J = 7.5 Hz, 1H), 7.44 (br. s., 1H), 7.38 (br. s., 1H), 7.24 (t, J = 8.2 Hz, 1H), 6.76-6.52 (m, 2H), 3.67 (br s, 6H), 3.17 (d, J = 7.4 Hz, 4H), 2.53 (d, J = 19.1 Hz, 4H), 2.06-1.91 (m, 2H), 1.36-1.18 (m, 2H), 1.03 (br. s., 2H), 0.62 (br. s., 3H) | 1.63 A 588.1 | A |
| 154 | 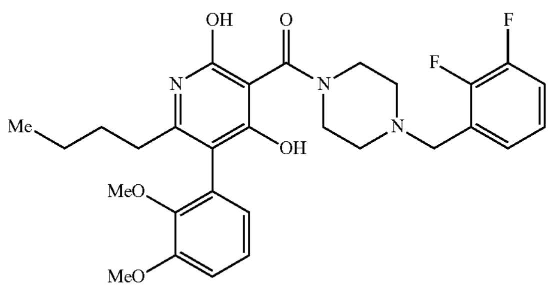 [SMILES: CCCCc1nc(O)c(C(=O)N2CCN(Cc3cccc(F)c3F)CC2)c(O)c1-c1cccc(OC)c1OC] | 6-butyl-3-{4-[(2,3-difluorophenyl)methyl]piperazine-1-carbonyl}-5-(2,3-dimethoxyphenyl)pyridine-2,4-diol | $^1$H NMR (500 MHz, DMSO-d6) δ 7.40-7.27 (m, 1H), 7.26-7.11 (m, 2H), 7.12-6.94 (m, 2H), 6.66 (d, J = 6.6 Hz, 1H), 3.81 (s, 3H), 3.60 (br s, 3H), 3.56 (br. s., 4H), 2.55 (s, 2H), 2.42 (br. s., 4H), 2.24-2.00 (m, 2H), 1.35 (d, J = 6.6 Hz, 2H), 1.14-1.01 (m, 2H), 0.66 (t, J = 7.2 Hz, 3H) | 1.55 A 542.0 | A |

The following compounds, Example 124 to Example 129, were prepared by the general procedures described for Examples 74.

TABLE 5

| Ex# | Structure | Name | Chiral Amine intermediate with Retention time (min) | NMR | Rt (min) method M + H | Human cAMP EC50 |
|---|---|---|---|---|---|---|
| 124 | 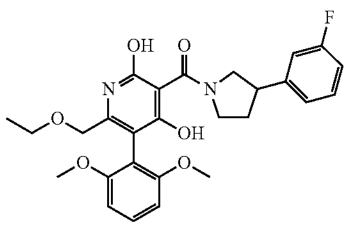 [SMILES: CCOCc1nc(O)c(C(=O)N2CCC(c3cccc(F)c3)C2)c(O)c1-c1c(OC)cccc1OC] | 5-(2,6-dimethoxyphenyl)-6-(ethoxymethyl)-3-[3-(3-fluorophenyl)pyrrolidine-1-carbonyl]pyridine-2,4-diol | Rt = 10.72 (isomer 2) Whelk-O 1 (R,R), 4.6 x 250 mm, 5 micron; mobile phase: 15% IPA/85% CO$_2$; Flow Conditions: 2.0 mL/min, 150 bar, 40° C., wavelength: 220 nm | $^1$H NMR (500 MHz, DMSO-d6) δ 7.43-7.28 (m, 2H), 7.15 (br. s., 2H), 7.05 (t, J = 8.5 Hz, 1H), 6.69 (d, J = 8.2 Hz, 2H), 3.88 (br. s., 1H), 3.69 (br s, 6H), 3.59-3.50 (m, 1H), , 3.42 (br s, 1H), 3.24 (br s, 2H), 3.16 (br s, 1H), 2.56-2.53 (m, 3H), 2.26 (br s, 1H), 2.04-1.94 (m, 1H), 0.00-0.93 (m = 3H) | 1.44 A 497.3 | A |
| 125 | 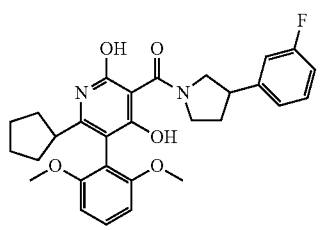 [SMILES: COc1cccc(OC)c1-c1c(C2CCCC2)nc(O)c(C(=O)N2CCC(c3cccc(F)c3)C2)c1O] | 6-cyclopentyl-5-(2,6-dimethoxyphenyl)-3-[3-(3-fluorophenyl)pyrrolidine-1-carbonyl]pyridine-2,4-diol | Rt = 10.72 (isomer 2) Whelk-O 1 (R,R), 4.6 x 250 mm, 5 micron; mobile phase: 15% IPA/85% CO$_2$; Flow Conditions: 2.0 mL/min, 150 bar, 40° C., wavelength: 220 nm | $^1$H NMR (500 MHz, DMSO-d6) δ 7.36 (d, J = 6.4 Hz, 1H), 7.29 (t, J = 8.2 Hz, 1H), 7.17 (br. s., 3H), 7.06 (t, J = 8.3 Hz, 1H), 6.68 (d, J = 8.2 Hz, 3H), 3.65 (br. s., 1H), 3.40 (br. s., 1H), 2.51 (br. s., 6H), 2.43 (br. s., 2H), 2.25 (br. s., 2H), 2.01 (br. s., 2H), 1.66 (br. s., 5H), 1.59 (br. s., 3H), 1.33 (br. s., 3H) | 1.79 A 507.1 | B |
| 126 | 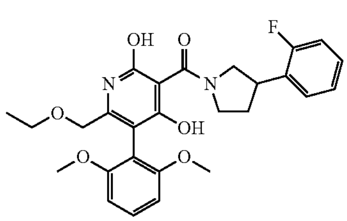 [SMILES: CCOCc1nc(O)c(C(=O)N2CCC(c3ccccc3F)C2)c(O)c1-c1c(OC)cccc1OC] | 5-(2,6-dimethoxyphenyl)-6-(ethoxymethyl)-3-[3-(2-fluorophenyl)pyrrolidine-1-carbonyl]pyridine-2,4-diol | Rt = 10.65 (isomer 2) Chiralpak IF, 4.6 x 250 mm, 5 micron; mobile phase: 15% IPA/90% CO$_2$; Flow Conditions: 2.0 mL/min, 150 bar, 40° C., wavelength: 220 nm | $^1$H NMR (500 MHz, DMSO-d6) δ 7.50-7.38 (m, 1H), 7.36-7.25 (m, 2H), 7.22-7.12 (m, 2H), 6.70 (d, J = 8.2 Hz, 2H), 3.88 (br. s., 2H), 3.74-3.35 (m, 5H), 3.28-3.18 (m, 2H), 2.51 (br. s., 6H), 2.33-2.16 (m, 1H), 2.17-1.77 (m, 1H), 0.97 (d, J = 6.0 Hz, 3H) | 0.89 D 497.4 | A |

TABLE 5-continued

| Ex# | Structure | Name | Chiral Amine intermediate with Retention time (min) | NMR | Rt (min) method M + H | Human cAMP EC50 |
|---|---|---|---|---|---|---|
| 127 | 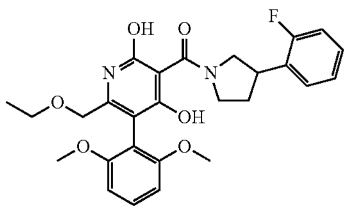 [SMILES: CCOCc1nc(O)c(C(=O)N2CCC(c3ccccc3F)C2)c(O)c1-c1c(OC)cccc1OC] | 5-(2,6-dimethoxyphenyl)-6-(ethoxymethyl)-3-[3-(2-fluorophenyl)pyrrolidine-1-carbonyl]pyridine-2,4-diol | Rt = 10.65 (isomer 1) Chiralpak IF, 4.6 x 250 mm, 5 micron; mobile phase: 15% IPA/90% $CO_2$; Flow Conditions: 2.0 mL/min, 150 bar, 40° C., wavelength: 220 nm | $^1$H NMR (500 MHz, DMSO-d6) δ 7.50-7.38 (m, 1H), 7.36-7.25 (m, 2H), 7.22-7.12 (m, 2H), 6.70 (d, J = 8.2 Hz, 2H), 3.88 (br. s., 2H), 3.74-3.35 (m, 5H), 3.28-3.18 (m, 2H), 2.51 (br. s., 6H), 2.33-2.16 (m, 1H), 2.17-1.77 (m, 1H), 0.97 (d, J = 6.0 Hz, 3H) | 0.89 D 497.4 | A |
| 128 | 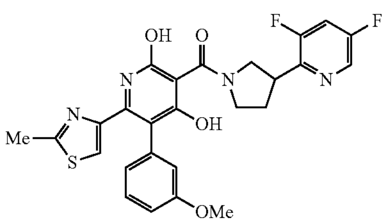 [SMILES: COc1cccc(-c2c(-c3csc(C)n3)nc(O)c(C(=O)N3CCC(c4ncc(F)cc4F)C3)c2O)c1] | 3-[3-(3,5-difluoropyridin-2-yl)pyrrolidine-1-carbonyl]-5-(3-methoxyphenyl)-6-(2-methyl-1,3-thiazol-4-yl)pyridine-2,4-diol | Rt = 4.80, (isomer 1) Whelko (4.6 x 250 mm, 5 micron; mobile phase: 10% IPA/90% $CO_2$; flow conditions: 3.0 mL/min, 140 bar, 40° C.; wavelength: 220 nm. | $^1$H NMR (500 MHz, DMSO-d6) δ 8.49 (br. s., 1H), 8.05-7.82 (m, 1H), 7.39-7.16 (m, 1H), 6.93 (d, J = 7.9 Hz, 1H), 6.85-6.57 (m, 3H), 4.14-3.70 (m, 3H), 3.72 (s, 3H), 3.42 (br. s., 2H), 2.63 (br. s., 3H), 2.34-2.09 (m, 2H) | 1.37 A 525.2 | B |
| 129 | 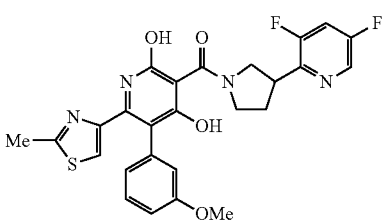 [SMILES: COc1cccc(-c2c(-c3csc(C)n3)nc(O)c(C(=O)N3CCC(c4ncc(F)cc4F)C3)c2O)c1] | 3-[3-(3,5-difluoropyridin-2-yl)pyrrolidine-1-carbonyl]-5-(3-methoxyphenyl)-6-(2-methyl-1,3-thiazol-4-yl)pyridine-2,4-diol | Rt = 3.86, (isomer 2) Whelko (4.6 x 250 mm, 5 micron; mobile phase: 10% IPA/90% $CO_2$; flow conditions: 3.0 mL/min, 140 bar, 40° C.; wavelength: 220 nm. | $^1$H NMR (500 MHz, DMSO-d6) δ 8.49 (br. s., 1H), 8.05-7.82 (m, 1H), 7.39-7.16 (m, 1H), 6.93 (d, J = 7.9 Hz, 1H), 6.85-6.57 (m, 3H), 4.14-3.70 (m, 3H), 3.72 (s, 3H), 3.42 (br. s., 2H), 2.63 (br. s., 3H), 2.34-2.09 (m, 2H) | 1.37 A 525.2 | A |

Example 130. 6-butyl-3-[3-(5-chloro-3-fluoropyridin-2-yl)pyrrolidine-1-carbonyl]-5-(2,6-dimethoxyphenyl)-4-hydroxy-1,2-dihydropyridin-2-one

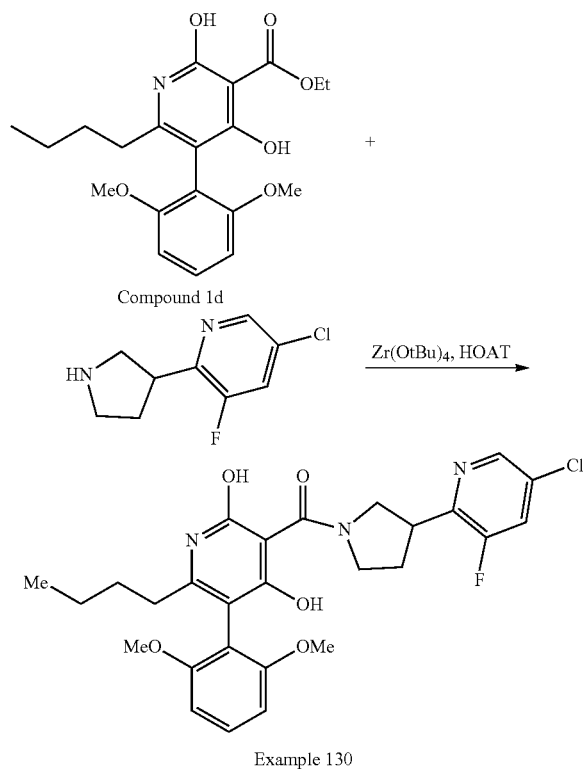

1-Hydroxy-7-azabenzotriazole (HOAT, 6.5 mg, 0.048 mmol) and zirconium (IV) tert-butoxide (0.02 mL, 0.05 mmol) were added to compound 1d and 5-chloro-3-fluoro-2-(pyrrolidin-3-yl)pyridine (prepared from chiral tert-butyl 3-(5-chloro-3-fluoropyridin-2-yl)pyrrolidine-1-carboxylate using the general route described for the preparation of compound 74c, isomer 2, Rt=8.20, Chiral analytical HPLC: Whelko (4.6×250 mm, 5 micron; mobile phase: 10% IPA/90% $CO_2$; flow condition: 3.0 mL/min, 140 bar, 40° C.; wavelength: 220 nm.) in toluene (1.5 mL). The reaction mixture was heated at 100° C. After 16 hours, the reaction mixture was allowed to cool and diluted with 1N HCl (4 mL), extracted with DCM (3×5 mL), the combined organic portions dried over $Na_2SO_4$, concentrated and purified via preparative LC/MS with the following conditions: Column: XBridge C18, 19×200 mm, 5-m particles; Mobile Phase A: 5:95 acetonitrile:water with 0.1% TFA; Mobile Phase B: 95:5 acetonitrile:water with 0.1% TFA; Gradient: 20-60% B over 25 minutes, then a 5-minute hold at 100% B; Flow: 20 mL/min. Fractions containing the desired product were combined and concentrated to give Example 130 (13 mg, 31% yield). LCMS (Method D) Rt=0.98, m/z=530.0 (M+H). $^1$H NMR (500 MHz, DMSO-d6) δ 8.49 (br. s., 1H), 8.06 (br. s., 1H), 7.32 (t, J=8.3 Hz, 1H), 6.70 (d, J=8.4 Hz, 2H), 3.67 (s, 6H), 3.93-3.70 (m, 2H), 3.65-3.38 (m, 3H), 2.35-2.22 (m, 1H), 2.18-1.96 (m, 3H), 1.33-1.24 (m, 2H), 1.14-0.98 (m, 2H), 0.64 (t, J=6.6 Hz, 3H). Human cAMP Potency range A The following compounds, Example 131 to Example 137, were prepared by the general procedures described for Examples 130

TABLE 6

| Ex# | Structure | Name | Chiral Amine intermediate with Retention time (min) | NMR | Rt (min) Method M + H | Human cAMP EC$_{50}$ |
|---|---|---|---|---|---|---|
| 131 | ![structure] | 3-[3-(2,4-difluorophenyl)pyrrolidine-1-carbonyl]-5-2,6-dimethoxyphenyl)-6-(ethoxymethyl)-4-hydroxy-1,2-dihydropyridin-2-one | Rt = 2.53 (isomer 1) Chiralpak IC, 4.6 × 250 mm, 5 micron; mobile phase: 10% IPA/90% CO$_2$; flow condition: 3.0 mL/min, 140 bar, 45° C.; wavelength: 220 nm | $^1$H NMR (500 MHz, METHANOL-d4) δ 17.49-7.34 (m, 2H), 6.96 (br. s., 2H), 6.75 (d, J = 8.5 Hz, 2H), 4.08 (s, 2H), 3.76 (s, 6H), 3.75-3.69 (m, 5H), 3.42 (d, J = 6.9 Hz, 2H), 2.45-2.30 (m, 1H), 2.21-2.10 (m, 1H), 1.15 (br. s., 3H) | 0.90 D 515.2 | A |

TABLE 6-continued

| Ex# | Structure | Name | Chiral Amine intermediate with Retention time (min) | NMR | Rt (min) Method M + H | Human cAMP EC$_{50}$ |
|---|---|---|---|---|---|---|
| 132 | 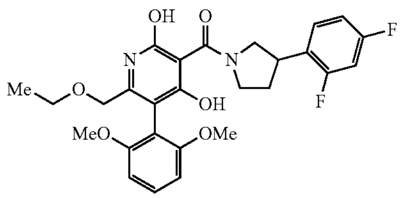 [SMILES: CCOCc1nc(O)c(C(=O)N2CCC(c3ccc(F)cc3F)C2)c(O)c1-c1c(OC)cccc1OC] | 3-[3-(2,4-difluorophenyl)pyrrolidine-1-carbonyl]-5-(2,6-dimethoxyphenyl)-6-(ethoxymethyl)-4-hydroxy-1,2-dihydropyridin-2-one | Rt = 2.78 (isomer 2) Chiralpak IC, 4.6 x 250 mm, 5 micron; mobile phase: 10% IPA/90% CO$_2$; flow condition: 3.0 mL/min, 140 bar, 45° C.; wavelength: 220 nm | $^1$H NMR (500 MHz, METHANOL-d4) δ 7.49-7.34 (m, 2H), 6.96 (br. s., 2H), 6.75 (d, J = 8.5 Hz, 2H), 4.08 (s, 2H), 3.86-13.58 (m, 11H), 3.42 (d, J = 6.9 Hz, 2H), 2.45-2.30 (m, 1H), 2.21-2.10 (m, 1H), 1.15 (br. s., 3H) | 0.90 D 515.2 | A |
| 133 | 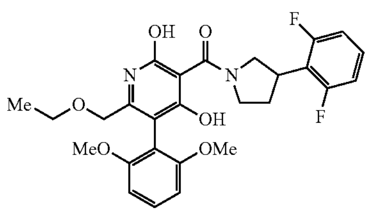 [SMILES: CCOCc1nc(O)c(C(=O)N2CCC(c3c(F)cccc3F)C2)c(O)c1-c1c(OC)cccc1OC] | 3-[3-(2,6-difluorophenyl)pyrrolidine-1-carbonyl]-5-(2,6-dimethoxyphenyl)-6-(ethoxymethyl)-4-hydroxy-1,2-dihydropyridin-2-one | Rt = 4.85, (isomer 2) Whelko (4.6 x 250 mm, 5 micron; mobile phase: 10% IPA/90% CO$_2$; flow condition: 3.0 mL/min, 140 bar, 40° C.; wavelength: 220 nm. | $^1$H NMR (500 MHz, METHANOL-d4) δ 7.40 (s, 1H), 7.36-7.26 (m, 1H), 6.99 (t, J = 8.5 Hz, 2H), 6.74 (d, J = 8.4 Hz, 2H), 4.07 (s, 2H), 4.01-3.59 (m, 11H), 3.54-3.37 (m, 2H), 2.56-2.38 (m, 1H), 2.36-2.16 (m, 1H), 1.15 (br. s., 3H) | 0.89 D 515.1 | A |
| 134 | 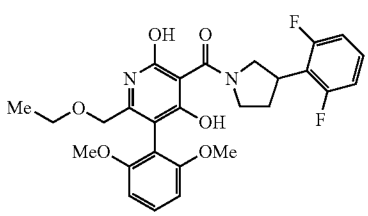 [SMILES: CCOCc1nc(O)c(C(=O)N2CCC(c3c(F)cccc3F)C2)c(O)c1-c1c(OC)cccc1OC] | 3-[3-(2,6-difluorophenyl)pyrrolidine-1-carbonyl]-5-(2,6-dimethoxyphenyl)-6-(ethoxymethyl)-4-hydroxy-1,2-dihydropyridin-2-one | Rt = 4.11, (isomer 1) Whelko (4.6 x 250 mm, 5 micron; mobile phase: 10% IPA/90% CO$_2$; flow condition: 3.0 mL/min, 140 bar, 40° C.; wavelength: 220 nm. | $^1$H NMR (500 MHz, METHANOL-d4) δ 7.40 (s, 1H), 7.36-7.26 (m, 1H), 6.99 (t, J = 8.5 Hz, 2H), 6.74 (d, J = 8.4 Hz, 2H), 4.07 (s, 2H), 4.01-3.59 (m, 11H), 3.54-3.37 (m, 2H), 2.56-2.38 (m, 1H), 2.36-2.16 (m, 1H), 1.15 (br. s., 3H) | 0.89 D 515.1 | A |

TABLE 6-continued

| Ex# | Structure | Name | Chiral Amine intermediate with Retention time (min) | NMR | Rt (min) Method M + H | Human cAMP EC$_{50}$ |
|---|---|---|---|---|---|---|
| 135 | (structure shown) | 6-butyl-3-[3-(5-chloro-3-fluoropyridin-2-yl)pyrrolidine-1-carbonyl]-5-(2,6-dimethoxyphenyl)-4-hydroxy-1,2-dihydropyridin-2-one | (structure shown) Rt = 6.80, (isomer 1) Whelko (4.6 x 250 mm, 5 micron; mobile phase: 10% IPA/90% CO$_2$; flow condition: 3.0 mL/min, 140 bar, 40° C.; wavelength: 220 nm. | $^1$H NMR (500 MHz, DMSO-d6) δ 8.49 (br. s., 1H), 8.06 (br. s., 1H), 7.32 (t, J = 8.3 Hz, 1H), 6.70 (d, J = 8.4 Hz, 2H), 3.93-3.38 (m, 11H), 2.35-2.22 (m, 1H), 2.18-1.96 (m, 3H), 1.33-1.24 (m, 2H), 1.14-0.98 (m, 2H), 0.64 (t, J = 6.6 Hz, 3H) | 0.98 D 530.0 | A |
| 136 | (structure shown) | 3-[(3S)-3-(benzyloxy)pyrrolidine-1-carbonyl]-6-butyl-5-(2,6-dimethoxyphenyl)pyridine-2,4-diol | Chiral commercial reagent | $^1$H NMR (500 MHz, DMSO-d6) δ 7.67-7.16 (m, 7H), 6.69 (d, J = 7.8 Hz, 2H), 4.51 (br. s., 2H), 4.27-4.14 (m, 1H), 3.71-3.60 (m, 4H), 2.55 (s, 6H), 2.16-1.89 (m, 4H), 1.39-1.24 (m, 2H), 1.07 (d, J = 7.2 Hz, 2H), 0.64 (t, J = 7.2 Hz, 3H) | 1.93 B 507.1 | A |
| 137 | (structure shown) | 3-[(3S)-3-(benzyloxy)pyrrolidine-1-carbonyl]-5-(2,6-dimethoxyphenyl)-6-(ethoxymethyl)pyridine-2,4-diol | Chiral commercial reagent | $^1$H NMR (500 MHz DMSO-d6) δ 7.52-7.19 (m, 6H), 6.85-6.50 (m, 2H), 4.63-4.41 (m, 2H), 4.20 (br. s., 1H), 3.90 (s, 2H), 3.78-3.52 (m, 10H), 3.30-3.20 (m, 1H), 2.55 (s, 3H), 2.11-1.93 (m, 2H), 0.98 (t, J = 7.0 Hz, 3H) | 0.94 D 507.1 | B |

Example 138. 6-butyl-5-(3-ethylphenyl)-4-hydroxy-3-{5-[(2-methyl-1,3-thiazol-4-yl)methyl]-1,3,4-oxadiazol-2-yl}-1,2-dihydropyridin-2-one

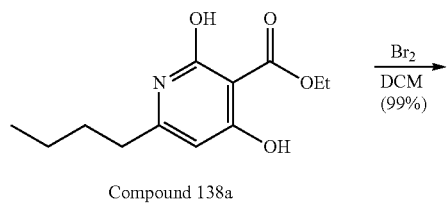

Compound 138a

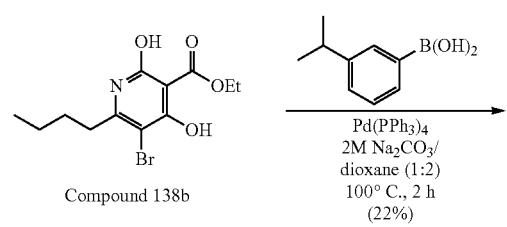

Compound 138b

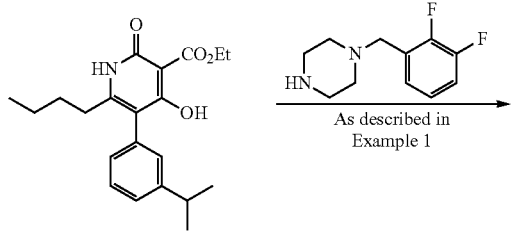

Compound 138c

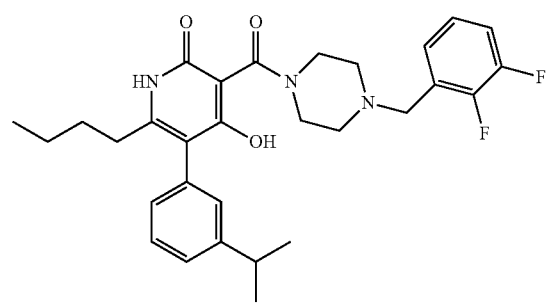

Example 138

Compound 138a. Ethyl 5-bromo-6-butyl-2,4-dihydroxynicotinate

Bromine (0.55 mL, 11 mmol) was added to compound 138a (1.7 g, 7.1 mmol; prepared as described in W2007/197478) in DCM (40 mL). After 15 minutes, the reaction mixture was concentrated under reduced pressure and purified by silica gel chromatography elution with 0 to 5% methanol/DCM to give compound 138b (2.2 g, 99% yield) as a white solid. LCMS (Method D) Rt=0.90 min, m/z=320.0 [M+H]$^+$. $^1$H NMR (500 MHz, CDCl$_3$) δ 14.28 (s, 1H), 12.09-11.75 (m, 1H), 4.45 (q, J=7.0 Hz, 2H), 2.95-2.71 (m, 2H), 1.80-1.64 (m, 2H), 1.52-1.37 (m, 5H), 0.98 (t, J=7.4 Hz, 3H).

Compound 138b. Ethyl 6-butyl-4-hydroxy-5-(3-isopropylphenyl)-2-oxo-1,2-dihydropyridine-3-carboxylate Compound 138a (100 mg, 0.31 mmol), (3-isopropylphenyl)boronic acid (77 mg, 0.47 mmol) and Pd(PPh$_3$)$_4$ (110 mg, 0.094 mmol) in 2M Na$_2$CO$_3$ (2 mL)/Dioxane (4 mL) were purged with nitrogen and heated to 100° C. After 2 hours, the reaction mixture was filtered, diluted with DMF/methanol and purified using reverse phase HPLC (Phenomemenx Luna AXIA 5 micron C18, 30×100 mm, 30 to 100% B over 10 minutes with 5 minute hold time, solvent A: 90% water/10% methanol/0.1% TFA, solvent B: 90% methanol/10% water/0.1% TFA, Flow rate 40 mL/min; detector at 254) to isolate compound 138b (25 mg, 22% yield). LCMS (Method D). Rt=1.05, m/z=384.0 [M+H]$^+$. $^1$H NMR (500 MHz, CHLOROFORM-d) δ 7.50-7.35 (m, 1H), 7.35-7.23 (m, 1H), 7.15-6.96 (m, 2H), 4.48 (d, J=6.6 Hz, 2H), 2.97 (dt, J=13.8, 6.9 Hz, 1H), 2.48 (t, J=7.7 Hz, 2H), 1.62-1.51 (m, 2H), 1.45 (t, J=6.6 Hz, 3H), 1.34-1.21 (m, 8H), 0.81 (t, J=7.3 Hz, 3H).

Example 138. 6-butyl-5-(3-ethylphenyl)-4-hydroxy-3-{5-[(2-methyl-1,3-thiazol-4-yl)methyl]-1,3,4-oxadiazol-2-yl}-1,2-dihydropyridin-2-one Example 138 was prepared from compound 138b using the method described for Example 1 (8.5%). LCMS (Method A). Rt=2.23, m/z=524.0 [M+H]$^+$. $^1$H NMR (500 MHz, DMSO-d6) δ 7.35-7.15 (m, 5H), 7.08-6.92 (m, 2H), 3.26-3.02 (m, 2H), 2.98-2.76 (m, 1H), 2.53 (m, 8H), 2.19 (br. s., 2H), 1.47-1.33 (m, 2H), 1.28-1.14 (m, 6H), 1.13-1.01 (m, 2H), 0.66 (t, J=7.2 Hz, 3H). Human cAMP Potency range A.

The following compounds, Example 139 to Example 147, were prepared by the general procedures described for Examples 138 and 74.

TABLE 7

| Ex# | Structure | Name | Chiral Amine intermediate with Retention time (min) | NMR | Rt (min) Method M + H | Human cAMP EC$_{50}$ |
|---|---|---|---|---|---|---|
| 139 | 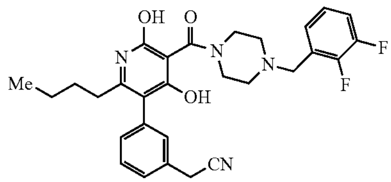 [SMILES: CCCCc1nc(O)c(C(=O)N2CCN(Cc3cccc(F)c3F)CC2)c(O)c1-c1cccc(CC#N)c1] | 2-[3-(2-butyl-5-{4-[(2,3-difluorophenyl)methyl]piperazine-1-carbonyl}-4,6-dihydroxypyridin-3-yl)phenyl]acetonitrile | achiral | $^1$H NMR (500 MHz, DMSO-d6) δ 7.59-7.01 (m, 7H), 4.51-4.23 (m, 2H), 4.06 (s, 2H), 2.53 (m, 8H), 2.30-2.14 (m, 2H), 1.50-1.33 (m, 2H), 1.13-1.00 (m, 2H), 0.68 (t, J = 7.3 Hz, 3H) | 1.42 A 521.3 | A |
| 140 | 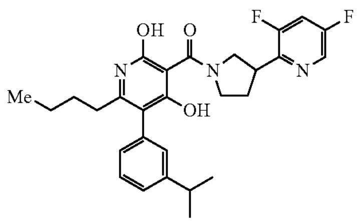 [SMILES: CCCCc1nc(O)c(C(=O)N2CCC(c3ncc(F)cc3F)C2)c(O)c1-c1cccc(C(C)C)c1] | 6-butyl-3-[3-(3,5-difluoropyridin-2-yl)pyrrolidine-1-carbonyl]-5-[3-(propan-2-yl)phenyl]pyridine-2,4-diol | Rt = 3.86, (isomer 2) Whelko (4.6 x 250 mm, 5 micron; mobile phase: 10% IPA/90% CO$_2$; flow condition: 3.0 mL/min, 140 bar, 40° C.; wavelength: 220 nm. | $^1$H NMR (500 MHz, DMSO-d6) δ 8.48 (br. s., 1H), 7.90 (br. s., 1H), 7.41-7.25 (m, 1H), 7.20 (d, J = 7.4 Hz, 1H), 7.10-6.94 (m, 2H), 4.06-3.29 (m, 5H), 2.98-2.81 (m, 1H), 2.33-2.04 (m, 4H), 1.39 (br. s., 2H), 1.20 (d, J = 6.8 Hz, 6H), 1.08 (d, J = 6.9 Hz, 2H), 0.71-0.59 (m, 3H) | 2.17 A 496.1 | A |
| 141 | 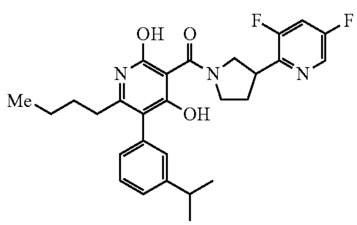 [SMILES: CCCCc1nc(O)c(C(=O)N2CCC(c3ncc(F)cc3F)C2)c(O)c1-c1cccc(C(C)C)c1] | 6-butyl-3-[3-(3,5-difluoropyridin-2-yl)pyrrolidine-1-carbonyl]-5-[3-(propan-2-yl)phenyl]pyridine-2,4-diol | Rt = 4.80, (isomer 1) Whelko (4.6 x 250 mm, 5 micron; mobile phase: 10% IPA/90% CO$_2$; flow condition: 3.0 mL/min, 140 bar, 40° C.; wavelength: 220 nm. | $^1$H NMR (500 MHz, DMSO-d6) δ 8.48 (br. s., 1H), 7.90 (br. s., 1H), 7.41-7.25 (m, 1H), 7.20 (d, J = 7.4 Hz, 1H), 7.10-6.94 (m, 2H), 4.06-3.29 (m, 5H), 2.98-2.81 (m, 1H), 2.33-2.04 (m, 4H), 1.39 (br. s., 2H), 1.20 (d, J = 6.8 Hz, 6H), 1.08 (d, J = 6.9 Hz, 2H), 0.71-0.59 (m, 3H) | 2.17 A 496.1 | A |

TABLE 7-continued

| Ex# | Structure | Name | Chiral Amine intermediate with Retention time (min) | NMR | Rt (min) Method M + H | Human cAMP EC$_{50}$ |
|---|---|---|---|---|---|---|
| 142 | 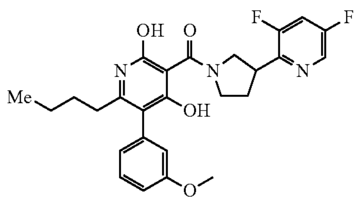 [SMILES: CCCCc1nc(O)c(C(=O)N2CCC(c3ncc(F)cc3F)C2)c(O)c1-c1cccc(OC)c1] | 6-butyl-3-[3-(3,5-difluoropyridin-2-yl)pyrrolidine-1-carbonyl]-5-(3-methoxyphenyl)pyridine-2,4-diol | Rt = 4.80, (isomer 1) Whelko (4.6 x 250 mm, 5 micron; mobile phase: 10% IPA/90% CO$_2$; flow condition: 3.0 mL/min, 140 bar, 40° C.; wavelength: 220 nm. | $^1$H NMR (500 MHz, DMSO-d6) δ 8.47 (br. s. 1H), 8.02-7.76 (m, 1H), 7.31 (s, 1H), 7.01-6.83 (m, 1H), 6.84-6.62 (m, 2H), 3.74 (s, 3H), 3.53 (br. s., 5H), 2.25 (br. s., 4H), 1.39 (br. s., 2H), 1.10 (d, J = 6.9 Hz, 2H), 0.68 (t, J = 6.8 Hz, 3H) | 1.88 B 484.0 | A |
| 143 | 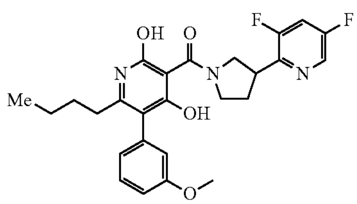 [SMILES: CCCCc1nc(O)c(C(=O)N2CCC(c3ncc(F)cc3F)C2)c(O)c1-c1cccc(OC)c1] | 6-butyl-3-[3-(3,5-difluoropyridin-2-yl)pyrrolidine-1-carbonyl]-5-(3-methoxyphenyl)pyridine-2,4-diol | Rt = 3.86, (isomer 2) Whelko (4.6 x 250 mm, 5 micron; mobile phase: 10% IPA/90% CO$_2$; flow condition: 3.0 mL/min, 140 bar, 40° C.; wavelength: 220 nm. | $^1$H NMR (500 MHz, DMS0-d6) δ 8.47 (br. s. 1H), 8.02-7.76 (m, 1H), 7.31 (s, 1H), 7.01-6.83 (m, 1H), 6.84-6.62 (m, 2H), 3.74 (s, 3H), 3.53 (br. s., 5H), 2.25 (br. s., 4H), 1.39 (br. s., 2H), 1.10 (d, J = 6.9 Hz, 2H), 10.68 (t, J = 6.8 Hz, 3H) | 1.88 B 484.0 | A |
| 144 | 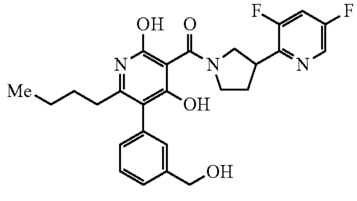 [SMILES: CCCCc1nc(O)c(C(=O)N2CCC(c3ncc(F)cc3F)C2)c(O)c1-c1cccc(CO)c1] | 6-butyl-3-[3-(3,5-difluoropyridin-2-yl)pyrrolidine-1-carbonyl]-5-[3-(hydroxymethyl)phenyl]pyridine-2,4-diol | Rt = 3.86, (isomer 2) Whelko (4.6 x 250 mm, 5 micron; mobile phase: 10% IPA/90% CO$_2$; flow condition: 3.0 mL/min, 140 bar, 40° C.; wavelength: 220 nm. | $^1$H NMR (500 MHz, DMSO-d6) δ 8.47 (br. s., 1H), 7.88 (br. s., 1H), 7.38-7.17 (m, 2H), 7.13-6.96 (m, 2H), 4.49 (s, 2H), 3.89 (s, 5H), 2.32-2.03 (m, 4H), 1.39 (br. s., 2H), 1.10 (br. s., 2H), 0.68 (br. s. 3H) | 1.27 A 484.2 | A |

TABLE 7-continued

| Ex# | Structure | Name | Chiral Amine intermediate with Retention time (min) | NMR | Rt (min) Method M + H | Human cAMP EC$_{50}$ |
|---|---|---|---|---|---|---|
| 145 | 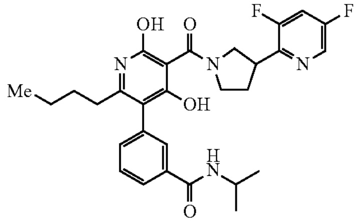 [SMILES: CCCCc1nc(O)c(C(=O)N2CCC(c3ncc(F)cc3F)C2)c(O)c1-c1cccc(C(=O)NC(C)C)c1] | 3-{2-butyl-5-[3-(3,5-difluoropyridin-2-yl)pyrrolidine-1-carbonyl]-4,6-dihydroxypyridin-3-yl}-N-(propan-2-yl)benzamide | Rt = 4.80, (isomer 1) Whelko (4.6 x 250 mm, 5 micron; mobile phase: 10% IPA/90% CO$_2$; flow condition: 3.0 mL/min, 140 bar, 40° C.; wavelength: 220 nm. | $^1$H NMR (500 MHz, DMSO-d6) δ 8.48 (br. s., 1H), 8.22 (d, J = 7.6 Hz, 1H), 7.91 (br. s., 1H), 7.83 (d, J = 7.6 Hz, 1H), 7.72 (br. s., 1H), 7.47 (t, J = 7.6 Hz, 1H), 7.35 (d, J = 7.3 Hz, 1H), 4.11 (d, J = 6.4 Hz, 1H), 3.96-3.36 (m, 5H), 2.24 (d, J = 7.3 Hz, 4H), 1.41 (br. s., 2H), 1.22-1.06 (m, 8H), 0.67 (t, J = 7.2 Hz, 3H) | 1.62 A 539.2 | A |
| 146 | 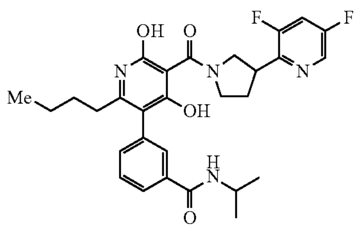 [SMILES: CCCCc1nc(O)c(C(=O)N2CCC(c3ncc(F)cc3F)C2)c(O)c1-c1cccc(C(=O)NC(C)C)c1] | 3-{2-butyl-5-[3-(3,5-difluoropyridin-2-yl)pyrrolidine-1-carbonyl]-4,6-dihydroxypyridin-3-yl}-N-(propan-2-yl)benzamide | Rt = 4.80, (isomer 1) Whelko (4.6 x 250 mm, 5 micron; mobile phase: 10% IPA/90% CO$_2$; flow condition: 3.0 mL/min, 140 bar, 40° C.; wavelength: 220 nm. | $^1$H NMR (500 MHz, DMSO-d6) δ 8.48 (br. s., 1H), 8.22 (d, J = 7.6 Hz, 1H), 7.91 (br. s., 1H), 7.83 (d, J = 7.6 Hz, 1H), 7.72 (br. s., 1H), 7.47 (t, J = 7.6 Hz, 1H), 7.35 (d, J = 7.3 Hz, 1H), 4.11 (d, J = 6.4 Hz, 1H), 3.96-3.36 (m, 5H), 2.24 (d, J = 7.3 Hz, 4H), 1.41 (br. s., 2H), 1.22-1.06 (m, 8H), 0.67 (t, J = 7.2 Hz, 3H) | 1.62 A 539.2 | A |

TABLE 7-continued

| Ex# | Structure | Name | Chiral Amine intermediate with Retention time (min) | NMR | Rt (min) Method M+H | Human cAMP EC$_{50}$ |
|---|---|---|---|---|---|---|
| 147 | 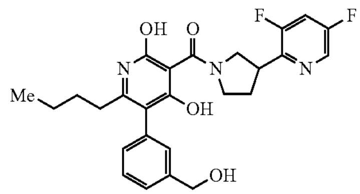 [SMILES: CCCCc1nc(O)c(C(=O)N2CCC(c3ncc(F)cc3F)C2)c(O)c1-c1cccc(CO)c1] | 6-butyl-3-[3-(3,5-difluoropyridin-2-yl)pyrrolidine-1-carbonyl]-5-[3-(hydroxymethyl)phenyl]pyridine-2,4-diol | Rt = 4.80, (isomer 1) Whelko (4.6 x 250 mm, 5 micron; mobile phase: 10% IPA/90% CO$_2$; flow condition: 3.0 mL/min, 140 bar, 40° C.; wavelength: 220 nm. | $^1$H NMR (500 MHz, DMSO-d6) δ 8.47 (br. s., 1H), 7.88 (br. s., 1H), 7.38-7.17 (m, 2H), 7.13-6.96 (m, 2H), 4.49 (s, 2H), 3.89 (s, 5H), 2.32-12.03 (m, 4H), 1.39 (br. s., 2H), 1.10 (br. s., 2H), 0.68 (br. s., 3H) | 1.27 A 484.2 | A |

Example 148. 6-butyl-3-[(3R)-3-phenylpyrrolidine-1-carbonyl]-5-[3-(propan-2-yl)phenyl]pyridine-2,4-diol

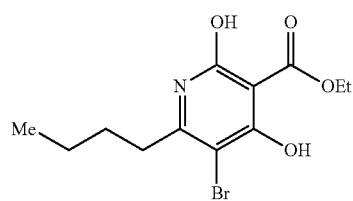

Compound 138b

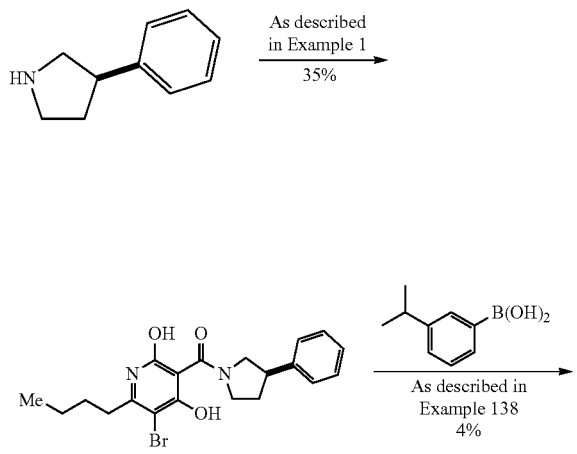

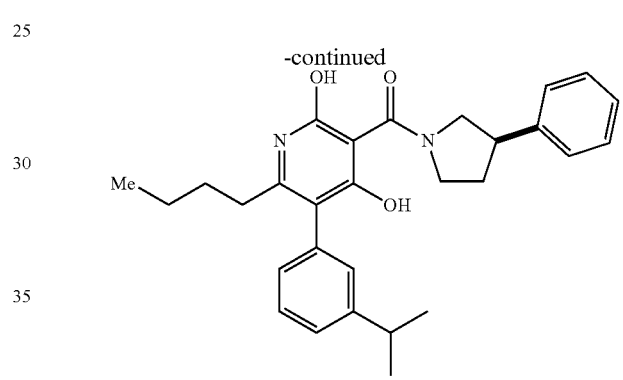

Example 148

Compound 148a. (R)-(5-bromo-6-butyl-2,4-dihydroxypyridin-3-yl)(3-phenylpyrrolidin-1-yl)methanone Compound 148a was prepared from compound 138b using the method described for Example 1 (35% yield). LCMS (Method D). Rt=0.97, m/z=421.0 [M+H]$^+$. $^1$H NMR (400 MHz, CHLOROFORM-d) δ 7.45-7.21 (m, 5H), 4.10-3.64 (m, 4H), 3.42 (br. s., 1H), 2.91-2.74 (m, 2H), 2.37 (br. s., 1H), 2.17-2.05 (m, 1H), 1.71 (quin, J=7.6 Hz, 2H), 1.46 (dq, J=14.8, 7.4 Hz, 2H), 1.06-0.89 (m, 3H).

Example 148. 6-butyl-3-[(3R)-3-phenylpyrrolidine-1-carbonyl]-5-[3-(propan-2-yl)phenyl]pyridine-2,4-diol Example 148 was prepared from compound 148a using the method described for Example 138 (4% yield). LCMS (Method D). Rt=2.31, m/z=459.0 [M+H]$^+$. $^1$H NMR (500 MHz, DMSO-d6) δ 7.42-7.18 (m, 7H), 7.10-6.98 (m, 2H), 3.89-3.32 (m, 4H), 2.90 (br. s., 1H), 2.24 (br. s., 3H), 2.11-1.90 (m, 1H), 1.40 (br. s., 2H), 1.26-1.14 (m, 7H), 1.08 (br. s., 2H), 0.66 (br. s., 3H). Human cAMP Potency range A.

Example 149. 5-(2,6-dimethoxyphenyl)-6-[(ethylamino)methyl]-3-[3-(3-fluorophenyl)pyrrolidine-1-carbonyl]pyridine-2,4-diol

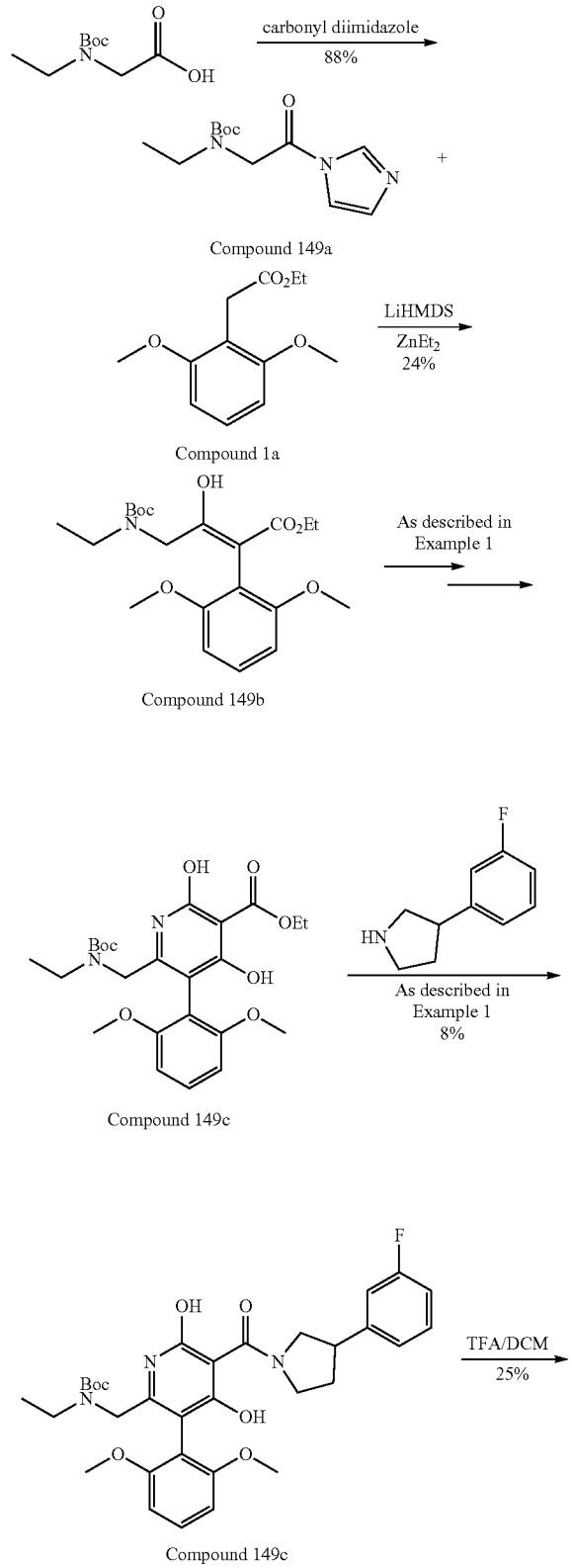

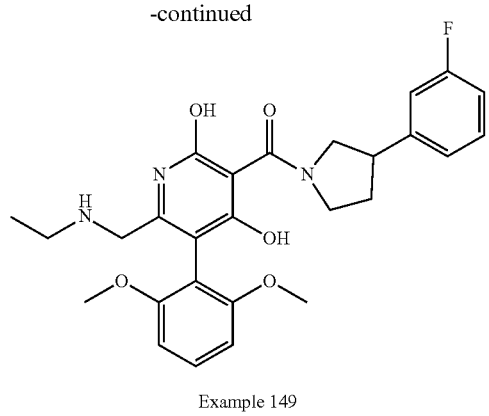

Example 149

Compound 149a. tert-Butyl (2-(1H-imidazol-1-yl)-2-oxoethyl)(ethyl)carbamate

Carbonyl diimidazole (176 mg, 1.10 mmol) was added to 2-((tert-butoxycarbonyl)(ethyl)amino)acetic acid (200 mg, 0.98 mmol) in THF (10 mL) at room temperature. After 18 hours, the reaction mixture was washed with $H_2O$, the organic portion separated and dried over $MgSO_4$, filtered, and concentrated under reduced pressure to give compound 149a as a yellow oil (220 mg, 88% yield). LCMS (Method E) Rt=1.57 min, m/z=252.2 [M+H]$^+$. $^1$H NMR (500 MHz, CHLOROFORM-d) δ 8.24 (br. s., 1H), 7.52 (t, J=1.5 Hz, 1H), 7.21-7.09 (m, 1H), 4.54 (s, 1H), 4.45 (br. s., 1H), 3.47 (d, J=6.3 Hz, 1H), 3.43-3.28 (m, 1H), 1.52 (s, 5H), 1.45 (d, J=5.0 Hz, 1H), 1.40 (br. s., 3H), 1.24-1.08 (m, 3H) Compound 149b. Ethyl 4-((tert-butoxycarbonyl)(ethyl)amino)-2-(2,6-dimethoxyphenyl)-3-oxobutanoate LiHMDS (1.0 mL, 1.0 mmol, 1M solution in THF) was added to compound 1a (160 mg, 0.71 mmol) in THF (1 mL) cooled to −78° C. After 10 minutes, the reaction mixture was allowed to stir at room temperature. After 1 hour, the reaction mixture was cooled back to −78° C. and diethylzinc (2M solution, 0.5 mL, 1 mmol) was added. The reaction mixture was allowed to warm to −20° C. over a period of 40 minutes. Compound 149a (217 mg, 0.856 mmol) in THF (0.5 mL) was added, and after 20 minutes, the reaction mixture was diluted with 1N HCl, extracted with DCM (2×), dried over $MgSO_4$, concentrated under reduced pressure and purified using silica gel chromatography to give compound 149b (70 mg, 24% yield). LCMS (Method E) Rt=2.02 min, m/z=410.4 [M+H]$^+$. $^1$H NMR (500 MHz, CHLOROFORM-d) δ 7.32-7.10 (m, 1H), 6.65-6.41 (m, 2H), 5.07-5.06 (m, 1H) 4.22-3.98 (m, 2H), 3.97-3.84 (m, 2H), 3.77-3.56 (m, 6H), 3.32-2.88 (m, 2H), 1.45-1.31 (m, 9H), 1.21-1.01 (m, 4H), 1.01-0.77 (m, 3H).

Compound 149c. ethyl 6-(((tert-butoxycarbonyl)(ethyl)amino)methyl)-5-(2,6-dimethoxyphenyl)-2,4-dihydroxynicotinate Compound 149c was prepared from compound 149b in 17% yield using the general method described in Example 1. LCMS (Method E) Rt=0.95 min, m/z=477.3 [M+H]$^+$. $^1$H NMR (500 MHz, CHLOROFORM-d) δ 7.39 (t, J=8.4 Hz, 1H), 6.66 (d, J=8.5 Hz, 2H), 4.46 (q, J=7.2 Hz, 2H), 4.06 (br. s., 2H), 3.89-3.67 (m, 6H), 3.07 (d, J=6.9 Hz, 2H), 1.49 (s, 9H), 1.47-1.41 (m, 3H), 0.91 (t, J=7.0 Hz, 3H).

Compound 149d. tert-butyl ((3-(2,6-dimethoxyphenyl)-5-(3-(3-fluorophenyl)pyrrolidine-1-carbonyl)-4,6-dihydroxypyridin-2-yl)methyl)(ethyl)carbamate Compound 149d was prepared from compound 149c and 3-(3-fluorophenyl)pyrrolidine (prepared from chiral tert-butyl 3-(3-fluorophenyl)pyrrolidine-1-carboxylate using the general route described for the preparation of compound 74c, isomer 2, Rt=10.72, Chiral analytical HPLC: Whelko (4.6×250 mm, 5 micron; mobile phase: 10% IPA/90% $CO_2$; flow condition: 3.0 mL/min, 140 bar, 40° C.; wavelength: 220 nm) using the method described in Example 1 (8% yield). LCMS (Method A) Rt=1.96 min, m/z=596.0 [M+H]$^+$. $^1$H NMR (500 MHz, DMSO-$d_6$) δ 7.37 (d, J=6.1 Hz, 1H), 7.28 (br. s., 1H), 7.19 (br. s., 1H), 7.15 (br. s., 1H), 7.06 (t, J=8.2 Hz, 1H), 6.76-6.61 (m, 2H), 3.90-3.84 (m, 2H), 3.65 (br. m., 3H), 2.89-2.73 (m, 3H), 2.51 (br. s., 6H), 2.26 (br. s., 1H), 1.98-1.89 (br. m., 2H), 1.33-1.26 (br. m., 9H), 0.75 (br. s., 3H)

Example 149. 5-(2,6-dimethoxyphenyl)-6-[(ethylamino)methyl]-3-[3-(3-fluorophenyl)pyrrolidine-1-carbonyl]pyridine-2,4-diol TFA (0.1 mL) was added to compound 149d (12 mg, 0.020 mmol) in DCM (1 mL) at room temperature. After 3 hours, the reaction mixture was concentrated under reduced pressure, and purified via preparative LC/MS with the following conditions: Column: XBridge C18, 19×200 mm, 5-m particles; Mobile Phase A: 5:95 acetonitrile:water with 10-mM ammonium acetate; Mobile Phase B: 95:5 acetonitrile:water with 10-mM ammonium acetate; Gradient: 0-100% B over 15 minutes, then a 3-minute hold at 100% B; Flow: 20 mL/min to give Example 149 (2.5 mg, 25%). LCMS (Method A) Rt=1.094 min, m/z=496.4 [M+H]$^+$. $^1$H NMR (500 MHz, DMSO-$d_6$) δ 7.44-7.27 (m, 2H), 7.18 (d, J=9.3 Hz, 2H), 7.07 (t, J=7.9 Hz, 1H), 6.71 (d, J=8.2 Hz, 2H), 3.68 (br s, 6H), 3.17 (br s, 2H), 2.56-2.53 (m, 2H), 2.40-2.14 (m., 3H), 2.13-1.95 (m, 1H), 1.90 (br s, 3H), 0.85 (br s, 3H). Human cAMP Potency range C.

The following compounds, Example 150 to Example 151, were prepared by the general procedures described for Examples 149 and 74

TABLE 8

| Ex# | Structure | Name | Chiral Amine intermediate with Retention time (min) | NMR | Rt (min) Method M + H | Human cAMP EC$_{50}$ |
|---|---|---|---|---|---|---|
| 150 | 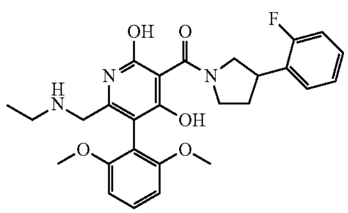 [SMILES: CCNCc1nc(O)c(C(=O)N2CCC(c3ccccc3F)C2)c(O)c1-c1c(OC)cccc1OC] | 5-(2,6-dimethoxyphenyl)-6-[(ethylamino)methyl]-3-[3-(2-fluorophenyl)pyrrolidine-1-carbonyl]pyridine-2,4-diol | Rt = 10.65, (isomer 1) Chiralpak IF, 4.6 x 250 mm, 5 micron; mobile phase: 15% IPA/90% $CO_2$; Flow Condition: 2.0 mL/min, 150 bar, 40° C., wavelength: 220 nm | $^1$H NMR (500 MHz, DMSO-d6) δ 7.41 (br. s., 1H), 7.37-7.27 (m, 2H), 7.19 (t, J = 7.0 Hz, 2H), 6.71 (d, J = 8.3 Hz, 2H), 3.67 (br. s., 6H), 3.22-3.15 (m, 2H), 2.56-2.53 (m, 2H) (2.33 (br s, 2H), 2.25 (br. s., 1H), 2.10-1.96 (m, 1H), 1.91 (br s, 3H), 0.88-0.81 (m, 3H) | 1.26 B 495.9 | B |
| 151 | 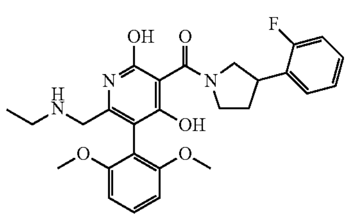 [SMILES: CCNCc1nc(O)c(C(=O)N2CCC(c3ccccc3F)C2)c(O)c1-c1c(OC)cccc1OC] | 5-(2,6-dimethoxyphenyl)-6-[(ethylamino)methyl]-3-[3-(2-fluorophenyl)pyrrolidine-1-carbonyl]pyridine-2,4-diol | Rt = 10.65, (isomer 2) Chiralpak IF, 4.6 x 250 mm, 5 micron; mobile phase: 15% IPA/90% $CO_2$; Flow Condition: 2.0 mL/min, 150 bar, 40° C., wavelength: 220 nm | $^1$H NMR (500 MHz, DMSO-d6) δ 7.40 (br. s., 1H), 7.37-7.26 (m, 2H), 7.23-7.12 (m, 2H), 6.70 (d, J = 8.2 Hz, 2H), 3.69 (br s, 6H), 3.22-3.15 (m, 2H), 2.56-2.53 (m, 2H), 2.34 (br s, 2H), 2.34 (br s, 2H), 2.25 (br s, 1H), 2.10-1.96 (m, 1H), 1.90 (br s, 3H), 0.88-0.81 (m, 3H) | 1.10 A 496.3 | B |

Example 152. methyl (S)-(2-(6-butyl-5-(2,6-dimethoxyphenyl)-4-hydroxy-2-oxo-1,2-dihydropyridine-3-carboxamido)-3-cyclohexylpropanoyl)glycinate

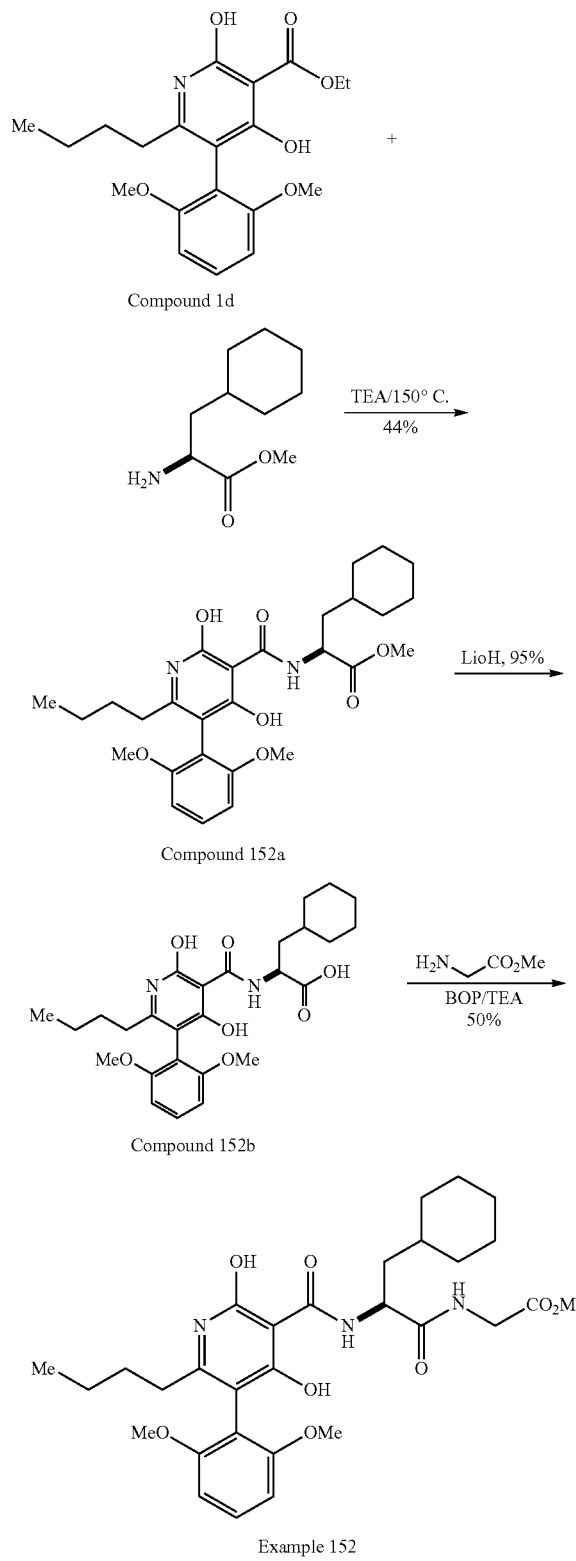

Compound 152a. methyl (S)-2-(6-butyl-5-(2,6-dimethoxyphenyl)-4-hydroxy-2-oxo-1,2-dihydropyridine-3-carboxamido)-3-cyclohexylpropanoate To a stirred solution of compound 1d (50 mg, 0.13 mmol) in DMF (2 mL) was added (S)-methyl 2-amino-3-cyclohexylpropanoate (30 mg, 0.16 mmol) and Et$_3$N (0.037 mL, 0.27 mmol). The reaction mixture was heated to 150° C. in a sealed reaction vessel under microwave irradiation for 1 h, allowed to cool to room temperature, concentrated in vacuo and diluted with EtOAc. The organic layer was washed with 0.1M HCl, dried over MgSO$_4$, filtered and concentrated in vacuo. The residue was added to a silica gel (12 g) column and was eluted with 0-100% EtOAc in hexanes. The fractions containing Compound 152a were collected as a clear liquid and the solvent removed under reduced pressure to yield Compound 152a as a colorless oil (30 mg, 44% yield). LCMS (Method A) retention time=2.50 min, m/z=514.9 (M+H). $^1$H NMR (500 MHz, DMSO-D6) δ 10.63 (d, J=7.3 Hz, 1H), 7.34 (t, J=8.5 Hz, 1H), 6.71 (d, J=8.5 Hz, 2H), 4.51-4.55 (m, 1H), 3.66 (s, 6H), 3.52 (s, 3H), 3.17 (d, J=5.2 Hz, 1H), 2.14 (t, J=7.6 Hz, 2H), 1.54-1.76 (m, 7H), 1.28-1.36 (m, 3H), 1.04-1.24 (m, 5H), 0.86-1.01 (m, 2H), 0.64 (t, J=7.3 Hz, 3H).

Compound 152b. (S)-2-(6-butyl-5-(2,6-dimethoxyphenyl)-4-hydroxy-2-oxo-1,2-dihydropyridine-3-carboxamido)-3-cyclohexylpropanoic acid To a stirred solution of compound 152a (25 mg, 0.049 mmol) in THF (5 mL) was added lithium hydroxide monohydrate (6.1 mg, 0.15 mmol) in water (3 mL). The reaction mixture was stirred at RT for 16 h then concentrated in vacuo and the residue dissolved in EtOAc. The organic layer was washed with 0.1 M HCl (pH=4). The aq layer was extracted with EtOAc 5×. The combined organic layers were dried over MgSO$_4$, filtered and concentrated in vacuo to give compound 152b (23 mg, 95% yield) as a white solid. LCMS (Method A) retention time=1.72 min, m/z=501.0 (M+H). $^1$H NMR (500 MHz, DMSO-D6) δ 10.53 (d, J=7.6 Hz, 1H), 7.95 (s, 1H), 7.34 (t, J=8.2 Hz, 1H), 6.71 (d, J=8.2 Hz, 2H), 4.38-4.45 (m, 1H), 3.68 (s, 6H), 2.14 (t, J=7.3 Hz, 2H), 1.55-1.79 (m, 7H), 1.28-1.40 (m, 3H), 1.05-1.23 (m, 5H), 0.86-1.01 (m, 2H), 0.66 (t, J=7.0 Hz, 3H).

Example 152. Methyl (S)-(2-(6-butyl-5-(2,6-dimethoxyphenyl)-4-hydroxy-2-oxo-1,2-dihydropyridine-3-carboxamido)-3-cyclohexylpropanoyl)glycinate To a stirred solution of compound 152b (30 mg, 0.060 mmol) in THF (3 mL) was added BOP (29 mg, 0.066 mmol) and Et$_3$N (0.025 mL, 0.18 mmol). After 15 min, methyl 2-aminoacetate hydrochloride (9.0 mg, 0.072 mmol) in THF (1 mL) was added and the reaction mixture was stirred for 2 hrs. The reaction mixture was concentrated in vacuo and diluted with EtOAc. The organic layer was washed with sat NaHCO$_3$, saturated NH$_4$Cl. The organic layer was dried over MgSO$_4$, filtered and concentrated in vacuo. The residue was purified via preparative LC/MS with the following conditions: Column: XBridge C18, 19×200 mm, 5-Lm particles; Mobile Phase A: 5:95 acetonitrile:water with 10-mM ammonium acetate; Mobile Phase B: 95:5 acetonitrile:water with 10-mM ammonium acetate; Gradient: 40-80% B over 20 minutes, then a 5 minute hold at 100% B; Flow: 20 mL/min. Fractions containing the compound 152 were combined and dried via centrifugal evaporation. The residue was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 40-80% B over 19 minutes, then a 5-minute hold at 100% B; Flow: 20 mL/min. Fractions containing the Example 152 (16 mg, 50%) were combined and dried via centrifugal evaporation. LCMS (Method A) Rt=2.18 min, m/z=572.5 [M+H]$^+$. $^1$H NMR (500 MHz, DMSO-d6) δ 10.55 (br s, 1H), 8.62 (br s, 1H), 7.34 (t, J=7.6 Hz, 1H), 6.71 (d, J=8.2 Hz, 2H), 4.57 (br s, 1H), 3.83-3.89 (m, 2H), 3.68 (s, 6H), 3.63 (s, 3H), 2.14 (br s, 2H), 1.70-1.80 (m, 2H), 1.51-1.70 (m, 5H), 1.27-1.40 (m, 3H), 1.05-1.26 (m, 5H), 0.89-0.97 (m, 2H), 0.64 (t, J=7.3 Hz, 3H). Human cAMP Potency range A.

What is claimed is:

1. A compound having Formula (II):

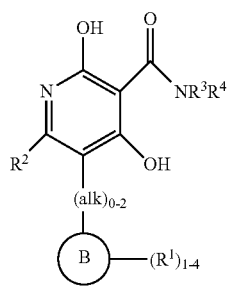

(II)

or a stereoisomer, a tautomer, or a pharmaceutically acceptable salt thereof, wherein:
ring B is independently selected from:

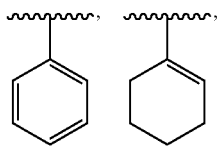

and 6-membered heteroaryl;

$R^1$ is independently selected from: F, Cl, Br, $NO_2$, —$(CH_2)_nOR^b$, —$(CH_2)_nC(=O)R^b$, —$(CH_2)_nNR^aR^a$, —$(CH_2)_nCN$, —$(CH_2)_nC(=O)NR^aR^a$, —$(CH_2)_n$ $NR^aC(=O)R^b$, $C_{1-4}$ alkyl substituted with 0-3 $R^e$ and $C_{3-6}$ cycloalkyl substituted with 0-3 $R^e$;

$R^2$ is independently selected from: $C_{1-5}$ alkyl substituted with 0-3 $R^e$; $C_{2-5}$ alkenyl substituted with 0-3 $R^e$, aryl substituted with 0-3 $R^e$, heterocyclyl substituted with 0-3 $R^e$, and $C_{3-6}$ cycloalkyl substituted with 0-3 $R^e$; provided when $R^2$ is $C_{1-5}$ alkyl, the methylene unit except the one attached to the pyridine ring may be replaced by O, NH, and S;

$R^3$ and $R^4$ together with the nitrogen atom to which they are both attached form a heterocyclic ring or a spiro heterocyclic ring selected from:

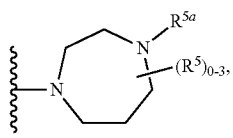

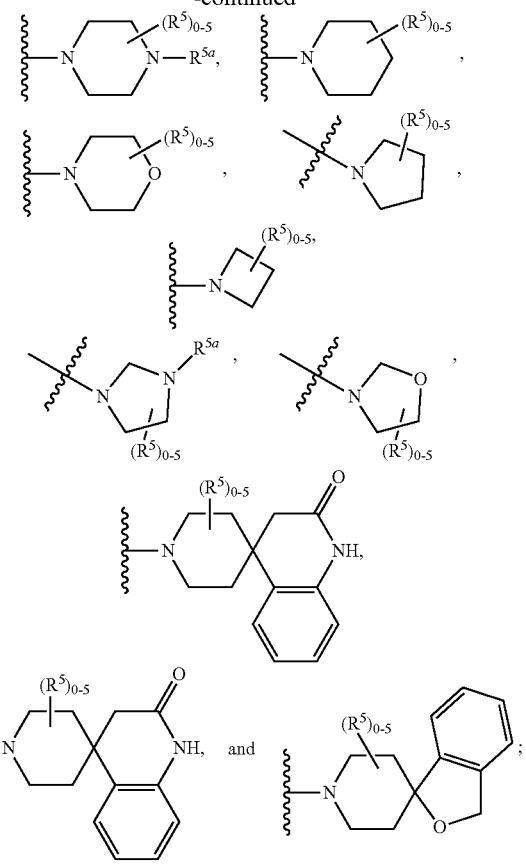

$R^5$ is independently at each occurrence, selected from: OH, —$(CH_2)_n$-aryl, —$(CH_2)_n$—$C_{3-6}$ cycloalkyl and —$(CH_2)_n$-heterocycle, each substituted with 0-3 $R^6$;

$R^{5a}$ is independently at each occurrence, selected from: —$(CR^7R^7)_n$—$C_{3-10}$ carbocycle and —$(CR^7R^7)_n$-heterocycle, —$C(=O)$—$C_{3-10}$ carbocycle, each substituted with 0-3 $R^6$;

$R^6$ is independently selected from: H, F, Cl, Br, —$OR^b$, =O, —$(CH_2)_nC(=O)R^b$, —$(CH_2)_nC(=O)OR^b$, —$(CH_2)_nNR^aR^a$, CN, —$(CH_2)_nC(=O)NR^aR^a$, —$NHC(=O)OR^b$, $C_{1-4}$ alkyl substituted with 0-3 $R^e$, $(CH_2)_n$—$C_{3-6}$ carbocyclyl substituted with 0-3 $R^e$, and —$(CH_2)_n$-heterocyclyl substituted with 0-3 $R^e$;

$R^7$ is, independently at each occurrence, selected from: H, $C_{1-4}$ alkyl, and $(CH_2)_n$—$C_{3-12}$ carbocyclyl substituted with 0-3 $R^e$;

$R^a$, at each occurrence, is independently selected from H, $C_{1-6}$ alkyl substituted with 0-5 $R^e$, —$(CH_2)_n$—$C_{3-10}$ carbocyclyl substituted with 0-5 $R^e$, and —$(CH_2)_n$-heterocyclyl substituted with 0-5 $R^e$; or $R^a$ and $R^a$ together with the nitrogen atom to which they are both attached form a heterocyclic ring substituted with 0-5 $R^e$;

$R^b$, at each occurrence, is independently selected from H, $C_{1-6}$ alkyl substituted with 0-5 $R^e$, $C_{2-6}$ alkenyl substituted with 0-5 $R^e$, $C_{2-6}$ alkynyl substituted with 0-5 $R^e$, —$(CH_2)_n$—$C_{3-10}$carbocyclyl substituted with 0-5 $R^e$, and —$(CH_2)_n$-heterocyclyl substituted with 0-5 $R^e$;

$R^e$, at each occurrence, is independently selected from $C_{1-6}$ alkyl (optionally substituted with F and Cl), OH, $OCH_3$, $OCF_3$, —$(CH_2)_n$—$C_{3-6}$ cycloalkyl, —$(CH_2)_n$—

$C_{4-6}$ heterocyclyl, —$(CH_2)_n$-aryl, —$(CH_2)_n$-heteroaryl, F, Cl, Br, CN, $NO_2$, =O, $CO_2H$;

$R^g$, at each occurrence, is independently selected from H, F, Cl, Br, CN, OH, $C_{1-5}$alkyl (optimally substituted with halogen and OH);

n is independently selected from zero, 1, 2, 3, and 4; and p, at each occurrence, is independently selected from zero, 1, and 2.

2. The compound according to claim 1 having Formula (IIIa):

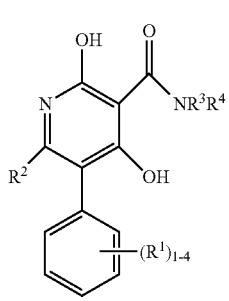

or a stereoisomer, a tautomer, or a pharmaceutically acceptable salt thereof, wherein:

$R^1$ is independently selected from: F, Cl, —$(CH_2)_n$OH, C(=O)$NR^aR^a$, $C_{1-4}$ alkyl, and $OC_{1-4}$ alkyl;

$R^2$ is independently selected from: $C_{1-5}$ alkyl substituted with 0-3 $R^e$; $C_{2-5}$ alkenyl, aryl substituted with 0-3 $R^e$, heteroaryl substituted with 0-3 $R^e$, $C_{3-6}$ cycloalkyl and —$(CH_2)_{1-4}OC_{1-5}$alkyl, and —$(CH_2)_{1-3}OC_{3-6}$cycloalkyl;

$R^3$ and $R^4$ together with the nitrogen atom to which they are both attached form a heterocyclic ring or a spiro heterocyclic ring selected from:

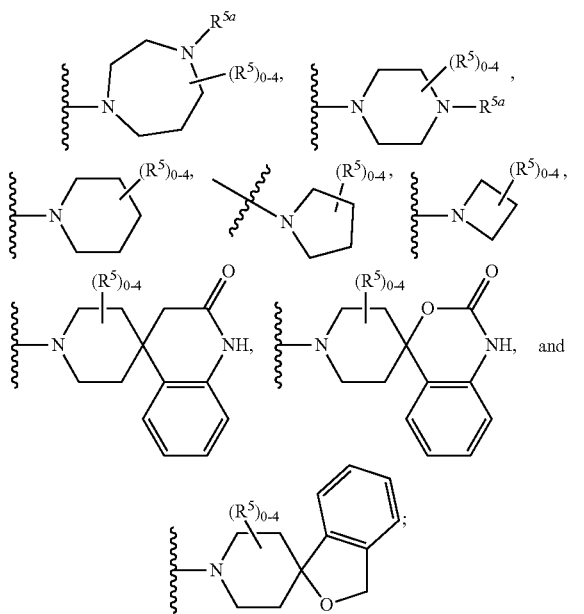

$R^5$ is independently at each occurrence, selected from: OH, —$(CH_2)_n$-aryl, —$(CH_2)_n$—$C_{3-6}$ cycloalkyl and —$(CH_2)_n$-heterocycle, each substituted with 0-3 $R^6$;

$R^{5a}$ is independently at each occurrence, selected from: —$(CR^7R^7)_n$—$C_{3-10}$ carbocycle and —$(CR^7R^7)_n$-heterocycle, —C(=O)—$C_{3-10}$ carbocycle, each substituted with 0-3 $R^6$;

$R^6$ is independently selected from: H, F, Cl, Br, —$OR^b$, =O, —$(CH_2)_nC(=O)R^b$, —$(CH_2)_nC(=O)OR^b$, —$(CH_2)_nNR^aR^a$, CN, —$(CH_2)_nC(=O)NR^aR^a$, $C_{1-4}$ alkyl substituted with 0-3 $R^e$, $(CH_2)_n$—$C_{3-6}$ carbocyclyl substituted with 0-3 $R^e$, and —$(CH_2)_n$-heterocyclyl substituted with 0-3 $R^e$;

$R^7$ is, independently at each occurrence, selected from: H, $C_{1-4}$ alkyl, and $(CH_2)_n$—$C_{3-12}$ carbocyclyl substituted with 0-3 $R^e$;

$R^a$, at each occurrence, is independently selected from H, $C_{1-6}$ alkyl substituted with 0-5 $R^e$, —$(CH_2)_n$—$C_{3-10}$carbocyclyl substituted with 0-5 $R^e$, and —$(CH_2)_n$-heterocyclyl substituted with 0-5 $R^e$; or $R^a$ and $R^a$ together with the nitrogen atom to which they are both attached form a heterocyclic ring substituted with 0-5 $R^e$;

$R^b$, at each occurrence, is independently selected from H, $C_{1-6}$ alkyl substituted with 0-5 $R^e$, $C_{2-6}$ alkenyl substituted with 0-5 $R^e$, $C_{2-6}$ alkynyl substituted with 0-5 $R^e$, —$(CH_2)_n$—$C_{3-10}$carbocyclyl substituted with 0-5 $R^e$, and —$(CH_2)_n$-heterocyclyl substituted with 0-5 $R^e$;

$R^e$, at each occurrence, is independently selected from $C_{1-6}$ alkyl (optionally substituted with F and Cl), OH, $OCH_3$, $OCF_3$, —$(CH_2)_n$—$C_{3-6}$ cycloalkyl, —$(CH_2)_n$—$C_{4-6}$ heterocyclyl, —$(CH_2)_n$-aryl, —$(CH_2)_n$-heteroaryl, F, Cl, Br, CN, $NO_2$, =O, $CO_2H$; and n is independently selected from zero, 1, 2, 3, and 4.

3. The compound according to claim 2 or a stereoisomer, a tautomer, or a pharmaceutically acceptable salt thereof, wherein:

$R^5$ is independently at each occurrence, selected from:

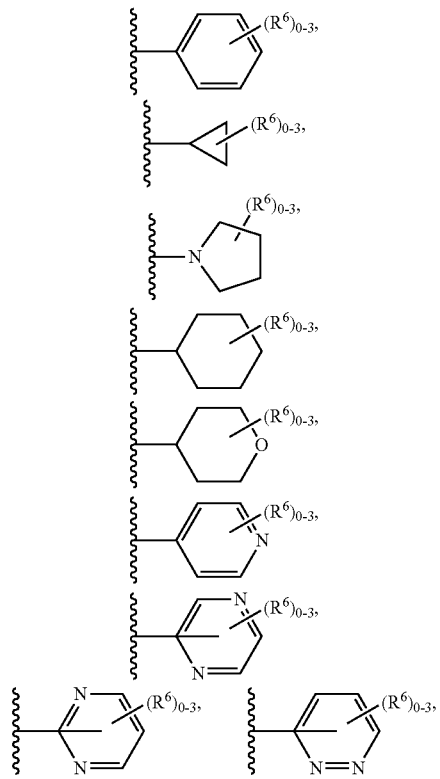

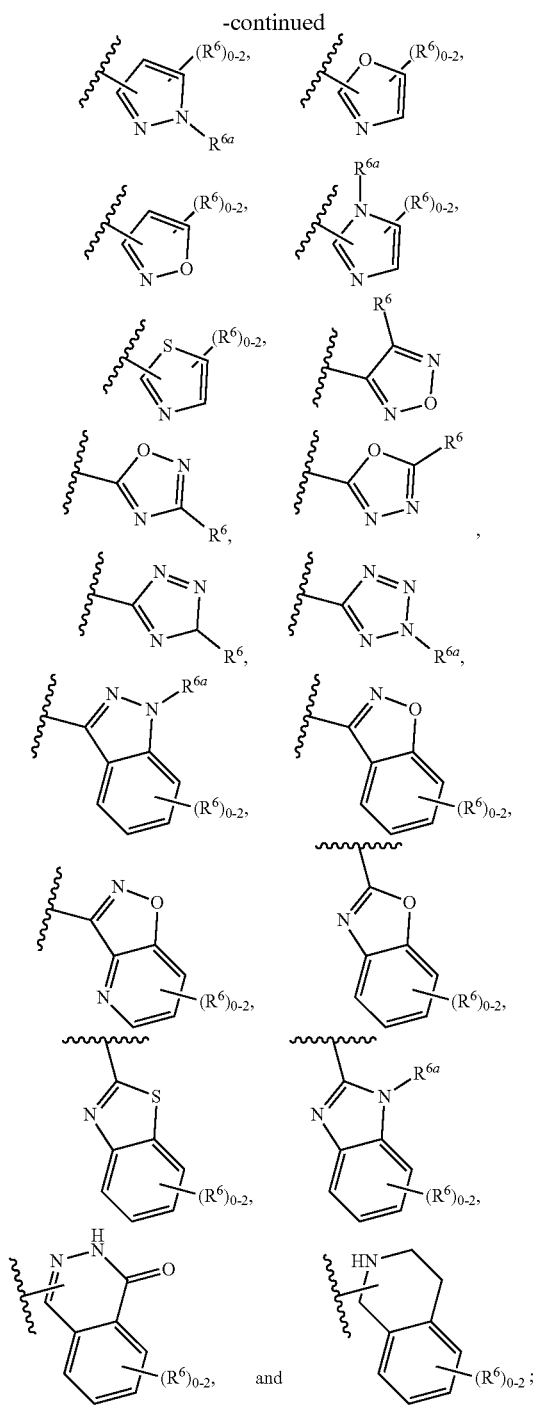

and $R^6$ is independently selected from: H, F, Cl, Br, —OCH$_3$, —OCF$_3$, =O, CN, CH$_3$, CF$_3$—(CH$_2$)$_n$-aryl, —(CH$_2$)$_n$—C$_{3-6}$ cycloalkyl substituted with 0-3 R$^e$, and —(CH$_2$)$_n$-heterocyclyl substituted with 0-3 R$^e$;

$R^{6a}$ is independently selected from: H, CH$_3$, aryl substituted with 0-3 R$^e$, and heterocyclyl substituted with 0-3 R$^e$;

$R^a$, at each occurrence, is independently selected from H, C$_{1-6}$ alkyl substituted with 0-5 R$^e$, —(CH$_2$)$_n$—C$_{3-10}$carbocyclyl substituted with 0-5 R$^e$, and —(CH$_2$)$_n$-heterocyclyl substituted with 0-5 R$^e$;

R$^e$, at each occurrence, is independently selected from C$_{1-6}$ alkyl (optionally substituted with F and Cl), OH, OCH$_3$, OCF$_3$, —(CH$_2$)$_n$—C$_{3-6}$ cycloalkyl, —(CH$_2$)$_n$—C$_{4-6}$ heterocyclyl, —(CH$_2$)$_n$-aryl, —(CH$_2$)$_n$-heteroaryl, F, Cl, Br, CN, NO$_2$, =O, CO$_2$H; and n is independently selected from zero, 1, 2, and 3.

4. The compound according to claim 2 or a stereoisomer, a tautomer, or a pharmaceutically acceptable salt thereof, wherein:

R$^3$ and R$^4$ together with the nitrogen atom to which they are both attached form a heterocyclic ring selected from:

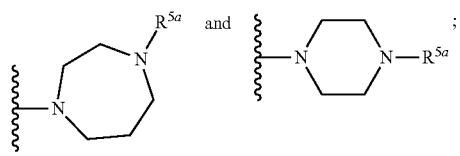

$R^{5a}$ is independently at each occurrence, selected from:

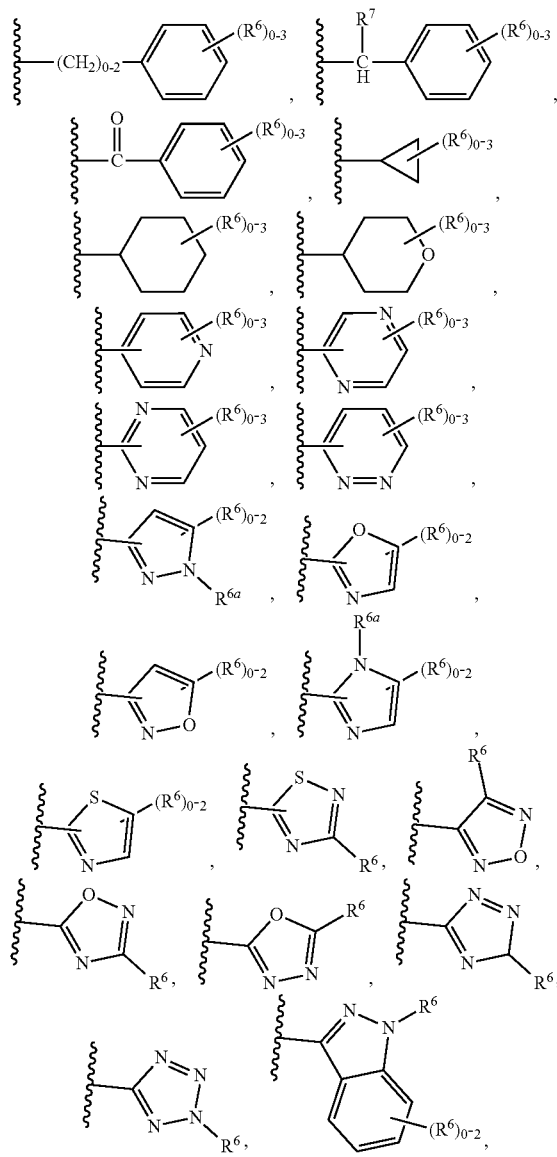

-continued

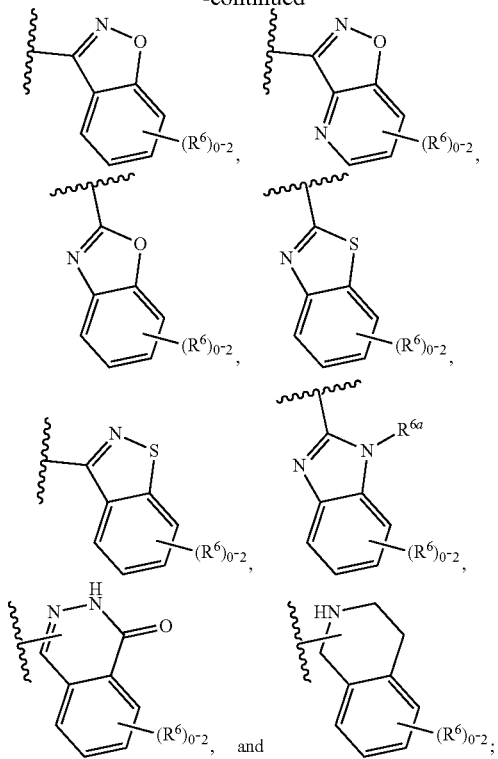

R[6] is independently selected from: H, F, Cl, Br, —OCH$_3$, —O(CH$_2$)$_{1-3}$OCH$_3$, —OCF$_3$, =O, CN, CH$_3$, CF$_3$—(CH$_2$)$_n$-aryl, —(CH$_2$)$_n$—C$_{3-6}$ cycloalkyl substituted with 0-3 R[e], and —(CH$_2$)$_n$-heterocyclyl substituted with 0-3 R[e];

R[6a] is independently selected from: H, CH$_3$, aryl substituted with 0-3 R[e], and heterocyclyl substituted with 0-3 R[e];

R[e], at each occurrence, is independently selected from C$_{1-6}$ alkyl (optionally substituted with F and Cl), OH, OCH$_3$, OCF$_3$, —(CH$_2$)$_n$—C$_{3-6}$ cycloalkyl, —(CH$_2$)$_n$—C$_{4-6}$ heterocyclyl, —(CH$_2$)$_n$-aryl, —(CH$_2$)$_n$-heteroaryl, F, Cl, Br, CN, NO$_2$, =O, CO$_2$H; and n is independently selected from zero, 1, 2, and 3.

5. The compound according to claim 2, or a stereoisomer, a tautomer, or a pharmaceutically acceptable salt thereof, wherein:

R[1] is independently selected from: F, Cl, OH, and OC$_{1-4}$ alkyl;

R[1a] is independently selected from: F, Cl, and C$_{1-2}$ alkyl;

R[2] is independently selected from: C$_{1-5}$ alkyl substituted with 0-3 R[e]; C$_{2-5}$ alkenyl, phenyl substituted with 0-3 R[e], 6-membered heteroaryl substituted with 0-3 R[e], C$_{3-6}$ cycloalkyl and CH$_2$O(CH$_2$)$_{1-3}$CH$_3$;

R[3] and R[4] together with the nitrogen atom to which they are both attached form a heterocyclic ring selected from:

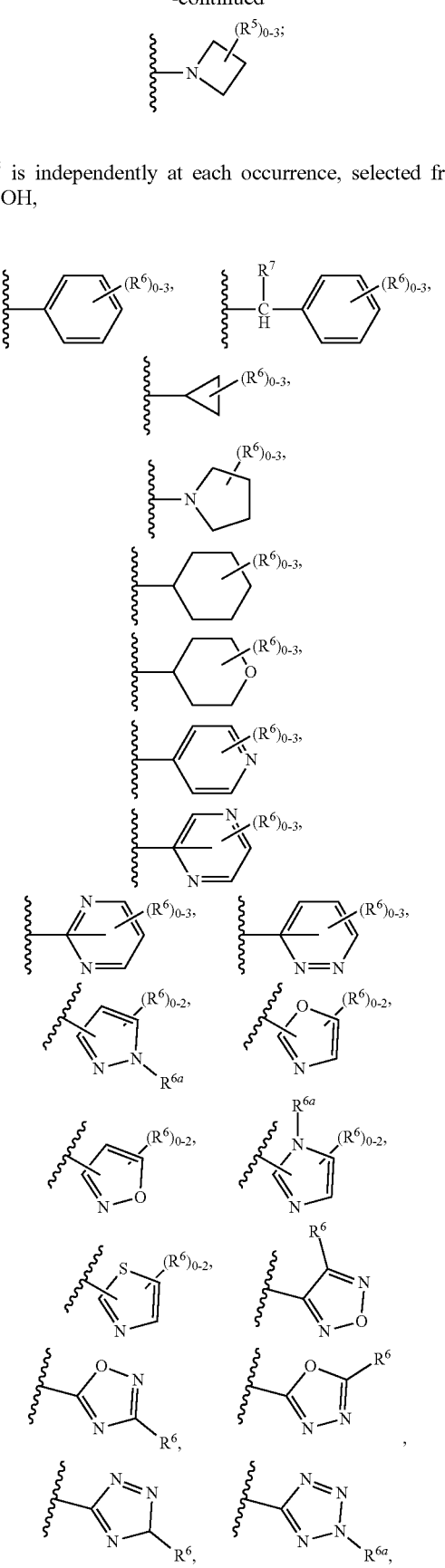

R[5] is independently at each occurrence, selected from: OH,

203

-continued

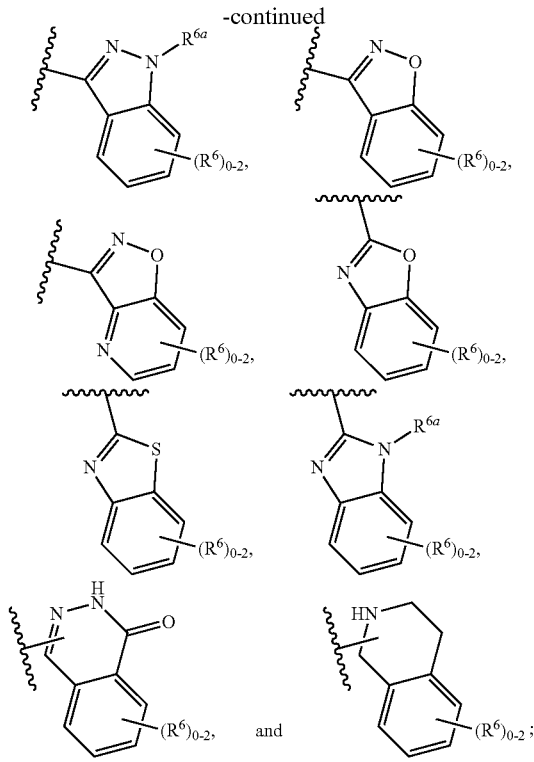

$R^6$ is independently selected from: H, F, Cl, Br, —OCH$_3$, —OCF$_3$, =O, CN, CH$_3$, CF$_3$, —C(=O)NH$_2$, —(CH$_2$)$_n$-aryl substituted with 0-3 R$^e$, —(CH$_2$)$_n$—C$_{3-6}$ cycloalkyl substituted with 0-3 R$^e$, and —(CH$_2$)$_n$-heterocyclyl substituted with 0-3 R$^e$;

$R^{6a}$ is independently selected from: H, CH$_3$, aryl substituted with 0-3 R$^e$, and heterocyclyl substituted with 0-3 R$^e$;

$R^a$, at each occurrence, is independently selected from H, C$_{1-6}$ alkyl substituted with 0-5 R$^e$, —(CH$_2$)$_n$—C$_{3-10}$ carbocyclyl substituted with 0-5 R$^e$, and —(CH$_2$)$_n$-heterocyclyl substituted with 0-5 R$^e$;

$R^e$, at each occurrence, is independently selected from C$_{1-6}$ alkyl (optionally substituted with F and Cl), OH, OCH$_3$, OCF$_3$, —(CH$_2$)$_n$—C$_{3-6}$ cycloalkyl, —(CH$_2$)$_n$—C$_{4-6}$ heterocyclyl, —(CH$_2$)$_n$-aryl, —(CH$_2$)$_n$-heteroaryl, F, Cl, Br, CN, NO$_2$, =O, CO$_2$H; and n is independently selected from zero, 1, 2, and 3.

6. The compound according to claim 2 having Formula (IV):

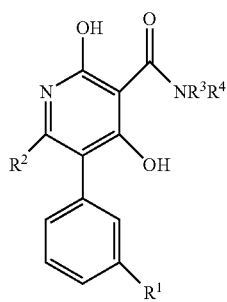

204 or a stereoisomer, a tautomer, or a pharmaceutically acceptable salt thereof, wherein:

$R^1$ is independently selected from: —CH$_2$OH, —OCH$_3$, —OCF$_3$, OCH$_2$Ph, —C(=O)NR$^a$R$^a$, —NR$^a$R$^a$, CH$_3$, CH$_2$CH$_3$, CH(CH$_3$)$_2$, and cyclopropyl;

$R^2$ is independently selected from: C$_{1-5}$ alkyl substituted with 0-3 R$^e$; C$_{2-5}$ alkenyl, phenyl substituted with 0-3 R$^e$, 6-membered heteroaryl substituted with 0-3 R$^e$, C$_{3-6}$ cycloalkyl and CH$_2$O(CH$_2$)$_{1-3}$CH$_3$;

$R^3$ and $R^4$ together with the nitrogen atom to which they are both attached form a heterocyclic ring selected from:

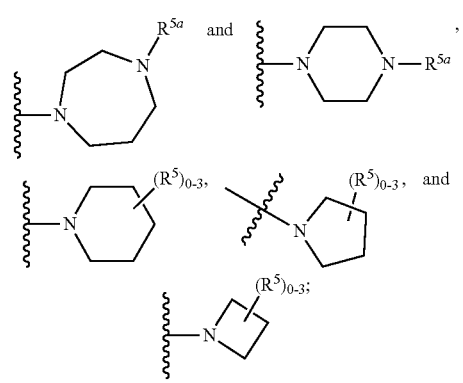

$R^{5a}$ is independently at each occurrence, selected from:

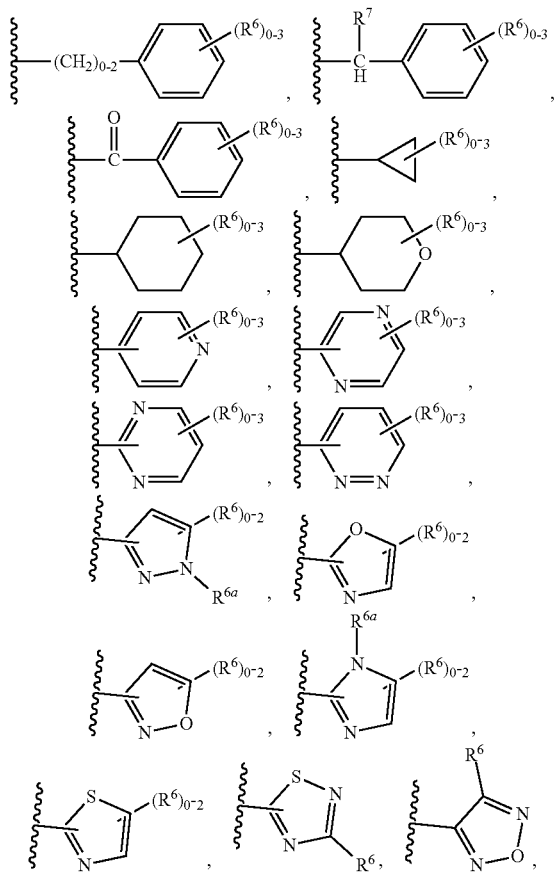

R⁵ is independently at each occurrence, selected from: OH,

R⁶ is independently selected from: H, F, Cl, Br, —OCH₃, —OCF₃, =O, CN, CH₃, CF₃, —C(=O)NH₂, —(CH₂)ₙ-aryl substituted with 0-3 Rᵉ, —(CH₂)ₙ—C₃₋₆ cycloalkyl substituted with 0-3 Rᵉ, and —(CH₂)ₙ-heterocyclyl substituted with 0-3 Rᵉ;

R⁶ᵃ is independently selected from: H, CH₃, aryl substituted with 0-3 Rᵉ, and heterocyclyl substituted with 0-3 Rᵉ;

Rᵃ, at each occurrence, is independently selected from H, C₁₋₆ alkyl substituted with 0-5 Rᵉ, —(CH₂)ₙ—C₃₋₁₀carbocyclyl substituted with 0-5 Rᵉ, and —(CH₂)ₙ-heterocyclyl substituted with 0-5 Rᵉ;

Rᵉ, at each occurrence, is independently selected from C₁₋₆ alkyl (optionally substituted with F and Cl), OH, OCH₃, OCF₃, —(CH₂)ₙ—C₃₋₆ cycloalkyl, —(CH₂)ₙ—C₄₋₆ heterocyclyl, —(CH₂)ₙ-aryl, —(CH₂)ₙ-heteroaryl, F, Cl, Br, CN, NO₂, =O, CO₂H; and n is independently selected from zero, 1, 2, and 3.

7. The compound according to claim 6, or a stereoisomer, a tautomer, or a pharmaceutically acceptable salt thereof, wherein:
$R^1$ is independently selected from: —CH$_2$OH, —C(=O)NHCH(CH$_3$)$_2$, CH$_3$, CH$_2$CH$_3$, and CH(CH$_3$)$_2$;
$R^2$ is independently selected from: CH$_2$(CH$_2$)$_{1-3}$CH$_3$ and CH$_2$O(CH$_2$)$_{1-3}$CH$_3$;
$R^3$ and $R^4$ together with the nitrogen atom to which they are both attached form

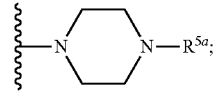

$R^{5a}$ is

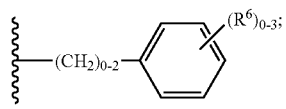

$R^6$ is independently selected from: H, F, Cl, Br, CH$_3$, and CF$_3$.

8. The compound according to claim 6, or a stereoisomer, a tautomer, or a pharmaceutically acceptable salt thereof, wherein:
$R^1$ is independently selected from: —CH$_2$OH, —C(=O)NHCH(CH$_3$)$_2$, CH$_3$, CH$_2$CH$_3$, and CH(CH$_3$)$_2$;
$R^2$ is independently selected from: CH$_2$(CH$_2$)$_{1-3}$CH$_3$ and CH$_2$O(CH$_2$)$_{1-3}$CH$_3$;
$R^3$ and $R^4$ together with the nitrogen atom to which they are both attached form

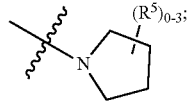

$R^5$ is independently at each occurrence, selected from:

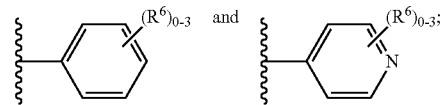

and
$R^6$ is independently selected from: H, F, Cl, Br, CH$_3$, and CF$_3$.

9. The compound according to claim 1, wherein the compound is selected from the group consisting of:
6-butyl-5-(2,6-dimethoxyphenyl)-3-[4-(4-methoxybenzoyl)piperazine-1-carbonyl]pyridine-2,4-diol (1);
6-butyl-5-(2,6-dimethoxyphenyl)-3-[4-(1-methyl-1H-imidazol-2-yl)piperazine-1-carbonyl]pyridine-2,4-diol (3);
6-butyl-5-(2,6-dimethoxyphenyl)-3-[4-hydroxy-4-(pyridin-3-yl)piperidine-1-carbonyl]pyridine-2,4-diol (4);
6-butyl-5-(2,6-dimethoxyphenyl)-3-[4-(3-propyl-1,2,4-oxadiazol-5-yl)piperidine-1-carbonyl]pyridine-2,4-diol (5);
6-butyl-3-[4-(5-chloropyridin-2-yl)piperazine-1-carbonyl]-5-(2,6-dimethoxyphenyl)pyridine-2,4-diol (6);
6-butyl-5-(2,6-dimethoxyphenyl)-3-{4-[4-(2-methoxyethoxy)phenyl]piperazine-1-carbonyl}pyridine-2,4-diol (7);
6-butyl-5-(2,6-dimethoxyphenyl)-3-[2-(pyridin-2-yl)pyrrolidine-1-carbonyl]pyridine-2,4-diol (8);
6-butyl-3-{3-[4-(2-chloro-4-methoxy-5-methylphenyl)-5-methyl-1,3-thiazol-2-yl]pyrrolidine-1-carbonyl}-5-(2,6-dimethoxyphenyl)pyridine-2,4-diol (9);
methyl N-(4-{4-[6-butyl-5-(2,6-dimethoxyphenyl)-2,4-dihydroxypyridine-3-carbonyl]piperazin-1-yl}phenyl)carbamate (10);
6-butyl-5-(2,6-dimethoxyphenyl)-3-{4-[3-(trifluoromethyl)pyridin-2-yl]piperazine-1-carbonyl}pyridine-2,4-diol (11);
6-butyl-5-(2,6-dimethoxyphenyl)-3-[4-(2-methoxyphenyl)piperazine-1-carbonyl]pyridine-2,4-diol (12);
6-butyl-5-(2,6-dimethoxyphenyl)-3-{4-[4-(trifluoromethyl)pyrimidin-2-yl]piperazine-1-carbonyl}pyridine-2,4-diol (13);
3-(4-benzylpiperidine-1-carbonyl)-6-butyl-5-(2,6-dimethoxyphenyl)pyridine-2,4-diol (14);
6-butyl-5-(2,6-dimethoxyphenyl)-3-[4-(diphenylmethyl)piperazine-1-carbonyl]pyridine-2,4-diol (16);
6-butyl-5-(2,6-dimethoxyphenyl)-3-[4-(4-methyl-1H-imidazol-5-yl)piperidine-1-carbonyl]pyridine-2,4-diol (17);
6-butyl-5-(2,6-dimethoxyphenyl)-3-[4-(4-methoxyphenyl)piperazine-1-carbonyl]pyridine-2,4-diol (18);
6-butyl-5-(2,6-dimethoxyphenyl)-3-[4-(2-methoxyphenyl)piperidine-1-carbonyl]pyridine-2,4-diol (19);
6-butyl-5-(2,6-dimethoxyphenyl)-3-{4-[3-(furan-2-yl)-1H-pyrazol-5-yl]piperidine-1-carbonyl}pyridine-2,4-diol (20);
6-butyl-5-(2,6-dimethoxyphenyl)-3-[4-(pyridazin-3-yl)piperazine-1-carbonyl]pyridine-2,4-diol (21);
6-butyl-5-(2,6-dimethoxyphenyl)-3-[4-(pyridin-4-yl)piperazine-1-carbonyl]pyridine-2,4-diol (22);
6-butyl-3-[4-(2-chlorophenyl)piperidine-1-carbonyl]-5-(2,6-dimethoxyphenyl)pyridine-2,4-diol (23);
4-{1-[6-butyl-5-(2,6-dimethoxyphenyl)-2,4-dihydroxypyridine-3-carbonyl]piperidin-4-yl}benzamide (24);
5-(2,6-dimethoxyphenyl)-6-(ethoxymethyl)-3-[(3S)-3-phenylpyrrolidine-1-carbonyl]pyridine-2,4-diol (25);
5-(2,6-dimethoxyphenyl)-6-(ethoxymethyl)-3-[(3R)-3-phenylpyrrolidine-1-carbonyl]pyridine-2,4-diol (26);
6-butyl-5-(2,6-dimethoxyphenyl)-3-[(3R)-3-phenylpyrrolidine-1-carbonyl]pyridine-2,4-diol (28);
6-butyl-5-(2,6-dimethoxyphenyl)-3-[(3S)-3-phenylpyrrolidine-1-carbonyl]pyridine-2,4-diol (29);
6-butyl-5-(2,6-dimethoxyphenyl)-3-(4-phenylpiperazine-1-carbonyl)pyridine-2,4-diol (30);
6-butyl-3-{4-[(4-chlorophenyl)methyl]piperazine-1-carbonyl}-(2,6-dimethoxyphenyl)pyridine-2,4-diol (31);
3-[4-(1,3-benzoxazol-2-yl)piperidine-1-carbonyl]-6-butyl-5-(2,6-dimethoxyphenyl)pyridine-2,4-diol (32);
6-butyl-3-[3-(3-chlorophenyl)azetidine-1-carbonyl]-5-(2,6-dimethoxyphenyl)pyridine-2,4-diol (34);
6-butyl-3-[3-(2-chlorophenyl)pyrrolidine-1-carbonyl]-5-(2,6-dimethoxyphenyl)pyridine-2,4-diol (35);
6-butyl-3-[3-(3-chlorophenyl)pyrrolidine-1-carbonyl]-5-(2,6-dimethoxyphenyl)pyridine-2,4-diol (37);
6-butyl-3-[3-(3-chlorophenyl)pyrrolidine-1-carbonyl]-5-(2,6-dimethoxyphenyl)pyridine-2,4-diol (38);
6-butyl-5-(2,6-dimethoxyphenyl)-3-[3-(4-fluorophenyl)pyrrolidine-1-carbonyl]pyridine-2,4-diol (39);

6-butyl-5-(2,6-dimethoxyphenyl)-3-[3-(4-fluorophenyl) pyrrolidine-1-carbonyl]pyridine-2,4-diol (40);
3-(4-benzoylpiperazine-1-carbonyl)-6-butyl-5-(2,6-dimethoxyphenyl)pyridine-2,4-diol (41);
6-butyl-5-(2,6-dimethoxyphenyl)-3-[4-(3-fluorobenzoyl) piperazine-1-carbonyl]pyridine-2,4-diol (42);
6-butyl-5-(2,6-dimethoxyphenyl)-3-{4-[(4-fluorophenyl) methyl]piperazine-1-carbonyl}pyridine-2,4-diol (43);
6-butyl-5-(2,6-dimethoxyphenyl)-3-{4-[(2-fluorophenyl) methyl]piperazine-1-carbonyl}pyridine-2,4-diol (44);
6-butyl-5-(2,6-dimethoxyphenyl)-3-{4-[(3-fluorophenyl) methyl]piperazine-1-carbonyl}pyridine-2,4-diol (45);
6-butyl-5-(2,6-dimethoxyphenyl)-3-(4-hydroxy-4-phenylpiperidine-1-carbonyl)pyridine-2,4-diol (46);
6-butyl-3-[4-(4-chlorophenyl)-4-hydroxypiperidine-1-carbonyl]-5-(2,6-dimethoxyphenyl)pyridine-2,4-diol (47);
3-[4-(1,3-benzothiazol-2-yl)piperidine-1-carbonyl]-6-butyl-5-(2,6-dimethoxyphenyl)pyridine-2,4-diol (48);
3-[4-(1,2-benzothiazol-3-yl)piperazine-1-carbonyl]-6-butyl-5-(2,6-dimethoxyphenyl)pyridine-2,4-diol (49);
1'-[6-butyl-5-(2,6-dimethoxyphenyl)-2,4-dihydroxypyridine-3-carbonyl]-1,2-dihydrospiro[3,1-benzoxazine-4,4'-piperidine]-2-one (50);
3-[4-(1,3-benzoxazol-2-yl)piperazine-1-carbonyl]-6-butyl-5-(2,6-dimethoxyphenyl)pyridine-2,4-diol (51);
6-butyl-5-(2,6-dimethoxyphenyl)-3-[4-(1-phenyl-1H-1,2,3,4-tetrazol-5-yl)piperazine-1-carbonyl]pyridine-2,4-diol (52);
6-butyl-5-(2,6-dimethoxyphenyl)-3-[4-(1-phenyl-1H-1,2,3,4-tetrazol-5-yl)-1,4-diazepane-1-carbonyl]pyridine-2,4-diol (53);
3-[4-(1,3-benzothiazol-2-yl)piperazine-1-carbonyl]-6-butyl-5-(2,6-dimethoxyphenyl)pyridine-2,4-diol (54);
6-butyl-5-(2,6-dimethoxyphenyl)-3-[4-(1H-imidazol-4-yl)piperidine-1-carbonyl]pyridine-2,4-diol (55);
6-butyl-3-[4-(3-chlorophenyl)piperidine-1-carbonyl]-5-(2,6-dimethoxyphenyl)pyridine-2,4-diol (56);
6-butyl-3-[4-(2-chlorophenyl)piperazine-1-carbonyl]-5-(2,6-dimethoxyphenyl)pyridine-2,4-diol (57);
6-butyl-3-[4-(3-chlorophenyl)piperazine-1-carbonyl]-5-(2,6-dimethoxyphenyl)pyridine-2,4-diol (58);
6-butyl-5-(2,6-dimethoxyphenyl)-3-[4-(pyridin-2-yl)piperazine-1-carbonyl]pyridine-2,4-diol (59);
6-butyl-5-(2,6-dimethoxyphenyl)-3-[4-(3-phenyl-1,2,4-thiadiazol-5-yl)piperazine-1-carbonyl]pyridine-2,4-diol (60);
6-butyl-5-(2,6-dimethoxyphenyl)-3-[4-(pyrrolidin-1-yl) piperidine-1-carbonyl]pyridine-2,4-diol (61);
6-butyl-5-(2,6-dimethoxyphenyl)-3-(4-phenylpiperidine-1-carbonyl)pyridine-2,4-diol (62);
6-butyl-3-(4-cyclohexylpiperazine-1-carbonyl)-5-(2,6-dimethoxyphenyl)pyridine-2,4-diol (63);
6-butyl-5-(2,6-dimethoxyphenyl)-3-({3H-spiro[2-benzofuran-1,4'-piperidine]-1'-yl}carbonyl)pyridine-2,4-diol (64);
6-butyl-5-(2,6-dimethoxyphenyl)-3-[4-(6-fluoro-1,2-benzoxazol-3-yl)piperidine-1-carbonyl]pyridine-2,4-diol (65);
1-[6-butyl-5-(2,6-dimethoxyphenyl)-2,4-dihydroxypyridine-3-carbonyl]-2',3'-dihydro-1'H-spiro[piperidine-4,4'-quinoline]-2'-one (66);
6-butyl-5-(2,6-dimethoxyphenyl)-3-[4-(5-phenyl-1H-pyrazol-3-yl)piperidine-1-carbonyl]pyridine-2,4-diol (67);
6-butyl-3-[4-(4-chlorophenyl)piperazine-1-carbonyl]-5-(2,6-dimethoxyphenyl)pyridine-2,4-diol (68);
6-butyl-5-(2,6-dimethoxyphenyl)-3-{4-[3-(pyridin-3-vi)-1,2,4-oxadiazol-5-yl]piperidine-1-carbonyl}pyridine-2,4-diol (69);
6-(Ethoxymethyl)-5-(4-fluoro-2,6-dimethoxyphenyl)-3-[(3R)-3-phenylpyrrolidine-1-carbonyl]pyridine-2,4-diol) (70);
6-butyl-5-(3-fluoro-2,6-dimethoxyphenyl)-3-[(3R)-3-phenylpyrrolidine-1-carbonyl]pyridine-2,4-diol (71);
6-butyl-3-[3-(2-chlorophenyl)pyrrolidine-1-carbonyl]-5-(2,6-dimethoxyphenyl)pyridine-2,4-diol (72);
(6-butyl-5-(2,6-dimethoxyphenyl)-2,4-dihydroxypyridin-3-yl)(3-(5-chloropyridin-2-yl)pyrrolidin-1-yl)methanone (74);
6-butyl-3-[3-(5-chloropyridin-2-yl)pyrrolidine-1-carbonyl]-5-(2,6-dimethoxyphenyl)pyridine-2,4-diol (75);
3-[3-(5-chloropyridin-2-yl)pyrrolidine-1-carbonyl]-5-(2,6-dimethoxyphenyl)-6-(ethoxymethyl)pyridine-2,4-diol (76);
3-[3-(5-chloropyridin-2-yl)pyrrolidine-1-carbonyl]-5-(2,6-dimethoxyphenyl)-6-(ethoxymethyl)pyridine-2,4-diol (77);
6-butyl-5-(2,6-dimethoxyphenyl)-3-[3-(3-fluoropyridin-2-yl)pyrrolidine-1-carbonyl]pyridine-2,4-diol (78);
6-butyl-5-(2,6-dimethoxyphenyl)-3-[3-(5-fluoropyridin-2-yl)pyrrolidine-1-carbonyl]pyridine-2,4-diol (79);
6-butyl-5-(2,6-dimethoxyphenyl)-3-[3-(5-fluoropyridin-2-yl)pyrrolidine-1-carbonyl]pyridine-2,4-diol (80);
6-butyl-5-(2,6-dimethoxyphenyl)-3-[3-(3-fluoropyridin-2-yl)pyrrolidine-1-carbonyl]pyridine-2,4-diol (81);
6-butyl-3-[3-(3,5-difluoropyridin-2-yl)pyrrolidine-1-carbonyl]-5-(2,6-dimethoxyphenyl)pyridine-2,4-diol (82);
6-butyl-3-[3-(3,5-difluoropyridin-2-yl)pyrrolidine-1-carbonyl]-5-(2,6-dimethoxyphenyl)pyridine-2,4-diol (83);
3-[3-(3,5-difluoropyridin-2-yl)pyrrolidine-1-carbonyl]-5-(2,6-dimethoxyphenyl)-6-(ethoxymethyl)pyridine-2,4-diol (84);
3-[3-(3,5-difluoropyridin-2-yl)pyrrolidine-1-carbonyl]-5-(2,6-dimethoxyphenyl)-6-(ethoxymethyl)pyridine-2,4-diol (85);
(5-(2,6-dimethoxyphenyl)-6-(4-fluorophenyl)-2,4-dihydroxypyridin-3-yl)(3-(2-fluorophenyl)pyrrolidin-1-yl) methanone (86);
(3-(3,5-difluoropyridin-2-yl)pyrrolidin-1-yl)(5-(2,6-dimethoxyphenyl)-6-(4-fluorophenyl)-2,4-dihydroxypyridin-3-yl)methanone (87);
5-(2,6-dimethoxyphenyl)-3-{4-[(3-fluorophenyl)methyl] piperazine-1-carbonyl}-(2 methoxyethyl)pyridine-2,4-diol (88);
5-(2,6-dimethoxyphenyl)-6-(ethoxymethyl)-3-{4-[(2-fluorophenyl)methyl]piperazine-1-carbonyl}pyridine-2,4-diol (89);
5-(2,6-dimethoxyphenyl)-6-(ethoxymethyl)-3-{4-[(3-fluorophenyl)methyl]piperazine-1-carbonyl}pyridine-2,4-diol (90);
6-(ethoxymethyl)-3-{4-[(3-fluorophenyl)methyl]piperazine-1-carbonyl}-5-(2-methoxyphenyl)pyridine-2,4-diol (91);
6-butyl-5-(2,6-dimethoxyphenyl)-3-(4-phenoxypiperidine-1-carbonyl)pyridine-2,4-diol (92);
6-butyl-3-{4-[(2,4-dichlorophenyl)methyl]piperazine-1-carbonyl}-5-(2,6-dimethoxyphenyl)pyridine-2,4-diol (93);
6-butyl-3-{4-[(2,3-dichlorophenyl)methyl]piperazine-1-carbonyl}-5-(2,6-dimethoxyphenyl)pyridine-2,4-diol (94);
6-butyl-52-(2,5-dimethoxyphenyl-[(3S)-3-phenylpyrrolidine-1-carbonyl]pyridine-2,4-diol (96);

6-butyl-5-(2,5-dimethoxyphenyl)-3-[(3R)-3-phenylpyrrolidine-1-carbonyl]pyridine-2,4-diol (97);

N-{1-[6-butyl-5-(2,6-dimethoxyphenyl)-2,4-dihydroxypyridine-3-carbonyl]azetidin-3-yl}benzamide (98);

6-butyl-5-(2,6-dimethoxyphenyl)-2,4-dihydroxy-N-methyl-N-(2-phenoxyethyl)pyridine-3-carboxamide (99);

6-butyl-3-{4-[(5-chloropyridin-2-yl)oxy]piperidine-1-carbonyl}-5-(2,6-dimethoxyphenyl)pyridine-2,4-diol (100);

6-butyl-5-(2,6-dimethoxyphenyl)-3-[4-(pyridin-2-ylmethyl)piperazine-1-carbonyl]pyridine-2,4-diol (101);

6-butyl-3-{4-[(2,3-dichlorophenyl)methyl]piperazine-1-carbonyl}-5-(2,5-dimethoxyphenyl)pyridine-2,4-diol (103);

3-{4-[(2,3-dichlorophenyl)methyl]piperazine-1-carbonyl}-5-(2,6-dimethoxyphenyl)-6-(ethoxymethyl)pyridine-2,4-diol (104);

6-butyl-3-[4-(5-chloropyridine-2-carbonyl)piperazine-1-carbonyl]-5-(2,6-dimethoxyphenyl)pyridine-2,4-diol (105);

6-butyl-5-(2,6-dimethoxyphenyl)-3-{4-[(2-methylphenyl)methyl]piperidine-1-carbonyl}pyridine-2,4-diol (106);

6-butyl-5-(2,6-dimethoxyphenyl)-3-(4-{[3-(trifluoromethyl)phenyl]methyl}piperazine-1-carbonyl)pyridine-2,4-diol (107);

6-butyl-3-{4-[(2,3-difluorophenyl)methyl]piperazine-1-carbonyl}-5-(2,6-dimethoxyphenyl)pyridine-2,4-diol (108);

6-butyl-3-[4-(cyclohexylmethyl)piperazine-1-carbonyl]-5-(2,6-dimethoxyphenyl)pyridine-2,4-diol (109);

6-butyl-3-{4-[(2,3-difluorophenyl)methyl]piperazine-1-carbonyl}-5-(2,5-dimethoxyphenyl)pyridine-2,4-diol (110);

6-butyl-3-[4-(cyclopropylmethyl)piperazine-1-carbonyl]-5-(2,6-dimethoxyphenyl)pyridine-2,4-diol (111);

6-butyl-3-{4-[(2,3-dichlorophenyl)methyl]piperazine-1-carbonyl}-5-(2,3-dimethoxyphenyl)pyridine-2,4-diol (112);

3-{4-[(2-bromo-5-fluorophenyl)methyl]piperidine-1-carbonyl}-6-butyl-5-(2,6-dimethoxyphenyl)pyridine-2,4-diol (113);

3-{4-[(2,3-difluorophenyl)methyl]piperazine-1-carbonyl}-5-(2,6-dimethoxyphenyl)-6-(ethoxymethyl)pyridine-2,4-diol (114);

6-butyl-5-(2,6-dimethoxyphenyl)-3-{3-[(3-fluoropyridin-2-yl)oxy]azetidine-1-carbonyl}pyridine-2,4-diol (115);

6-butyl-3-{3-[(2,3-difluorophenyl)methoxy]azetidine-1-carbonyl}-5-(2,6-dimethoxyphenyl)pyridine-2,4-diol (116);

N-{1-[6-butyl-5-(2,6-dimethoxyphenyl)-2,4-dihydroxypyridine-3-carbonyl]azetidin-3-yl}-2,3-difluorobenzene-1-sulfonamide (118);

6-butyl-3-[4-(2,3-difluorobenzoyl)piperazine-1-carbonyl]-5-(2,6-dimethoxyphenyl)pyridine-2,4-diol (119);

6-butyl-5-(2,6-dimethoxyphenyl)-3-{4-[(3-fluoropyridin-2-yl)methyl]piperazine-1-carbonyl}pyridine-2,4-diol (120);

6-butyl-5-(2,6-dimethoxyphenyl)-3-{4-[(2-fluoro-3-methylphenyl)methyl]piperazine-1-carbonyl}pyridine-2,4-diol (121);

6-butyl-3-{4-[(2,5-difluorophenyl)methyl]piperazine-1-carbonyl}-5-(2,6-dimethoxyphenyl)pyridine-2,4-diol (122);

6-butyl-3-{4-[(6-chloropyridin-2-yl)methyl]piperazine-1-carbonyl}-5-(2,6-dimethoxyphenyl)pyridine-2,4-diol (123);

5-(2,6-dimethoxyphenyl)-6-(ethoxymethyl)-3-[3-(3-fluorophenyl)pyrrolidine-1-carbonyl]pyridine-2,4-diol (124);

6-cyclopentyl-5-(2,6-dimethoxyphenyl)-3-[3-(3-fluorophenyl)pyrrolidine-1-carbonyl]pyridine-2,4-diol (125);

5-(2,6-dimethoxyphenyl)-6-(ethoxymethyl)-3-[3-(2-fluorophenyl)pyrrolidine-1-carbonyl]pyridine-2,4-diol (126);

5-(2,6-dimethoxyphenyl)-6-(ethoxymethyl)-3-[3-(2-fluorophenyl)pyrrolidine-1-carbonyl]pyridine-2,4-diol (127);

3-[3-(3,5-difluoropyridin-2-yl)pyrrolidine-1-carbonyl]-5-(3-methoxyphenyl)-6-(2-methyl-1,3-thiazol-4-yl)pyridine-2,4-diol (128);

3-[3-(3,5-difluoropyridin-2-yl)pyrrolidine-1-carbonyl]-5-(3-methoxyphenyl)-6-(2-methyl-1,3-thiazol-4-yl)pyridine-2,4-diol (129);

6-butyl-3-[3-(5-chloro-3-fluoropyridin-2-yl)pyrrolidine-1-carbonyl]-5-(2,6-dimethoxyphenyl)-4-hydroxy-1,2-dihydropyridin-2-one (130);

3-[3-(2,4-difluorophenyl)pyrrolidine-1-carbonyl]-5-(2,6-dimethoxyphenyl)-6-(ethoxymethyl)-4-hydroxy-1,2-dihydropyridin-2-one (131);

3-[3-(2,4-difluorophenyl)pyrrolidine-1-carbonyl]-5-(2,6-dimethoxyphenyl)-6-(ethoxymethyl)-4-hydroxy-1,2-dihydropyridin-2-one (132);

3-[3-(2,6-difluorophenyl)pyrrolidine-1-carbonyl]-5-(2,6-dimethoxyphenyl)-6-(ethoxymethyl)-4-hydroxy-1,2-dihydropyridin-2-one (133);

3-[3-(2,6-difluorophenyl)pyrrolidine-1-carbonyl]-5-(2,6-dimethoxyphenyl)-6-(ethoxymethyl)-4-hydroxy-1,2-dihydropyridin-2-one (134);

6-butyl-3-[3-(5-chloro-3-fluoropyridin-2-yl)pyrrolidine-1-carbonyl]-5-(2,6-dimethoxyphenyl)-4-hydroxy-1,2-dihydropyridin-2-one (135);

3-[(3S)-3-(benzyloxy)pyrrolidine-1-carbonyl]-6-butyl-5-(2,6-dimethoxyphenyl)pyridine-2,4-diol (136);

3-[(3S)-3-benzyloxy)pyrrolidine-1-carbonyl]-5-(2,6-dimethoxyphenyl)-6-(ethoxymethyl)pyridine-2,4-diol (137);

6-butyl-5-(3-ethylphenyl)-4-hydroxy-3-{5-[(2-methyl-1,3-thiazol-4-yl)methyl]-1,3,4-oxadiazol-2-yl}-1,2-dihydropyridin-2-one (138);

2-[3-(2-butyl-5-{4-[(2,3-difluorophenyl)methyl]piperazine-1-carbonyl}-4,6-dihydroxypyridin-3-yl)phenyl]acetonitrile (139);

6-butyl-3-[3-(3,5-difluoropyridin-2-yl)pyrrolidine-1-carbonyl]-5-[3-(propan-2-yl)phenyl]pyridine-2,4-diol (140);

6-butyl-3-[3-(3,5-difluoropyridin-2-yl)pyrrolidine-1-carbonyl]-5-[3-(propan-2-yl)phenyl]pyridine-2,4-diol (141);

6-butyl-3-[3-(3,5-difluoropyridin-2-yl)pyrrolidine-1-carbonyl]-5-(3-methoxyphenyl)pyridine-2,4-diol (142);

6-butyl-3-[3-(3,5-difluoropyridin-2-yl)pyrrolidine-1-carbonyl]-5-(3-methoxyphenyl)pyridine-2,4-diol (143);

6-butyl-3-[3-(3,5-difluoropyridin-2-yl)pyrrolidine-1-carbonyl]-5-[3-(hydroxymethyl)phenyl]pyridine-2,4-diol (144);

3-{2-butyl-5-[3-(3,5-difluoropyridin-2-yl)pyrrolidine-1-carbonyl]-4,6-dihydroxypyridin-3-yl}-N-(propan-2-yl)benzamide (145);

3-{2-butyl-5-[3-(3,5-difluoropyridin-2-yl)pyrrolidine-1-carbonyl]-4,6-dihydroxypyridin-3-yl}-N-(propan-2-yl)benzamide (146);

6-butyl-3-[3-(3,5-difluoropyridin-2-yl)pyrrolidine-1-carbonyl]-5-[3-(hydroxymethyl)phenyl]pyridine-2,4-diol (147);

6-butyl-3-[(3R)-3-phenylpyrrolidine-1-carbonyl]-5-[3-(propan-2-yl)phenyl]pyridine-2,4-diol (148);

5-(2,6-dimethoxyphenyl)-6-[(ethylamino)methyl]-3-[3-(3-fluorophenyl)pyrrolidine-1-carbonyl]pyridine-2,4-diol (149);

5-(2,6-dimethoxyphenyl)-6-[(ethylamino)methyl]-3-[3-(2-fluorophenyl)pyrrolidine-1-carbonyl]pyridine-2,4-diol (150);

5-(2,6-dimethoxyphenyl)-6-[(ethylamino)methyl]-3-[3-(2-fluorophenyl)pyrrolidine-1-carbonyl]pyridine-2,4-diol (151);

6-butyl-3-[4-(2,3-dichlorobenzoyl)piperazine-1-carbonyl]-5-(2,6-dimethoxyphenyl)pyridine-2,4-diol (153);

6-butyl-3-{4-[(2,3-difluorophenyl)methyl]piperazine-1-carbonyl}-5-(2,3-dimethoxyphenyl)pyridine-2,4-diol (154), or a stereoisomer, a tautomer, or a pharmaceutically acceptable salt thereof.

10. A pharmaceutical composition, comprising a pharmaceutically acceptable carrier and a compound of claim 1, or a stereoisomer, a tautomer, or a pharmaceutically acceptable salt thereof.

* * * * *

UNITED STATES PATENT AND TRADEMARK OFFICE
CERTIFICATE OF CORRECTION

PATENT NO. : 10,392,347 B2
APPLICATION NO. : 15/767364
DATED : August 27, 2019
INVENTOR(S) : Soong-Hoon Kim et al.

It is certified that error appears in the above-identified patent and that said Letters Patent is hereby corrected as shown below:

In the Claims

In Claim 1, Column 196, Lines 27-34 (Approx.), delete

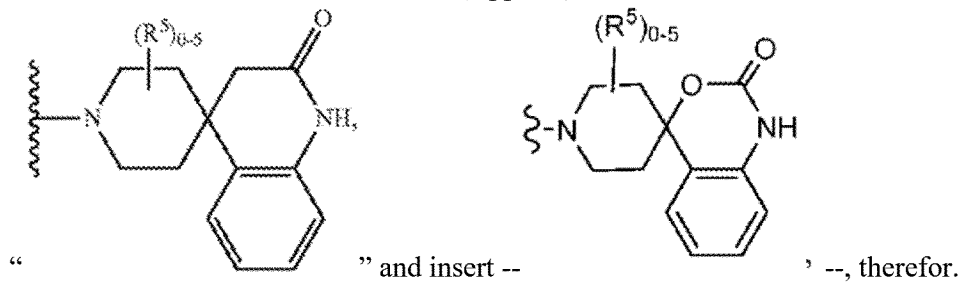

" and insert -- ' --, therefor.

In Claim 3, Column 198, Line 53 (Approx.), above

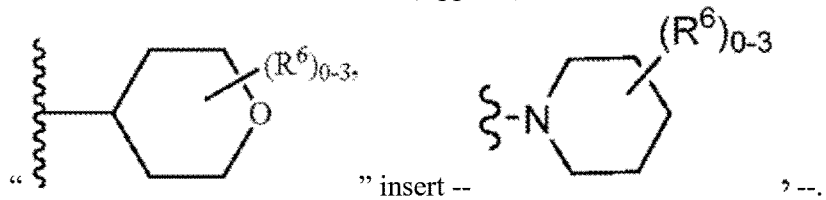

" insert -- ' --.

In Claim 3, Column 199, Lines 12-16 (Approx.), after " 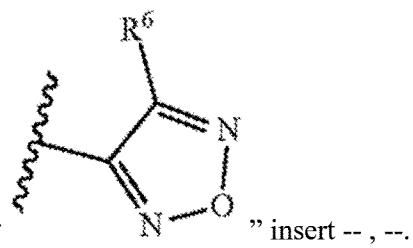 " insert --, --.

Signed and Sealed this
Twenty-third Day of June, 2020

Andrei Iancu
*Director of the United States Patent and Trademark Office*

In Claim 4, Column 200, Lines 28-32 (Approx.), delete "  " and insert
-- 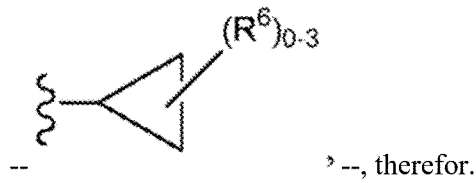 --, therefor.
In Claim 4, Column 200, Lines 33-41 (Approx.), delete
" 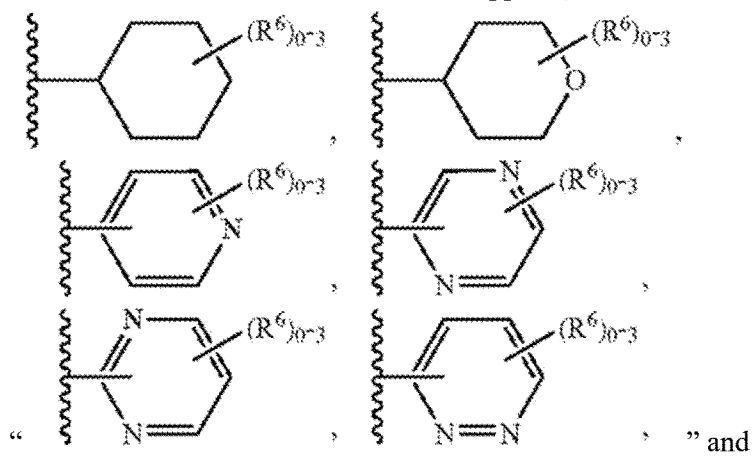 " and
insert -- 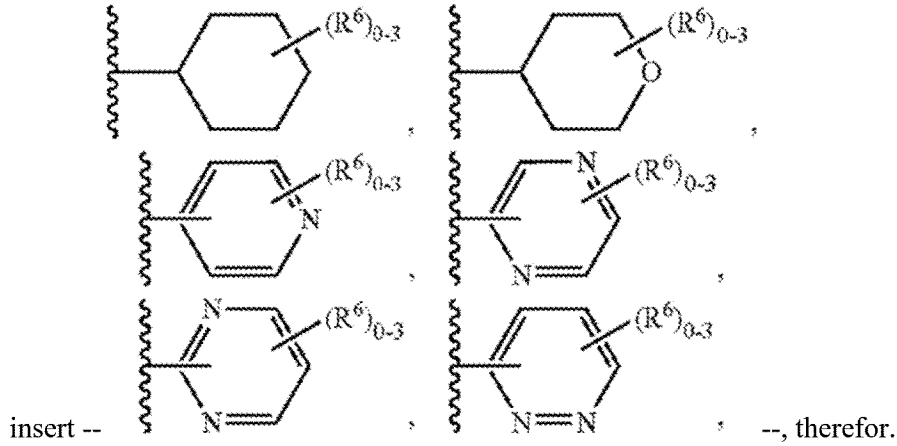 --, therefor.

In Claim 4, Column 200, Lines 42-51 (Approx.), delete
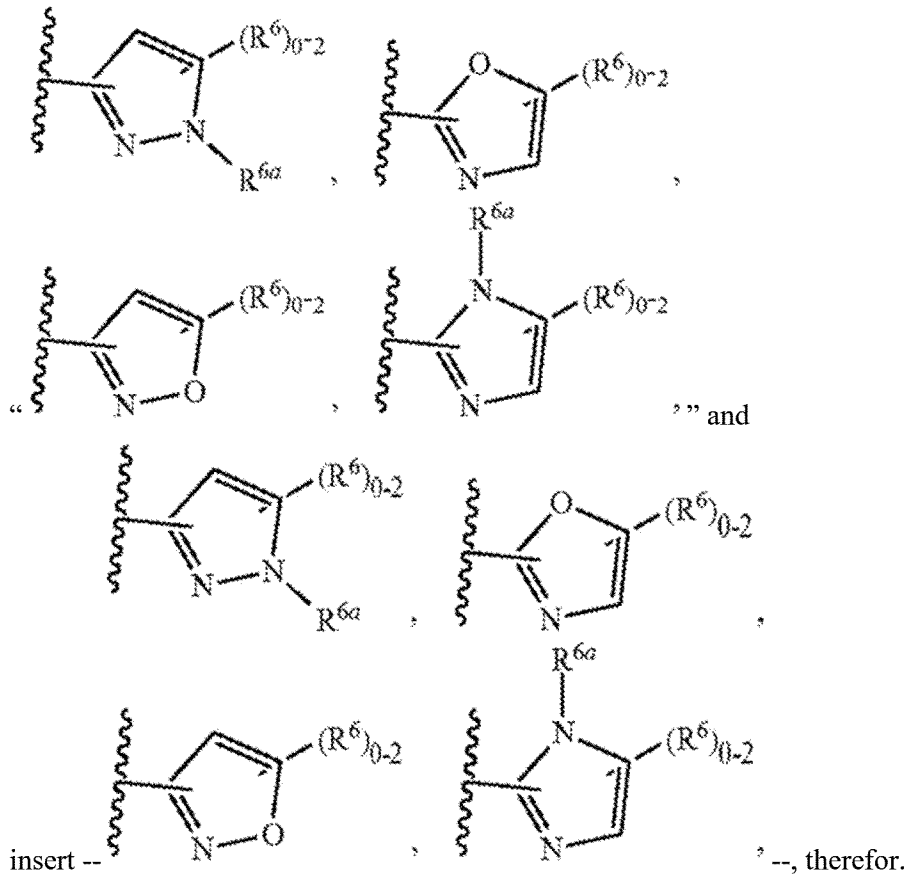
insert -- ... --, therefor.
In Claim 4, Column 200, Lines 52-55 (Approx.), delete
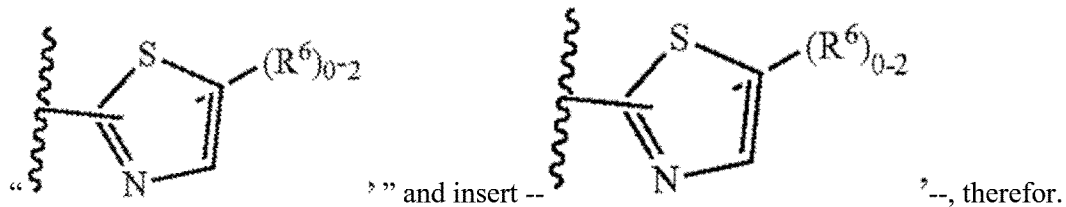
" " and insert -- " --, therefor.
In Claim 4, Column 200, Lines 61-67 (Approx.), delete
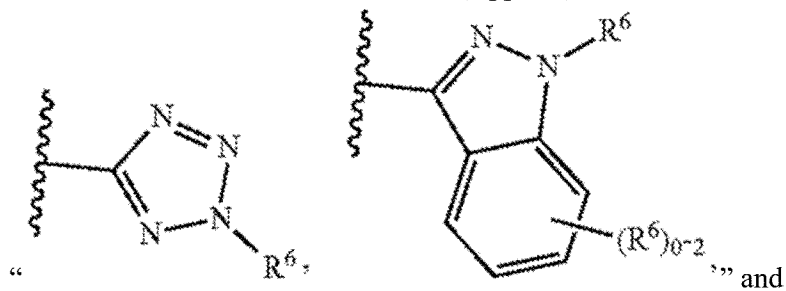
" " and insert -- 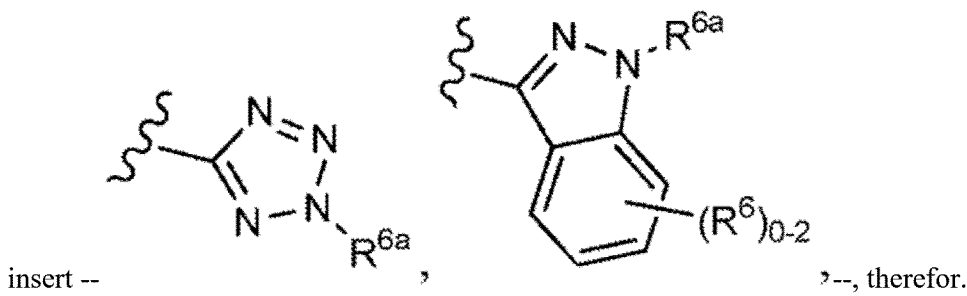 --, therefor.
In Claim 4, Column 201, Lines 1-7 (Approx.), delete
" 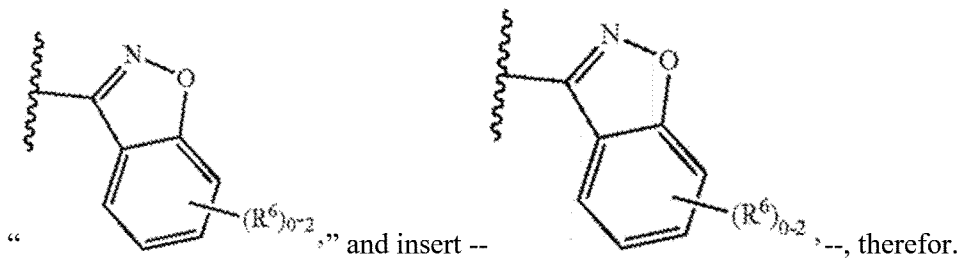 ," and insert -- --, therefor.
In Claim 4, Column 201, Lines 1-7 (Approx.), delete
" 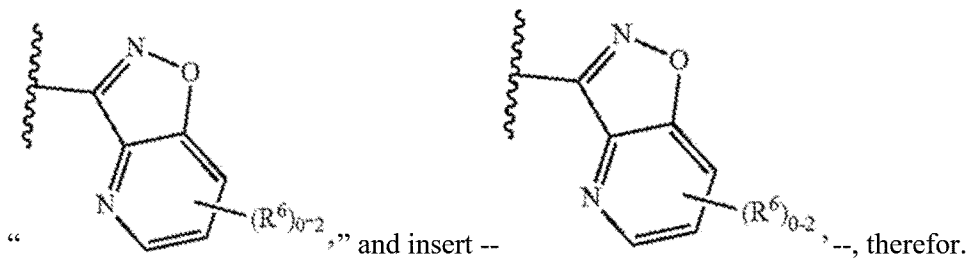 ," and insert -- --, therefor.

CERTIFICATE OF CORRECTION (continued)
U.S. Pat. No. 10,392,347 B2

In Claim 4, Column 201, Lines 8-29 (Approx.), delete

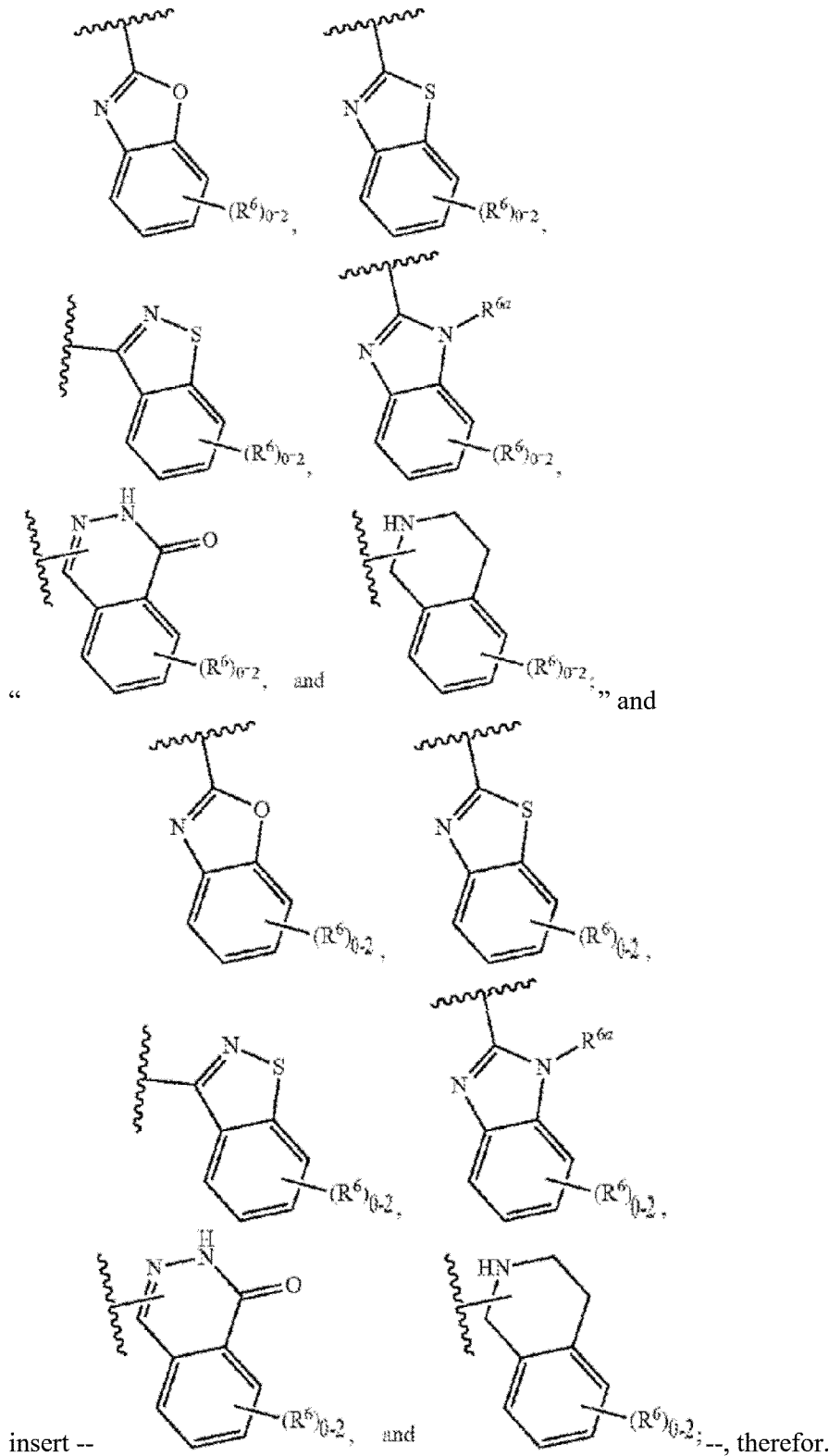

" , and insert -- , and ; --, therefor.

In Claim 5, Column 202, Lines 54-57 (Approx.), after " 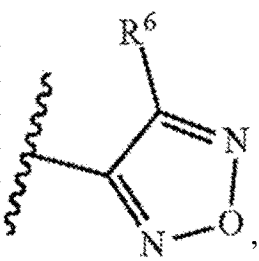 " insert -- , --.
In Claim 6, Column 204, Lines 37-42 (Approx.), delete
" 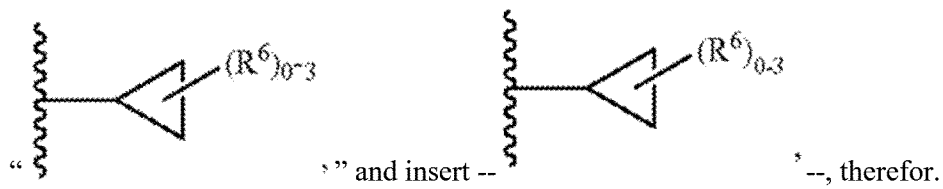 " and insert -- -- , therefor.
In Claim 6, Column 204, Lines 43-52 (Approx.), delete
" 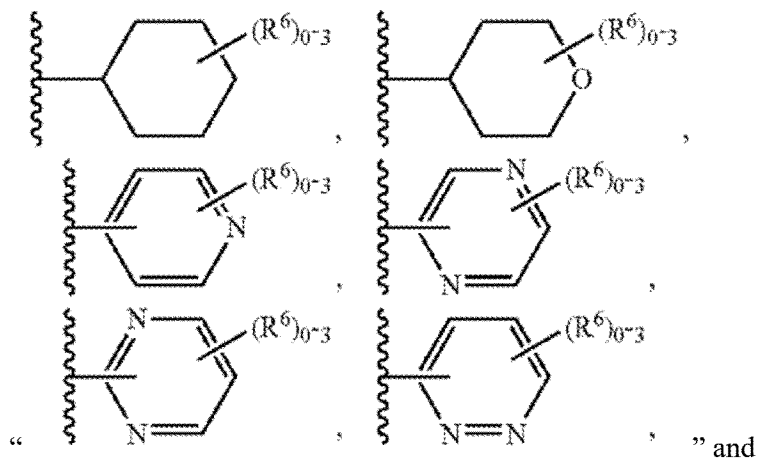 " and insert -- 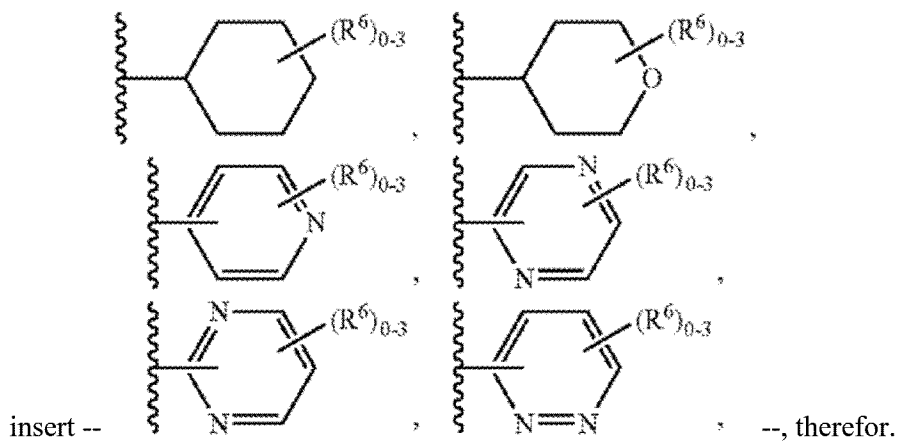 --, therefor.

In Claim 6, Column 204, Lines 53-62 (Approx.), delete
insert -- 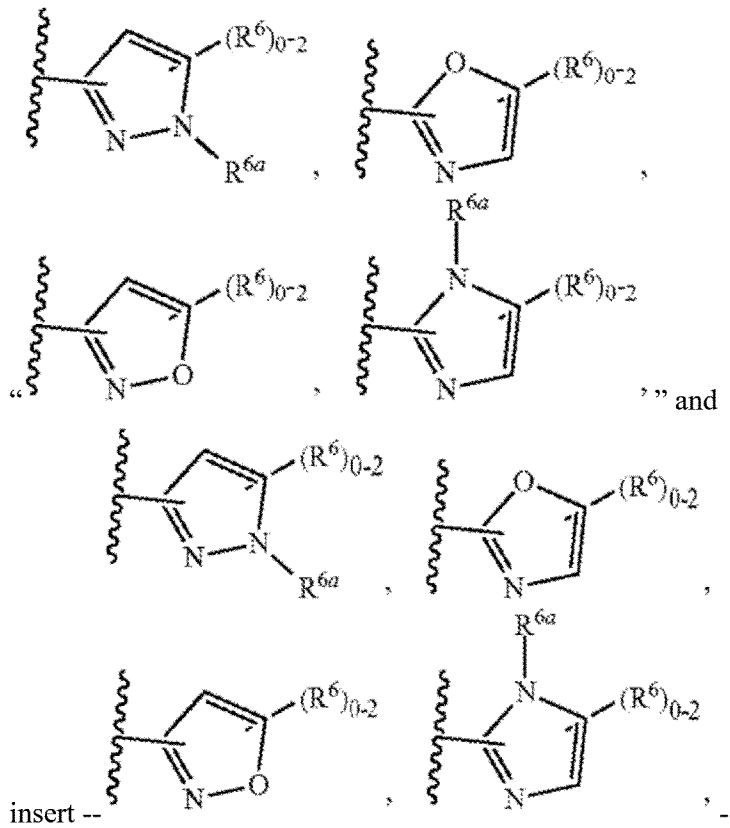 -- , therefor.
In Claim 6, Column 204, Lines 63-66 (Approx.), delete " 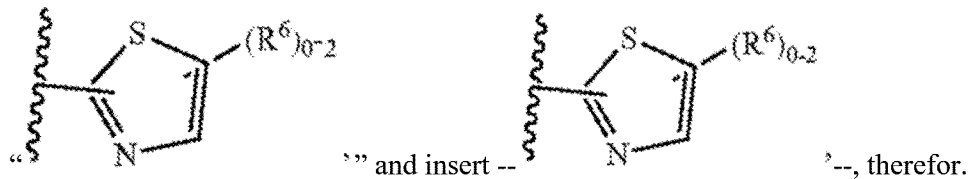 " and insert -- -- , therefor.
In Claim 6, Column 205, Lines 7-12 (Approx.), delete " 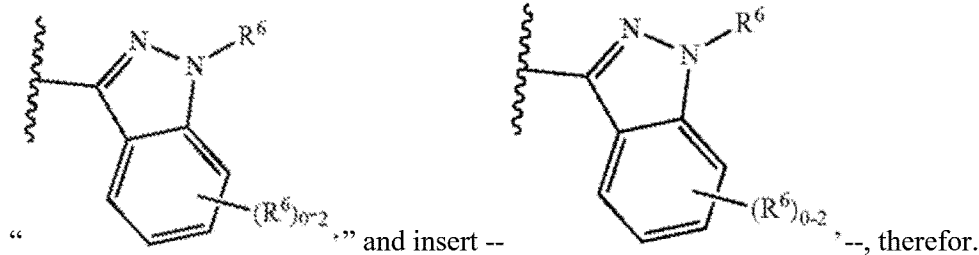 " and insert -- -- , therefor.

In Claim 6, Column 205, Lines 14-42 (Approx.), delete
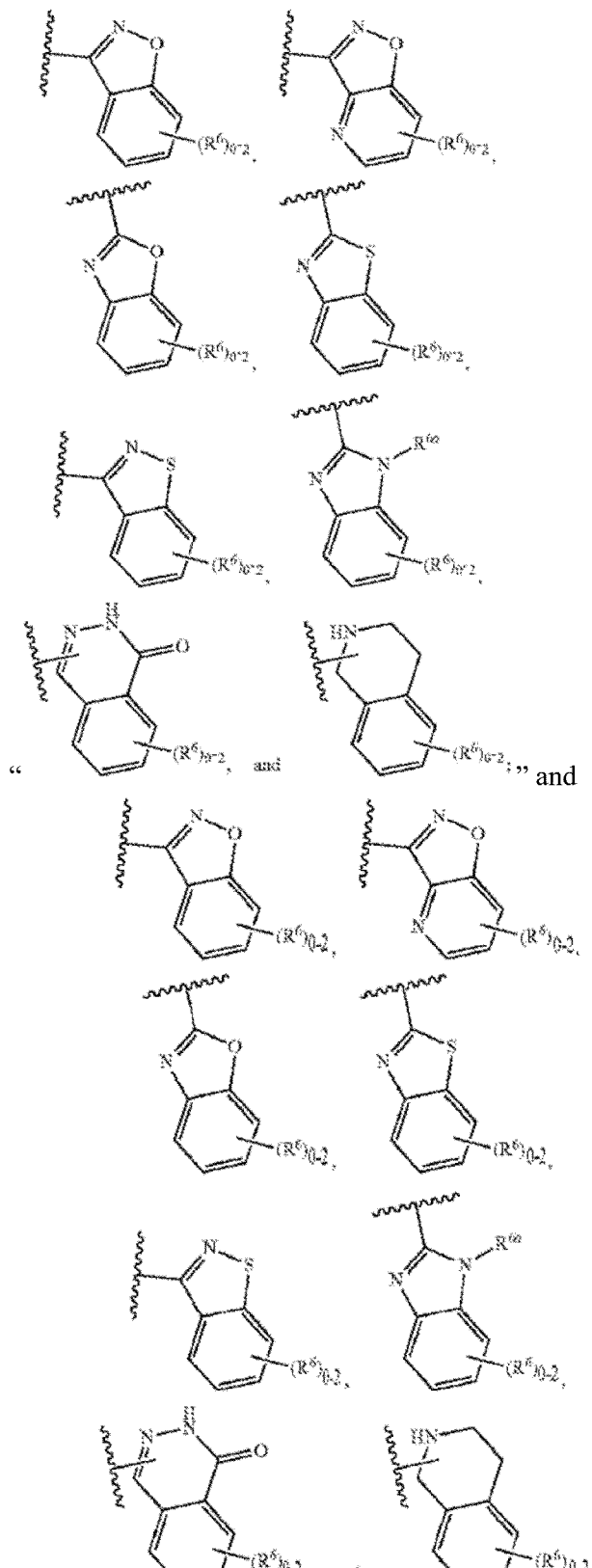
insert --                                                                                    --, therefor.

In Claim 6, Column 205, Lines 49-63 (Approx.), delete " 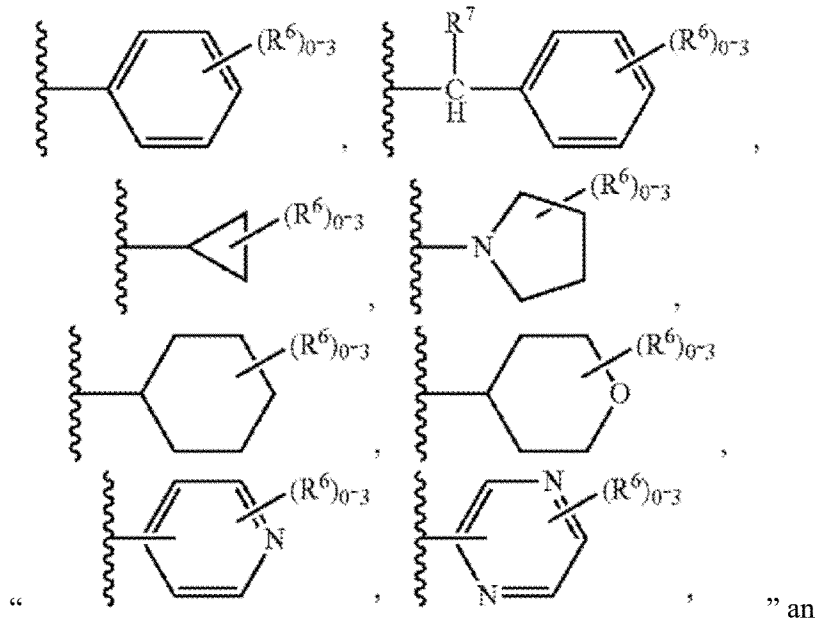 " and insert -- 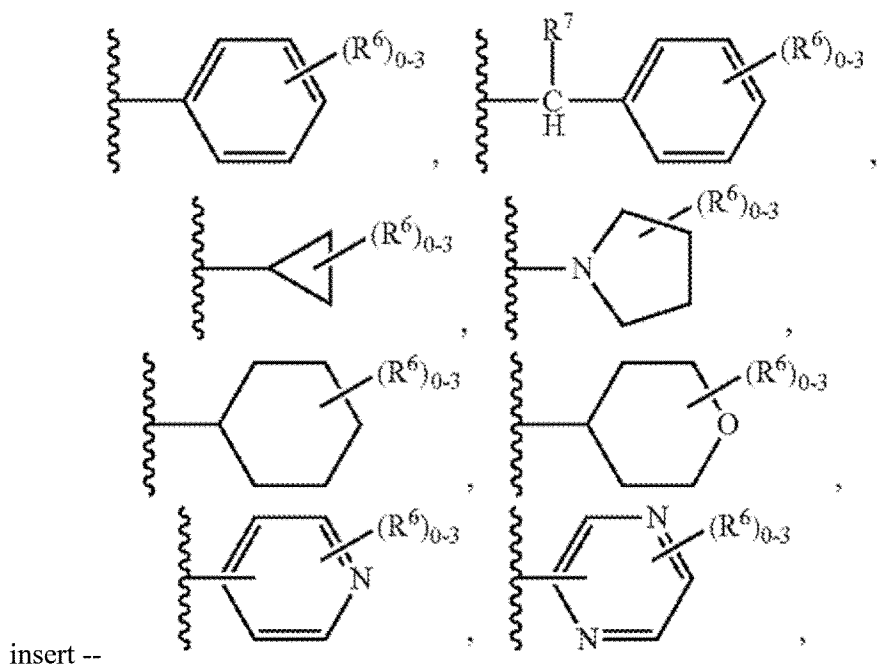 --, therefor.
In Claim 6, Column 205, Lines 64-67 (Approx.), delete 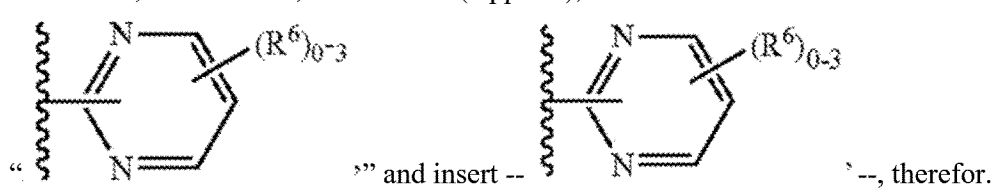 therefor.

CERTIFICATE OF CORRECTION (continued)
U.S. Pat. No. 10,392,347 B2

In Claim 6, Column 205, Lines 64-67 (Approx.), delete

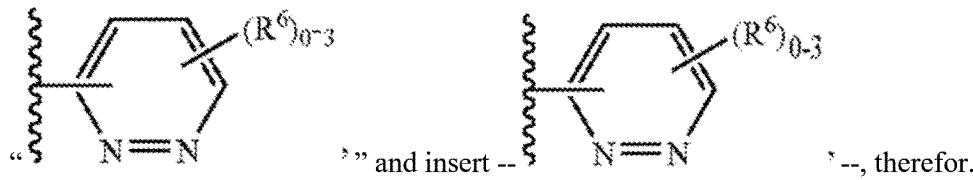

" and insert -- -- , therefor.

In Claim 6, Column 206, Lines 1-11 (Approx.), delete

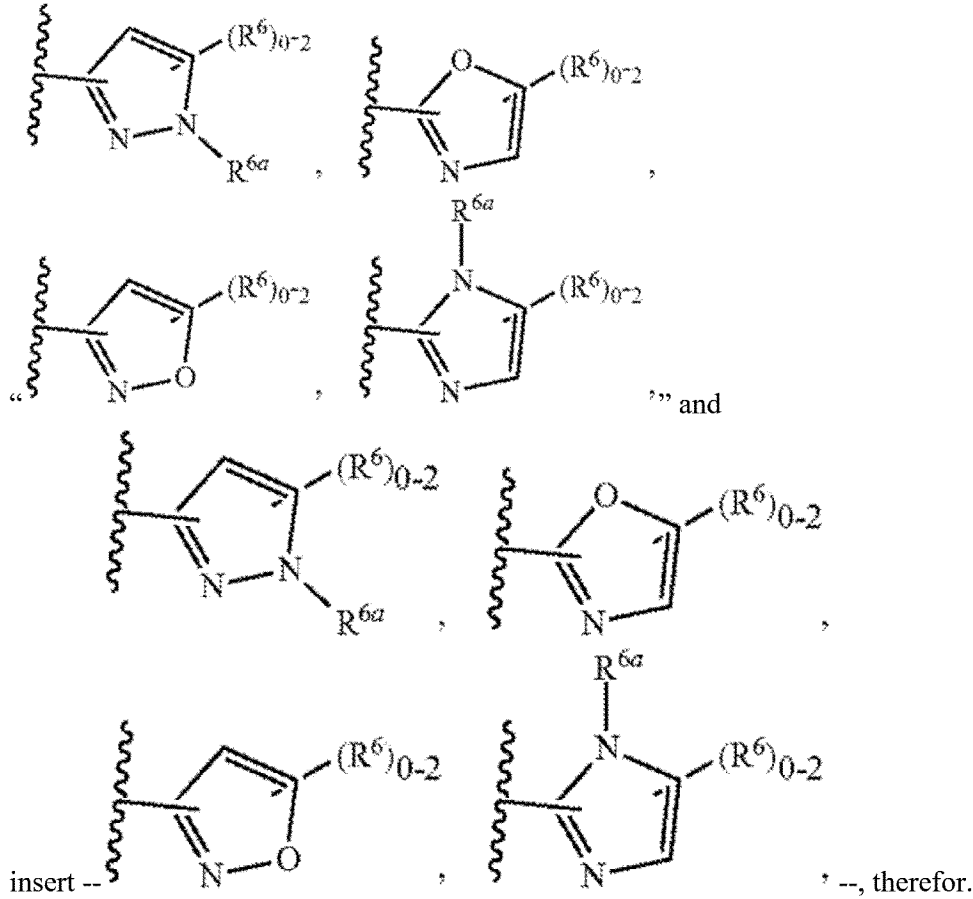

-- , therefor.

In Claim 6, Column 206, Lines 12-16 (Approx.), delete

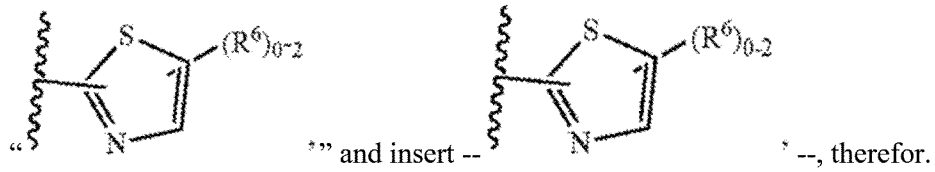

" and insert -- -- , therefor.

In Claim 6, Column 206, Lines 22-48 (Approx.), delete
" 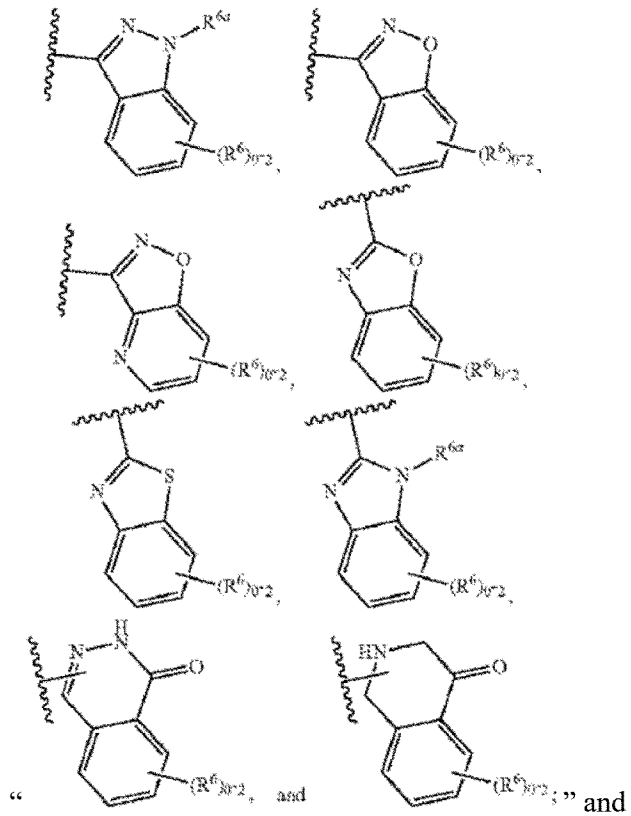 and " and
insert -- 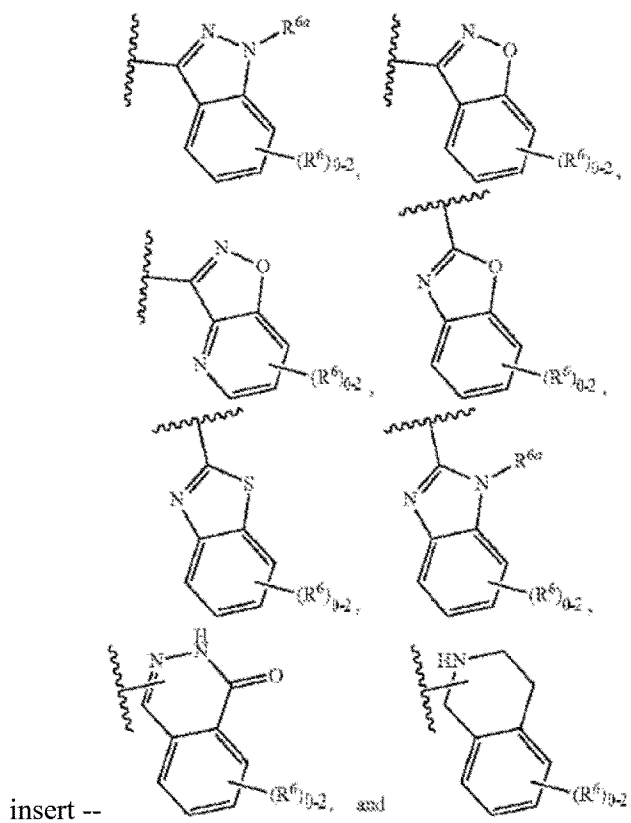 --, therefor.

In Claim 7, Column 207, Lines 22 (Approx.), after " 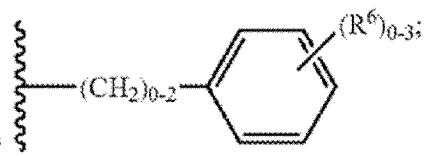 " insert -- and --.

In Claim 9, Column 208, Lines 54-55, delete "carbonyl}-(2,6-" and insert -- carbonyl}-5-(2,6- --, therefor.

In Claim 9, Column 210, Line 1, delete "(pyridin-3-vi)" and insert -- (pyridin-3-yl) --, therefor.

In Claim 9, Column 210, Line 47, delete "-(2 methoxyethyl)" and insert -- -6-(2-methoxyethyl) --, therefor.

In Claim 9, Column 210, Line 66, delete "6-butyl-52-(2,5-dimethoxyphenyl-[(3S)" and insert -- 6-butyl-5-(2,5-dimethoxyphenyl-3-[(3S) --, therefor.

In Claim 9, Column 211, Line 12 (Approx.), delete "(pyri din" and insert -- (pyridin --, therefor.

In Claim 9, Column 212, Line 43, delete "3-benzyloxy)" and insert -- 3-(benzyloxy) --, therefor.